United States Patent
Pellicciari et al.

(10) Patent No.: US 12,186,317 B2
(45) Date of Patent: Jan. 7, 2025

(54) INHIBITORS OF ALPHA-AMINO-BETA-CARBOXYMUCONIC ACID SEMIALDEHYDE DECARBOXYLASE

(71) Applicant: TES Pharma S.r.l., Perugia (IT)

(72) Inventors: Roberto Pellicciari, Perugia (IT); Paride Liscio, Perugia (IT); Nicola Giacche, Perugia (IT); Francesca De Franco, Perugia (IT)

(73) Assignee: TES PHARMA S.R.L., Perugia (IT)

( * ) Notice: Subject to any disclaimer, the term of this patent is extended or adjusted under 35 U.S.C. 154(b) by 0 days.

(21) Appl. No.: 18/447,130

(22) Filed: Aug. 9, 2023

(65) Prior Publication Data

US 2023/0381177 A1 Nov. 30, 2023

Related U.S. Application Data

(63) Continuation of application No. 17/325,068, filed on May 19, 2021, which is a continuation of application No. PCT/EP2019/081799, filed on Nov. 19, 2019.

(60) Provisional application No. 62/769,959, filed on Nov. 20, 2018.

(51) Int. Cl.
| | |
|---|---|
| *A61K 31/513* | (2006.01) |
| *A61K 31/4418* | (2006.01) |
| *A61K 31/4436* | (2006.01) |
| *A61K 31/5377* | (2006.01) |
| *A61P 1/16* | (2006.01) |
| *C07D 213/70* | (2006.01) |
| *C07D 239/56* | (2006.01) |
| *C07D 409/04* | (2006.01) |
| *C07D 409/12* | (2006.01) |
| *C07D 409/14* | (2006.01) |

(52) U.S. Cl.
CPC ........ *A61K 31/513* (2013.01); *A61K 31/4418* (2013.01); *A61K 31/4436* (2013.01); *A61K 31/5377* (2013.01); *A61P 1/16* (2018.01); *C07D 213/70* (2013.01); *C07D 239/56* (2013.01); *C07D 409/04* (2013.01); *C07D 409/12* (2013.01); *C07D 409/14* (2013.01)

(58) Field of Classification Search
CPC .............. C07D 213/70; A61K 31/5377; A61K 31/4418; A61K 31/513
See application file for complete search history.

(56) References Cited

U.S. PATENT DOCUMENTS

| | | | |
|---|---|---|---|
| 2,530,570 A | 11/1950 | Druey | |
| 3,914,250 A | 10/1975 | Kim | |
| 3,980,781 A | 9/1976 | Snell et al. | |
| 4,062,950 A | 12/1977 | Frommer et al. | |
| 4,174,439 A | 11/1979 | Rauenbusch et al. | |
| 4,189,438 A | 2/1980 | Umezawa et al. | |
| 4,242,453 A | 12/1980 | Umezawa et al. | |
| 4,254,256 A | 3/1981 | Otani et al. | |
| 4,273,765 A | 6/1981 | Suhara et al. | |
| 4,405,644 A | 9/1983 | Kabbe et al. | |
| 4,451,455 A | 5/1984 | Vertesy et al. | |
| 4,452,813 A | 6/1984 | Fujii et al. | |
| 4,598,089 A | 7/1986 | Hadvary et al. | |
| 4,623,714 A | 11/1986 | Vertesy et al. | |
| 4,634,765 A | 1/1987 | Liu | |
| 4,639,436 A | 1/1987 | Junge et al. | |
| 4,701,559 A | 10/1987 | Horii et al. | |
| 4,746,680 A | 5/1988 | Jeffery et al. | |
| 4,751,237 A | 6/1988 | Chabala et al. | |
| 4,806,564 A | 2/1989 | Chabala et al. | |
| 4,806,570 A | 2/1989 | Jeffery et al. | |
| 4,816,477 A | 3/1989 | Girotra et al. | |
| 4,847,271 A | 7/1989 | Chabala et al. | |
| 4,973,587 A | 11/1990 | Ward et al. | |
| 4,983,597 A | 1/1991 | Yang et al. | |
| 5,013,837 A | 5/1991 | Ward et al. | |
| 5,081,122 A | 1/1992 | Ward | |
| 5,091,418 A | 2/1992 | Sawada et al. | |
| 5,091,524 A | 2/1992 | Vertesy et al. | |
| 5,112,820 A | 5/1992 | Ward | |
| 5,120,729 A | 6/1992 | Chabala et al. | |
| 5,157,116 A | 10/1992 | Ducep et al. | |
| 5,182,298 A | 1/1993 | Helms et al. | |

(Continued)

FOREIGN PATENT DOCUMENTS

| | | |
|---|---|---|
| CN | 103864699 A | 6/2014 |
| CN | 107207483 A | 9/2017 |
| EA | 021088 B1 | 4/2015 |
| EA | 022069 B1 | 10/2015 |
| EP | 0318860 A2 | 6/1989 |
| EP | 0411703 A1 | 2/1991 |
| EP | 1010691 A2 | 6/2000 |
| EP | 0658546 B1 | 5/2001 |
| EP | 1258476 A1 | 11/2002 |
| EP | 1044970 B1 | 1/2003 |
| JP | H02169571 A | 6/1990 |

(Continued)

OTHER PUBLICATIONS

Kahn et al. (Natural Product Research (2018) 32:1161-1169, published on line May 11, 2017). (Year: 2017).*

(Continued)

*Primary Examiner* — Marcos L Sznaidman
(74) *Attorney, Agent, or Firm* — Cooley LLP

(57) ABSTRACT

The present disclosure discloses compounds capable of modulating the activity of α-amino-β-carboxymuconic acid semialdehyde decarboxylase (ACMSD), which are useful for the prevention and/or the treatment of diseases and disorders associated with defects in NAD$^+$ biosynthesis, e.g., metabolic disorders, neurodegenerative diseases, chronic inflammatory diseases, kidney diseases, and diseases associated with ageing. The present application also discloses pharmaceutical compositions comprising said compounds and the use of such compounds as a medicament.

12 Claims, No Drawings

(56) References Cited

U.S. PATENT DOCUMENTS

| | | | |
|---|---|---|---|
| 5,192,772 A | 3/1993 | Yoshikuni et al. |
| 5,217,877 A | 6/1993 | Sawada et al. |
| 5,292,736 A | 3/1994 | Kumar et al. |
| 5,391,571 A | 2/1995 | Mewshaw et al. |
| 5,436,272 A | 7/1995 | Scheinbaum |
| 5,451,677 A | 9/1995 | Fisher et al. |
| 5,504,078 A | 4/1996 | Ducep et al. |
| 5,512,565 A | 4/1996 | Mewshaw et al. |
| 5,521,283 A | 5/1996 | DiMarchi et al. |
| 5,532,237 A | 7/1996 | Gallant et al. |
| 5,552,522 A | 9/1996 | DiMarchi et al. |
| 5,552,523 A | 9/1996 | Basinski et al. |
| 5,552,524 A | 9/1996 | Basinski et al. |
| 5,602,151 A | 2/1997 | Mewshaw et al. |
| 5,624,941 A | 4/1997 | Barth et al. |
| 5,705,515 A | 1/1998 | Fisher et al. |
| 5,739,106 A | 4/1998 | Rink et al. |
| 6,001,836 A | 12/1999 | Poindexter et al. |
| 6,028,084 A | 2/2000 | Barth et al. |
| 6,140,354 A | 10/2000 | Dax et al. |
| 6,191,160 B1 | 2/2001 | Gao et al. |
| 6,258,837 B1 | 7/2001 | Fukami et al. |
| 6,313,298 B1 | 11/2001 | Gao et al. |
| 6,326,375 B1 | 12/2001 | Fukami et al. |
| 6,329,395 B1 | 12/2001 | Dugar et al. |
| 6,335,345 B1 | 1/2002 | Fukami et al. |
| 6,337,332 B1 | 1/2002 | Carpino |
| 6,340,683 B1 | 1/2002 | Marzabadi et al. |
| 6,358,951 B1 | 3/2002 | Carpino |
| 6,365,633 B1 | 4/2002 | Cheetham et al. |
| 2002/0006964 A1 | 1/2002 | Young et al. |
| 2002/0022637 A1 | 2/2002 | Li et al. |
| 2002/0049196 A1 | 4/2002 | Carpino et al. |
| 2002/0103199 A1 | 8/2002 | Corbett et al. |
| 2003/0087821 A1 | 5/2003 | Beeley et al. |
| 2003/0232860 A1 | 12/2003 | Harada et al. |
| 2009/0076033 A1* | 3/2009 | Robl .................. A61P 9/10 514/247 |
| 2018/0134667 A1 | 5/2018 | Pellicciari |
| 2022/0354848 A9 | 11/2022 | Pellicciari et al. |

FOREIGN PATENT DOCUMENTS

| | | |
|---|---|---|
| JP | H10237049 A | 9/1998 |
| JP | 2000256190 A | 9/2000 |
| JP | 2002114768 A | 4/2002 |
| JP | 2004250400 A | 9/2004 |
| JP | 2007145828 A | 6/2007 |
| JP | 2013226269 A | 11/2013 |
| JP | 2017529389 A | 10/2017 |
| NZ | 504256 A | 1/2003 |
| WO | WO-9409134 A2 | 4/1994 |
| WO | WO-9614307 A1 | 5/1996 |
| WO | WO-9623513 A1 | 8/1996 |
| WO | WO-9623514 A1 | 8/1996 |
| WO | WO-9623515 A1 | 8/1996 |
| WO | WO-9623516 A1 | 8/1996 |
| WO | WO-9623517 A1 | 8/1996 |
| WO | WO-9623518 A1 | 8/1996 |
| WO | WO-9623519 A1 | 8/1996 |
| WO | WO-9623520 A1 | 8/1996 |
| WO | WO-9633159 A1 | 10/1996 |
| WO | WO-9719682 A1 | 6/1997 |
| WO | WO-9720820 A1 | 6/1997 |
| WO | WO-9720821 A1 | 6/1997 |
| WO | WO-9720822 A1 | 6/1997 |
| WO | WO-9720823 A2 | 6/1997 |
| WO | WO-9727847 A1 | 8/1997 |
| WO | WO-9727857 A1 | 8/1997 |
| WO | WO-9728115 A1 | 8/1997 |
| WO | WO-9728137 A1 | 8/1997 |
| WO | WO-9729079 A1 | 8/1997 |
| WO | WO-9822128 A1 | 5/1998 |
| WO | WO-9827063 A1 | 6/1998 |
| WO | WO-9831227 A1 | 7/1998 |
| WO | WO-9833765 A1 | 8/1998 |
| WO | WO-9837061 A1 | 8/1998 |
| WO | WO-9841519 A1 | 9/1998 |
| WO | WO-9843635 A1 | 10/1998 |
| WO | WO-9843636 A1 | 10/1998 |
| WO | WO-9900123 A1 | 1/1999 |
| WO | WO-9902499 A1 | 1/1999 |
| WO | WO-9943813 A1 | 9/1999 |
| WO | WO-9951600 A1 | 10/1999 |
| WO | WO-9964002 A1 | 12/1999 |
| WO | WO-0010967 A1 | 3/2000 |
| WO | WO-0010968 A2 | 3/2000 |
| WO | WO-0064880 A1 | 11/2000 |
| WO | WO-0068197 A1 | 11/2000 |
| WO | WO-0069849 A1 | 11/2000 |
| WO | WO-0074679 A1 | 12/2000 |
| WO | WO-0102379 A1 | 1/2001 |
| WO | WO-0107027 A2 | 2/2001 |
| WO | WO-0107409 A1 | 2/2001 |
| WO | WO-0109120 A1 | 2/2001 |
| WO | WO-0114376 A1 | 3/2001 |
| WO | WO-0123387 A2 | 4/2001 |
| WO | WO-0123388 A2 | 4/2001 |
| WO | WO-0123389 A2 | 4/2001 |
| WO | WO-0127060 A1 | 4/2001 |
| WO | WO-0127068 A1 | 4/2001 |
| WO | WO-0144201 A1 | 6/2001 |
| WO | WO-0156592 A1 | 8/2001 |
| WO | WO-0158869 A2 | 8/2001 |
| WO | WO-0162341 A2 | 8/2001 |
| WO | WO-0162737 A2 | 8/2001 |
| WO | WO-0162738 A1 | 8/2001 |
| WO | WO-0164632 A1 | 9/2001 |
| WO | WO-0164633 A1 | 9/2001 |
| WO | WO-0164634 A1 | 9/2001 |
| WO | WO-0166548 A1 | 9/2001 |
| WO | WO-0168609 A1 | 9/2001 |
| WO | WO-0170337 A1 | 9/2001 |
| WO | WO-0170708 A1 | 9/2001 |
| WO | WO-0174782 A1 | 10/2001 |
| WO | WO-0174844 A2 | 10/2001 |
| WO | WO-0177094 A1 | 10/2001 |
| WO | WO-0182925 A1 | 11/2001 |
| WO | WO-0185098 A2 | 11/2001 |
| WO | WO-0185173 A1 | 11/2001 |
| WO | WO-0185690 A1 | 11/2001 |
| WO | WO-0185714 A1 | 11/2001 |
| WO | WO-0185730 A1 | 11/2001 |
| WO | WO-0187335 A2 | 11/2001 |
| WO | WO-0187834 A1 | 11/2001 |
| WO | WO-0189528 A1 | 11/2001 |
| WO | WO-0190090 A1 | 11/2001 |
| WO | WO-0190091 A1 | 11/2001 |
| WO | WO-0190092 A1 | 11/2001 |
| WO | WO-0191752 A1 | 12/2001 |
| WO | WO-0194300 A1 | 12/2001 |
| WO | WO-0196302 A1 | 12/2001 |
| WO | WO-0204433 A2 | 1/2002 |
| WO | WO-0206245 A1 | 1/2002 |
| WO | WO-0208250 A2 | 1/2002 |
| WO | WO-0210169 A1 | 2/2002 |
| WO | WO-0211715 A2 | 2/2002 |
| WO | WO-0212166 A2 | 2/2002 |
| WO | WO-0212178 A1 | 2/2002 |
| WO | WO-0214291 A1 | 2/2002 |
| WO | WO-0215845 A2 | 2/2002 |
| WO | WO-0215909 A1 | 2/2002 |
| WO | WO-0220488 A2 | 3/2002 |
| WO | WO-0220530 A1 | 3/2002 |
| WO | WO-0222592 A2 | 3/2002 |
| WO | WO-0226707 A1 | 4/2002 |
| WO | WO-0226743 A1 | 4/2002 |
| WO | WO-0232888 A1 | 4/2002 |
| WO | WO-0232897 A1 | 4/2002 |
| WO | WO-0236596 A2 | 5/2002 |
| WO | WO-0240456 A1 | 5/2002 |
| WO | WO-0240457 A1 | 5/2002 |
| WO | WO-0244152 A1 | 6/2002 |

(56) References Cited

FOREIGN PATENT DOCUMENTS

| | | |
|---|---|---|
| WO | WO-0248106 A2 | 6/2002 |
| WO | WO-0248124 A2 | 6/2002 |
| WO | WO-0248152 A2 | 6/2002 |
| WO | WO-0249648 A1 | 6/2002 |
| WO | WO-02051232 A2 | 7/2002 |
| WO | WO-02051809 A1 | 7/2002 |
| WO | WO-02051838 A1 | 7/2002 |
| WO | WO-02051844 A1 | 7/2002 |
| WO | WO-02059095 A1 | 8/2002 |
| WO | WO-02059107 A1 | 8/2002 |
| WO | WO-02059108 A1 | 8/2002 |
| WO | WO-02059117 A1 | 8/2002 |
| WO | WO-02062764 A1 | 8/2002 |
| WO | WO-02067869 A2 | 9/2002 |
| WO | WO-02068387 A2 | 9/2002 |
| WO | WO-02068388 A2 | 9/2002 |
| WO | WO-02076949 A1 | 10/2002 |
| WO | WO-02083128 A1 | 10/2002 |
| WO | WO-03000180 A2 | 1/2003 |
| WO | WO-03000181 A2 | 1/2003 |
| WO | WO-03000250 A1 | 1/2003 |
| WO | WO-03000449 A1 | 1/2003 |
| WO | WO-03002530 A2 | 1/2003 |
| WO | WO-03002531 A2 | 1/2003 |
| WO | WO-03002553 A2 | 1/2003 |
| WO | WO-03002593 A2 | 1/2003 |
| WO | WO-03004496 A1 | 1/2003 |
| WO | WO-03007887 A2 | 1/2003 |
| WO | WO-03007949 A1 | 1/2003 |
| WO | WO-03009847 A1 | 2/2003 |
| WO | WO-03023561 A2 | 3/2003 |
| WO | WO-03026591 A2 | 4/2003 |
| WO | WO-03027637 A2 | 4/2003 |
| WO | WO-03057235 A2 | 7/2003 |
| WO | WO-2008061740 A1 | 5/2008 |
| WO | WO-2011006158 A2 | 1/2011 |
| WO | WO-2015138326 A1 | 9/2015 |
| WO | WO-2016030534 A1 | 3/2016 |
| WO | WO-2018125983 A1 | 7/2018 |

OTHER PUBLICATIONS

Ballatore, C., et al., "Carboxylic Acid (Bio)Isosteres in Drug Design," ChemMedChem, 2013, vol. 8(3), pp. 385-395.

Brandt, W. et al., Inhibitors of the RET tyrosine kinase based on a 2-(alkylsulfanyl)-4-(3-thienyl) nicotinonitrile scaffold. European Journal of Medicinal Chemistry, Jul. 1, 2010, vol. 45, No. 7, pp. 2919-2927.

Bundegaard, H., Design of Prodrugs, p. 1-92, Elesevier, New York-Oxford (1985).

Cho, "SIRT3 as a Regulator of Non-alcoholic Fatty Liver Disease," Journal of Lifestyle Medicine, 2014, vol. 4, No. 2, 80-85.

Chu et al., "A Theoretical Study on the Modeling of Human 2-Amino-3-Carboxymuconic Acid 6-Semialdehyde Decarboxylase (ACMSD) Action with Substrates and Inhibitors", Chemical Journey of Chinese Universities, 2008, vol. 26, No. 12, pp. 2398-2402.

Database Accession No. 1082473-69-5, dated Dec. 9, 2008, 3 pages.

Database Registry [Online] Chemical Abstracts Service, Columbus, Ohio, US; Nov. 19, 2007, retrieved from STN Database accession No. 954850-51-2, 3 pages.

Database Registry [Online] Chemical Abstracts Service, Columbus, Ohio, US; Feb. 23, 2014, retrieved from STN Database accession No. 1552449-54-3, 2 pages.

Database Registry [Online] Chemical Abstracts Service, Columbus, Ohio, US; Feb. 26, 2009, retrieved from STN Database accession No. 1112336-45-4, 3 pages.

Database Registry [Online] Chemical Abstracts Service, Columbus, Ohio, US; Oct. 30, 2007, Database accession No. 951908-78-4, 2 pages.

Database Registry [Online] Chemical Abstracts Service, Columbus, Ohio, US; Dec. 9, 2008, Database accession No. 1082369-53-6, 3 pages.

Database Registry [Online] Chemical Abstracts Service, Columbus, Ohio, US; retrieved from Registry; STN Database accession No. 1017053-26-7 dated Apr. 24, 2008, 2 pages.

Database Registry [Online] Chemical Abstracts Service, Columbus, Ohio, US; retrieved from Registry; STN Database accession No. 1082520-77-1, dated Dec. 9, 2008, 3 pages.

Database Registry [Online] Chemical Abstracts Service, Columbus, Ohio, US; retrieved from Registry; STN Database accession No. 1082540-59-7, dated Dec. 10, 2008 2 pages.

Database Registry [Online] Chemical Abstracts Service, Columbus, Ohio, US; retrieved from Registry; STN Database accession No. 874606-82-3, dated Feb. 19, 2006, 2 pages.

Database Registry [Online] Chemical Abstracts Service, Columbus, Ohio, US; XP002750885, retrieved from Registry; STN Database accession No. 1029777-12-5, dated Jun. 22, 2008, 3 pages.

De Gregorio et al. "Relevance of SIRT1-NF-κB Axis as Therapeutic Target to Ameliorate Inflammation in Liver Disease" nt. J. Mol. Sci. 2020, 21, 3858, pp. 1-24; doi:10.3390/ijms21113858.

Del Mar-Grasa, M. et al., Daily Oral Oleoyl-Estrone Gavage Induces a Dose-Dependent Loss of Fat in Wistar Rats, Obesity Research, 9:202-209 (2001).

Dela Cruz et al. "Mitochondrial Dysfunction and Damage Associated Molecular Patterns (DAMPs) in Chronic Inflammatory Diseases" Mitochondrion. Jul. 2018; 41: 37-44.

Ding et al. "Emerging roles of SIRT1 in fatty liver diseases" Int. J. Biol. Sci. 2017, vol. 13, 852-867.

Djouder, "Boosting NAD+ for the prevention and treatment of liver cancer" Molecular & Cellular Oncology 2:4, e1001199; Oct./Nov./Dec. 2015.

Emma et al. "Mitochondrial dysfunction in inherited renal disease and acute kidney injury" Nature Reviews Nephrology 12:267-280 (May 2016).

Galvin et al. "The Hallmarks of Mitochondrial Dysfunction in Chronic Kidney Disease" Kidney Int. Nov. 2017 ; 92(5): 1051-1057.

Giner-Sorolla, A. et al., Fluorine-containing Pyrimidines and Purines: Synthesis and Properties of Trifluoromethyl Pyrimidines and Purines. J. Am. Chem. Soc., Nov. 1, 1958, vol. 80, No. 21, pp. 5744-5752.

Guarino et al. "Nicotinamide and NAFLD: Is There Nothing New Under the Sun?" Metabolites 9:180, pp. 1-17(2019).

International Search Report and Written Opinion issued by the International Searching Authority for Application PCT/EP2019/081799, Apr. 2, 2020, 15 pages.

Kiec-Kononowicz, K. et al., "Importance of the lipophilic group in carbamates having histamine H3-receptor antagonist activity", Pharmazie, 55:349-355 (2000).

Kümmerer, K., "Pharmaceuticals in the Environment", Annual Review of Environment and Resources (2010); 35: 57-75.

Krishnamurthy et al. "Involvement of Kynurenine Pathway in Hepatocellular Carcinoma" Cancers 13( 5180), pp. 1-18 (2021).

Kwak et al. "Mitochondrial metabolism and diabetes" Journal of Diabetes Investigation vol. 1 Issue Oct. 5, 2010, 161-169.

Lazewska, D. et al., "Piperidine-containing histamine H3-receptor antagonists of the carbamate series: variation of the spacer length", Pharmazie, 56:927-932 (2001).

Middleton et al. "Mitochondrial Dysfunction and Liver Disease: role, relevance, and potential for therapeutic modulation" Therapeutic Advances in Gastroenterology 2021; vol. 14: 1-19.

Nicolson, "Mitochondrial Dysfunction and Chronic Disease: Treatment With Natural Supplements" Integrative Medicine, 4:35-43 (Aug. 2014).

Norman et al., "Structure-Activity Relationships of a Series of Pyrrolo [3,2-d]pyrimidine Derivatives and Related Compounds as Neuropeptide Y5 Receptor Antagonists", J. Med. Chem. 43:4288-4312 (2000).

Pellicciari et al., "-Amino—carboxymuconate-e-semialdehyde Decarboxylase (ACMSD) Inhibitors as Novel Modulators of De Novo Nicotinamide Adenine Dinucleotide (NAD+) Biosynthesis," Journal of Medicinal Chemistry, 745-759 (2018).

Physician's Desk Reference 1080-1086, (56th ed. 2002).

Reidemeister, S. et al., "Substituted N-phenylcarbamates as histamine H3 receptor antagonists with improved in vivo potency", Pharmazie, 55:83-6 (2000).

(56) References Cited

OTHER PUBLICATIONS

Sasse, A. et al. "Benzophenone Derivatives and Related Compounds as Potent Histamine H3-Receptor Antagonists and Potential PET/SPECT Ligands", Arch. Pharm., (Weinheim), 334:45-52 (2001).
Sasse, A. et al., "New Histamine H3-Receptor Ligands of the Proxifan Series: Imoproxifan and Other Selective Antagonists with High Oral in Vivo Potency", J. Med. Chem. 43:3335-3343 (2000).
Wei, Q., et al. "Mouse model of ischemic acute kidney injury: technical notes and trick", Am. J. Physiol-Rena, (2012), 303(11), F1487-F1494.
Zhou et al. "Hepatic NAD+ deficiency as a therapeutic target for non-alcoholic fatty liver disease in ageing" British Journal of Pharmacology (2016) 173 2352-2368.
Singh et al., "QSAR Studies of Uracil-Containing Histone Deacetylase Inhibitors," Asian Journal of Chemistry, 2008, vol. 20, No. 8, pp. 6208-6212.

\* cited by examiner

INHIBITORS OF ALPHA-AMINO-BETA-CARBOXYMUCONIC ACID SEMIALDEHYDE DECARBOXYLASE

CROSS REFERENCE TO RELATED APPLICATIONS

This application is a continuation of U.S. application Ser. No. 17/325,068, filed May 19, 2021, which is a continuation of PCT Application No. PCT/EP2019/081799, filed Nov. 19, 2019, which claims the benefit of U.S. Provisional Application No. 62/769,959, filed Nov. 20, 2018, the content of each of which is incorporated herein by reference in its entirety.

FIELD OF THE DISCLOSURE

The present disclosure relates to compounds capable of modulating the activity of α-amino-β-carboxymuconic acid semialdehyde decarboxylase (ACMSD). The compounds of the disclosure may be used in methods for the prevention and/or the treatment of diseases and disorders associated with defects in $NAD^+$ biosynthesis, e.g., metabolic disorders, neurodegenerative diseases, chronic inflammatory diseases, kidney diseases, and diseases associated with ageing.

BACKGROUND OF THE DISCLOSURE

ACMSD is a critical enzyme for tryptophan metabolism, and regulates $NAD^+$ biosynthesis from tryptophan. ACMSD is a zinc-dependent amidohydrolase that participates in picolinic acid (PA), quinolinic acid (QA) and $NAD^+$ homeostasis. ACMSD stands at a branch point of the $NAD^+$ biosynthetic pathway from tryptophan and determines the final fate of the amino acid, i.e., transformation into PA, complete oxidation through the citric acid cycle, or conversion into $NAD^+$ through QA synthesis.

ACMSD has been purified from liver, kidney, and brain human tissues. There are two isoforms ACMSD1 and ACMSD2 derived from a differential splicing of ACMSD gene transcription but only ACMSD1 is endowed with enzymatic activity. ACMSD1 directs ACMS (α-amino-ω-carboxymuconic acid semialdehyde) to the acetyl-CoA pathway, and when ACMSD1 is inhibited, ACMS is nonenzymatically converted to quinolinic acid (QA) leading to the formation of $NAD^+$ and an increase in the intracellular level of $NAD^+$.

Increased levels of $NAD^+$ have been shown to protect against neuronal degeneration, improve muscle function and oxidative metabolism in mice, and enhance lifespan in worms. Whilst reduced levels of $NAD^+$ have been associated with a range of pathophysiological states including type 2 diabetes (T2D), hyperlipidemia (elevated cholesterol and TAGs), mitochondrial diseases, neutropenia, cancers, and kidney disorders.

The inhibition of ACMSD thus represents a novel approach to increase $NAD^+$ levels and modify disease pathophysiologies associated with defects in $NAD^+$ biosynthesis.

SUMMARY OF THE DISCLOSURE

It is an object of embodiments of the disclosure to provide novel series of compounds capable of modulating the activity of α-amino-β-carboxymuconic acid semialdehyde decarboxylase (ACMSD), which compounds are useful for the prevention and/or the treatment of diseases and disorders associated with defects in $NAD^+$ biosynthesis, e.g., metabolic disorders, neurodegenerative diseases, chronic inflammatory diseases, kidney diseases, and diseases associated with ageing.

Compounds of Formula (I) or (II), as defined herein, may be used in the treatment of a disease or disorder in which ACMSD plays a role. The disclosure features methods of treating a disease or disorder associated with abnormalities in $NAD^+$ biosynthesis by administering to subjects suffering from or susceptible to developing the disease or disorder a therapeutically effective amount of one or more compounds that increases intracellular $NAD^+$ by ACMSD1 inhibition, in an amount sufficient to activate sirtuins (SIRTs) and the downstream targets of SIRTs, such as PGC-1α, FoxO1 and/or superoxide dismutase (SOD). The methods of the present disclosure can be used in the treatment of $NAD^+$ dependent diseases by inhibiting ACMSD. Inhibition of ACMSD may provide a novel approach to the prevention and treatment of metabolic disorders, neurodegenerative diseases, chronic inflammatory diseases, kidney diseases, diseases associated with ageing and other ACMSD dependent diseases, or diseases characterized by defective $NAD^+$ synthesis.

The present disclosure provides a compound represented by Formula (I):

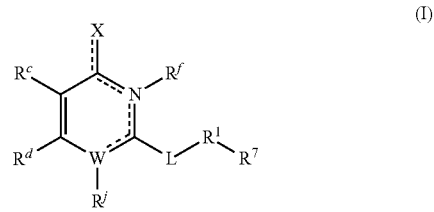

(I)

and pharmaceutically acceptable salts and tautomers thereof, wherein:

X is H, S, $SR^2$, $NR^2$, $NR^2R^{2'}$, O, OH, $OR^h$, F, Br, or Cl;
W is N or C;
(i) when W is N, then: L is —$(C(R^5)_2)_m CH=CH(C(R^5)_2)_p$—,

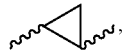

—$(C(R^5)_2)_m Y^1 (C(R^5)_2)_p$—, —$(C(R^5)_2)_m Y^1 (C(R^5)_2)_p$-cyclopropyl-, —$(C(R^5)_2)_m Y^1 CH=CH$—, —$(C(R^5)_2)_m NR^3 C=(O)(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—;

(ii) when W is C, then: L is —$(C(R^5)_2)_m CH=CH(C(R^5)_2)_p$—, —$(C(R^5)_2)_o$—, —$(C(R^5)_2)_m Y^1 (C(R^5)_2)_p$—,

—$(C(R^5)_2)_m Y^1 CH=CH$—, —$(C(R^5)_2)_m C=(O)(CH_2)_p$—, —$(C(R^5)_2)_m C=(O)O(C(R^5)_2)_p$—, —$(C(R^5)_2)_m C=(O)NR^3 (C(R^5)_2)_p$—, —$(C(R^5)_2)_m NR^3 C=(O)(C(R^5)_2)_p$—, —$(C(R^5)_2)_m$phenyl(C $(R^5)_2)_p$—, —$(C(R^5)_2)_m$pyridinyl$(C(R^5)_2)_p$—, or —$(C(R^5)_2)_m$thiophenyl$(C(R^5)_2)_p$—;

$Y^1$ is O, $NR^4$, or $S(O)_q$;

each $Y^2$ is independently O, NH or S;

$R^1$ is absent or $C_6$-$C_{10}$ arylene or heteroarylene, wherein the heteroarylene comprises one or two 5- to 7-membered rings and 1-4 heteroatoms selected from N, O and S, and wherein the $C_6$-$C_{10}$ arylene or heteroarylene are optionally substituted with one to two $R^e$;

$R^2$ is H or $C_1$-$C_4$ alkyl;

$R^{2'}$ is H, $C_1$-$C_4$ alkyl, or $C_3$-$C_7$ cycloalkyl; or $R^2$ and $R^{2'}$ together with the nitrogen atom to which they are attached form a 3- to 7-membered heterocycloalkyl ring comprising 1-3 additional heteroatoms selected from N, O and S;

$R^3$ is H or $C_1$-$C_4$ alkyl;

$R^4$ is H or $C_1$-$C_4$ alkyl;

each $R^5$ is independently at each occurrence H or $C_1$-$C_4$ alkyl;

each $R^6$ is independently at each occurrence H or $C_1$-$C_4$ alkyl;

$R^7$ is H, A, B, or C;

A is —$(C(R^6)_2)_r CO_2 R^x$, —$Y^2(C(R^6)_2)_r CO_2 R^x$, —$(CH_2)_r$tetrazole, —$(CH_2)_r$oxadiazolone, —$(CH_2)_r$tetrazolone, —$(CH_2)_r$thiadiazolol, —$(CH_2)_r$isoxazol-3-ol, —$(CH_2)_r P(O)(OH)OR^x$, —$(CH_2)_r S(O)_2 OH$, —$(CH_2)_r C(O)NHCN$, or —$(CH_2)_r C(O)NHS(O)_2$alkyl, wherein —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol are optionally substituted with $C_1$-$C_6$ alkyl, B is —$(C(R^6)_2)_r S(O)_2 OC_1$-$C_4$ alkyl, —$O(C(R^6)_2)_r S(O)_2 OC_1$-$C_4$ alkyl, —$Y^2(C(R^6)_2)_r C(O)NR^g R^{g'}$, —$Y^2(C(R^6)_2)_r S(O)_2 NR^g R^{g'}$, —$(CH_2)_r C(O)NR^g R^{g'}$, —$(CH_2)_r S(O)_2 NR^g R^{g'}$, —$(CH_2)_r C(O)NHS(O)_2 NR^g R^{g'}$, —$(C(R^6)_2)_r CO_2 R$, —$(C(R^6)_2)_r NH CO_2 R^x$, —$(C(R^6)_2)_r P(O)(OR^x)_2$, —$O(C(R^6)_2)_r P(O)(OR^x)_2$, —$(C(R^6)_2)_r S(O)_2 OH$, —$O(C(R^6)_2)_r S(O)_2 OH$, —$(C(R^6)_2)_r P(O)_2 OR^x$, or —$O(C(R^6)_2)_r P(O)_2 OR^x$, C is —$(CH_2)_r CN$, —$(CH_2)_s OH$, halogen, —$(C(R^6)_2)_r C_6$-$C_{10}$ aryl, —$(C(R^6)_2)_r S$—$C_6$-$C_{10}$ aryl, —$(C(R^6)_2)_r$heteroaryl, —$O(C(R^6)_2)_r$heteroaryl, —$O(C(R^6)_2)_r$heterocycloalkyl, —$O(C(R^6)_2)_r OH$, —$OR^v$, —$(C(R^6)_2)_r C(O)NHCN$, —$CH=CHCO_2 R^x$, or —$(C(R^6)_2)_r C(O)NHS(O)_2 C_1$-$C_4$ alkyl, wherein the aryl and heteroaryl are substituted with one to three substituents each independently selected from $C_1$-$C_6$ alkyl, $C_1$-$C_6$ haloalkyl, halogen, and OH, and wherein the heterocycloalkyl is substituted with one to two =O or =S;

$R^c$ is H, $C_1$-$C_6$ alkyl, $C_1$-$C_6$ haloalkyl, halogen, —CN, —$OR^x$, or —$CO_2 R^x$;

$R^d$ is methyl, $CF_3$, $CR^f F_2$, —$(C(R^6)_2)_t C_6$-$C_{10}$ aryl, —$(C(R^6)_2)_t$-5- or 6-membered heteroaryl, —$(C(R^6)_2)_t$-5- or 6-membered cycloalkyl, optionally substituted $C_6$-$C_{10}$ aryl, optionally substituted 5- or 6-membered heteroaryl, or optionally substituted 5- or 6-membered cycloalkyl;

each $R^e$ is independently at each occurrence $C_1$-$C_6$ alkyl, $C_2$-$C_6$ alkenyl, $C_2$-$C_6$ alkynyl, halogen, $C_1$-$C_6$ haloalkyl, —$NHR^z$, —OH, or —CN;

$R^f$ is absent, H, or methyl;

$R^g$ is H, $C_1$-$C_6$ alkyl, OH, —$S(O)_2(C_1$-$C_6$ alkyl), or $S(O)_2 N(C_1$-$C_6$ alkyl$)_2$;

$R^{g'}$ is H, $C_1$-$C_6$ alkyl, $C_3$-$C_7$ cycloalkyl, 4- to 7-membered heterocycloalkyl ring comprising 1-3 heteroatoms selected from N, O and S, $C_6$-$C_{10}$ aryl, or 5- to 7-membered heteroaryl comprising 1-3 heteroatoms selected from N, O and S, wherein the alkyl is optionally substituted with one or more substituents independently selected from halogen and —OH, and wherein the cycloalkyl, heterocycloalkyl, aryl and heteroaryl are optionally substituted with one or more substituents independently selected from $C_1$-$C_6$ alkyl, halogen, and —OH;

$R^h$ is H, $C_1$-$C_4$ alkyl, or 3- to 7-membered heterocycloalkyl ring comprising 1-3 heteroatoms selected from N, O and S, wherein the alkyl is optionally substituted with one or more substituents each independently selected from $NH_2$, $C_1$-$C_4$ alkylamino, $C_1$-$C_4$ dialkylamino, and $C(O)NH_2$; and wherein the heterocycloalkyl is optionally substituted with one or more substituents each independently selected from $C_1$-$C_6$ alkyl and $C_1$-$C_6$ haloalkyl;

$R^i$ is (i) —$(CH_2)_s OC(O)C_1$-$C_6$ alkyl, wherein the alkyl is substituted with one or more $NH_2$; (ii) $(CH_2 CH_2 O)_n CH_2 CH_2 OH$; or (iii) $C_1$-$C_6$ alkyl substituted with one or more substituents each independently selected from OH and 4- to 7-membered heterocycloalkyl comprising 1 to 3 heteroatoms selected from O, N, or S;

$R^j$ is absent, H, $C_1$-$C_6$ alkyl, or —CN;

each $R^x$ is independently at each occurrence H, $C_1$-$C_6$ alkyl, or $C_6$-$C_{10}$ aryl;

each $R^y$ and $R^z$ is independently H, $C_1$-$C_6$ alkyl, or $C_1$-$C_6$ haloalkyl;

each m, p, q, r, and t is independently 0, 1 or 2;

n is 0, 1, 2, or 3;

s is 1 or 2;

o is 0, 1, 2, 3, or 4; and

═══ represents a single bond or a double bond; and provided that when X is O; $R^f$ is H; W is C; $R^j$ is —CN; L is —$SCH_2$—; $R^1$ is phenylene or pyridine; then $R^7$ is not —COOH;

when X is O; $R^f$ is H; W is C; R is —CN; L is —$SCH_2$—; $R^1$ is phenylene or pyridine; and $R^7$ is tetrazole; then $R^c$ is not H;

when X is O; $R^f$ is H; W is C; $R^j$ is —CN; L is —S—$C(R^5)_2$ or —$SCH_2 CH_2$—; $R^1$ is absent; then $R^7$ is not COOH or tetrazole;

when X is O, $R^f$ is H; W is N; $R^j$ is absent; $R^d$ is methyl, optionally substituted 5- to 10-membered aryl, optionally substituted 5- or 6-membered heteroaryl, or optionally substituted 5- or 6-membered cycloalkyl; L is —$SCH_2$— or —$OCH_2$—; and $R^1$ is phenylene; then $R^7$ is not —COOH, —$CH_2 COOH$, and when X is O, $R^f$ is H, W is N, $R^j$ is absent, L is —$NHCH_2$—, —$CH_2 NH$—, or —NH—C(O)—, and $R^1$ is phenylene, then $R^d$ is not phenyl.

The present disclosure provides a compound represented by Formula (II):

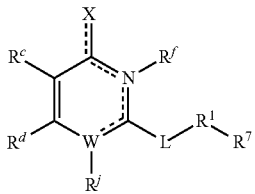

and pharmaceutically acceptable salts and tautomers thereof, wherein:

X is H, S, $SR^2$, $NR^2$, $NR^2R^{2'}$, O, OH, $OR^h$, F, Br, or Cl;
W is N or C;
  (i) when W is N, then: L is $-(C(R^5)_2)_m CH=CH(C(R^5)_2)_p-$,

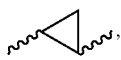

$-(C(R^5)_2)_m Y^1 (C(R^5)_2)_p-$, $-(C(R^5)_2)_m Y^1 (C(R^5)_2)_p$-cyclopropyl-, $-(C(R^5)_2)_m Y^1 CH=CH-$, $-(C(R^5)_2)_m NR^3 C=(O)(C(R^5)_2)_p-$, $-(C(R^5)_2)_m phenyl(C(R^5)_2)_p-$, $-(C(R^5)_2)_m pyridinyl(C(R^5)_2)_p-$, or $-(C(R^5)_2)_m thiophenyl(C(R^5)_2)_p-$;

(ii) when W is C, then: L is $-(C(R^5)_2)_m CH=CH(C(R^5)_2)_p-$, $-(C(R^5)_2)_o-$, $-(C(R^5)_2)_m Y^1 (C(R^5)_2)_p-$,

$(C(R^5)_2)_m Y^1 CH=CH-$, $-(C(R^5)_2)_m C=(O)(CH_2)_p-$, $-(C(R^5)_2)_m C=(O)O(C(R^5)_2)_p-$, $-(C(R^5)_2)_m C=(O)NR^3 (C(R^5)_2)_p-$, $-(C(R^5)_2)_m NR^3 C=(O)(C(R^5)_2)_p-$, $-(C(R^5)_2)_m phenyl(C(R^5)_2)_p-$, $-(C(R^5)_2)_m pyridinyl(C(R^5)_2)_p-$, or $-(C(R^5)_2)_m thiophenyl(C(R^5)_2)_p-$;

$Y^1$ is O, $NR^4$, or $S(O)_q$;
each $Y^2$ is independently O, NH or S;
$R^1$ is absent, $C_6$-$C_{10}$ arylene, heteroarylene, or $C_3$-$C_8$cycloalkylene, wherein the heteroarylene comprises one or two 5- to 7-membered rings and 1-4 heteroatoms selected from N, O and S, and wherein the $C_6$-$C_{10}$ arylene, heteroarylene, and $C_3$-$C_8$cycloalkylene are optionally substituted with one to two $R^e$;
$R^2$ is H or $C_1$-$C_4$ alkyl;
$R^{2'}$ is H, $C_1$-$C_4$ alkyl, or $C_3$-$C_7$ cycloalkyl; or
$R^2$ and $R^{2'}$ together with the nitrogen atom to which they are attached form a 3- to 7-membered heterocycloalkyl ring comprising 1-3 additional heteroatoms selected from N, O and S;
$R^3$ is H or $C_1$-$C_4$ alkyl;
$R^4$ is H or $C_1$-$C_4$ alkyl;
each $R^5$ is independently at each occurrence H or $C_1$-$C_4$ alkyl;
each $R^6$ is independently at each occurrence H or $C_1$-$C_4$ alkyl;
$R^7$ is H, A, B, or C;
A is $-(C(R^6)_2)_r CO_2 R^x$, $-Y^2(C(R^6)_2)_r CO_2 R^x$, $-(C(R^6)_2)_r$tetrazole, $-(C(R^6)_2)_r$oxadiazolone, $-(C(R^6)_2)_r$tetrazolone, $-(C(R^6)_2)_r$thiadiazolol, $-(C(R^6)_2)_r$ isoxazol-3-ol, $-(C(R^6)_2)_r P(O)(OH)OR^x$, $-(C(R^6)_2)_r S(O)_2 OH$, $-(C(R^6)_2)_r C(O)NHCN$, or $-(C(R^6)_2)_r C(O)NHS(O)_2$alkyl, wherein $-(C(R^6)_2)_r$tetrazole, $-(C(R^6)_2)_r$oxadiazolone, $-(C(R^6)_2)_r$tetrazolone, $-(C(R^6)_2)_r$thiadiazolol, $-(C(R^6)_2)_r$ isoxazol-3-ol are optionally substituted with $C_1$-$C_6$ alkyl, B is $-(C(R^6)_2)_r S(O)_2 OC_1$-$C_4$ alkyl, $-O(C(R^6)_2)_r S(O)_2 OC_1$-$C_4$ alkyl, $-Y^2(C(R^6)_2)_r C(O)NR^g R^{g'}$, $-Y^2(C(R^6)_2)_r S(O)_2 NR^g R^{g'}$, $-(C(R^6)_2)_r C(O)NR^g R^{g'}$, $-(C(R^6)_2)_r S(O)_2 NR^g R^{g'}$, $-(C(R^6)_2)_r C(O)NHS(O)_2 NR^g R^{g'}$, $-(C(R^6)_2)_r CO_2 R'$, $-(C(R^6)_2)_r NH_2 CO_2 R^x$, $-(C(R^6)_2)_r P(O)(OR^x)_2$, $-O(C(R^6)_2)_r P(O)(OR^x)_2$, $-(C(R^6)_2)_r S(O)_2 OH$, $-O(C(R^6)_2)_r S(O)_2 OH$, $-(C(R^6)_2)_r P(O)_2 OR^x$, or $-O(C(R^6)_2)_r P(O)_2 OR^x$, C is $-(CH_2)_r CN$, $-(CH_2)_s OH$, halogen, $-(C(R^6)_2)_r C_6$-$C_{10}$ aryl, $-(C(R^6)_2)_r S$-$C_6$-$C_{10}$ aryl, $-(C(R^6)_2)_r$heteroaryl, $-O(C(R^6)_2)_r$heteroaryl, $-O(C(R^6)_2)_r$heterocycloalkyl, $-O(C(R^6)_2)_r OH$, $-OR^y$, $-(C(R^6)_2)_r C(O)NHCN$, $-CH=CHCO_2 R^x$, or $-(C(R^6)_2)_r C(O)NHS(O)_2 C_1$-$C_4$ alkyl, wherein the aryl and heteroaryl are substituted with one to three substituents each independently selected from $C_1$-$C_6$ alkyl, $C_1$-$C_6$ haloalkyl, halogen, and OH, and wherein the heterocycloalkyl is substituted with one to two =O or =S;

$R^c$ is H, $C_1$-$C_6$ alkyl, $C_1$-$C_6$ haloalkyl, halogen, $-CN$, $-OR^x$, or $-CO_2 R^x$;

$R^d$ is methyl, $CF_3$, $CR^f F_2$, $-(C(R^6)_2)_r C_6$-$C_{10}$ aryl, $-(C(R^6)_2)_r$-5- or 6-membered heteroaryl, $-(C(R^6)_2)_r$-5- or 6-membered cycloalkyl, optionally substituted $C_6$-$C_{10}$ aryl, optionally substituted 5- or 6-membered heteroaryl, or optionally substituted 5- or 6-membered cycloalkyl;

each $R^e$ is independently at each occurrence $C_1$-$C_6$ alkyl, $C_2$-$C_6$ alkenyl, $C_2$-$C_6$ alkynyl, halogen, $C_1$-$C_6$ haloalkyl, $-NHR^z$, $-OH$, or $-CN$;

$R^f$ is absent, H, or methyl;

$R^g$ is H, $C_1$-$C_6$ alkyl, OH, $-S(O)_2(C_1$-$C_6$ alkyl), or $S(O)_2 N(C_1$-$C_6$ alkyl)$_2$;

$R^{g'}$ is H, $C_1$-$C_6$ alkyl, $C_3$-$C_7$ cycloalkyl, 4- to 7-membered heterocycloalkyl ring comprising 1-3 heteroatoms selected from N, O and S, $C_6$-$C_{10}$ aryl, or 5- to 7-membered heteroaryl comprising 1-3 heteroatoms selected from N, O and S, wherein the alkyl is optionally substituted with one or more substituents independently selected from halogen and $-OH$, and wherein the cycloalkyl, heterocycloalkyl, aryl and heteroaryl are optionally substituted with one or more substituents independently selected from $C_1$-$C_6$ alkyl, halogen, and $-OH$;

$R^h$ is H, $C_1$-$C_4$ alkyl, or 3- to 7-membered heterocycloalkyl ring comprising 1-3 heteroatoms selected from N, O and S, wherein the alkyl is optionally substituted with one or more substituents each independently selected from $NH_2$, $C_1$-$C_4$ alkylamino, $C_1$-$C_4$ dialkylamino, and $C(O)NH_2$; and wherein the heterocycloalkyl is optionally substituted with one or more substituents each independently selected from $C_1$-$C_6$ alkyl and $C_1$-$C_6$ haloalkyl;

$R^i$ is (i) $-(CH_2)_s OC(O)C_1$-$C_6$ alkyl, wherein the alkyl is substituted with one or more $NH_2$; (ii) $(CH_2CH_2O)_n CH_2CH_2OH$; or (iii) $C_1$-$C_6$ alkyl substituted with one or more substituents each independently selected from OH and 4- to 7-membered heterocycloalkyl comprising 1 to 3 heteroatoms selected from O, N, or S;

$R^j$ is absent, H, $C_1$-$C_6$ alkyl, or $-CN$;

each $R^x$ is independently at each occurrence H, $C_1$-$C_6$ alkyl, or $C_6$-$C_{10}$ aryl;

each $R^y$ and $R^z$ is independently H, $C_1$-$C_6$ alkyl, or $C_1$-$C_6$ haloalkyl;

each m, p, q, r, and t is independently 0, 1 or 2;

n is 0, 1, 2, or 3;

s is 1 or 2;

o is 0, 1, 2, 3, or 4; and

=== represents a single bond or a double bond; and provided that when X is O; $R^f$ is H; W is C; $R^j$ is —CN; L is —$SCH_2$—; $R^1$ is phenylene or pyridine; then $R^7$ is not —COOH;

when X is O; $R^f$ is H; W is C; $R^j$ is —CN; L is —$SCH_2$—; $R^1$ is phenylene or pyridine; and $R^7$ is tetrazole; then $R^c$ is not H;

when X is O; $R^f$ is H; W is C; $R^j$ is —CN; L is —S—$C(R^5)_2$ or —$SCH_2CH_2$—; $R^1$ is absent; then $R^7$ is not COOH or tetrazole;

when X is O, $R^f$ is H; W is N; $R^j$ is absent; $R^d$ is methyl, optionally substituted 5- to 10-membered aryl, optionally substituted 5- or 6-membered heteroaryl, or optionally substituted 5- or 6-membered cycloalkyl; L is —$SCH_2$— or —$OCH_2$—; and $R^1$ is phenylene; then $R^7$ is not —COOH, —$CH_2COOH$,

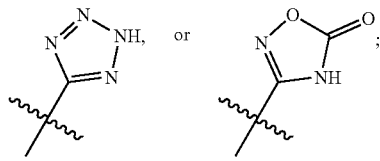 [SMILES: *c1nn[nH]n1 ; "or" ; *c1noc(=O)[nH]1 ; ";"]

and when X is O, $R^f$ is H, W is N, $R^j$ is absent, L is —$NHCH_2$—, —$CH_2NH$—, or —NH—C(O)—, and $R^1$ is phenylene, then $R^d$ is not phenyl.

Another aspect of the present disclosure provides a pharmaceutical composition comprising a compound of Formula (I) or (II), or a pharmaceutically acceptable salt thereof, and at least one of a pharmaceutically acceptable carrier, diluent, or excipient.

Another aspect of the present disclosure provides a compound of Formula (I) or (II) for use as a medicament. Another aspect of the present disclosure provides a pharmaceutical composition comprising a compound of Formula (I) or (II) for use as a medicament.

Another aspect of the present disclosure provides a method of treating a disease or disorder by inhibition of α-amino-β-carboxymuconate-ε-semialdehyde decarboxylase (ACMSD) comprising administering to the subject suffering from or susceptible to developing the disease or disorder a therapeutically effective amount of one or more compounds of Formula (I) or (II). Another aspect of the present disclosure provides a method of preventing a disease or disorder by inhibition of α-amino-β-carboxymuconate-ε-semialdehyde decarboxylase (ACMSD) comprising administering to the subject suffering from or susceptible to developing the disease or disorder a therapeutically effective amount of one or more compounds of Formula (I) or (II). Another aspect of the present disclosure provides a method of reducing the risk of a disease or disorder by inhibition of α-amino-β-carboxymuconate-ε-semialdehyde decarboxylase (ACMSD) comprising administering to the subject suffering from or susceptible to developing the disease or disorder a therapeutically effective amount of one or more compounds of Formula (I) or (II).

Another aspect of the present disclosure provides a method of treating a disease or disorder associated with reduced nicotinamide adenine dinucleotide ($NAD^+$) levels comprising administering to the subject suffering from or susceptible to developing a disease or disorder associated with reduced $NAD^+$ levels a therapeutically effective amount of one or more compounds of Formula (I) or (II). Another aspect of the present disclosure provides a method of preventing a disease or disorder associated with reduced nicotinamide adenine dinucleotide ($NAD^+$) levels comprising administering to the subject suffering from or susceptible to developing a disease or disorder associated with reduced $NAD^+$ levels a therapeutically effective amount of one or more compounds of Formula (I) or (II). Another aspect of the present disclosure provides a method of reducing the risk of a disease or disorder associated with reduced nicotinamide adenine dinucleotide ($NAD^+$) levels comprising administering to the subject suffering from or susceptible to developing a disease or disorder associated with reduced $NAD^+$ levels a therapeutically effective amount of one or more compounds of Formula (I) or (II).

Another aspect of the present disclosure provides a method of treating a disorder associated with mitochondrial dysfunction comprising administering to the subject suffering from or susceptible to developing a metabolic disorder a therapeutically effective amount of one or more compounds of Formula (I) or (II) that increases intracellular nicotinamide adenine dinucleotide ($NAD^+$). Another aspect of the present disclosure provides a method of preventing a disorder associated with mitochondrial dysfunction comprising administering to the subject suffering from or susceptible to developing a metabolic disorder a therapeutically effective amount of one or more compounds of Formula (I) or (II) that increases intracellular nicotinamide adenine dinucleotide ($NAD^+$). Another aspect of the present disclosure provides a method of reducing the risk of a disorder associated with mitochondrial dysfunction comprising administering to the subject suffering from or susceptible to developing a metabolic disorder a therapeutically effective amount of one or more compounds of Formula (I) or (II) that increases intracellular nicotinamide adenine dinucleotide ($NAD^+$).

Another aspect of the present disclosure provides a method of promoting oxidative metabolism comprising administering to the subject suffering from or susceptible to developing a metabolic disorder a therapeutically effective amount of one or more compounds of Formula (I) or (II) that increases intracellular nicotinamide adenine dinucleotide ($NAD^+$).

Another aspect of the present disclosure provides a compound of Formula (I) or (II) for use in treating a disease or disorder by inhibition of α-amino-β-carboxymuconate-ε-semialdehyde decarboxylase (ACMSD). Another aspect of the present disclosure provides a compound of Formula (I) or (II) for use in preventing a disease or disorder by inhibition of α-amino-β-carboxymuconate-ε-semialdehyde decarboxylase (ACMSD). Another aspect of the present disclosure provides a compound of Formula (I) or (II) for use in reducing the risk of a disease or disorder by inhibition of α-amino-β-carboxymuconate-ε-semialdehyde decarboxylase (ACMSD).

Another aspect of the present disclosure provides a compound of Formula (I) or (II) for use in treating a disease or disorder associated with reduced nicotinamide adenine dinucleotide ($NAD^+$) levels. Another aspect of the present disclosure provides a compound of Formula (I) or (II) for use in preventing a disease or disorder associated with reduced nicotinamide adenine dinucleotide (NAD$^+$) levels. Another aspect of the present disclosure provides a compound of Formula (I) or (II) for use in reducing the risk of a disease or disorder associated with reduced nicotinamide adenine dinucleotide (NAD$^+$) levels.

Another aspect of the present disclosure provides a compound of Formula (I) or (II) that increases intracellular nicotinamide adenine dinucleotide (NAD$^+$) for use in treating a disorder associated with mitochondrial dysfunction. Another aspect of the present disclosure provides a compound of Formula (I) or (II) that increases intracellular nicotinamide adenine dinucleotide (NAD$^+$) for use in preventing a disorder associated with mitochondrial dysfunction. Another aspect of the present disclosure provides a compound of Formula (I) or (II) that increases intracellular nicotinamide adenine dinucleotide (NAD$^+$) for use in reducing the risk of a disorder associated with mitochondrial dysfunction.

Another aspect of the present disclosure provides a compound of Formula (I) or (II) that increases intracellular nicotinamide adenine dinucleotide (NAD$^+$) for use in promoting oxidative metabolism.

Another aspect of the present disclosure provides use of a compound of Formula (I) or (II) for treating a disease or disorder by inhibition of α-amino-β-carboxymuconate-ε-semialdehyde decarboxylase (ACMSD). Another aspect of the present disclosure provides use of a compound of Formula (I) or (II) for preventing a disease or disorder by inhibition of α-amino-β-carboxymuconate-ε-semialdehyde decarboxylase (ACMSD). Another aspect of the present disclosure provides use of a compound of Formula (I) or (II) for reducing the risk of a disease or disorder by inhibition of α-amino-β-carboxymuconate-ε-semialdehyde decarboxylase (ACMSD).

Another aspect of the present disclosure provides use of a compound of Formula (I) or (II) for treating a disease or disorder associated with reduced nicotinamide adenine dinucleotide (NAD$^+$) levels. Another aspect of the present disclosure provides use of a compound of Formula (I) or (II) for preventing a disease or disorder associated with reduced nicotinamide adenine dinucleotide (NAD$^+$) levels. Another aspect of the present disclosure provides use of a compound of Formula (I) or (II) for reducing the risk of a disease or disorder associated with reduced nicotinamide adenine dinucleotide (NAD$^+$) levels.

Another aspect of the present disclosure provides use of a compound of Formula (I) or (II) that increases intracellular nicotinamide adenine dinucleotide (NAD$^+$) for treating a disorder associated with mitochondrial dysfunction. Another aspect of the present disclosure provides use of a compound of Formula (I) or (II) that increases intracellular nicotinamide adenine dinucleotide (NAD$^+$) for preventing a disorder associated with mitochondrial dysfunction. Another aspect of the present disclosure provides use of a compound of Formula (I) or (II) that increases intracellular nicotinamide adenine dinucleotide (NAD$^+$) for reducing the risk of a disorder associated with mitochondrial dysfunction.

Another aspect of the present disclosure provides use of a compound of Formula (I) or (II) that increases intracellular nicotinamide adenine dinucleotide (NAD$^+$) for promoting oxidative metabolism.

Another aspect of the present disclosure provides use of a compound of Formula (I) or (II) in the manufacture of a medicament for treating a disease or disorder by inhibition of α-amino-β-carboxymuconate-ε-semialdehyde decarboxylase (ACMSD). Another aspect of the present disclosure provides use of a compound of Formula (I) or (II) in the manufacture of a medicament for preventing a disease or disorder by inhibition of α-amino-β-carboxymuconate-ε-semialdehyde decarboxylase (ACMSD). Another aspect of the present disclosure provides use of a compound of Formula (I) or (II) in the manufacture of a medicament for reducing the risk of a disease or disorder by inhibition of α-amino-β-carboxymuconate-ε-semialdehyde decarboxylase (ACMSD).

Another aspect of the present disclosure provides use of a compound of Formula (I) or (II) in the manufacture of a medicament for treating a disease or disorder associated with reduced nicotinamide adenine dinucleotide (NAD$^+$) levels. Another aspect of the present disclosure provides use of a compound of Formula (I) or (II) in the manufacture of a medicament for preventing a disease or disorder associated with reduced nicotinamide adenine dinucleotide (NAD$^+$) levels. Another aspect of the present disclosure provides use of a compound of Formula (I) or (II) in the manufacture of a medicament for reducing the risk of a disease or disorder associated with reduced nicotinamide adenine dinucleotide (NAD$^+$) levels.

Another aspect of the present disclosure provides use of a compound of Formula (I) or (II) that increases intracellular nicotinamide adenine dinucleotide (NAD$^+$) in the manufacture of a medicament for treating a disorder associated with mitochondrial dysfunction. Another aspect of the present disclosure provides use of a compound of Formula (I) or (II) that increases intracellular nicotinamide adenine dinucleotide (NAD$^+$) in the manufacture of a medicament for preventing a disorder associated with mitochondrial dysfunction. Another aspect of the present disclosure provides use of a compound of Formula (I) or (II) that increases intracellular nicotinamide adenine dinucleotide (NAD$^+$) in the manufacture of a medicament for reducing the risk of a disorder associated with mitochondrial dysfunction.

Another aspect of the present disclosure provides use of a compound of Formula (I) or (II) that increases intracellular nicotinamide adenine dinucleotide (NAD$^+$) in the manufacture of a medicament for promoting oxidative metabolism.

In certain aspects, the compounds of the present disclosure may be administered alone or in combination with other compounds, including other ACMSD modulating compounds, or other therapeutic agents.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar to or equivalent to those described herein can be used in the practice and testing of the disclosure, suitable methods and materials are described below. All publications, patent applications, patents, and other references mentioned herein are incorporated by reference. The references cited herein are not admitted to be prior art to the claimed disclosure. In the case of conflict, the present specification, including definitions, will control. In addition, the materials, methods, and examples are illustrative only and not intended to be limiting.

Other features and advantages of the disclosure will be apparent from the following detailed description and claims.

DETAILED DESCRIPTION OF THE DISCLOSURE

All references, including any patent or patent application, cited in this specification are hereby incorporated by reference. No admission is made that any reference constitutes prior art. Further, no admission is made that any of the prior art constitutes part of the common general knowledge in the art.

As used throughout this disclosure, the following terms, unless otherwise indicated, shall be understood to have the following meanings. If a term is missing, the conventional term as known to one skilled in the art controls.

As used herein, the terms "including," "containing," and "comprising" are used in their open, non-limiting sense. Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The articles "a" and "an" as used in this disclosure may refer to one or more than one (i.e., to at least one) of the grammatical object of the article. By way of example, "an element" may mean one element or more than one element.

The term "and/or" as used in this disclosure may mean either "and" or "or" unless indicated otherwise.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The term "alkyl" as used herein refers to a saturated, straight or branched hydrocarbon chain. The hydrocarbon chain preferably contains from one to eight carbon atoms ($C_{1-8}$-alkyl), more preferred from one to six carbon atoms ($C_{1-6}$-alkyl), in particular from one to four carbon atoms ($C_{1-4}$-alkyl), including methyl, ethyl, propyl, isopropyl, butyl, isobutyl, secondary butyl, tertiary butyl, pentyl, isopentyl, neopentyl, tertiary pentyl, hexyl, isohexyl, heptyl and octyl. In a preferred embodiment "alkyl" represents a $C_{1-4}$-alkyl group, which may in particular include methyl, ethyl, propyl, isopropyl, butyl, isobutyl, secondary butyl, and tertiary butyl. Correspondingly, the term "alkylene" means the corresponding biradical (-alkyl-).

The term "cycloalkyl" or "carbocycle" as used herein refers to a cyclic alkyl group, preferably containing from three to ten carbon atoms ($C_{3-10}$-cycloalkyl or $C_{3-10}$-carbocycle), such as from three to eight carbon atoms ($C_{3-8}$-cycloalkyl or $C_{3-10}$-carbocycle), preferably from three to six carbon atoms ($C_{3-6}$-cycloalkyl or $C_{3-10}$-carbocycle), including cyclopropyl, cyclobutyl, cyclopentyl, cyclohexyl, cycloheptyl and cyclooctyl. Furthermore, the term "cycloalkyl" as used herein may also include polycyclic groups such as for example bicyclo[2.2.2]octyl, bicyclo[2.2.1]heptanyl, decalinyl and adamantyl. Correspondingly, the term "cycloalkylene" means the corresponding biradical (-cycloalkyl-).

Alkyl and cycloalkyl groups may be optionally substituted with 1-4 substituents. Examples of substituents on alkyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The term "alkenyl" as used herein refers to a straight or branched hydrocarbon chain or cyclic hydrocarbons containing one or more double bonds, including di-enes, tri-enes and poly-enes. Typically, the alkenyl group comprises from two to eight carbon atoms ($C_{2-8}$-alkenyl), such as from two to six carbon atoms ($C_{2-6}$-alkenyl), in particular from two to four carbon atoms ($C_{2-4}$-alkenyl), including at least one double bond. Examples of alkenyl groups include ethenyl; 1- or 2-propenyl; 1-, 2- or 3-butenyl, or 1,3-but-dienyl; 1-, 2-, 3-, 4- or 5-hexenyl, or 1,3-hex-dienyl, or 1,3,5-hex-trienyl; 1-, 2-, 3-, 4-, 5-, 6-, or 7-octenyl, or 1,3-octadienyl, or 1,3,5-octatrienyl, or 1,3,5,7-octatetraenyl, or cyclohexenyl. Correspondingly, the term "alkenylene" means the corresponding biradical (-alkenyl-). Alkenyl groups may be optionally substituted with 1-4 substituents. Examples of substituents on alkenyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The term "alkynyl" as used herein refers to a straight or branched hydrocarbon chain containing one or more triple bonds, including di-ynes, tri-ynes and poly-ynes. Typically, the alkynyl group comprises of from two to eight carbon atoms ($C_{2-8}$-alkynyl), such as from two to six carbon atoms ($C_{2-6}$-alkynyl), in particular from two to four carbon atoms ($C_{2-4}$-alkynyl), including at least one triple bond. Examples of preferred alkynyl groups include ethynyl; 1- or 2-propynyl; 1-, 2- or 3-butynyl, or 1,3-but-diynyl; 1-, 2-, 3-, 4- or 5-hexynyl, or 1,3-hex-diynyl, or 1,3,5-hex-triynyl; 1-, 2-, 3-, 4-, 5-, 6-, or 7-octynyl, or 1,3-oct-diynyl, or 1,3,5-oct-triynyl, or 1,3,5,7-oct-tetraynyl. Correspondingly, the term "alkynylene" means the corresponding biradical (-alkynyl-). Alkynyl groups may be optionally substituted with 1-4 substituents. Examples of substituents on alkynyl groups include, but are not limited to, alkyl, alkenyl, alkynyl, halogen, haloalkyl, alkoxy, heteroaryl, aryl, carbocyclyl, hydroxyl, carbamoyl, oxo, and —CN.

The terms "halo" and "halogen" as used herein refer to fluoro, chloro, bromo or iodo. Thus a trihalomethyl group represents, e.g., a trifluoromethyl group, or a trichloromethyl group. Preferably, the terms "halo" and "halogen" designate fluoro or chloro.

The term "haloalkyl" as used herein refers to an alkyl group, as defined herein, which is substituted one or more times with one or more halogen. Examples of haloalkyl groups include, but are not limited to, trifluoromethyl, difluoromethyl, pentafluoroethyl, trichloromethyl, etc.

The term "alkoxy" as used herein refers to an "alkyl-O—" group, wherein alkyl is as defined above.

The term "hydroxyalkyl" as used herein refers to an alkyl group (as defined hereinabove), which alkyl group is substituted one or more times with hydroxy. Examples of hydroxyalkyl groups include HO—$CH_2$—, HO—$CH_2$—$CH_2$— and $CH_3$—CH(OH)—.

The term "oxy" as used herein refers to an "—O—" group.

The term "oxo" as used herein refers to an "=O" group.

The term "amine" as used herein refers to primary (R—$NH_2$, R≠H), secondary ((R)$_2$—NH, (R)$_2$≠H) and tertiary ((R)$_3$—N, R≠H) amines. A substituted amine is intended to mean an amine where at least one of the hydrogen atoms has been replaced by the substituent.

The term "carbamoyl" as used herein refers to a "H₂N(C=O)—" group.

The term "aryl" as used herein, unless otherwise indicated, includes carbocyclic aromatic ring systems derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, biphenyl, indenyl, naphthyl, anthracenyl, phenanthrenyl, pentalenyl, azulenyl, and biphenylenyl. Preferred "aryl" is phenyl, naphthyl or indanyl, in particular phenyl, unless otherwise stated. Any aryl used may be optionally substituted. Correspondingly, the term "arylene" means the corresponding biradical (-aryl-). Aryl groups may be optionally substituted with 1-4 substituents. Examples of substituents on aryl groups include, but are not limited to, alkyl, alkenyl, alkynyl, halogen, haloalkyl, alkoxy, heteroaryl, aryl, carbocyclyl, hydroxyl, and —CN.

The term "heteroaryl" as used herein, refers to aromatic groups containing one or more heteroatoms selected from O, S, and N, preferably from one to four heteroatoms, and more preferably from one to three heteroatoms. Heteroaryl furthermore includes bi-, tri- and polycyclic groups, wherein at least one ring of the group is aromatic, and at least one of the rings contains a heteroatom selected from O, S, and N. Heteroaryl also include ring systems substituted with one or more oxo moieties. Examples of preferred heteroaryl moieties include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, phteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, azaindolyl, pyrazolinyl, 1,2,4-oxadiazol-5(4H)-one, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-). Heteroaryl groups may be optionally substituted with 1-4 substituents. Examples of substituents on heteroaryl groups include, but are not limited to, alkyl, alkenyl, alkynyl, halogen, haloalkyl, alkoxy, heteroaryl, aryl, carbocyclyl, hydroxyl, and —CN.

The term "heterocyclyl" as used herein, refers to cyclic non-aromatic groups containing one or more heteroatoms selected from O, S, and N, preferably from one to four heteroatoms, and more preferably from one to three heteroatoms. Heterocyclyl furthermore includes bi-, tri- and polycyclic non-aromatic groups, and at least one of the rings contains a heteroatom selected from O, S, and N. Heterocyclyl also include ring systems substituted with one or more oxo moieties. Examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholino, thiomorpholino, 1,4-oxathianyl, benzofuranyl, isobenzofuranyl, indazolyl, benzimidazolyl, quinolinyl, isoquinolinyl, chromayl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocylylene" means the corresponding biradical (-heterocyclyl-). Heterocyclyl groups may be optionally substituted with 1-4 substituents. Examples of substituents on heterocyclyl groups include, but are not limited, to alkyl, alkenyl, alkynyl, halogen, haloalkyl, alkoxy, heteroaryl, aryl, carbocyclyl, hydroxyl, and —CN.

The term "N-heterocyclic ring" as used herein, refers to a heterocyclyl or a heteroaryl, as defined hereinabove, having at least one nitrogen atom, and being bound via a nitrogen atom. Examples of such N-heterocyclic rings are pyrrolidinyl, pyrrolyl, 3H-pyrrolyl, pyrazolyl, pyrazolidinyl, imidazolyl, imidazolidinyl, 3H-pyrazolyl, 1,2-oxazolyl, 1,2-thiazolyl, 1,3-thiazolyl, piperidinyl, pyridinyl, pyridazinyl, pyrazinyl, piperazinyl, morpholino, pyridinyl, pyridazinyl, pyrimidinyl, pyrazolyl, pyrazinyl, tetrazolyl, etc.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. Accordingly, it should be understood that the definition of compounds of Formula (I) or (II) include each and every individual isomer corresponding to the Formula: Formula (I) or (II), including cis-trans isomers, stereoisomers and tautomers, as well as racemic mixtures of these and pharmaceutically acceptable salts thereof. Hence, the definition of compounds of Formula (I) or (II) are also intended to encompass all R- and S-isomers of a chemical structure in any ratio, e.g., with enrichment (i.e., enantiomeric excess or diastereomeric excess) of one of the possible isomers and corresponding smaller ratios of other isomers. In addition, a crystal polymorphism may be present for the compounds represented by Formula (I) or (II). It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers".

Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J Chem. Soc.* 1951 (London), 612; Cahn et al., *Experientia* 1956, 12, 81; Cahn, *J Chem. Educ.* 1964, 41, 116).

Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula (I) or (II) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formulae (I) can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, a "subject" or "subject in need thereof" is a subject having a disease or disorder associated with α-amino-β-carboxymuconate-ε-semialdehyde decarboxylase (ACMSD) dysfunction or inhibited by α-amino-β-carboxymuconate-ε-semialdehyde decarboxylase (ACMSD). A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Compounds

The present disclosure relates to compounds of Formula (I):

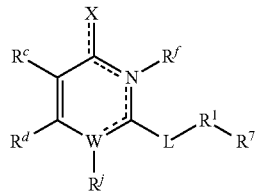

(I)

and pharmaceutically acceptable salts and tautomers thereof, wherein the substituents are as described herein.

The present disclosure relates to compounds of Formula (II):

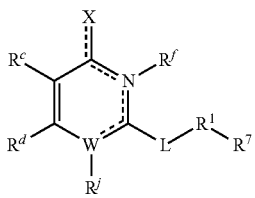

(II)

and pharmaceutically acceptable salts and tautomers thereof, wherein the substituents are as described herein.

In certain embodiments of Formula (I) or (II), wherein W is N, the present disclosure relates to compounds of Formula (I-1):

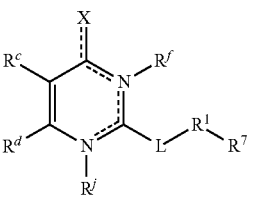

(I-1)

and pharmaceutically acceptable salts and tautomers thereof, wherein the substituents are as described herein for Formula (I) and (II).

In certain embodiments of Formula (I) or (II), wherein W is C, the present disclosure relates to compounds of Formula (I-2):

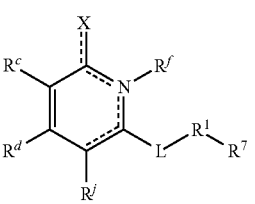

(I-2)

and pharmaceutically acceptable salts and tautomers thereof, wherein the substituents are as described herein for Formula (I) and (II).

In certain embodiments of Formula (I) or (II), wherein $R^1$ is phenyl, the present disclosure relates to compounds of Formula (I-3):

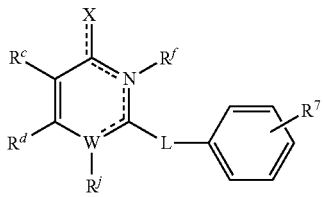

(I-3)

and pharmaceutically acceptable salts and tautomers thereof, wherein the substituents are as described herein for Formula (I) and (II).

In certain embodiments of Formula (I) or (II), wherein $R^1$ is absent, the present disclosure relates to compounds of Formula (I-4):

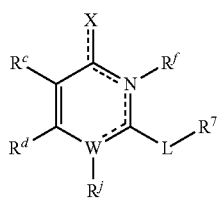

(I-4)

and pharmaceutically acceptable salts and tautomers thereof, wherein the substituents are as described herein for Formula (I) and (II).

As described above, X is H, S, $SR^2$, $NR^2$, $NR^2R^{2'}$, O, OH, $OR^h$, F, Br, or Cl. In certain embodiments, X is O, OH, $OR^h$, F, Br, or Cl. In certain embodiments, X is H, S, $SR^2$, $NR^2$, or $NR^2R^{2'}$. In certain embodiments, X is H. In certain embodiments, X is S. In certain embodiments, X is $SR^2$. In certain embodiments, X is $NR^2$. In certain embodiments, X is $NR^2R^{2'}$. In certain embodiments, X is O. In certain embodiments, X is OH. In certain embodiments, X is $OR^h$. In certain embodiments, X is F. In certain embodiments, X is Br. In certain embodiments, X is Cl.

As described above, $R^2$ is H or $C_1$-$C_4$ alkyl. In certain embodiments, $R^2$ is H. In certain embodiments, $R^2$ is $C_1$-$C_4$ alkyl. In certain embodiments, $R^2$ is —$CH_3$.

As described above, $R^{2'}$ is H, $C_1$-$C_4$ alkyl, or $C_3$-$C_7$ cycloalkyl. In certain embodiments, $R^{2'}$ is H. In certain embodiments, $R^{2'}$ is $C_1$-$C_4$ alkyl. In certain embodiments, $R^{2'}$ is $C_3$-$C_7$ cycloalkyl.

As described above, $R^2$ and $R^{2'}$ together with the nitrogen atom to which they are attached form a 3- to 7-membered heterocycloalkyl ring comprising 1-3 additional heteroatoms selected from N, O and S. In certain embodiments, $R^2$ and $R^{2'}$ together with the nitrogen atom to which they are attached form a 6-membered heterocycloalkyl ring.

As described above, $R^h$ is H, $C_1$-$C_4$ alkyl, or 3- to 7-membered heterocycloalkyl ring comprising 1-3 heteroatoms selected from N, O and S, wherein the alkyl is optionally substituted with one or more substituents each independently selected from $NH_2$, $C_1$-$C_4$ alkylamino, $C_1$-$C_4$ dialkylamino, and $C(O)NH_2$; and wherein the heterocycloalkyl is optionally substituted with one or more substituents each independently selected from $C_1$-$C_6$ alkyl and $C_1$-$C_6$ haloalkyl. In certain embodiments, $R^h$ is H. In certain embodiments, $R^h$ is $C_1$-$C_4$ alkyl, wherein the alkyl is optionally substituted with one or more substituents each independently selected from $NH_2$, $C_1$-$C_4$ alkylamino, $C_1$-$C_4$ dialkylamino, and $C(O)NH_2$. In certain embodiments, $R^h$ is 3- to 7-membered heterocycloalkyl ring comprising 1-3 heteroatoms selected from N, O and S, wherein the heterocycloalkyl is optionally substituted with one or more substituents each independently selected from $C_1$-$C_6$ alkyl and $C_1$-$C_6$ haloalkyl.

As described above, $R^f$ is absent, H, or methyl. In certain embodiments, $R^f$ is absent. In certain embodiments, $R^f$ is H. In certain embodiments, $R^f$ is methyl.

As described above, W is N or C. In certain embodiments, W is N. In certain embodiments, W is C.

As described above, $R^j$ is absent, H, $C_1$-$C_6$ alkyl, or —CN. In certain embodiments, $R^j$ is absent. In certain embodiments, $R^j$ is H. In certain embodiments, $R^j$ is $C_1$-$C_6$ alkyl. In certain embodiments, $R^j$ is —CN.

In certain embodiments, W is N and $R^j$ is absent. In certain embodiments, W is C and $R^j$ is H, $C_1$-$C_6$ alkyl, or —CN. In certain embodiments, W is C and $R^j$ is —CN.

As described above, $R^c$ is H, $C_1$-$C_6$ alkyl, $C_1$-$C_6$ haloalkyl, halogen, —CN, —$OR^c$, or —$CO_2R^x$. In certain embodiments, $R^c$ is H. In certain embodiments, $R^c$ is $C_1$-$C_6$ alkyl. In certain embodiments, $R^c$ is $C_1$-$C_6$ haloalkyl. In certain embodiments, $R^c$ is halogen. In certain embodiments, $R^c$ is —CN. In certain embodiments, $R^c$ is —$OR^x$. In certain embodiments, $R^c$ is —$CO_2R^x$.

As described above, $R^x$ is independently at each occurrence H, $C_1$-$C_6$ alkyl, or $C_6$-$C_{10}$ aryl. In certain embodiments, $R^x$ is H. In certain embodiments, $R^x$ is $C_1$-$C_6$ alkyl. In certain embodiments, $R^x$ is $C_6$-$C_{10}$ aryl.

As described above, $R^d$ is methyl, $CF_3$, $CR^fF_2$, —$(C(R^6)_2)_tC_6$-$C_{10}$ aryl, —$(C(R^6)_2)_t$-5- or 6-membered heteroaryl, —$(C(R^6)_2)_t$-5- or 6-membered cycloalkyl, optionally substituted $C_6$-$C_{10}$ aryl, optionally substituted 5- or 6-membered heteroaryl, or optionally substituted 5- or 6-membered cycloalkyl.

In certain embodiments, $R^d$ is methyl. In certain embodiments, $R^d$ is $CF_3$. In certain embodiments, $R^d$ is $CR^fF_2$. In certain embodiments, $R^d$ is —$(C(R^6)_2)_tC_6$-$C_{10}$ aryl. In certain embodiments, $R^d$ is —$CH_2C_6$-$C_{10}$ aryl. In certain embodiments, $R^d$ is —$CH_2C_6$aryl. In certain embodiments, $R^d$ is —$(C(R^6)_2)_t$-5- or 6-membered heteroaryl. In certain embodiments, $R^d$ is —$(C(R^6)_2)_t$-5- or 6-membered cycloalkyl. In certain embodiments, $R^d$ is optionally substituted $C_6$-$C_{10}$ aryl. In certain embodiments, $R^d$ is optionally substituted 5- or 6-membered heteroaryl. In certain embodiments, $R^d$ is optionally substituted 5- or 6-membered cycloalkyl.

As described above, $R^f$ is absent, H, or methyl. In certain embodiments, $R^f$ is absent. In certain embodiments, $R^f$ is H. In certain embodiments, $R^f$ is methyl.

As described above, t is 0, 1, or 2. In certain embodiments, t is 0. In certain embodiments, t is 1. In certain embodiments, t is 2.

As described above, when W is N, then L is —$(C(R^5)_2)_mCH=CH(C(R^5)_2)_p$—,

,

—$(C(R^5)_2)_mY^1(C(R^5)_2)_p$—, —$(C(R^5)_2)_mY^1(C(R^5)_2)_p$-cyclopropyl-, —$(C(R^5)_2)_mY^1CH=CH$—, —$(C(R^5)_2)_mNR^3C=(O)(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—.

In certain embodiments, W is N and L is —$(C(R^5)_2)_mCH=CH(C(R^5)_2)_p$—. In certain embodiments, W is N and L is

.

In certain embodiments, W is N and L is —$(C(R^5)_2)_mY^1(C(R^5)_2)_p$—. In certain embodiments, W is N and L is —$(C(R^5)_2)_mY^1(C(R^5)_2)_p$-cyclopropyl-. In certain embodiments, W is N and L is —$(C(R^5)_2)_mY^1CH=CH$—. In certain embodiments, W is N and L is —$(C(R^5)_2)_mNR^3C=(O)(C(R^5)_2)_p$—. In certain embodiments, W is N and L is —$(C(R^5)_2)_m$phenyl$(C(R^5)_2)_p$—. In certain embodiments, W is N and L is —$(C(R^5)_2)_m$pyridinyl$(C(R^5)_2)_p$—. In certain embodiments, W is N and L is —$(C(R^5)_2)_m$thiophenyl$(C(R^5)_2)_p$—. In certain embodiments, W is N and L is —$(C(R^5)_2)_mY^1(C(R^5)_2)_p$, such as —$SCH_2$— or —$NHCH_2$—. In certain embodiments, W is N and L is —$SCH_2$—. In certain embodiments, W is N and L is —$NHCH_2$—.

As described above, when W is C, L is —$(C(R^5)_2)_mCH=CH(C(R^5)_2)_p$—, —$(C(R^5)_2)_o$—, —$(C(R^5)_2)_mY^1(C(R^5)_2)_p$—,

,

—$(C(R)_2)_m$ $Y^1CH=CH$—, —$(C(R^5)_2)_mC=(O)(CH_2)_p$—, —$(C(R^5)_2)_mC=(O)O(C(R^5)_2)_p$—, —$(C(R^5)_2)_mC=(O)NR^3(C(R^5)_2)_p$—, —$(C(R^5)_2)_mNR^3C=(O)(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—.

In certain embodiments, W is C and L is —$(C(R^5)_2)_mCH=CH(C(R^5)_2)_p$—. In certain embodiments, W is C and L is —$(C(R^5)_2)_o$—. In certain embodiments, W is C and L is —$(C(R^5)_2)_mY^1(C(R^5)_2)_p$—. In certain embodiments, W is C and L is

.

In certain embodiments, W is C and L is —$(C(R^5)_2)_m Y^1CH=CH$—. In certain embodiments, W is C and L is —$(C(R^5)_2)_mC=(O)(CH_2)_p$—. In certain embodiments, W is C and L is —$(C(R^5)_2)_mC=(O)O(C(R^5)_2)_p$—. In certain embodiments, W is C and L is —$(C(R^5)_2)_mC=(O)NR^3(C(R^5)_2)_p$—. In certain embodiments, W is C and L is —$(C(R^5)_2)_mNR^3C=(O)(C(R^5)_2)_p$—. In certain embodiments, W is C and L is —$(C(R^5)_2)_m$phenyl$(C(R^5)_2)_p$—. In certain embodiments, W is C and L is —$(C(R^5)_2)_m$pyridinyl$(C(R^5)_2)_p$—. In certain embodiments, W is C and L is —$(C(R^5)_2)_m$thiophenyl$(C(R^5)_2)_p$—.

As described above, $Y^1$ is O, $NR^4$, or $S(O)_q$. In certain embodiments, $Y^1$ is O. In certain embodiments, $Y^1$ is $NR^4$. As described above, $R^4$ is H or $C_1$-$C_4$ alkyl. In certain embodiments, $R^4$ is H. In certain embodiments, $R^4$ is $C_1$-$C_4$ alkyl.

In certain embodiments, $Y^1$ is $S(O)_q$. As described above, q is 0, 1, or 2. In certain embodiments, q is 0. In certain embodiments, $Y^1$ is S. In certain embodiments, q is 1. In certain embodiments, q is 2.

As described above, each $R^5$ is independently at each occurrence H or $C_1$-$C_4$ alkyl. In certain embodiments, $R^5$ is H. In certain embodiments, $R^5$ is $C_1$-$C_4$ alkyl.

As described above, $R^3$ is H or $C_1$-$C_4$ alkyl. In certain embodiments, $R^3$ is H. In certain embodiments, $R^3$ is $C_1$-$C_4$ alkyl.

As described above, each m and p is independently 0, 1 or 2. In certain embodiments, m is 0. In certain embodiments, m is 1. In certain embodiments, m is 2. In certain embodiments, p is 0. In certain embodiments, p is 1. In certain embodiments, p is 2.

As described above, o is 0, 1, 2, 3, or 4. In certain embodiments, o is 0. In certain embodiments, o is 1. In certain embodiments, o is 2. In certain embodiments, o is 3. In certain embodiments, o is 4.

As described above, $R^1$ is absent or $C_6$-$C_{10}$ arylene or heteroarylene, wherein the heteroarylene comprises one or two 5- to 7-membered rings and 1-4 heteroatoms selected from N, O and S, and wherein the $C_6$-$C_{10}$ arylene or heteroarylene are optionally substituted with one to two R. In certain embodiments, $R^1$ is absent. In certain embodiments, $R^1$ is $C_6$-$C_{10}$ arylene, which is optionally substituted with one to two R. In certain embodiments, $R^1$ is heteroarylene, wherein the heteroarylene comprises one or two 5- to 7-membered rings and 1-4 heteroatoms selected from N, O and S, and optionally substituted with one to two R. In certain embodiments of Formula (II), $R^1$ is $C_3$-$C_8$cycloalkylene, such as $C_3$cycloalkylene, $C_4$cycloalkylene, $C_5$cycloalkylene, $C_6$cycloalkylene, $C_7$cycloalkylene, or $C_8$cycloalkylene As described above, each R is independently at each occurrence $C_1$-$C_6$ alkyl, $C_2$-$C_6$ alkenyl, $C_2$-$C_6$ alkynyl, halogen, $C_1$-$C_6$ haloalkyl, —$NHR^z$, —OH, or —CN.

As described above, $R^7$ is H, A, B, or C. In certain embodiments, $R^7$ is H. In certain embodiments, $R^7$ is A. In certain embodiments, $R^7$ is B. In certain embodiments, $R^7$ is C.

As described above for Formula (I), A is —$C(R^6)_2)_rCO_2R^x$, —$Y^2(C(R^6)_2)_rCO_2R^x$, —$(CH_2)_r$tetrazole, —$(CH_2)_r$oxadiazolone, —$(CH_2)_r$tetrazolone, —$(CH_2)_r$thiadiazolol, —$(CH_2)_r$isoxazol-3-ol, —$(CH_2)_rP(O)(OH)OR^x$, —$(CH_2)_rS(O)_2OH$, —$(CH_2)_rC(O)NHCN$, or —$(CH_2)_rC(O)NHS(O)_2$alkyl, wherein —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol are optionally substituted with $C_1$-$C_6$ alkyl.

As described above for Formula (II), A is —$C(R^6)_2)_rCO_2R^x$, —$Y^2(C(R^6)_2)_rCO_2R^x$, —$(C(R^6)_2)_r$tetrazole, —$(C(R^6)_2)_r$oxadiazolone, —$(C(R^6)_2)_r$tetrazolone, —$(C(R^6)_2)_r$thiadiazolol, —$(C(R^6)_2)_r$ isoxazol-3-ol, —$(C(R^6)_2)_rP(O)(OH)OR^x$, —$(C(R^6)_2)_rS(O)_2OH$, —$(C(R^6)_2)_rC(O)NHCN$, or —$(C(R^6)_2)_rC(O)NHS(O)_2$alkyl, wherein —$(C(R^6)_2)_r$tetrazole, —$(C(R^6)_2)_r$oxadiazolone, —$(C(R^6)_2)_r$tetrazolone, —$(C(R^6)_2)_r$thiadiazolol, —$(C(R^6)_2)_r$ isoxazol-3-ol are optionally substituted with $C_1$-$C_6$ alkyl. In certain embodiments, A is —$(C(R^6)_2)_r$tetrazole. In certain embodiments, A is —$(C(R^6)_2)_r$oxadiazolone. In certain embodiments, A is —$(C(R^6)_2)_r$tetrazolone. In certain embodiments, A is —$(C(R^6)_2)_r$thiadiazolol. In certain embodiments, A is —$(C(R^6)_2)_r$ isoxazol-3-ol. In certain embodiments, A is —$(C(R^6)_2)_rP(O)(OH)OR^x$. In certain embodiments, A is —$(C(R^6)_2)_rS(O)_2OH$. In certain embodiments, A is —$(C(R^6)_2)_rC(O)NHCN$. In certain embodiments, A is —$(C(R^6)_2)_rC(O)NHS(O)_2$alkyl.

In certain embodiments, A is —$(C(R^6)_2)_rCO_2R^x$. In certain embodiments, A is —$Y^2(C(R^6)_2)_rCO_2R^x$. In certain embodiments, A is —$(CH_2)_r$tetrazole. In certain embodiments, A is —$(CH_2)_r$oxadiazolone. In certain embodiments, A is —$(CH_2)_r$tetrazolone. In certain embodiments, A is —$(CH_2)_r$thiadiazolol. In certain embodiments, A is —$(CH_2)_r$ isoxazol-3-ol.

In certain embodiments, A is —$(CH_2)_rP(O)(OH)OR^x$. In certain embodiments, A is —$(CH_2)_rS(O)_2OH$. In certain embodiments, A is —$(CH_2)_rC(O)NHCN$. In certain embodiments, A is —$(CH_2)_rC(O)NHS(O)_2$alkyl. In certain embodiments, —$(CH_2)_r$tetrazole, —$(CH_2)_r$oxadiazolone, —$(CH_2)_r$tetrazolone, —$(CH_2)_r$thiadiazolol, —$(CH_2)_r$ isoxazol-3-ol are optionally substituted with $C_1$-$C_6$ alkyl. In certain embodiments, A is —$(C(R^6)_2)_rCO_2R^x$ or —$(CH_2)_r$tetrazole, wherein —$(CH_2)_r$tetrazole is optionally substituted with $C_1$-$C_6$ alkyl. In certain embodiments, A is —$(C(R^6)_2)_r$COOH or —$(CH_2)_r$tetrazole, wherein —$(CH_2)_r$tetrazole is optionally substituted with $C_1$-$C_6$ alkyl. In certain embodiments, A is —COOH, —$CH_2$COOH, -tetrazole, or —$(CH_2)$tetrazole, wherein tetrazole and —$(CH_2)_r$tetrazole are optionally substituted with $C_1$-$C_6$ alkyl.

As described above for Formula (I), B is —$(C(R^6)_2)_rS(O)_2OC_1$-$C_4$ alkyl, —$O(C(R^6)_2)_rS(O)_2OC_1$-$C_4$ alkyl, —$Y^2(C(R^6)_2)_rC(O)NR^gR^{g'}$, —$Y^2(C(R^6)_2)_rS(O)_2NR^gR^{g'}$, —$(CH_2)_rC(O)NR^gR^{g'}$, —$(CH_2)_rS(O)_2NR^gR^{g'}$, —$(CH_2)_rC(O)NHS(O)_2NR^gR^{g'}$, —$(C(R^6)_2)_rCO_2R^i$, —$(C(R^6)_2)_rNH_2CO_2R^x$, —$(C(R^6)_2)_rP(O)(OR^x)_2$, —$O(C(R^6)_2)_rP(O)(OR^x)_2$, —$(C(R^6)_2)_rS(O)_2OH$, —$O(C(R^6)_2)_rS(O)_2OH$, —$(C(R^6)_2)_rP(O)_2OR^x$, or —$O(C(R^6)_2)_rP(O)_2OR^x$.

As described above for Formula (II), is —$(C(R^6)_2)_rS(O)_2OC_1$-$C_4$ alkyl, —$O(C(R^6)_2)_rS(O)_2OC_1$-$C_4$ alkyl, —$Y^2(C(R^6)_2)_rC(O)NR^gR^{g'}$, —$Y^2(C(R^6)_2)_rS(O)_2NR^gR^{g'}$, —$(C(R^6)_2)_rC(O)NR^gR^{g'}$, —$(C(R^6)_2)_rS(O)_2NR^gR^{g'}$, —$(C(R^6)_2)_rC(O)NHS(O)_2NR^gR^{g'}$, —$(C(R^6)_2)_rCO_2R$, —$(C(R^6)_2)_rNH_2CO_2R^x$, —$(C(R^6)_2)_rP(O)(OR^x)_2$, —$O(C(R^6)_2)_rP(O)(OR^x)_2$, —$(C(R^6)_2)_rS(O)_2OH$, —$O(C(R^6)_2)_rS(O)_2OH$, —$(C(R^6)_2)_rP(O)_2OR^x$, or —$O(C(R^6)_2)_rP(O)_2OR^x$. In certain embodiments, B is —$(C(R^6)_2)_rC(O)NR^gR^{g'}$. In certain embodiments, B is —$(C(R^6)_2)_rS(O)_2NR^gR^{g'}$. In certain embodiments, B is —$(C(R^6)_2)_rC(O)NHS(O)_2NR^gR^{g'}$.

In certain embodiments, B is —$(C(R^6)_2)_rS(O)_2OC_1$-$C_4$ alkyl. In certain embodiments, B is —$O(C(R^6)_2)_rS(O)_2OC_1$-$C_4$ alkyl. In certain embodiments, B is —$Y^2(C(R^6)_2)_rC(O)NR^gR^{g'}$. In certain embodiments, B is —$Y^2(C(R^6)_2)_rS(O)_2NR^gR^{g'}$. In certain embodiments, B is —$Y^2(C(R^6)_2)_rC(O)NR^gR^{g'}$. In certain embodiments, B is —$(CH_2)_rS(O)_2NR^gR^{g'}$. In certain embodiments, B is —$(CH_2)_rC(O)NHS(O)_2NR^gR^{g'}$. In certain embodiments, B is —$(C(R^6)_2)_rCO_2R^i$. In certain embodiments, B is —$(C(R^6)_2)_rNH_2CO_2R^x$. In certain embodiments, B is —$(C(R^6)_2)_rP(O)(OR^x)_2$. In certain embodiments, B is —$O(C(R^6)_2)_rP(O)(OR^x)_2$. In certain embodiments, B is —$(C(R^6)_2)_rS(O)_{20}H$. In certain embodiments, B is —$O(C(R^6)_2)_rS(O)_2OH$. In certain embodiments, B is —$(C(R^6)_2)_rP(O)_2OR^x$. In certain embodiments, B is —$O(C(R^6)_2)_rP(O)_2OR^x$.

As described above, C is —$(CH_2)_r$CN, —$(CH_2)_s$OH, halogen, —$(C(R^6)_2)_rC_6$-$C_{10}$ aryl, —$(C(R^6)_2)_r$S—$C_6$-$C_{10}$ aryl, —$(C(R^6)_2)_r$heteroaryl, —$O(C(R^6)_2)_r$heteroaryl, —$O(C(R^6)_2)_r$heterocycloalkyl, —$O(C(R^6)_2)_r$OH, —$OR^y$, —$(C(R^6)_2)_rC(O)NHCN$, —CH═$CHCO_2R^x$, or —$(C(R^6)_2)_rC(O)NHS(O)_2C_1$-$C_4$ alkyl, wherein the aryl and heteroaryl are substituted with one to three substituents each independently selected from $C_1$-$C_6$ alkyl, $C_1$-$C_6$ haloalkyl, halogen, and OH, and wherein the heterocycloalkyl is substituted with one to two ═O or ═S;

In certain embodiments, C is —$(CH_2)_r$CN. In certain embodiments, C is —$(CH_2)_s$OH. In certain embodiments, C is halogen. In certain embodiments, C is —$(C(R^6)_2)_r C_6$-$C_{10}$ aryl. In certain embodiments, C is —$(C(R^6)_2)_r$S—$C_6$-$C_{10}$ aryl. In certain embodiments, C is —$(C(R^6)_2)_r$heteroaryl. In certain embodiments, C is —$O(C(R^6)_2)_r$heteroaryl. In certain embodiments, C is-$O(C(R^6)_2)_r$heterocycloalkyl. In certain embodiments, C is —$O(C(R^6)_2)_r$OH. In certain embodiments, C is —$OR^y$. In certain embodiments, C is —$(C(R^6)_2)_r$C(O)NHCN. In certain embodiments, C is —CH=CHCO$_2$R$^x$. In certain embodiments, C is —$(C(R^6)_2)_r$C(O)NHS(O)$_2$C$_1$-C$_4$ alkyl. In the above, the aryl and heteroaryl are substituted with one to three substituents each independently selected from C$_1$-C$_6$ alkyl, C$_1$-C$_6$ haloalkyl, halogen, and OH, and wherein the heterocycloalkyl is substituted with one to two =O or =S.

As described above, each R$^6$ is independently at each occurrence H or C$_1$-C$_4$ alkyl. In certain embodiments, R$^6$ is H. In certain embodiments, R$^6$ is C$_1$-C$_4$ alkyl.

As described above, each R$^x$ is independently at each occurrence H, C$_1$-C$_6$ alkyl, or C$_6$-C$_{10}$ aryl. In certain embodiments, R$^x$ is H. In certain embodiments, R$^x$ is C$_1$-C$_6$ alkyl. In certain embodiments, R$^x$ is C$_6$-C$_{10}$ aryl.

As described above, each Y$^2$ is independently O, NH or S. In certain embodiments, Y$^2$ is O. In certain embodiments, Y$^2$ is NH. In certain embodiments, Y$^2$ is S.

As described above, each r independently is 0, 1 or 2. In certain embodiments, r is 0. In certain embodiments, r is 1. In certain embodiments, r is 2.

As described above, s is 1 or 2. In certain embodiments, s is 1. In certain embodiments, s is 2.

As described above, R$^g$ is H, C$_1$-C$_6$ alkyl, OH, —S(O)$_2$(C$_1$-C$_6$ alkyl), or —S(O)$_2$N(C$_1$-C$_6$ alkyl)$_2$.

As described above, R$^{g'}$ is H, C$_1$-C$_6$ alkyl, C$_3$-C$_7$ cycloalkyl, 4- to 7-membered heterocycloalkyl ring comprising 1-3 heteroatoms selected from N, O and S, C$_6$-C$_{10}$ aryl, or 5- to 7-membered heteroaryl comprising 1-3 heteroatoms selected from N, O and S, wherein the alkyl is optionally substituted with one or more substituents independently selected from halogen and —OH, and wherein the cycloalkyl, heterocycloalkyl, aryl and heteroaryl are optionally substituted with one or more substituents independently selected from C$_1$-C$_6$ alkyl, halogen, and —OH.

In some embodiments, the present disclosure provides a compound of formula (I) having one, two, or three of the following features:
a) W is N;
b) R$^c$ is CN;
c) R$^d$ is 5- or 6-membered heteroaryl, such as thiophenyl;
d) L is —$(C(R^5)_2)_m Y^1 (C(R^5)_2)_p$, such as —SCH$_2$—;
e) R$^1$ is phenylene;
f) R$^7$ is A, such as COOH or tetrazole.

In some embodiments, the present disclosure provides a compound of formula (I) having one, two, or three of the following features:
a) W is N;
b) R$^d$ is CF$_3$;
c) L is —$(C(R^5)_2)_m Y^1 (C(R^5)_2)_p$, such as —SCH$_2$—;
d) R$^1$ is phenylene;
e) R$^7$ is A, such as COOH or tetrazole.

In some embodiments, the present disclosure provides a compound of formula (I) having one, two, or three of the following features:
a) W is N;
b) R$^c$ is CN;
c) R$^d$ is 5- or 6-membered heteroaryl, such as thiophenyl;
d) L is —$(C(R^5)_2)_m Y^1 (C(R^5)_2)_p$, such as —SCH$_2$—;
e) R$^1$ is absent;
f) R$^7$ is A, such as COOH or tetrazole.

In some embodiments, the present disclosure provides a compound of formula (I) having one, two, or three of the following features:
a) W is N;
b) R$^d$ is CF$_3$;
c) L is —$(C(R^5)_2)_m Y^1 (C(R^5)_2)_p$, such as —SCH$_2$—;
d) R$^1$ is absent;
e) R$^7$ is A, such as COOH or tetrazole.

In some embodiments, the present disclosure provides a compound of formula (I) having one, two, or three of the following features:
a) W is C;
b) R$^d$ is —$(C(R^6)_2)_r C_6$-$C_{10}$ aryl or —$(C(R^6)_2)_r$-5- or 6-membered heteroaryl);
c) L is —$(C(R^5)_2)_m Y^1 (C(R^5)_2)_p$, such as —SCH$_2$—;
d) R$^1$ is phenylene;
e) R$^7$ is A, such as COOH or tetrazole.

In some embodiments, the present disclosure provides a compound of formula (I) having one, two, or three of the following features:
a) W is C;
b) R$^d$ is —CF$_3$;
c) L is —$(C(R^5)_2)_m Y^1 (C(R^5)_2)_p$, such as —SCH$_2$—;
d) R$^1$ is phenylene;
e) R$^7$ is A, such as COOH or tetrazole.

In some embodiments, the present disclosure provides a compound of formula (I) having one, two, or three of the following features:
a) W is N;
b) R$^c$ is CN;
c) R$^d$ is 5- or 6-membered heteroaryl, such as thiophenyl;
d) L is —$(C(R^5)_2)_m Y^1 (C(R^5)_2)_p$, such as —SCH$_2$—;
e) R$^1$ is phenylene;
f) R$^7$ is A, such as —$(C(R^6)_2)_r$CO$_2$R$^x$ or —(CH$_2$)$_r$tetrazole.

In some embodiments, the present disclosure provides a compound of formula (I) having one, two, or three of the following features:
a) W is N;
b) R$^d$ is CF$_3$;
c) L is —$(C(R^5)_2)_m Y^1 (C(R^5)_2)_p$, such as —SCH$_2$—;
d) R$^1$ is phenylene;
e) R$^7$ is A, such as —$(C(R^6)_2)_r$CO$_2$R$^x$ or —(CH$_2$)$_r$tetrazole.

In some embodiments, the present disclosure provides a compound of formula (I) having one, two, or three of the following features:
a) W is N;
b) R$^c$ is CN;
c) R$^d$ is 5- or 6-membered heteroaryl, such as thiophenyl;
d) L is —$(C(R^5)_2)_m Y^1 (C(R^5)_2)_p$, such as —SCH$_2$—;
e) R$^1$ is absent;
f) R$^7$ is A, such as —$(C(R^6)_2)_r$CO$_2$R$^x$ or —(CH$_2$)$_r$tetrazole.

In some embodiments, the present disclosure provides a compound of formula (I) having one, two, or three of the following features:
a) W is N;
b) R$^d$ is CF$_3$;
c) L is —$(C(R^5)_2)_m Y^1 (C(R^5)_2)_p$, such as —SCH$_2$—;
d) R$^1$ is absent;
e) R$^7$ is A, such as —$(C(R^6)_2)_r$CO$_2$R$^x$ or —(CH$_2$)$_r$tetrazole.

In some embodiments, the present disclosure provides a compound of formula (I) having one, two, or three of the following features:

a) W is C;
b) $R^d$ is —$(C(R^6)_2)_tC_6$-$C_{10}$ aryl or —$(C(R^6)_2)_t$-5- or 6-membered heteroaryl);
c) L is —$(C(R^5)_2)_mY^1(C(R^5)_2)_p$, such as —$SCH_2$—;
d) $R^f$ is phenylene;
e) $R^7$ is A, such as —$(C(R^6)_2)_rCO_2R^x$ or —$(CH_2)_r$tetrazole.

In some embodiments, the present disclosure provides a compound of formula (I) having one, two, or three of the following features:

a) W is C;
b) $R^d$ is —$CF_3$;
c) L is —$(C(R^5)_2)_mY^1(C(R^5)_2)_p$, such as —$SCH_2$—;
d) $R^f$ is phenylene;
e) $R^7$ is A, such as —$(C(R^6)_2)_rCO_2R^x$ or —$(CH_2)_r$tetrazole.

In certain embodiments, with certain above features for Formula (I), the present disclosure provides a compound of formula (Ia) having at least one of the following features:

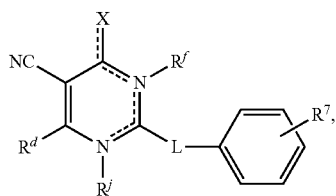

(Ia)

and pharmaceutically salts and tautomers thereof, wherein a) $R^d$ is 5- or 6-membered heteroaryl;
b) L is —$(C(R^5)_2)_mY^1(C(R^5)_2)_p$;
c) $R^7$ is A or C;
d) X, $R^d$, $R^f$, $R^j$, A, $R^5$, $Y^1$, m, and p are defined for Formula (I).

In certain embodiments, $R^d$ is thiophenyl. In certain embodiments, L is —$SCH_2$— or —$NHCH_2$—. In certain embodiments, $R^7$ is C. In certain embodiments, C is —$(C(R^6)_2)_rC_6$-$C_{10}$ aryl, substituted with one to three substituents each independently selected from $C_1$-$C_6$ alkyl, $C_1$-$C_6$ haloalkyl, halogen and OH. In certain embodiments, $R^7$ is A. In certain embodiments, A is —$(C(R^6)_2)_rCO_2R^x$ or —$(CH_2)_r$tetrazole, wherein —$(CH_2)_r$tetrazole is optionally substituted with $C_1$-$C_6$ alkyl. In certain embodiments, A is —$(C(R^6)_2)_rCOOH$ or —$(CH_2)_r$tetrazole, wherein —$(CH_2)_r$tetrazole is optionally substituted with $C_1$-$C_6$ alkyl. In certain embodiments, A is —COOH, —$CH_2$COOH, -tetrazole, or —$(CH_2)$tetrazole, wherein tetrazole and —$(CH_2)_r$tetrazole are optionally substituted with $C_1$-$C_6$ alkyl. In certain embodiments, Formula (Ia) has one, two, three or four of the features (a) to (d).

In certain embodiments, with certain above features for Formula (I), the present disclosure provides a compound of formula (Ib) having at least one of the following features:

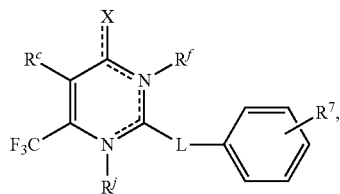

(Ib)

and pharmaceutically salts and tautomers thereof, wherein a) L is —$(C(R^5)_2)_mY^1(C(R^5)_2)_p$;
b) $R^7$ is A;
c) X, $R^c$, R, $R^j$, A, $R^5$, $Y^1$, m, and p are defined for Formula (I).

In certain embodiments, L is —$SCH_2$— or —$NHCH_2$—. In certain embodiments, A is —$(C(R^6)_2)_rCO_2R^x$ or —$(CH_2)_r$tetrazole, wherein —$(CH_2)_r$tetrazole is optionally substituted with $C_1$-$C_6$ alkyl. In certain embodiments, A is —$(C(R^6)_2)_rCOOH$ or —$(CH_2)_r$tetrazole, wherein —$(CH_2)_r$tetrazole is optionally substituted with $C_1$-$C_6$ alkyl. In certain embodiments, A is —COOH, —$CH_2$COOH, -tetrazole, or —$(CH_2)$tetrazole, wherein tetrazole and —$(CH_2)_r$tetrazole are optionally substituted with $C_1$-$C_6$ alkyl. In certain embodiments, Formula (Ib) has one, two, or three of the features (a) to (c).

In certain embodiments, with certain above features for Formula (I), the present disclosure provides a compound of formula (Ic) having at least one of the following features:

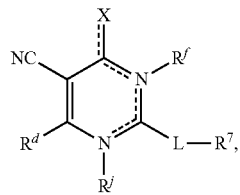

(Ic)

and pharmaceutically salts and tautomers thereof, wherein a) $R^d$ is 5- or 6-membered heteroaryl;
b) L is —$(C(R^5)_2)_mY^1(C(R^5)_2)_p$;
c) $R^7$ is A;
d) X, $R^d$, $R^f$, $R^j$, A, $R^5$, $Y^1$, m, and p are defined for Formula (I).

In certain embodiments, $R^d$ is thiophenyl. In certain embodiments, L is —$SCH_2$— or —$NHCH_2$—. In certain embodiments, A is —$(C(R^6)_2)_rCO_2R^x$ or —$(CH_2)_r$tetrazole, wherein —$(CH_2)_r$tetrazole is optionally substituted with $C_1$-$C_6$ alkyl. In certain embodiments, A is —$(C(R^6)_2)_rCOOH$ or —$(CH_2)_r$tetrazole, wherein —$(CH_2)_r$tetrazole is optionally substituted with $C_1$-$C_6$ alkyl. In certain embodiments, A is —COOH, —$CH_2$COOH, -tetrazole, or —$(CH_2)$tetrazole, wherein tetrazole and —$(CH_2)_r$tetrazole are optionally substituted with $C_1$-$C_6$ alkyl. In certain embodiments, Formula (Ic) has one, two, three or four of the features (a) to (d).

In certain embodiments, with certain above features for Formula (I), the present disclosure provides a compound of formula (Id) having at least one of the following features:

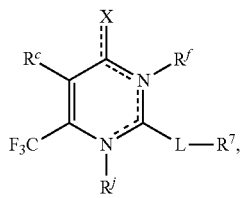

(Id)

and pharmaceutically salts and tautomers thereof, wherein
a) L is —(C(R$^5$)$_2$)$_m$Y$^1$(C(R$^5$)$_2$)$_p$;
b) R$^7$ is A;
c) X, R$^d$, R$^f$, R$^j$, A, R$^5$, Y$^1$, m, and p are defined for Formula (I).

In certain embodiments, L is —SCH$_2$— or —NHCH$_2$—. In certain embodiments, A is —(C(R$^6$)$_2$)$_r$CO$_2$R$^x$ or —(CH$_2$)$_r$tetrazole, wherein —(CH$_2$)$_r$tetrazole is optionally substituted with C$_1$-C$_6$ alkyl. In certain embodiments, A is —(C(R$^6$)$_2$)$_r$COOH or —(CH$_2$)$_r$tetrazole, wherein —(CH$_2$)$_r$tetrazole is optionally substituted with C$_1$-C$_6$ alkyl. In certain embodiments, A is —COOH, —CH$_2$COOH, -tetrazole, or —(CH$_2$)tetrazole, wherein tetrazole and —(CH$_2$)$_r$tetrazole are optionally substituted with C$_1$-C$_6$ alkyl. In certain embodiments, Formula (Id) has one, two, or three of the features (a) to (c).

In certain embodiments, with certain above features for Formula (I), the present disclosure provides a compound of formula (Ie) having at least one of the following features:

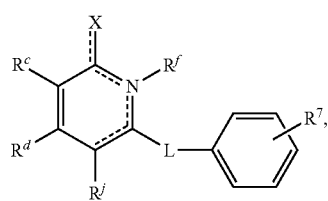

(Ie)

and pharmaceutically salts and tautomers thereof, wherein
a) R$^d$ is —(C(R$^6$)$_2$)$_t$C$_6$-C$_{10}$ aryl or —(C(R$^6$)$_2$)$_t$-5- or 6-membered heteroaryl);
b) L is —(C(R$^5$)$_2$)$_m$Y$^1$(C(R$^5$)$_2$)$_p$;
c) R$^7$ is A.
d) X, R$^d$, R, R$^j$, A, R$^5$, Y$^1$, m, and p are defined for Formula (I).

In certain embodiments, L is —SCH$_2$— or —NHCH$_2$—. In certain embodiments, A is —(C(R$^6$)$_2$)$_r$CO$_2$R$^x$ or —(CH$_2$)$_r$tetrazole, wherein —(CH$_2$)$_r$tetrazole is optionally substituted with C$_1$-C$_6$ alkyl. In certain embodiments, A is —(C(R$^6$)$_2$)$_r$COOH or —(CH$_2$)$_r$tetrazole, wherein —(CH$_2$)$_r$tetrazole is optionally substituted with C$_1$-C$_6$ alkyl. In certain embodiments, A is —COOH, —CH$_2$COOH, -tetrazole, or —(CH$_2$)tetrazole, wherein tetrazole and —(CH$_2$)$_r$tetrazole are optionally substituted with C$_1$-C$_6$ alkyl. In certain embodiments, Formula (Ie) has one, two, three, or four of the features (a) to (d).

In certain embodiments, with certain above features for Formula (I), the present disclosure provides a compound of formula (If) having at least one of the following features:

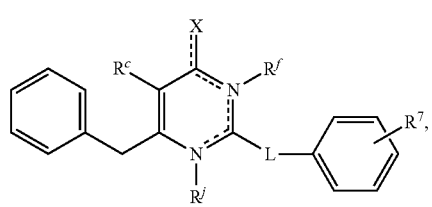

(If)

and pharmaceutically salts and tautomers thereof, wherein
a) L is —(C(R$^5$)$_2$)$_m$Y$^1$(C(R$^5$)$_2$)$_p$;
b) R$^7$ is A;
c) X, R$^c$, R, R$^j$, A, R$^5$, Y$^1$, m, and p are defined for Formula (I).

In certain embodiments, L is —SCH$_2$— or —NHCH$_2$—. In certain embodiments, A is —(C(R$^6$)$_2$)$_r$CO$_2$R$^x$ or —(CH$_2$)$_r$tetrazole, wherein —(CH$_2$)$_r$tetrazole is optionally substituted with C$_1$-C$_6$ alkyl. In certain embodiments, A is —(C(R$^6$)$_2$)$_r$COOH or —(CH$_2$)$_r$tetrazole, wherein —(CH$_2$)$_r$tetrazole is optionally substituted with C$_1$-C$_6$ alkyl. In certain embodiments, A is —COOH, —CH$_2$COOH, -tetrazole, or —(CH$_2$)tetrazole, wherein tetrazole and —(CH$_2$)$_r$tetrazole are optionally substituted with C$_1$-C$_6$ alkyl. In certain embodiments, R$^c$ is CN. In certain embodiments, Formula (If) has one, two, or three of the features (a) to (c).

In certain embodiments, with certain above features for Formula (I), the present disclosure provides a compound of formula (Ig) having at least one of the following features:

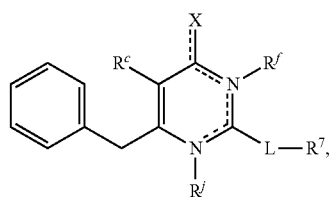

(Ig)

and pharmaceutically salts and tautomers thereof, wherein
a) L is —(C(R$^5$)$_2$)$_m$Y$^1$(C(R$^5$)$_2$)$_p$;
b) R$^7$ is A;
c) X, R$^d$, R$^f$, R$^j$, A, R$^5$, Y$^1$, m, and p are defined for Formula (I).

In certain embodiments, L is —SCH$_2$— or —NHCH$_2$—. In certain embodiments, A is —(C(R$^6$)$_2$)$_r$CO$_2$R$^x$ or —(CH$_2$)$_r$tetrazole, wherein —(CH$_2$)$_r$tetrazole is optionally substituted with C$_1$-C$_6$ alkyl. In certain embodiments, A is —(C(R$^6$)$_2$)$_r$COOH or —(CH$_2$)$_r$tetrazole, wherein —(CH$_2$)$_r$tetrazole is optionally substituted with C$_1$-C$_6$ alkyl. In certain embodiments, A is —COOH, —CH$_2$COOH, -tetrazole, or —(CH$_2$)tetrazole, wherein tetrazole and —(CH$_2$)$_r$tetrazole are optionally substituted with C$_1$-C$_6$ alkyl. In certain embodiments, Formula (Ig) has one, two, or three of the features (a) to (c).

In some embodiments, the compound of Formula (I) is a compound selected from:

| Cpd No. | Structure |
|---|---|
| I-1 | 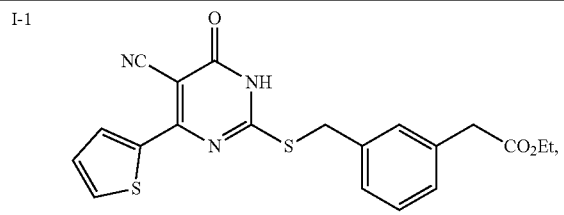 |
| I-2 | 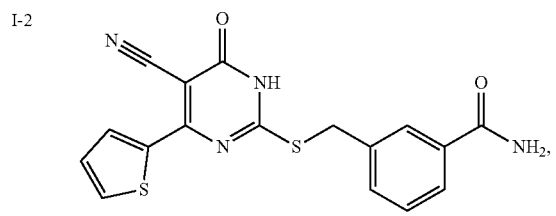 |
| I-3 | 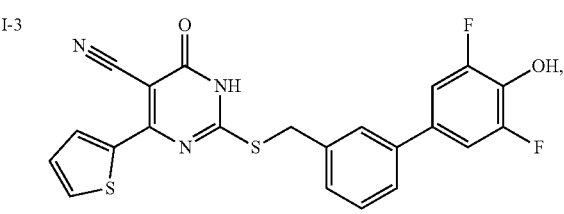 |
| I-4 | 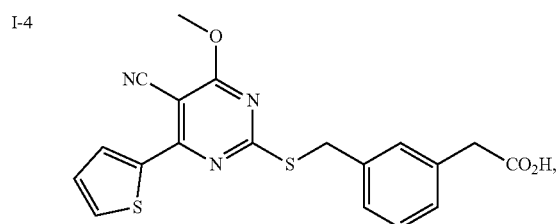 |
| I-5 | 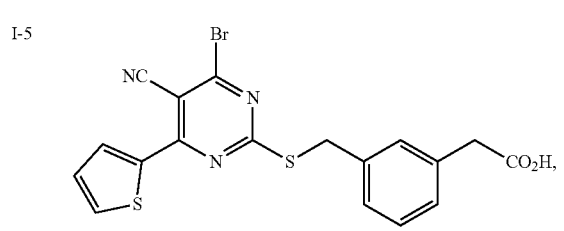 |
| I-6 | 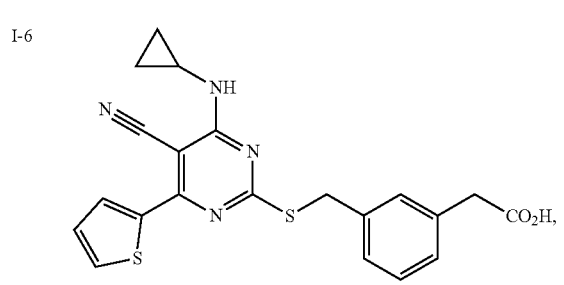 |
| I-7 | 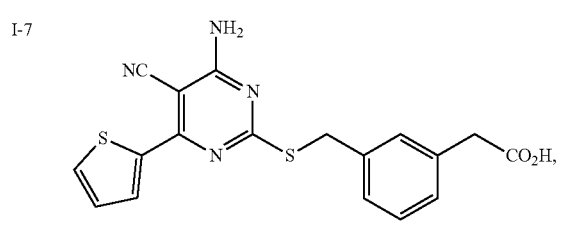 |
-continued
| Cpd No. | Structure |
|---|---|
| I-8 | 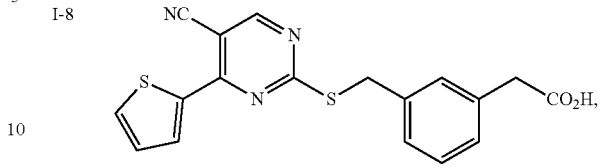 |
| I-9 | 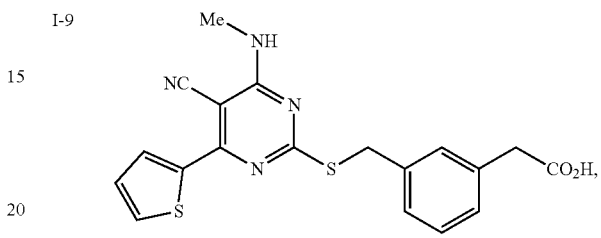 |
| I-10 | 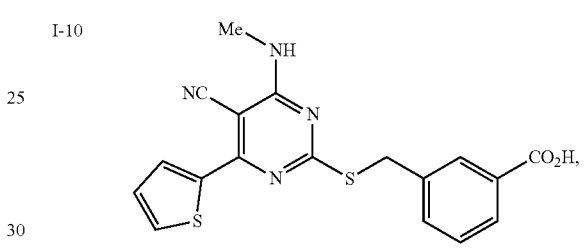 |
| I-11 | 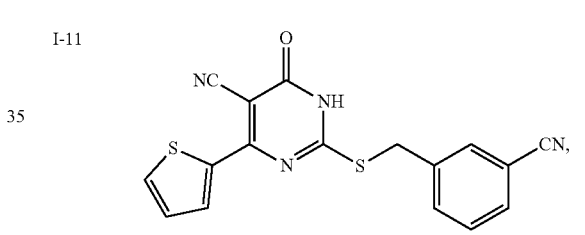 |
| I-12 | 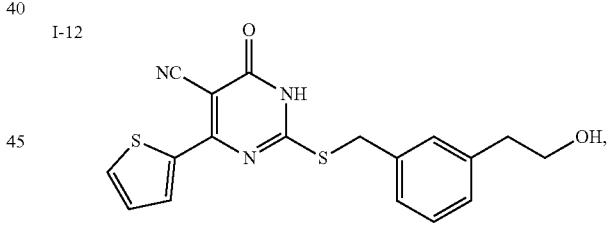 |
| I-13 | 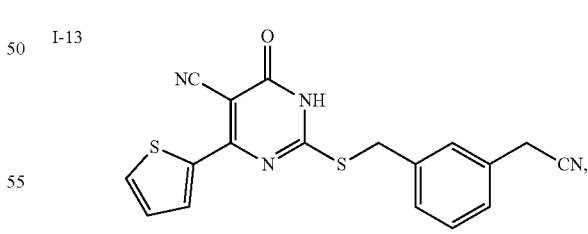 |
| I-14 | 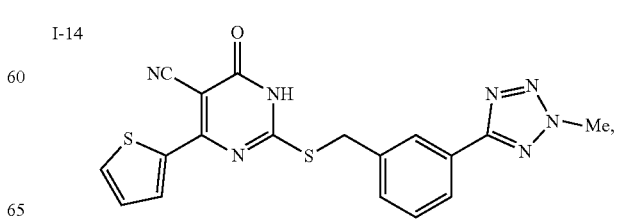 |

| Cpd No. | Structure |
|---|---|
| I-15 | 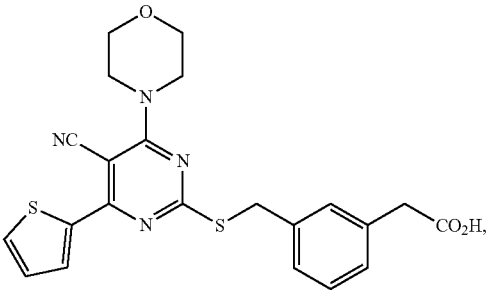 [SMILES: N#Cc1c(-c2cccs2)nc(SCc2cccc(CC(=O)O)c2)nc1N1CCOCC1] |
| I-16 | 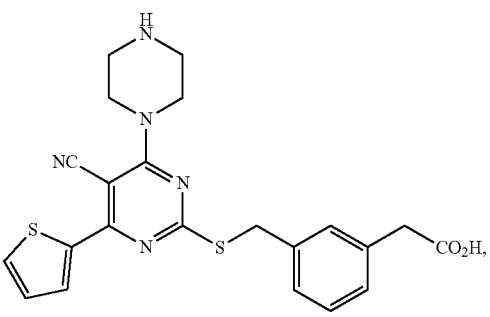 [SMILES: N#Cc1c(-c2cccs2)nc(SCc2cccc(CC(=O)O)c2)nc1N1CCNCC1] |
| I-17 | 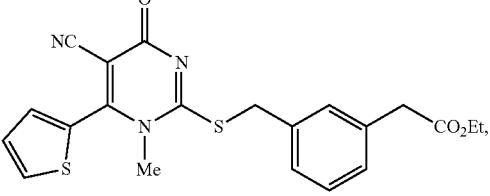 |
| I-18 | 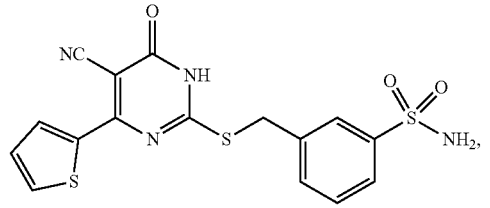 [SMILES: N#Cc1c(-c2cccs2)nc(SCc2cccc(S(N)(=O)=O)c2)[nH]c1=O] |
| I-19 | 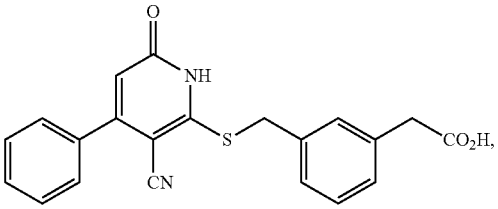 [SMILES: N#Cc1c(-c2ccccc2)cc(=O)[nH]c1SCc1cccc(CC(=O)O)c1] |
| I-20 | 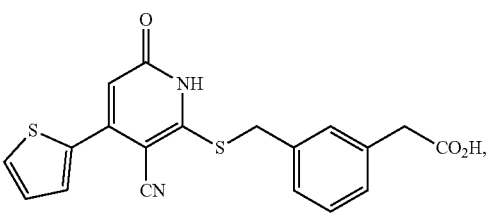 [SMILES: N#Cc1c(-c2cccs2)cc(=O)[nH]c1SCc1cccc(CC(=O)O)c1] |
| I-21 | 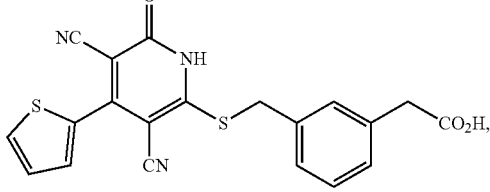 |
| I-22 | 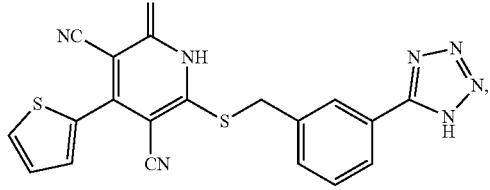 |
| I-23 | 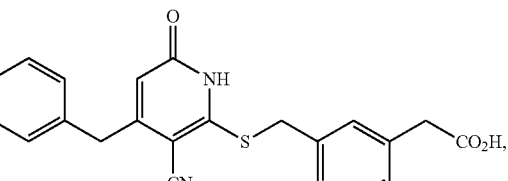 |
| I-24 | 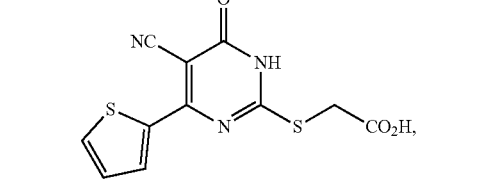 |
| I-25 | 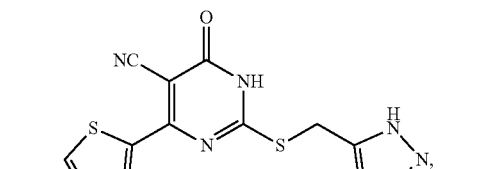 |
| I-26 | 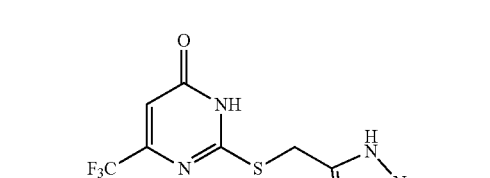 |
| I-27 | 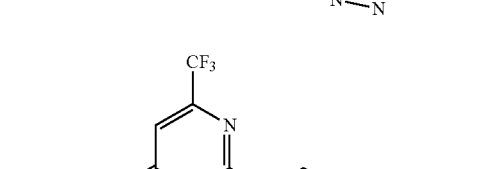 |

| Cpd No. | Structure |
|---|---|
| I-28 | 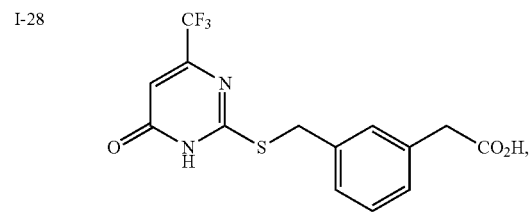 |
| I-29 | 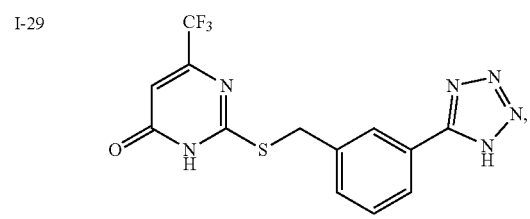 |
| I-30 | 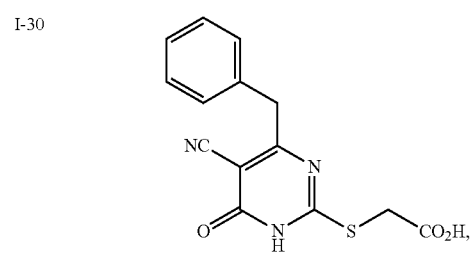 |
| I-31 | 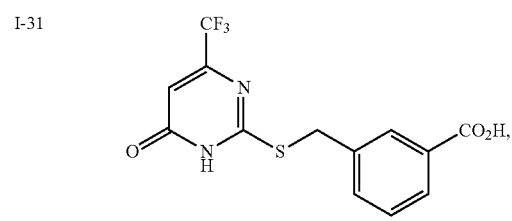 |
| I-32 | 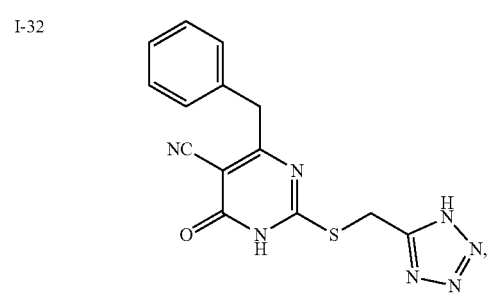 |
| I-33 | 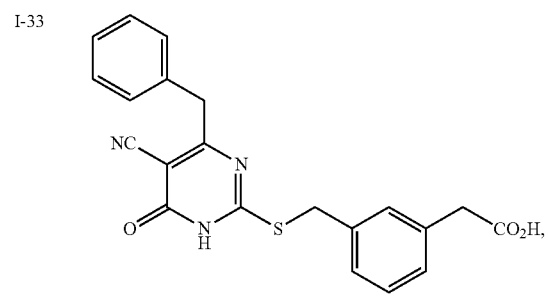 |
| I-34 | 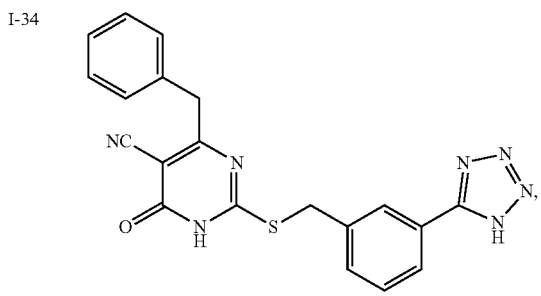 |
| I-35 | 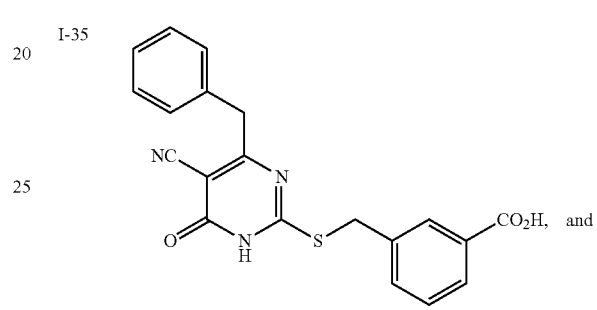 |
| I-36 | 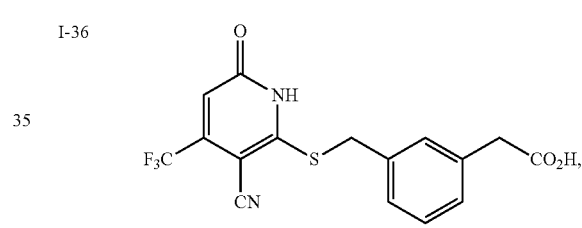 |
or a pharmaceutically acceptable salt or tautomer thereof.
In some embodiments, the compound of Formula (I) or (II) is a compound selected from:
| Cpd No. | Structure |
|---|---|
| I-37 | 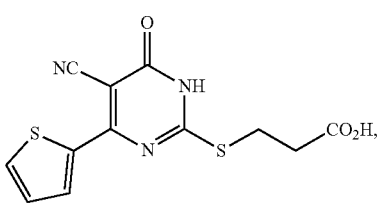 |
| I-38 | 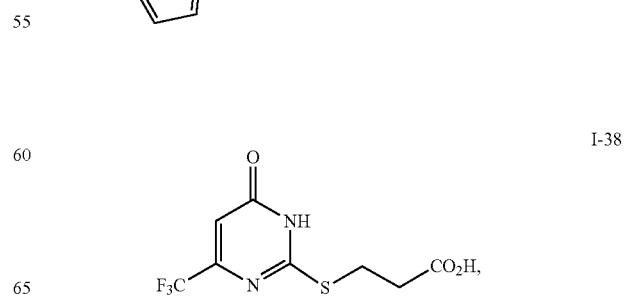 |

I-39
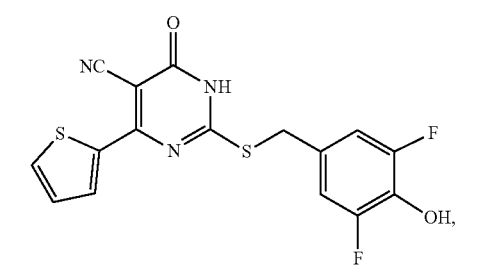
I-40
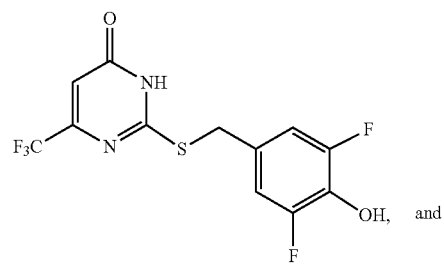
and
I-41
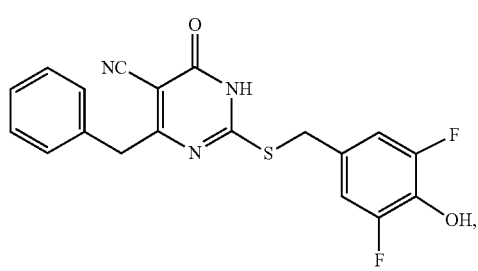
I-42
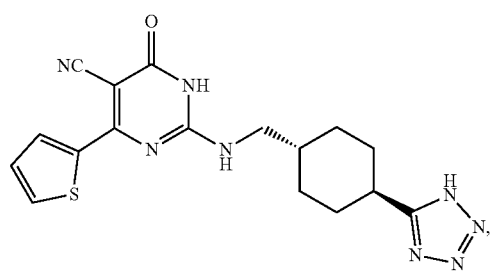
I-43
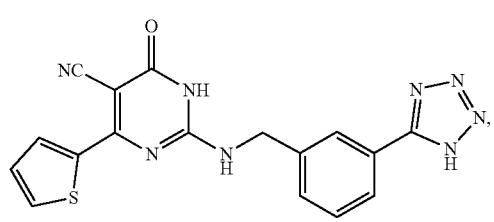
I-44
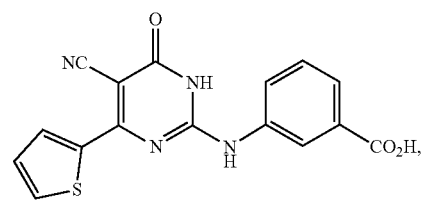
I-45
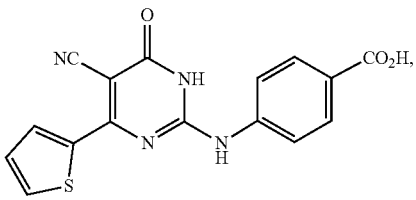
I-46
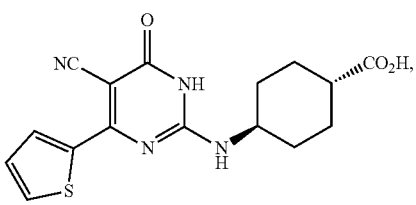
I-47
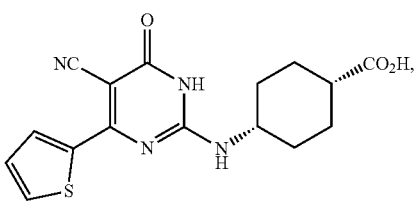
I-48
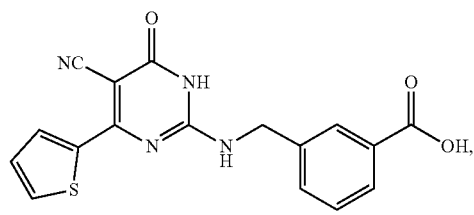
I-49
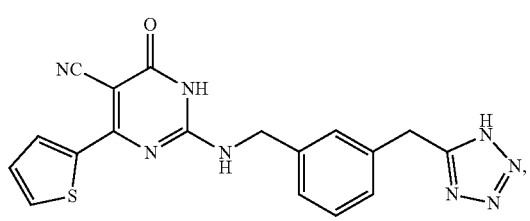
I-50
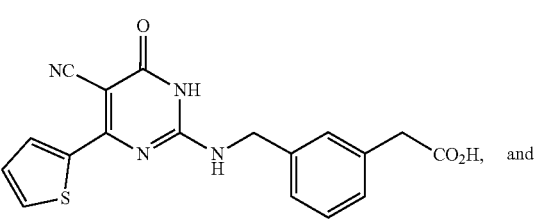
and
I-51
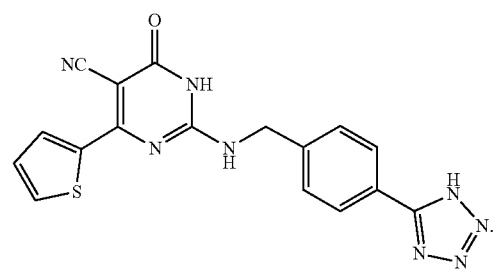

In some embodiments, the compound of Formula (I) is a compound, or a pharmaceutically acceptable salt or tautomer thereof, selected from:
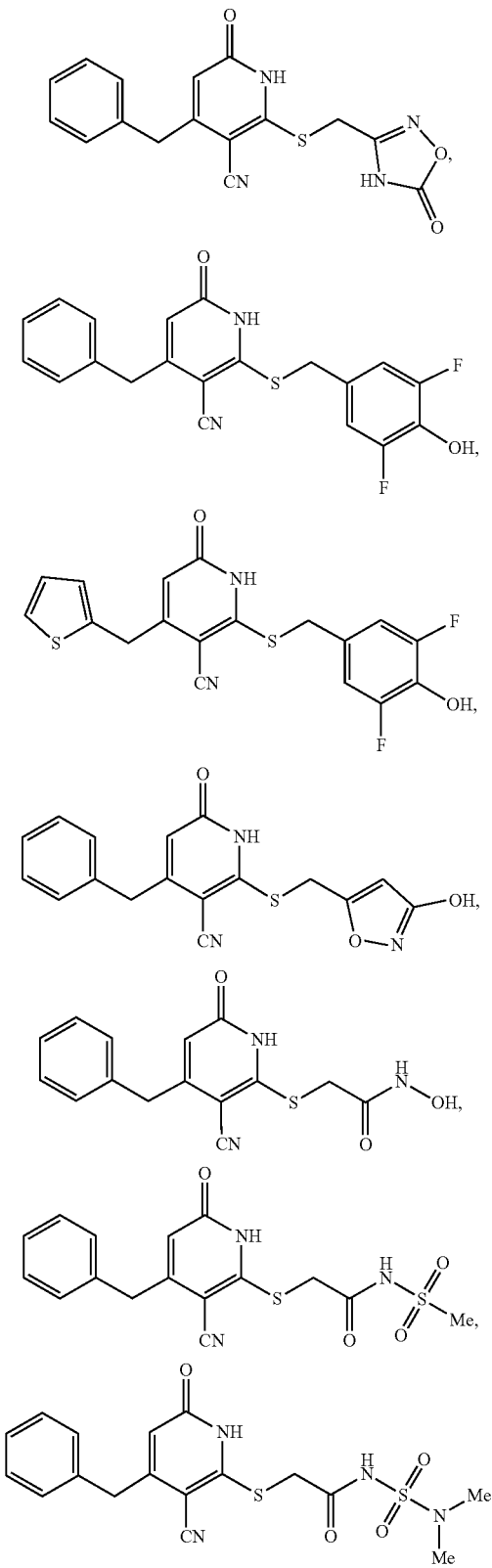
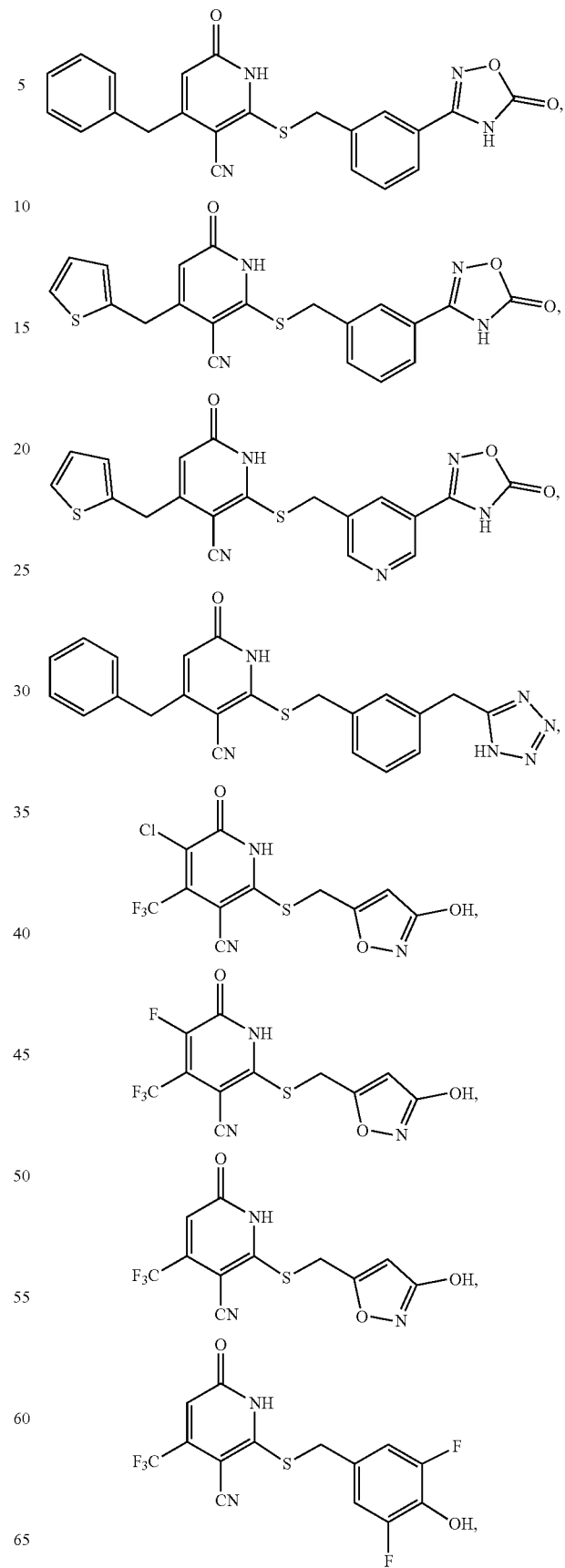

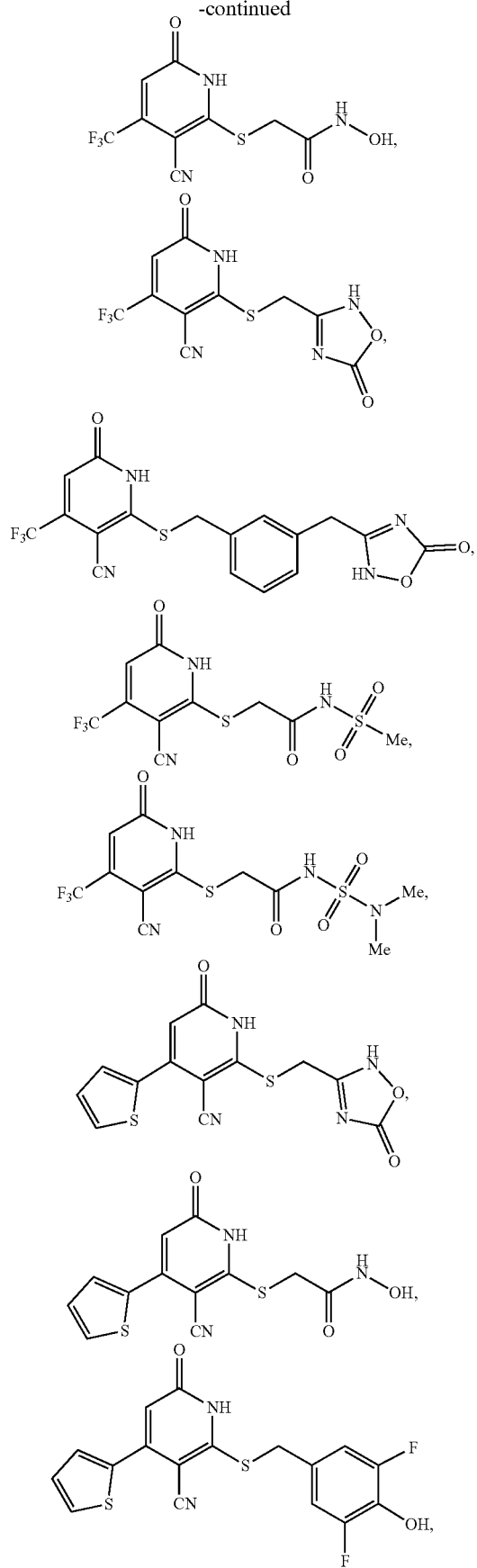
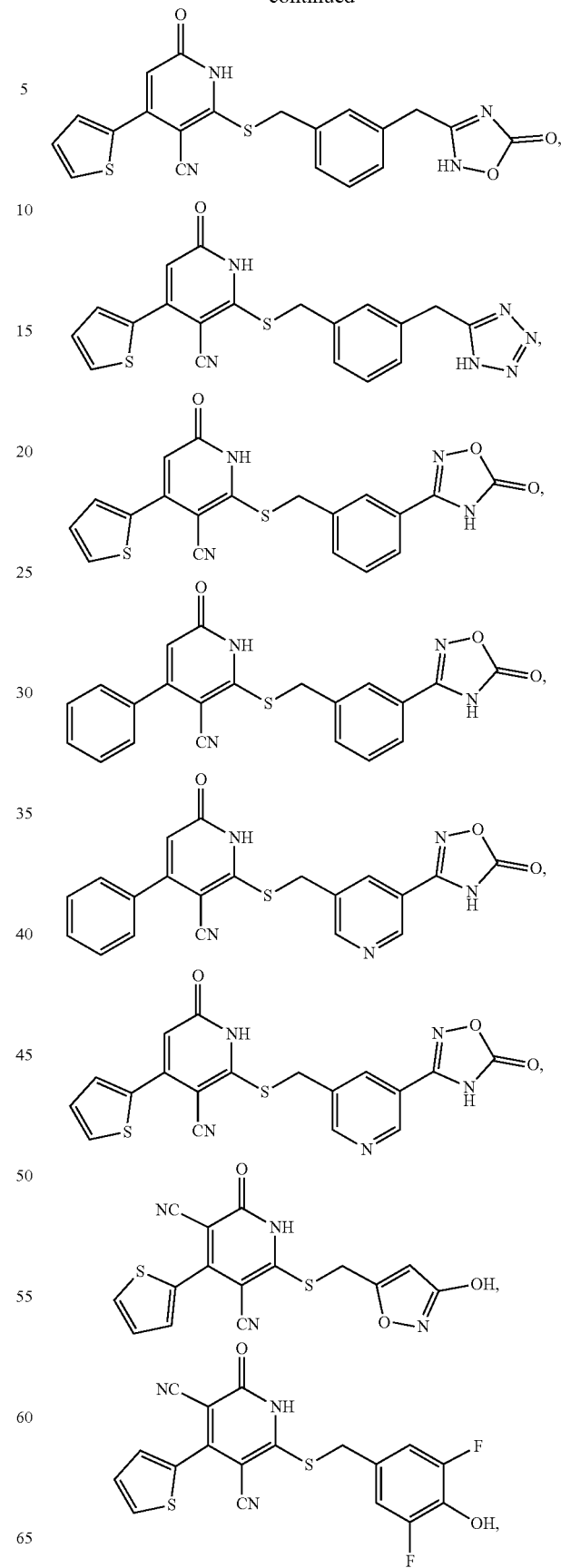

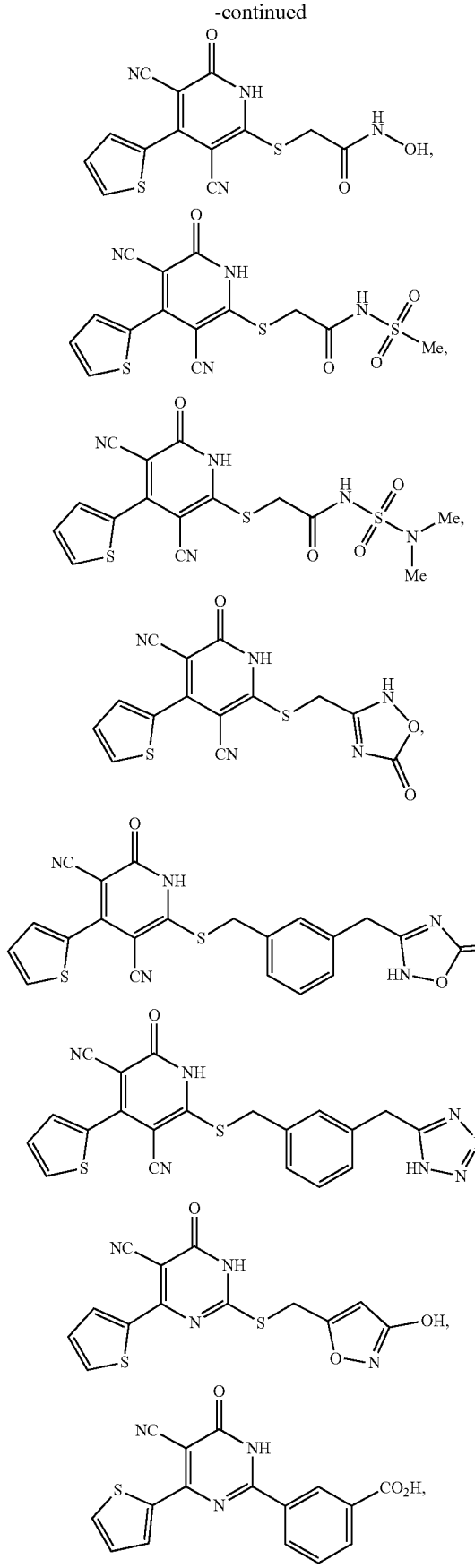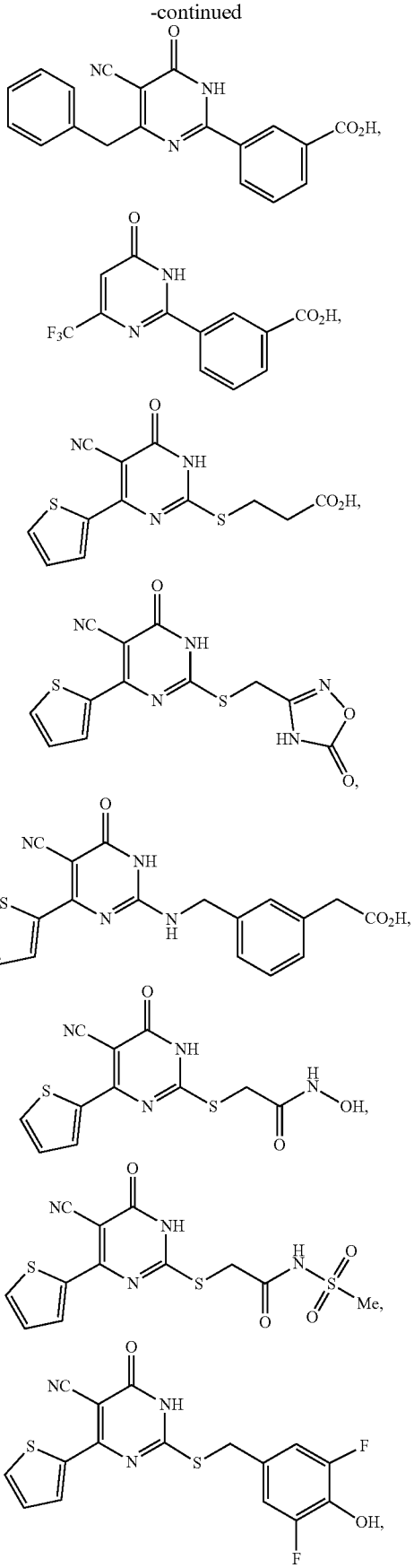

-continued
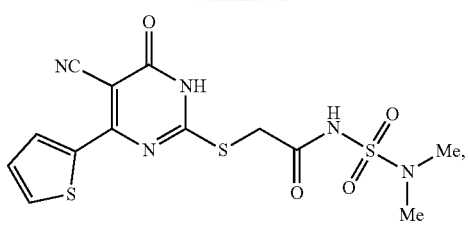
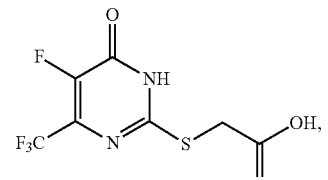
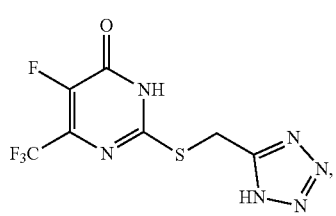
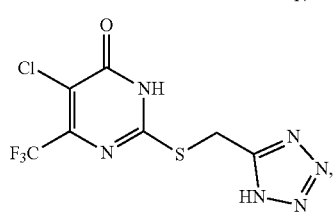
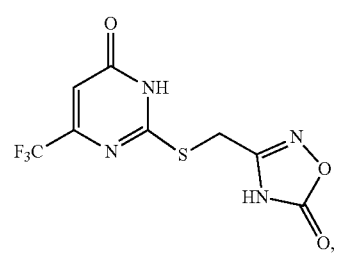
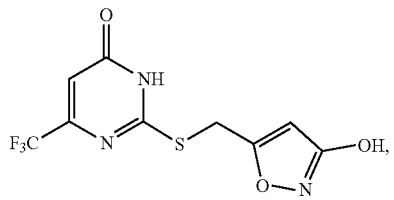
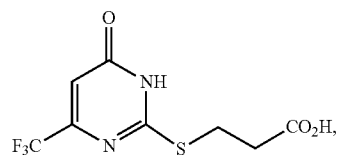
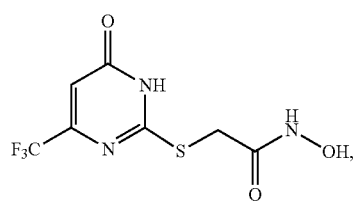
-continued
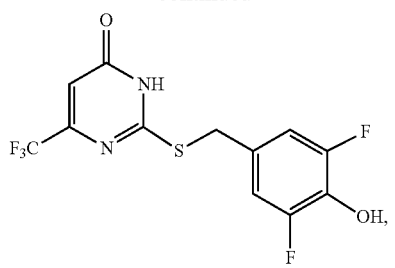
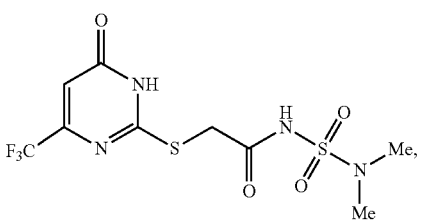
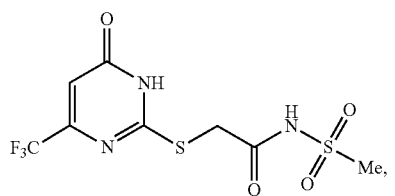
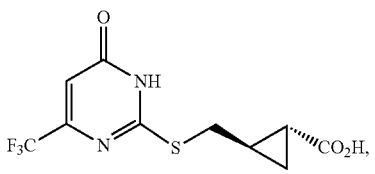
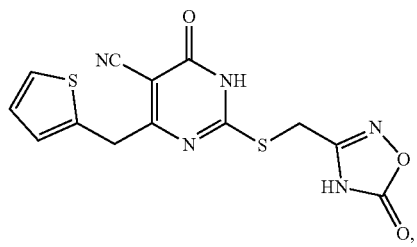
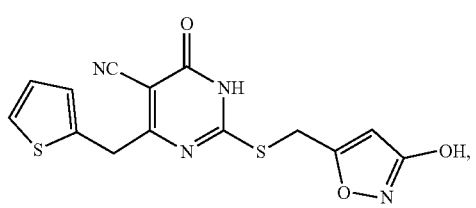
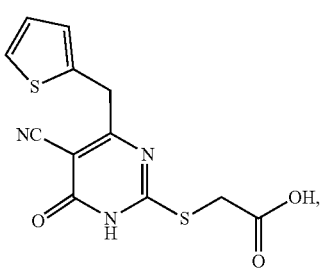

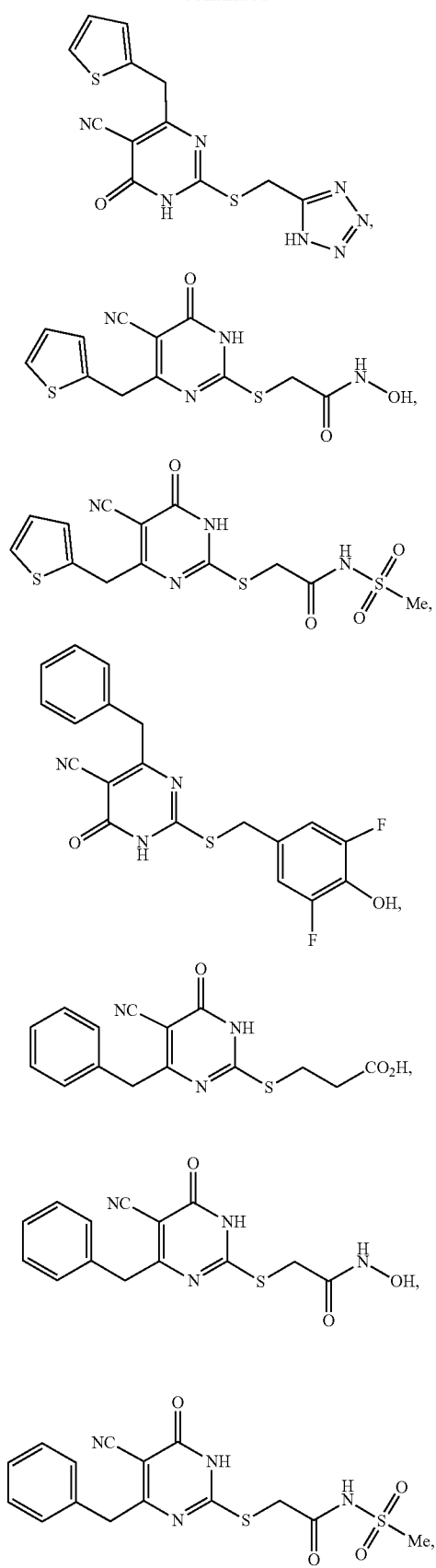
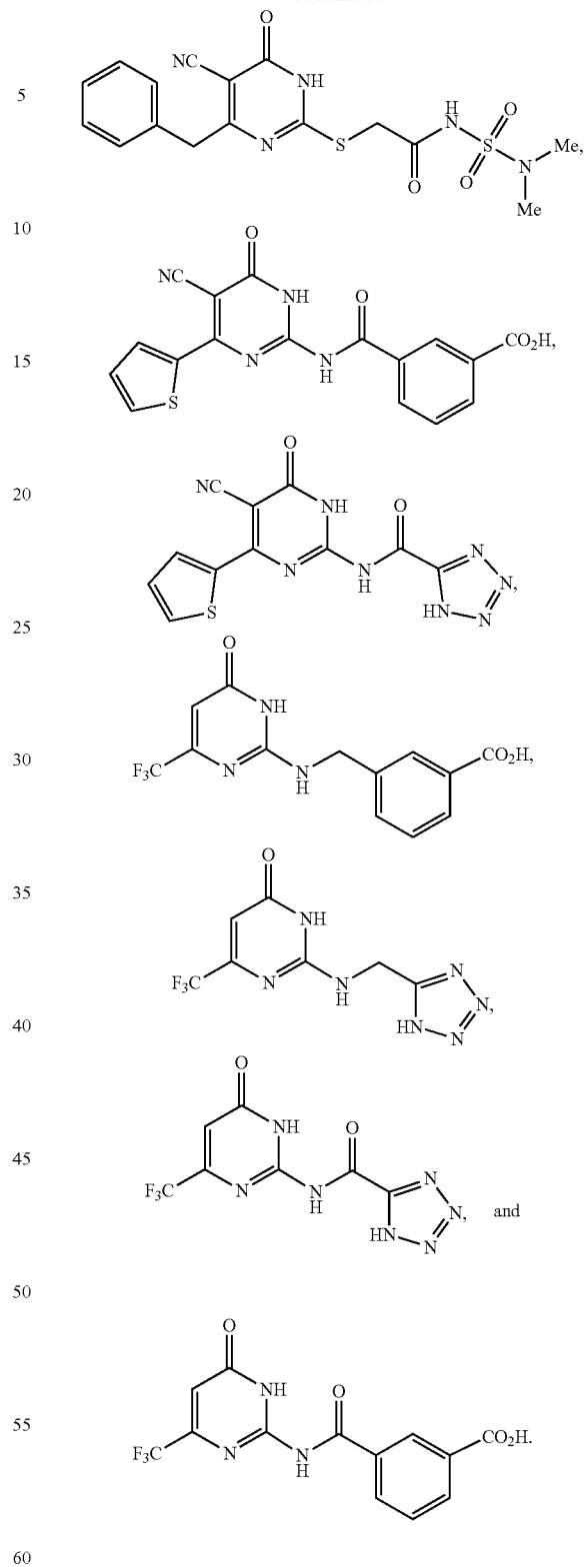
or a pharmaceutically acceptable salt or tautomer thereof.
In some embodiments, the compound of Formula (I) or (II) is a compound, or a pharmaceutically acceptable salt or tautomer thereof, selected from:

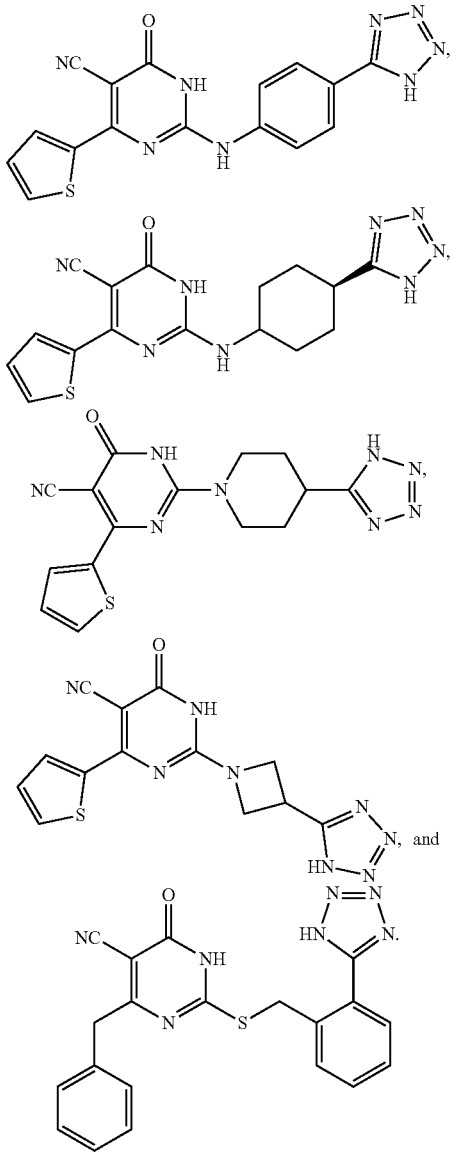

It should be understood, that such references are intended to encompass not only the above general formula, but also each and every of the embodiments, etc. discussed in the following. It should also be understood, that unless stated to the opposite, such references also encompass isomers, mixtures of isomers, pharmaceutically acceptable salts, solvates and prodrugs of the compounds of Formula (I) or (II).

Methods for the Preparation of Compounds

The compounds of the present disclosure (e.g., compounds of Formula (I)) can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Preferred methods include but are not limited to those methods described below. The final products of the reactions described herein may be isolated by conventional techniques, e.g., by extraction, crystallisation, distillation, chromatography, etc.

Compounds of the present disclosure can be synthesized by following the steps outlined in General Scheme A to F which comprise different sequences of assembling intermediates Ia-Ih and Ij-Io. Starting materials are either commercially available or made by known procedures in the reported literature or as illustrated. Useful steps that may be used in the preparation steps of the compounds will be known to the skilled person. The method below is given as a non-limiting example on how the compounds may be prepared.

General Scheme A

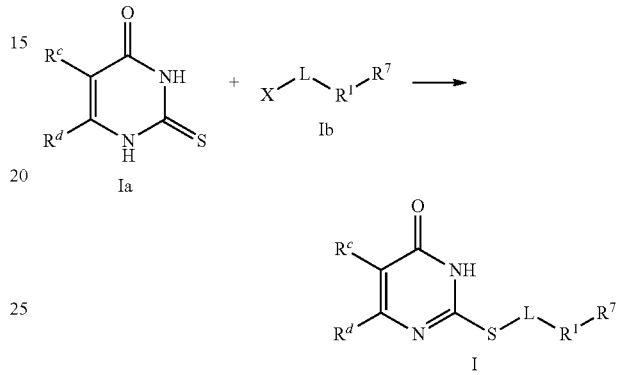

wherein $R^1$, $R^c$, $R^d$, and L are defined as in Formula (I).

The general way of preparing compounds of Formula (I) by using intermediates Ia, and Ib is outlined in General Scheme A. Coupling of Ia with Ib using a base, i.e., potassium carbonate ($K_2CO_3$), in a solvent, i.e., acetonitrile ($CH_3CN$), optionally at elevated temperature provides the desired produce of Formula (I). Bases that can be used include, but are not limited to, sodium carbonate ($Na_2CO_3$), potassium carbonate ($K_2CO_3$), N,N-diisopropylethylamine (DIPEA) and triethylamine. Solvents used in the coupling reaction can be polar or non-polar solvents. For example, the solvent can be acetonitrile ($CH_3CN$), acetone, or dimethylsulfoxide (DMSO).

General Scheme B

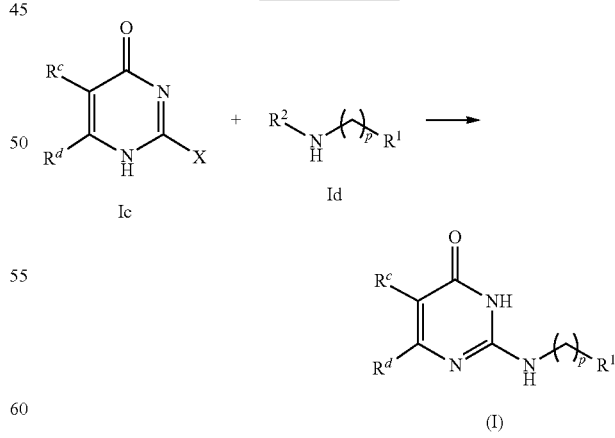

wherein X is a good leaving group, i.e., Cl, Br, —$SCH_3$, or $S(O)_2CH_3$, and $R^1$, $R^2$, $R^c$, $R^d$, and p are defined as in Formula (I).

Alternatively, compounds of Formula (I) can be prepared using intermediates Ic and Id as outlined in General Scheme B. Amination of Intermediate Ic with Ie using a base, i.e., sodium hydroxide (NaOH), potassium hydroxide (KOH), etc., in a solvent, i.e., methanol (MeOH), ethanol (EtOH), water (H₂O), etc., provides compounds of Formula (I).

subsequent treatment with a base, i.e., ammonia (NH₃). Cyclization of Intermediate Ik and Im using a base, i.e., sodium hydroxide (NaOH), potassium hydroxide (KOH), etc., in a solvent, i.e., dimethylacetamide (DMA), optionally at elevated temperature provides compounds of Formula (I).

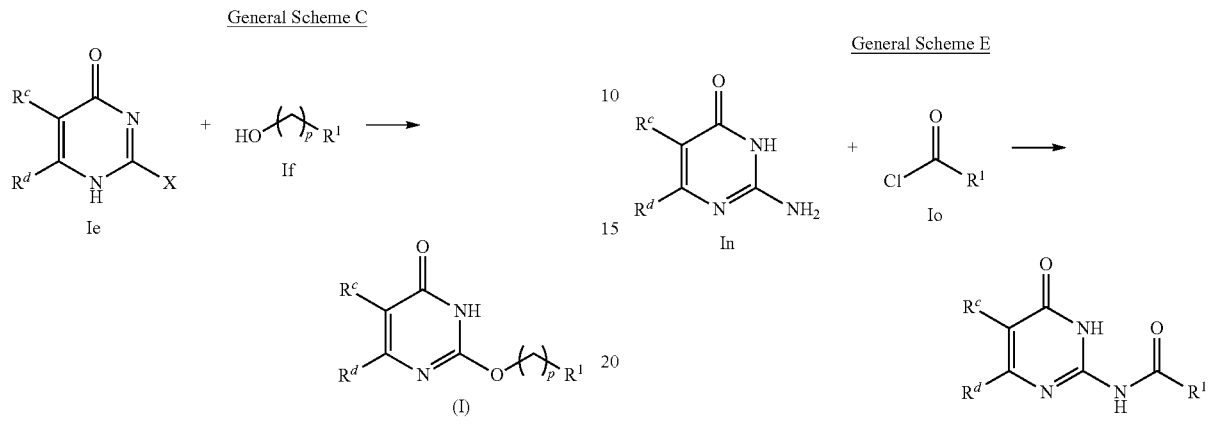

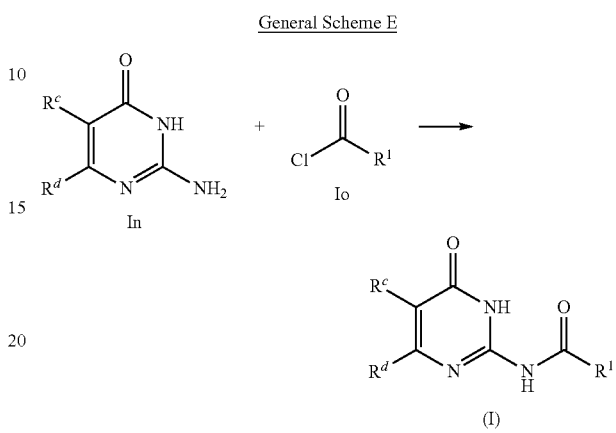

wherein X is a good leaving group, i.e., Cl, Br, —SCH₃, or S(O)₂CH₃, and $R^1$, $R^2$, $R^c$, $R^d$, and p are defined as in Formula (I).

Compounds of Formula (I) can also be prepared using intermediates Ie and If as outlined in General Scheme C. Amination of Intermediate Ie with If using a base, i.e., sodium hydroxide (NaOH), potassium hydroxide (KOH), etc., in a solvent, i.e., methanol (MeOH), ethanol (EtOH), water (H₂O), etc., provides compounds of Formula (I).

wherein and $R^1$, $R^c$, and $R^d$ are defined as in Formula (I).

Alternatively, compounds of Formula (I) can be prepared using intermediates In and Io as outlined in General Scheme D. Acylation of Intermediate In with Io using a base, i.e., sodium hydroxide (NaOH), potassium hydroxide (KOH), etc., in a solvent, i.e., methanol (MeOH), ethanol (EtOH), water (H₂O), etc., provides compounds of Formula (I).

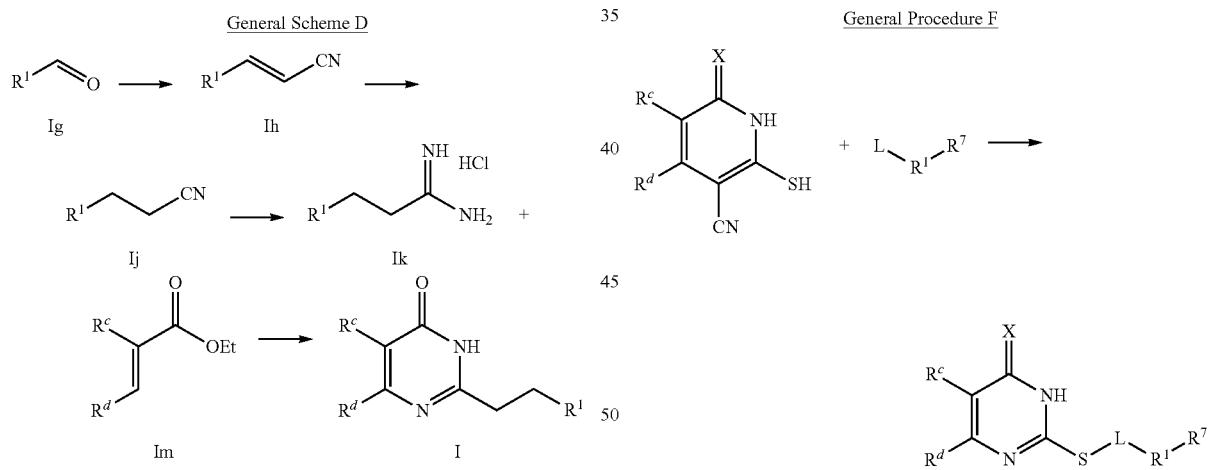

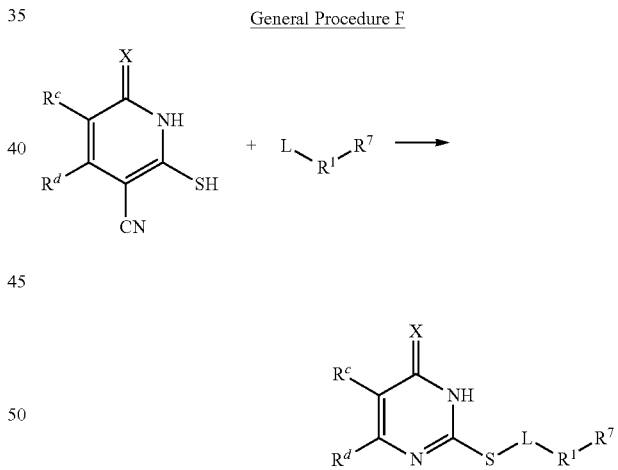

wherein and $R^1$, $R^c$, and $R^d$ are defined as in Formula (I).

Alternatively, compounds of Formula (I) can also be prepared using intermediates Ig, Ih, Ij, Ik, and Im as outlined in General Scheme D. Olefination of intermediate Ig using a base i.e., potassium carbonate (K₂CO₃) and diethyl (cyanomethyl)phosphonate in a solvent, i.e., tetrahydrofuran (THF), water (H₂O), optionally at an elevated temperature provides Intermediate Ih. Hydrogenation of Ih using a metal catalyst, i.e., palladium on carbon (Pd/C), platinum dioxide (PtO₂), etc, and hydrogen (H₂) gas in a solvent, i.e., ethanol (EtOH) and/or tetrahydrofuran (THF), provides Intermediate Ij. Intermediate Ik is obtained by treating Intermediate Ij with an acid, i.e., hydrochloric acid (HCl) in a solvent, i.e., ethanol (EtOH), dichloromethane (CH₂Cl₂), etc., and then wherein and L, $R^c$, $R^d$, $R^1$, and $R^7$ are defined as in Formula (I).

The general procedure for the synthesis of compounds (e.g., I-17 to I-30) with general Formula I include the final coupling between one equivalent of the corresponding substituted 6-mercapto-2-oxo-4,5-disubstituted-1,2-dihydropyridine derivative and a stoichiometric amount of the L-R¹-R⁷ intermediates using two equivalent of DIPEA as base and acetone as solvent to provide the final compound.

Alternatively, certain compounds of Formula (I) or (II) can be prepared using the schemes shown below and compounds of Formula (I) or (II) in general can be prepared based on the schemes shown below.

General Scheme G, 6-Oxo-2-[4-(1H-tetrazol-5-yl)-phenylamino]-4-thiophen-2-yl-1,6-dihydro-pyrimidine-5-carbonitrile
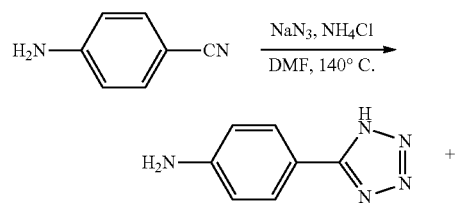
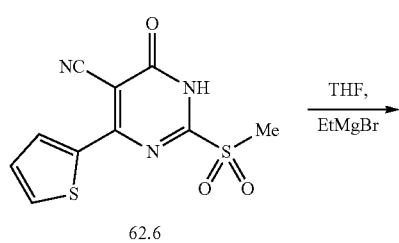
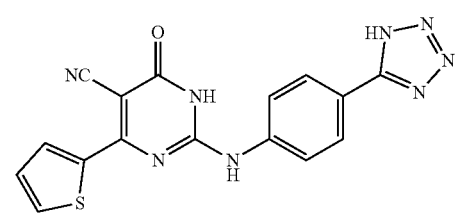
General Scheme H, 6-Oxo-2-[4-(1H-tetrazol-5-yl)-cyclohexylamino]-4-thiophen-2-yl-1,6-dihydro-pyrimidine-5-carbonitrile
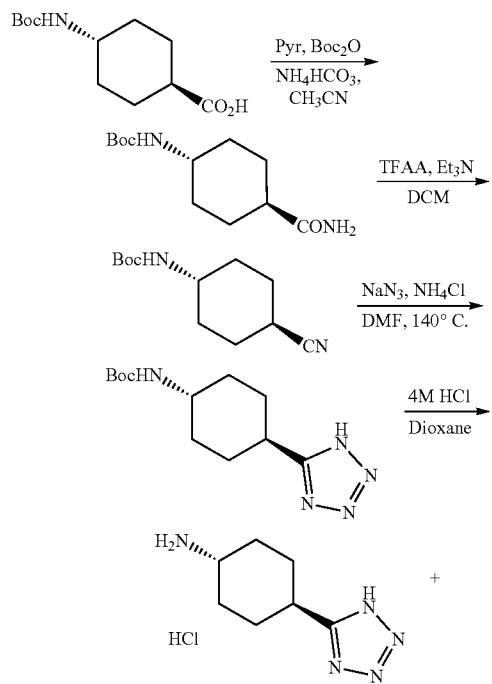
-continued
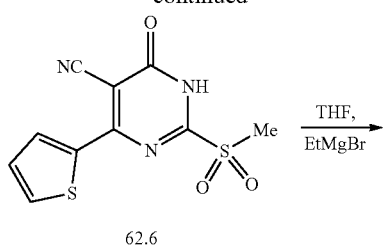
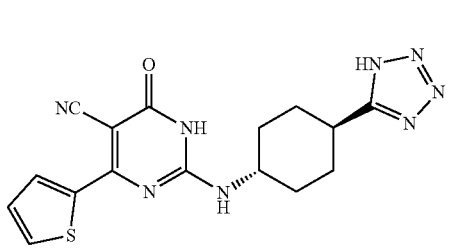
General Scheme I, 6-Oxo-2-[4-(1H-tetrazol-5-yl)-piperidin-1-yl]-4-thiophen-2-yl-1,6-dihydro-pyrimidine-5-carbonitrile
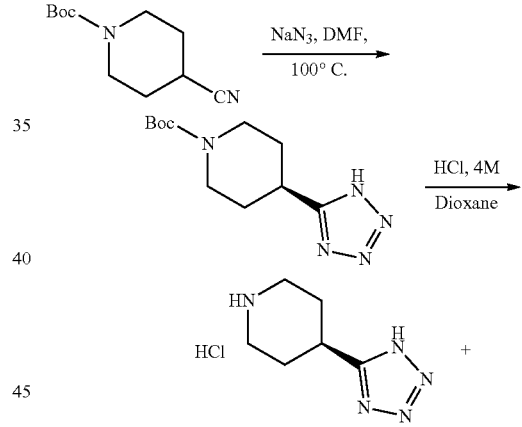
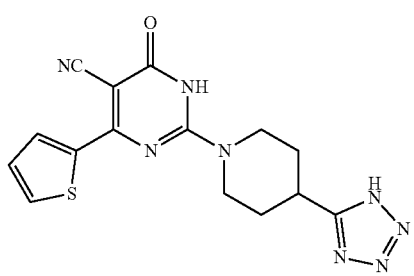

General Scheme J, 6-Oxo-2-[3-(1H-tetrazol-5-yl)-azetidin-1-yl]-4-thiophen-2-yl-1,6-dihydro-pyrimidine-5-carbonitrile

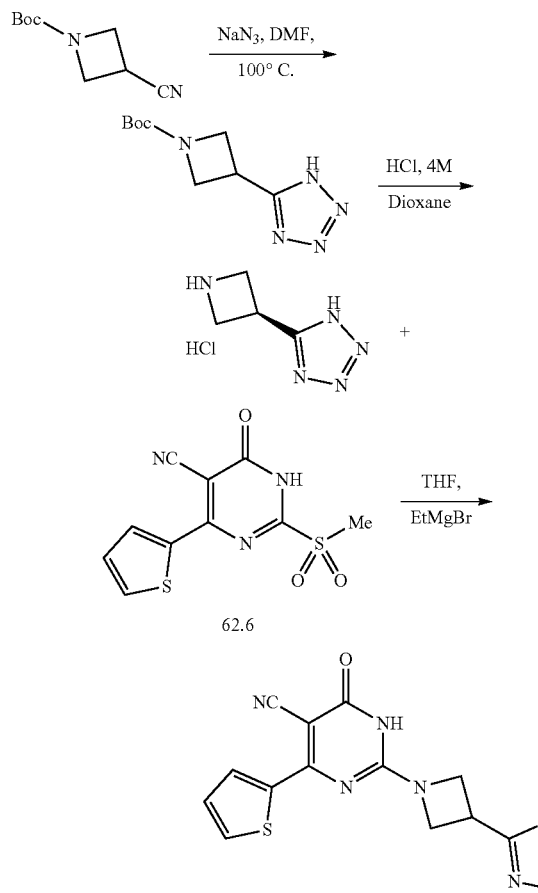

General Scheme K, 4-Benzyl-6-oxo-2-[2-(1H-tetrazol-5-yl)-benzylsulfanyl]-1,6-dihydro-pyrimidine-5-carbonitrile

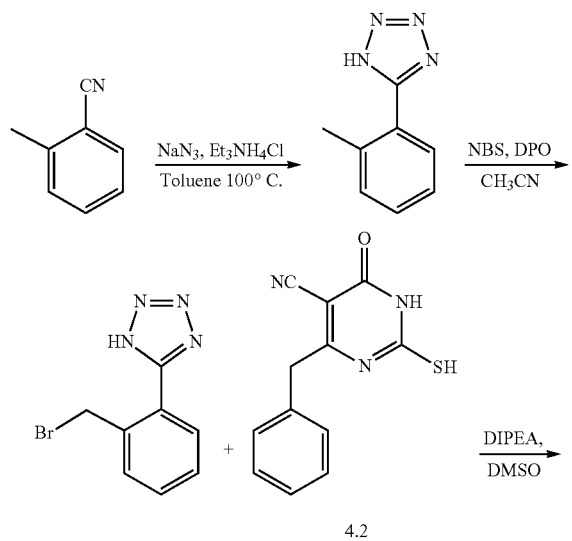

-continued

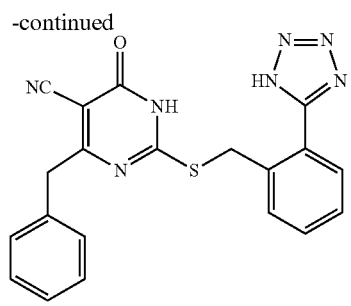

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R^1$, $R^2$, X, L, Y, $R^a$, $R^b$, $R^c$, $R^d$, $R^e$, $R^f$, $R^x$, $R^y$, $R^z$, m, n, p, q, r and other variables are as defined herein above, except where otherwise indicated. Furthermore, for synthetic purposes, the compounds of General Schemes A-E are merely representative with elected radicals to illustrate the general synthetic methodology of the compounds of Formula (I) as defined herein.

Pharmaceutical Compositions

The compound of Formula (I) or (II) may be provided in any form suitable for the intended administration, in particular including pharmaceutically acceptable salts, solvates and prodrugs of the compound of Formula (I) or (II).

Pharmaceutically acceptable salts refer to salts of the compounds of Formula (I) or (II) which are considered to be acceptable for clinical and/or veterinary use. Typical pharmaceutically acceptable salts include those salts prepared by reaction of the compounds of Formula (I) or (II) and a mineral or organic acid or an organic or inorganic base. Such salts are known as acid addition salts and base addition salts, respectively. It will be recognized that the particular counter-ion forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, PA, U.S.A., 1985 and more recent editions and in Encyclopedia of Pharmaceutical Technology.

Examples of pharmaceutically acceptable addition salts include acid addition salts formed with inorganic acids, e.g., hydrochloric, hydrobromic, sulfuric, nitric, hydroiodic, metaphosphoric, or phosphoric acid; and organic acids e.g., succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. It should be understood that all references to pharmaceutically acceptable salts include solvent addition forms (solvates) or crystal forms (polymorphs) as defined herein, of the same salt.

The compound of Formula (I) or (II), or a pharmaceutically acceptable salt thereof, may be provided in dissoluble or indissoluble forms together with a pharmaceutically acceptable solvent such as water, ethanol, and the like. Dissoluble forms may also include hydrated forms such as the mono-hydrate, the dihydrate, the hemihydrate, the trihydrate, the tetrahydrate, and the like.

The compound of Formula (I) or (II), or a pharmaceutically acceptable salt thereof, may be provided as a prodrug. The term "prodrug" used herein is intended to mean a compound which—upon exposure to certain physiological conditions—will liberate the compound of Formula (I) or (II), or a pharmaceutically acceptable salt thereof, which then will be able to exhibit the desired biological action. A typical example is a labile carbamate of an amine.

Since prodrugs are known to enhance numerous desirable qualities of pharmaceuticals (e.g., solubility, bioavailability, manufacturing, etc.), the compounds of the present disclosure can be delivered in prodrug form. Thus, the present disclosure is intended to cover prodrugs of the presently claimed compounds, methods of delivering the same and compositions containing the same. "Prodrugs" are intended to include any covalently bonded carriers that release an active parent drug of the present disclosure in vivo when such prodrug is administered to a subject. Prodrugs in the present disclosure are prepared by modifying functional groups present in the compound in such a way that the modifications are cleaved, either in routine manipulation or in vivo, to the parent compound. Prodrugs include compounds of the present disclosure wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., $C_{1-6}$ alkyl esters, e.g., methyl esters, ethyl esters, 2-propyl esters, phenyl esters, 2-aminoethyl esters, morpholinoethanol esters, etc.) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like. See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one aspect of this disclosure, there is provided a pharmaceutical composition comprising at, as an active ingredient, at least one compound of Formula (I) or (II), or a pharmaceutically acceptable salt thereof, as defined herein, and optionally one or more pharmaceutically acceptable excipients, diluents and/or carriers. The compounds of Formula (I) or (II), or a pharmaceutically acceptable salt thereof, may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

A "pharmaceutical composition" is a formulation containing the compounds of the present disclosure in a form suitable for administration to a subject. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The pharmaceutical compositions formed by combining a compound of Formula (I) or (II), or a pharmaceutically acceptable salt thereof, as defined herein, with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders, and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of Formula (I) or (II), or a pharmaceutically acceptable salt thereof, as defined herein, may suitably be combined with an oral, non-toxic, pharmaceutically acceptable carrier such as ethanol, glycerol, water, or the like. Furthermore, suitable binders, lubricants, disintegrating agents, flavouring agents, and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes, or the like. Lubricants include, e.g., sodium oleate, sodium stearate, magnesium stearate, sodium benzoate, sodium acetate, sodium chloride, or the like. Disintegrating agents include, e.g., starch, methyl cellulose, agar, bentonite, xanthan gum, sodium starch glycolate, crospovidone, croscarmellose sodium, or the like. Additional excipients for capsules include macrogels or lipids.

For the preparation of solid compositions such as tablets, the active compound of Formula (I) or (II), or a pharmaceutically acceptable salt thereof, is mixed with one or more excipients, such as the ones described above, and other pharmaceutical diluents such as water to make a solid pre-formulation composition containing a homogenous mixture of a compound of Formula (I) or (II), or a pharmaceutically acceptable salt thereof. The term "homogenous" is understood to mean that the compound of Formula (I) or (II), or a pharmaceutically acceptable salt thereof, is dispersed evenly throughout the composition so that the composition may readily be subdivided into equally effective unit dosage forms such as tablets or capsules.

Liquid compositions for either oral or parenteral administration of the compound of Formula (I) or (II), or a pharmaceutically acceptable salt thereof, include, e.g., aqueous solutions, syrups, elixirs, aqueous or oil suspensions and emulsion with edible oils such as cottonseed oil, sesame oil, coconut oil, or peanut oil. Suitable dispersing or suspending agents for aqueous suspensions include synthetic or natural gums such as tragacanth, alginate, acacia, dextran, sodium carboxymethylcellulose, gelatin, methylcellulose, or polyvinylpyrrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

The preparation of all these solutions under sterile conditions is readily accomplished by standard pharmaceutical techniques well known to those skilled in the art.

For example, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Depot injectable compositions are also contemplated as being within the scope of the present disclosure.

For parenteral administration, solutions containing a compound of Formula (I) or (II), or a pharmaceutically acceptable salt thereof, in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

In addition to the aforementioned ingredients, the compositions of a compound of Formula (I) or (II), or a pharmaceutically acceptable salt thereof, may include one or more additional ingredients such as diluents, buffers, flavouring agents, colourant, surface active agents, thickeners, preservatives, e.g., methyl hydroxybenzoate (including antioxidants), emulsifying agents and the like.

The term "therapeutically effective amount", as used herein, refers to an amount of a pharmaceutical agent to treat, ameliorate, or prevent an identified disease, disorder, or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or disorder to be treated is a disease or disorder associated with α-amino-β-carboxymuconate-ε-semialdehyde decarboxylase (ACMSD) dysfunction.

For any compound, the therapeutically effective amount can be estimated initially either in cell culture assays, e.g., in cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

A suitable dosage of the compound of Formula (I) or (II), or a pharmaceutically acceptable salt thereof, will depend on the age and condition of the patient, the severity of the disease to be treated and other factors well known to the practicing physician. The compound may be administered for example either orally, parenterally or topically according to different dosing schedules, e.g., daily or with intervals, such as weekly intervals. In general a single dose will be in the range from 0.01 to 500 mg/kg body weight, preferably from about 0.05 to 100 mg/kg body weight, more preferably between 0.1 to 50 mg/kg body weight, and most preferably between 0.1 to 25 mg/kg body weight. The compound may be administered as a bolus (i.e., the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

The compounds of Formula (I) or (II), or a pharmaceutically acceptable salt thereof, may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances, or preferably an active substance as described in the section "combination treatment" herein below.

Methods of Treatment

In another aspect, the present disclosure relates to a method of preventing, reducing the risk of, or ameliorating a disease or disorder in which α-amino-β-carboxymuconate-ε-semialdehyde decarboxylase (ACMSD) plays a role comprising administering to the subject in need thereof a therapeutically effective amount of one or more compounds of Formula (I) or (II), or a pharmaceutically acceptable salt thereof.

Another aspect of the present disclosure relates to a method of preventing, reducing the risk of, or ameliorating a disease or disorder in which α-amino-β-carboxymuconate-ε-semialdehyde decarboxylase (ACMSD) plays a role comprising administering to the subject in need thereof a therapeutically effective amount of a pharmaceutical composition comprising one or more compounds of Formula (I) or (II), or a pharmaceutically acceptable salt thereof, and at least one of a pharmaceutically acceptable carrier, diluent, or excipient.

Another aspect of the present disclosure relates to a method of treating, preventing, reducing the risk of, or ameliorating a disease or disorder by inhibition of α-amino-β-carboxymuconate-ε-semialdehyde decarboxylase (ACMSD) comprising administering to the subject suffering from or susceptible to developing the disease or disorder a therapeutically effective amount of one or more compounds of Formula (I) or (II), or a pharmaceutically acceptable salt thereof.

Another aspect of the present disclosure relates to a method of treating, preventing, reducing the risk of, or ameliorating a disease or disorder by inhibition of α-amino-β-carboxymuconate-ε-semialdehyde decarboxylase (ACMSD) comprising administering to the subject suffering from or susceptible to developing the disease or disorder associated with ACMSD a therapeutically effective amount of a pharmaceutical composition comprising one or more compounds of Formula (I) or (II), or a pharmaceutically acceptable salt thereof, and at least one of a pharmaceutically acceptable carrier, diluent, or excipient.

In another aspect, the present disclosure relates to a method of treating, preventing, reducing the risk of, or ameliorating a disease or disorder in which nicotinamide adenine dinucleotide ($NAD^+$) modulation plays a role comprising administering to the subject in need thereof a therapeutically effective amount of one or more compounds of Formula (I) or (II), or a pharmaceutically acceptable salt thereof.

In another aspect, the present disclosure relates to a method of treating, preventing, reducing the risk of, or ameliorating a disease or disorder in which nicotinamide adenine dinucleotide ($NAD^+$) modulation plays a role comprising administering to the subject in need thereof a therapeutically effective amount of a pharmaceutical composition comprising one or more compounds of Formula (I) or (II), or a pharmaceutically acceptable salt thereof, and at least one of a pharmaceutically acceptable carrier, diluent, or excipient.

In another aspect, the present disclosure relates to a method of treating, preventing, reducing the risk of, or ameliorating a disease or disorder associated with reduced nicotinamide adenine dinucleotide ($NAD^+$) levels comprising administering to the subject suffering from or susceptible to developing a disease or disorder associated with reduced $NAD^+$ levels a therapeutically effective amount of one or more compounds of Formula (I) or (II), or a pharmaceutically acceptable salt thereof.

In another aspect, the present disclosure relates to a method of treating, preventing, reducing the risk of, or ameliorating a disease or disorder associated with reduced nicotinamide adenine dinucleotide ($NAD^+$) levels comprising administering to the subject suffering from or susceptible to developing a disease or disorder associated with reduced $NAD^+$ levels a therapeutically effective amount of a pharmaceutical composition comprising one or more compounds of Formula (I) or (II), or a pharmaceutically acceptable salt thereof, and at least one of a pharmaceutically acceptable carrier, diluent, or excipient.

Another aspect of the present disclosure relates to a method of treating, preventing, reducing the risk of, or ameliorating a disorder associated with mitochondrial dysfunction comprising administering to the subject suffering from or susceptible to developing a metabolic disorder a therapeutically effective amount of one or more compounds of Formula (I) or (II), or a pharmaceutically acceptable salt thereof. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

Another aspect of the present disclosure relates to a method of treating, preventing, reducing the risk of, or ameliorating a disorder associated with mitochondrial dysfunction comprising administering to the subject suffering from or susceptible to developing a metabolic disorder a therapeutically effective amount of a pharmaceutical composition comprising one or more compounds of Formula (I) or (II), or a pharmaceutically acceptable salt thereof, and at least one of a pharmaceutically acceptable carrier, diluent, or excipient. In one embodiment, the disorder associated with mitochondrial dysfunction is an inherited mitochondrial disease, a common metabolic disorder, a neurodegenerative disease, an aging related disorder, a kidney disorder, or a chronic inflammatory disease. In a preferred embodiment, the disorder associated with mitochondrial dysfunction is a common metabolic disorder such as obesity or type II diabetes.

In another aspect, the present disclosure relates to a method of promoting oxidative metabolism comprising administering to the subject suffering from or susceptible to developing a metabolic disorder a therapeutically effective amount of one or more compounds of Formula (I) or (II), or a pharmaceutically acceptable salt thereof, that increases intracellular nicotinamide adenine dinucleotide ($NAD^+$).

In another aspect, the present disclosure relates to a method of promoting oxidative metabolism comprising administering to the subject suffering from or susceptible to developing a metabolic disorder a therapeutically effective amount of a pharmaceutical composition comprising one or more compounds of Formula (I) or (II), or a pharmaceutically acceptable salt thereof, and at least one of a pharmaceutically acceptable carrier, diluent, or excipient, that increases intracellular nicotinamide adenine dinucleotide ($NAD^+$).

In yet another aspect, the present disclosure relates to a method for the manufacture of a medicament for treating, preventing, reducing the risk of, or ameliorating a disease or condition that can be mediated by ACMSD inhibition, wherein the medicament comprises a compound of Formula (I) or (II), or a pharmaceutically acceptable salt thereof.

In another aspect, the present disclosure relates to a method for the manufacture of a medicament for treating, preventing, reducing the risk of, or ameliorating a disease or condition that can be mediated by ACMSD inhibition, wherein the medicament comprises a pharmaceutical composition comprising one or more compounds of Formula (I) or (II), or a pharmaceutically acceptable salt thereof, and at least one of a pharmaceutically acceptable carrier, diluent, or excipient.

In yet another aspect, the present disclosure relates to a compound for use in a method for treating, preventing, reducing the risk of, or ameliorating a disease or condition that can be mediated by ACMSD inhibition, wherein the compound comprises a compound of Formula (I) or (II), or a pharmaceutically acceptable salt thereof.

In another aspect, the present disclosure relates to a pharmaceutical composition for use in a method for treating, preventing, reducing the risk of, or ameliorating a disease or condition that can be mediated by ACMSD inhibition, wherein the composition comprises one or more compounds of compound of Formula (I) or (II), or a pharmaceutically acceptable salt thereof, and at least one of a pharmaceutically acceptable carrier, diluent, or excipient.

Another aspect of the present disclosure relates to the use of a compound of Formula (I) or (II), or a pharmaceutically acceptable salt thereof in the manufacture of a medicament for treating, preventing, reducing the risk of, or ameliorating a disease or disorder by inhibition of α-amino-β-carboxymuconate-ε-semialdehyde decarboxylase (ACMSD).

Another aspect of the present disclosure relates to the use of a pharmaceutical composition comprising one or more compounds of Formula (I) or (II), or a pharmaceutically acceptable salt thereof, and at least one of a pharmaceutically acceptable carrier, diluent, or excipient, in the manufacture of a medicament for treating, preventing, reducing the risk of, or ameliorating a disease or disorder by inhibition of α-amino-β-carboxymuconate-ε-semialdehyde decarboxylase (ACMSD).

In another aspect, the present disclosure relates to the use of a compound of a compound of Formula (I) or (II), or a pharmaceutically acceptable salt thereof in the manufacture of a medicament for treating, preventing, reducing the risk of, or ameliorating a disease or disorder associated with reduced nicotinamide adenine dinucleotide ($NAD^+$) levels.

In another aspect, the present disclosure relates to the use of a pharmaceutical composition comprising one or more compounds of Formula (I) or (II), or a pharmaceutically acceptable salt thereof, and at least one of a pharmaceutically acceptable carrier, diluent, or excipient, in the manufacture of a medicament for treating, preventing, reducing the risk of, or ameliorating a disease or disorder associated with reduced nicotinamide adenine dinucleotide ($NAD^+$) levels.

Another aspect of the present disclosure relates to the use of a compound of Formula (I) or (II), or a pharmaceutically acceptable salt thereof in the manufacture of a medicament for treating, preventing, reducing the risk of, or ameliorating a disorder associated with mitochondrial dysfunction.

Another aspect of the present disclosure relates to the use of a pharmaceutical composition comprising one or more compounds of Formula (I) or (II), or a pharmaceutically acceptable salt thereof, and at least one of a pharmaceutically acceptable carrier, diluent, or excipient, in the manufacture of a medicament for treating, preventing, reducing the risk of, or ameliorating a disorder associated with mitochondrial dysfunction.

In another aspect, the present disclosure relates to the use of a compound of a compound of Formula (I) or (II), or a pharmaceutically acceptable salt thereof, in the manufacture of a medicament for promoting oxidative metabolism.

In another aspect, the present disclosure relates to the use of a pharmaceutical composition comprising one or more compounds of Formula (I) or (II), or a pharmaceutically acceptable salt thereof, and at least one of a pharmaceutically acceptable carrier, diluent, or excipient, in the manufacture of a medicament for promoting oxidative metabolism.

Another aspect of the present disclosure relates to a compound of Formula (I) or (II), or a pharmaceutically acceptable salt thereof, for use in the manufacture of a medicament for treating, preventing, reducing the risk of, or ameliorating a disease or disorder by inhibition of α-amino-β-carboxymuconate-ε-semialdehyde decarboxylase (ACMSD).

Another aspect of the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use in the manufacture of a medicament for treating, preventing, reducing the risk of, or ameliorating a disease or disorder by inhibition of α-amino-β-carboxymuconate-ε-semialdehyde decarboxylase (ACMSD).

In another aspect, the present disclosure relates to a compound of Formula (I) or (II), or a pharmaceutically acceptable salt thereof for use as a medicament for treating, preventing, reducing the risk of, or ameliorating a disease or disorder associated with reduced nicotinamide adenine dinucleotide (NAD$^+$) levels.

In another aspect, the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use as a medicament for treating, preventing, reducing the risk of, or ameliorating a disease or disorder associated with reduced nicotinamide adenine dinucleotide (NAD$^+$) levels.

Another aspect of the present disclosure relates to a compound of Formula (I) or (II), or a pharmaceutically acceptable salt thereof for use as a medicament for treating, preventing, reducing the risk of, or ameliorating a disorder associated with mitochondrial dysfunction.

Another aspect of the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use as a medicament for treating, preventing, reducing the risk of, or ameliorating a disorder associated with mitochondrial dysfunction.

In another aspect, the present disclosure relates to a compound of Formula (I) or (II), or a pharmaceutically acceptable salt thereof for use as a medicament for promoting oxidative metabolism.

In another aspect, the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use as a medicament for promoting oxidative metabolism.

Another aspect of the present disclosure relates to a compound of Formula (I) or (II), or a pharmaceutically acceptable salt thereof for use in treating, preventing, reducing the risk of, or ameliorating a disease or disorder associated with reduced nicotinamide adenine dinucleotide (NAD$^+$) levels.

Another aspect of the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use in treating, preventing, reducing the risk of, or ameliorating a disease or disorder associated with reduced nicotinamide adenine dinucleotide (NAD$^+$) levels.

In another aspect, the present disclosure relates to a compound of Formula (I) or (II), or a pharmaceutically acceptable salt thereof for use in for treating, preventing, reducing the risk of, or ameliorating a disorder associated with mitochondrial dysfunction.

In another aspect, the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use in for treating, preventing, reducing the risk of, or ameliorating a disorder associated with mitochondrial dysfunction.

Another aspect of the present disclosure relates to a compound of Formula (I) or (II), or a pharmaceutically acceptable salt thereof for use in promoting oxidative metabolism.

Another aspect of the present disclosure relates to a pharmaceutical composition comprising one or more compounds of Formula (I) or (II), or a pharmaceutically acceptable salt thereof, and at least one of a pharmaceutically acceptable carrier, diluent, or excipient, for use in promoting oxidative metabolism.

In some embodiments, the disease or disorder associate with reduced nicotinamide adenine dinucleotide (NAD$^+$) levels is a chronic liver disease including, but is not limited to, primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency. In one embodiment, the common metabolic disorder is obesity or type II diabetes.

In some embodiments, the disorder associated with mitochondrial dysfunction is an inherited mitochondrial disease, a common metabolic disorder, a neurodegenerative disease, an aging related disorder, a kidney disorder, or a chronic inflammatory disease.

In another aspect, the present disclosure relates to a method of treating, preventing, reducing the risk of, or ameliorating a disease or disorder by inhibition of α-amino-β-carboxymuconate-ε-semialdehyde decarboxylase (ACMSD), comprising administering to a subject in need thereof, a therapeutically effective amount of a compound of Formula (I) or (II) or a pharmaceutical composition comprising a compound of Formula (I) or (II).

As used herein, "treating" or "treat" describes the management and care of a patient for the purpose of reversing, inhibiting, or combating a disease, condition, or disorder and includes the administration of a compound of the present disclosure (i.e., a compound of Formula (I) or (II)), or a pharmaceutically acceptable salt, prodrug, metabolite, polymorph or solvate thereof, to reverse the disease, condition, or disorder, eliminate the disease, condition, or disorder, or inhibit the process of the disease, condition, or disorder.

A compound of the present disclosure (i.e., a compound of Formula (I) or (II)), or a pharmaceutically acceptable salt, prodrug, metabolite, polymorph or solvate thereof, can also be used to prevent a disease, condition, or disorder or one or more symptoms of such disease, condition, or disorder. As used herein, "preventing" or "prevent" describes reducing or eliminating the onset of the symptoms or complications of the disease, condition, or disorder.

A compound of the present disclosure (i.e., a compound of Formula (I) or (II)), or a pharmaceutically acceptable salt, prodrug, metabolite, polymorph or solvate thereof, can also be used to alleviate one or more symptoms of such disease, condition, or disorder. As used herein, the term "alleviate" is meant to describe a process by which the severity of a sign or symptom of a disorder is decreased. Importantly, a sign or symptom can be alleviated without being eliminated. Preferably treatment is curative or ameliorating.

Clinical Conditions and Other Uses of Compounds

The compounds according to Formula (I) or (II), or a pharmaceutically acceptable form thereof, compositions, medicaments, and compounds for use, as defined herein, are useful for treatment of a disease or disorder in which α-amino-β-carboxymuconate-ε-semialdehyde decarboxylase (ACMSD) modulation plays a role. The compounds may be used either in human or in veterinary medicine and the patient may be any mammal, but especially a human. The treatment may include administering to any mammal, but especially a human, suffering from a disease or disorder in which α-amino-β-carboxymuconate-ε-semialdehyde decarboxylase (ACMSD) modulation plays a role, a therapeutically effective amount of a compound according to Formula (I) or (II), or a pharmaceutically acceptable salt thereof, as defined herein.

The present disclosure also relates to a compound of Formula (I) or (II), or a pharmaceutically acceptable salt thereof, as defined herein, for use in a disease or disorder associated with α-amino-β-carboxymuconate-ε-semialdehyde decarboxylase (ACMSD) dysfunction, such as obesity, type II diabetes and its complications (e.g., diabetic retinopathy and nephropathy), non-alcoholic fatty liver disease (NAFLD), non-alcoholic steatohepatitis (NASH), or chronic kidney disease.

By the term "disease or disorder associated with α-amino-β-carboxymuconate-ε-semialdehyde decarboxylase (ACMSD) dysfunction" is meant any disease characterized by reduced nicotinamide adenine dinucleotide ($NAD^+$) expression and/or activity in at least in some instances of the disease, or a disease which is ameliorated by elevation of the levels of $NAD^+$.

The methods, medicaments and compounds for use of the present disclosure are useful to treat, alleviate the symptoms of, or delay the onset of a disorder associated with aberrant mitochondrial function. Disorders associated with aberrant mitochondrial function include, for example, metabolic disorders, neurodegenerative disorders, aging related disorders, and chronic inflammatory disorders. Mitochondrial disorders also include diseases with inherited and/or acquired mitochondrial dysfunction (i.e., Charcot-Marie-Tooth disease, Type 2A2, Mitochondrial Encephalopathy Lactic Acidosis and Stroke (MELAS), Leigh syndrome, Barth syndrome, and Leber's optic neuropathy), fatty acid oxidation disorders, inherited forms of deafness and blindness, and metabolic abnormalities induced by exposure to toxic chemicals and/or drugs (e.g., cisplatin induced deafness).

Metabolic disorders include, for example, type II diabetes, obesity, hyperglycemia, glucose intolerance, insulin resistance (i.e., hyperinsulinemia, metabolic syndrome, syndrome X), hypercholesterolemia, hypertension, hyperlipoproteinemia, hyperlipidemia (e.g., dyslipidemia), hypertriglylceridemia, cardiovascular disease, atherosclerosis, peripheral vascular disease, kidney disease, ketoacidosis, thrombotic disorders, nephropathy, diabetic neuropathy, diabetic retinopathy, sexual dysfunction, dermatopathy, dyspepsia, hypoglycemia, cancer, and edema.

Neurodegenerative disorders include diseases such as photoreceptor degeneration (i.e., retinitis pigmentosa), Dementia, Alzheimer's disease, Parkinson's disease, and Huntington's disease.

Chronic inflammatory diseases include diseases such as celiac disease, vasculitis, lupus, chronic obstructive pulmonary disease (COPD), irritable bowel disease, atherosclerosis, arthritis, and psoriasis.

Aging related disorders include diseases such as cancer, dementia, cardiovascular disease (i.e., arteriosclerosis), hypertension, diabetes mellitus (type I or type II), arthritis, cataracts, Alzheimer's disease, macular degeneration, and osteoporosis.

The subject can be suffering from or susceptible to developing a metabolic disorder. Subjects suffering from or at risk of developing a metabolic disorder are identified by methods known in the art. For example, diabetes can be diagnosed by measuring fasting blood glucose levels or insulin or by glucose tolerance test. Normal adult glucose levels are between about 60-126 mg/dl. Normal insulin levels are about 7 mU/mL±3 mU. Hypertension can be diagnosed by a blood pressure reading consistently at or above about 140/90. Cardiovascular disease can be diagnosed by measuring cholesterol levels. For example, LDL cholesterol above about 137 or total cholesterol above about 200 is indicative of cardiovascular disease. Hyperglycemia can be diagnosed by a blood glucose level higher than about 10 mmol/l (180 mg/dl). Glucose intolerance can be diagnosed by glucose levels of 140 to 199 mg per dL (7.8 to 11.0 mmol) after conducting a 75 g oral two-hour glucose tolerance test. Insulin resistance can be diagnosed by a fasting serum insulin level of greater than approximately 60 pmol/L. Hypoglycemia can be diagnosed by a blood glucose level lower than about 2.8 to 3.0 mmol/L (50 to 54 mg/dl). Obesity can be diagnosed, for example, by body mass index. Body mass index (BMI) is measured in $kg/m^2$ (or $lb/in^2 \times 704.5$). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e., fat mass impedes current), estimates % fat) can be measured. The parameters for normal, overweight, or obese individuals are as follows: Underweight: BMI<18.5; Normal: BMI about 18.5 to about 24.9; Overweight: BMI=about 25 to about 29.9. Overweight individuals are characterized as having a waist circumference of >94 cm for men or >80 cm for women and waist to hip ratios of ≥0.95 in men and ≥0.80 in women. Obese individuals are characterized as having a BMI of 30 to 34.9, being greater than 20% above "normal" weight for height, having a body fat percentage>30% for women and 25% for men, and having a waist circumference>102 cm (40 inches) for men or 88 cm (35 inches) for women. Individuals with severe or morbid obesity are characterized as having a BMI of ≥35.

The methods described herein may lead to a reduction in the severity or the alleviation of one or more symptoms of a metabolic disorder. For example, symptoms of diabetes include elevated fasting blood glucose levels, blood pressure at or above 140/90 mm/Hg; abnormal blood fat levels, such as high-density lipoproteins (HDL) less than or equal to 35 mg/dL, or triglycerides greater than or equal to 250 mg/dL (mg/dL=milligrams of glucose per deciliter of blood). Efficacy of treatment is determined in association with any known method for diagnosing the metabolic disorder. Alleviation of one or more symptoms of the metabolic disorder indicates that the compound confers a clinical benefit.

The methods of the present disclosure are useful to treat, alleviate the symptoms of, or delay the onset of a kidney disorder. Kidney disorders include acute kidney injury (AKI) and chronic kidney disease (CKD).

The subject can be suffering from or susceptible to developing acute kidney injury (AKI). The acute kidney injury can be characterized by one or more clinical criteria or conditions (i.e., an abrupt decrease in the ability of the kidneys to excrete nitrogenous waste products from the blood, resulting in azotemia). Subjects suffering from or at risk of developing acute kidney injury (AKI) are identified by methods known in the art. For example, the acute kidney injury can be characterized by an increase in serum creatinine by at least 50% over baseline, an absolute increase in serum creatinine of at least 0.3 mg/dL over baseline, a reduction in glomerular filtration rate of at least 25% compared to baseline, a decrease in urine output to 0.5 ml per kilogram of body weight or less per hour persisting for at least 6 hours, or any combination thereof. An acute kidney injury may be caused by ischemia, drugs or toxic agents (i.e., radiocontrast media, a non-steroidal anti-inflammatory drug (NSAID), alcohol, or a chemotherapy agent), viruses, and obstruction.

The subject can be suffering from or susceptible to developing chronic kidney disease (CKD). Chronic kidney disease (CKD) is defined as either (1) having kidney damage as defined by structural or functional abnormalities of the kidney for 3 months or longer with or without a decreased glomerular filtration rate (GFR) or (2) having a GFR of less than 60 mL/min/1.73 m$^2$ for 3 months or longer with or without kidney damage. Subjects suffering from or at risk of developing a chronic kidney disease (CKD) are identified by methods known in the art. Structural or functional abnormalities are manifested by symptoms such as either pathologic abnormalities or markers of kidney damage, including abnormalities identified in imaging studies or the composition of blood or urine.

For example, CKD can be diagnosed by testing for specific marker. For example, markers of kidney damage include a plasma creatinine concentration of above about 1.6 mg/dL and a blood urea nitrogen (BUN) concentration of above about 20 mg/dL. Typically, both of these markers are elevated in individuals with CKD. Additional markers of kidney damage can include hematuria (i.e., any detectable amount of blood in the urine), proteinuria (i.e., protein concentrations in urine above about 100 mg/dL), albuminuria (i.e., albumin concentrations in urine above about 100 mg/dL), an intact parathyroid hormone (PTH) concentration in the blood above about 150 pg/mL, or blood phosphate levels of above about 4.5 mg/dL. One specific marker of kidney disease is a GFR rate above normal (i.e., a GFR above about 90 mL/min/1.73 m$^2$), however a below normal GFR also indicates CKD.

The methods of the present disclosure are useful to treat, alleviate the symptoms of, or delay the onset of non-alcoholic fatty liver disease (NAFLD) and/or non-alcoholic steatohepatitis (NASH). The subject can be suffering from or susceptible to developing non-alcoholic fatty liver disease (NAFLD) and/or non-alcoholic steatohepatitis (NASH). Subjects suffering from or at risk of developing a non-alcoholic fatty liver disease (NAFLD) and/or non-alcoholic steatohepatitis (NASH) are identified by methods known in the art. For example, NAFLD and/or NASH can be diagnosed by liver biopsy.

Non-alcoholic fatty liver disease (NAFLD), as defined herein, is a disease with fat deposition in the liver, which occurs in patients whose alcohol ingestion history is not long enough to cause liver injury. Non-alcoholic fatty liver disease (NAFLD) can be further classified into simple fatty liver, steatohepatitis and cirrhosis. Nonalcoholic steatohepatitis (NASH) refers to a pathology associated with inflammation, liver cell necrosis, ballooning and fibrosis. The onset of nonalcoholic simple fatty liver is induced by fat deposition in liver cells, and this fat accumulation is defined by the balance between increasing factors (influx and synthesis of fats in liver cells) and decreasing factors (catabolism of fats and their release from liver cells). Once damage of liver cells occurs, in addition to this fat deposition, nonalcoholic simple fatty liver will progress to nonalcoholic steatohepatitis. Nonalcoholic steatohepatitis is progressive and may finally progress to cirrhosis and hepatocellular carcinoma.

Combination Treatment

In another aspect, the disclosure includes a compound of Formula (I) or (II), or a pharmaceutically acceptable salt thereof, for use in a combination therapy. A compound, compositions, medicaments and compounds for use of Formula (I) or (II), or a pharmaceutically acceptable salt thereof, may also be used to advantage in combination with one or more other therapeutic agents. Such therapeutic agents include, but are not limited to other ACMSD inhibitors; anti-diabetic agents such as PPARγ agonists, PPARα/γ dual agonists, PPARS agonists, biguanides, protein tyrosine phosphatase-1B (PTP-1B), dipeptidyl peptidase IV (DPP-IV) inhibitors, sulfonylureas, meglitinides, alpha glucoside hydrolase inhibitors, alpha-amylase inhibitors, insulin secreatagogues, A2 antagonists, insulin or insulin mimetics, glycogen phosphorylase inhibitors, GLP-1 agonists, non-thiazolidinediones, glycokinase, and 11 β HSD-1 inhibitor; anti-obesity agents such as uncoupling Protein (UCP-1, UCP-2, and UCP-3) activators, P3 adrenergic receptor (P3), thyroid hormone β agonists, fatty acid synthase (PAS) inhibitors, phosphodieterase (PDE) inhibitors, lipase inhibitors, serotonin reuptake inhibitors, monoamine reuptake inhibitors, Mc4r agonists, 5HT2c agonists, growth hormone secretagogue (GHS) agonists, CNTF derivatives, ciliary neurotrophic factors (CNTh), cholecystokinin-A (CCK-A) agonists, opioid antagonists, orexin antagonists, acyl-estrogens, leptin, NPY 5 antagonists, neuropeptide Y5 (NPY5) antagonists, neuropeptide Y2 (NPY2) agonists, melanin-concentrating hormone receptor (MCHLR) antagonists and melanin-concentrating hormone 2 receptor (MCH2R), MCH1R antagonists, neuropeptide Y1, ghrelin antagonists, cannabinoid receptor 1 (CB-1), serotonin (5HT) transport inhibitors, CCK-A agonists and histamine 3 (H3) antagonist/inverse agonists; cholesterol lower agents such as 3-hydroxy-3-methylglutaryl-coenzyme A (HMG CoA) reductase inhibitors, HMG-CoA synthase inhibitors, squalene epoxidase inhibitors, fibric acids, bile acid-binding resins probucol and niacin (nicotinic acid); compounds that boost NAD$^+$ levels such as NAD$^+$ precursors (i.e., nicotinamide ribose (NA), nicotinamide mononucleotide (NMN), nicotinic acid (NA) and nicotinamide); and compounds that inhibit NAD+ consumption such as PARP inhibitors and CD38 inhibitors.

PPARγ agonists useful in the present disclosure include, but are not limited to, glitazones (e.g., balaglitazone, ciglitazone, darglitazone, englitazone, isaglitazone (MCC-555), pioglitazone, rosiglitazone, troglitazone, CLX-0921, 5-BTZD, and the like); GW-0207, LG-100641, LY-300512, LY-519818, R483 (Roche), T131 (Tularik), and compounds disclosed in WO97/27857, 97/28115, 97/28137 and 97/27847; and pharmaceutically acceptable salts or esters thereof. PPARα/γ dual agonists useful in the present disclosure, include, but are not limited to, CLX-0940, GW-1536, GW1929, GW-2433, KRP-297, L-796449, LR-90, MK-0767, SB 219994, and muraglitazar, and pharmaceutically acceptable salts or esters thereof. KRP-297 is 5-[(2,4-Dioxo-5-thiazolidinyl)methyl]-2-methoxy-N-[[4-(trifluoromethyl)phenyl]methyl]benzamide, and pharmaceutically acceptable salts or esters thereof. PPARδ agonists useful in the present disclosure include, but are not limited to, GW 501516, GW 590735, and compounds disclosed in JP 10237049, WO 02/14291, and WO 2018/125983; and pharmaceutically acceptable salts or esters thereof.

Biguanides useful in the present disclosure include, but are not limited to, buformin, metformin, and phenformin, and pharmaceutically acceptable salts or esters thereof. Metformin (Glucophage®) is indicated for patients with non-insulin dependent diabetes mellitus, particularly those with refractory obesity. Physician's Desk Reference® page 1080-1086, (56th ed. 2002).

Protein tyrosine phosphatase-1B (PTP-1B) inhibitors useful in the present disclosure include, but are not limited to, A-401,674, KR 61639, OC-060062, OC-83839, OC-297962, MC52445, MC52453, and the compounds disclosed in WO 02/26707, WO 02/26743, JP 2002114768, and pharmaceutically acceptable salts or esters thereof.

Dipeptidyl peptidase IV (DPP-IV) inhibitors, such as isoleucine thiazolidide; NVP-DPP728; P32/98; and LAP 237, P 3298, TSL 225, valine pyrrolidide, TMC-2A/2B/2C, CD-26 inhibitors, FE 999011, P9310/K364, VIP 0177, DPP4, SDZ 274A444; and the compounds disclosed in WO 03/00449; WO 03/004496; EP 1 258 476; WO 02/083128; WO 021062764; WO 03/000250; WO 03/002530; WO 03/002531; WO 03/002553; WO 03/002593; WO 03/000180; and WO 03/000181.

Sulfonylureas useful in the present disclosure include, but are not limited to, acetohexamide, chloropropamide, diabinese, glibenclamide, glipizide, glyburide, glimepiride, gliclazide, glipentide, gliquidone, glisolamide, tolazamide, and tolbutamide, pharmaceutically acceptable salts or esters thereof. Meglitinides useful in the present disclosure include, but are not limited to, repaglinide and nateglinide, and pharmaceutically acceptable salts or esters thereof.

Alpha glucoside hydrolase inhibitors (or glucoside inhibitors) useful in the present disclosure include, but are not limited to, acarbose, adiposine, camiglibose, emiglitate, miglitol, voglibose, pradimicin-Q, salbostatin, CKD-711, MDL-25,637, MDL-73,945, and MOR 14, and pharmaceutically acceptable salts or esters thereof, and the compounds disclosed in U.S. Pat. Nos. 4,062,950, 4,174,439, 4,254,256, 4,701,559, 4,639,436, 5,192,772, 4,634,765, 5,157,116, 5,504,078, 5,091,418, 5,217,877, and 5,091,524. Alpha-amylase inhibitors useful in the present disclosure include, but are not limited to, tendamistat, trestatin, and A1-3688, and pharmaceutically acceptable salts and esters thereof, and the compounds disclosed in U.S. Pat. Nos. 4,451,455, 4,623,714, and 4,273,765.

Insulin secreatagogues useful in the present disclosure include, but are not limited to, linogliride and A-4166, and pharmaceutically acceptable salts and esters thereof.

Fatty acid oxidation inhibitors useful in the present disclosure include, but are not limited to, clomoxir, and etomoxir, and pharmaceutically acceptable salts and esters thereof. A2 antagonists useful in the present disclosure include, but are not 'limited to, midaglizole, isaglidole, deriglidole, idazoxan, earoxan, fluparoxan, and pharmaceutically acceptable salts and esters thereof. Insulin or insulin mimetics useful in the present disclosure include, but are not limited to, biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH2), and pharmaceutically acceptable salts or esters thereof.

Glycogen phosphorylase inhibitors useful in the present disclosure include, but are not limited to, CP-368, 296, CP-316,819, BAYR3401, and compounds disclosed in WO 01/94300, and WO 02/20530, and pharmaceutically acceptable salts or esters thereof. GLP-1 agonists useful in the present disclosure include, but are not limited to, exendin-3 and exendin-4, and compounds disclosed in US 2003087821 and NZ 504256, and pharmaceutically acceptable salts or esters thereof.

Non-thiazolidinediones useful in the present disclosure include, but are not limited to, JT-501, and farglitazar (GW-2570/GI-262579), and pharmaceutically acceptable salts or esters thereof. Glycokinase activators useful in this disclosure, include, but are not limited to, fused heteroaromatic compounds such as those disclosed in US 2002103199, and isoindolin-1-one-substituted propionamide compounds such as those disclosed in WO 02/48106.

Serotonin (5HT) transport inhibitors useful in this disclosure include, but are not limited to, paroxetine, fluoxetine, fenfluramine, fluvoxamine, sertraline, and imipramine. Norepinephrine (NE) transport inhibitors useful in this disclosure include, but are not limited to, GW 320659, despiramine, talsupram, and nomifensine. Cannabinoid receptor 1 (CB-1) antagonist/inverse agonists useful in the present disclosure include: U.S. Pat. Nos. 5,532,237, 4,973,587, 5,013,837, 5,081,122, 5,112,820, 5,292,736, 5,624,941 and 6,028,084, and PCT Application Nos. WO 96/33159, WO 98/33765, WO98/43636, WO98/43635, WO 01/09120, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 01/64634, and WO 03/007887, and EPO Application No. EP-658546. Specific CB-1 antagonists/inverse agonists useful in the present disclosure include, but are not limited to, rimonabant (Sanofi Synthelabo), SR-147778 (Sanofi Synthelabo), BAY 65-2520 (Bayer), and SLY 319 (Solvay). CCK-A agonists useful in the present disclosure include GI 181771, and SR 146,131. Ghrelin antagonists useful in the present disclosure, include: PCT Application Nos. WO 01/87335, and WO 02/08250. Histamine 3 (H3) antagonist/inverse agonists useful in the present disclosure include: PCT Application No. WO 02/15905, and O-[3-(1H-imidazol4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001)), benzophenone derivatives and related compounds (Sasse, A. et al. Arch. Pharm. (Weinheim) 334:45-52 (2001)), substituted N-phenyl carbamates (Reidemeister, S. et al., Pharmazie, 55:83-6 (2000)), and proxifan derivatives (Sasse, A. et al., J. Med. Chem. 43:3335-43 (2000)). Specific H3 antagonists/inverse agonists useful in the present disclosure include, but are not limited to, thioperamide, 3-(1H-imidazol-4-yl)propyl N-4-pentenyl)carbamate, clobenpropit, iodophenpropit, imoproxifan, GT2394 (Gliatech), and A331440.

Melanin-concentrating hormone receptor (MCHLR) antagonists and melanin-concentrating hormone 2 receptor (MCH2R) agonist/antagonists useful in the present disclosure include PCT Patent Application Nos. WO 01/82925, WO 01/87834, WO 02/06245, WO 02/04433, and WO 02/51809, and Japanese Patent Application No. JP 13226269. Specific MCH1R antagonists useful in the present disclosure include, but are not limited to, T-226296 (Takeda), SB 568849, and SNAP 7941. Neuropeptide Y1 (NPY1) antagonists useful in the present disclosure, include: U.S. Pat. No. 6,001,836, and PCT Application Nos. WO 96/14307, WO 01/23387, WO 99/51600, WO 01/85690, WO 01/85098, WO 01/85173, and WO 01/89528. Specific examples of NPY1 antagonists useful in the present disclosure include, but are not limited to, BIBP3226, J-115814, BIBO 3304, LY-357897, CP-671906, and GI-264879A. Neuropeptide Y2 (NPY2) agonists useful in the present disclosure, include, but are not limited to, peptide YY (PYY), and PYY3_36, peptide YY analogs, PYY agonists, and the compounds disclosed in WO 03/026591, WO 03/057235, and WO 03/027637. Neuropeptide Y5 (NPY5) antagonists useful in the present disclosure, include, but are not limited to, the compounds described in: U.S. Pat. Nos. 6,140,354, 6,191,160, 6,258,837, 6,313,298, 6,337,332, 6,329,395, and 6,340,683, 6,326,375, 6,329,395, 6,337,332, 6,335,345, European Patent Nos. EP-01010691, and EP 01044970, and PCT-International Patent Publication Nos. WO 97/19682, WO 97/20820, WO 97/20821, WO 97/20822, WO 97/20823, WO 98/27063, WO 00/107409, WO00/185714, WO 00/185730, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, and WO 01/14376. Specific NPY5 antagonists useful in the combinations of the present disclosure, include, but are not limited to GW-569180A, GW-594884A, GW-587081X, GW-548118X, FR 235,208, FR226928, FR 240662, FR252384, 1229U91, GI-264879A, CGP71683A, LY-377897, LY366377, PD-160170, SR-120562A, SR-120819A, JCF-104, and H409/22. Additional specific NPY5 antagonists useful in the combinations of the present disclosure, include, but are not limited to the compounds described in Norman et al., J. Med. Chem. 43:42884312 (2000). Leptin includes, but is not limited to, recombinant human leptin (PEG-OB, Hoffman La Roche) and recombinant methionyl human leptin (Amgen). Leptin derivatives (e.g., truncated forms of leptin) useful in the present disclosure include: U.S. Pat. Nos. 5,552,524, 5,552,523, 5,552, 522, 5,521,283, and PCT International Publication Nos. WO 96/23513, WO 96/23514, WO 96/23515, WO 96/23516, WO 96/23517, WO 96/23518, WO 96/23519, and WO 96/23520.

Opioid antagonists useful in the present disclosure include: PCT Application No. WO 00/21509. Specific opioid antagonists useful in the present disclosure include, but are not limited to, nalmefene (Revex®), 3-methoxynaltrexone, naloxone, and naltrexone. Orexin antagonists useful in the present disclosure include: PCT Patent Application Nos. WO 01/96302, WO 01/68609, WO 02/51232, WO 02/51838, and WO 03/023561. Specific orexin antagonists useful in the present disclosure include, but are not limited to, SB-334867-A. Acyl-estrogens useful in the present disclosure include oleoyl-estrone (del Mar-Grasa, M. et al., Obesity Research, 9:202-9 (2001)). Cholecystokinin-A (CCK-A) agonists useful in the present disclosure include U.S. Pat. No. 5,739,106. Specific CCK-A agonists include, but are not limited to, AR-R 15849, GI181771, JMv-180, A-71378, A-71623 and SR146131. Specific ciliary neurotrophic factors (CNTh) useful in the present disclosure include, but are not limited to, GI-181771 (GlaxoSmithKline), SR146131 (Sanofi Synthelabo), butabindide, PD170,292, PD 149164 (Pfizer). CNTF derivatives useful in the present disclosure include, but are not limited to, axokine (Regeneron), and PCT Application Nos. WO 94/09134, WO 98/22128, and WO 99/43813. Growth hormone secretagogue (GHS) agonists useful in the present disclosure include: U.S. Pat. No. 6,358,951, and U.S. Patent Application Nos. 2002/049196 and 2002/022637, and PCT Application Nos. WO 01/56592, and WO 02/32888. Specific GHS agonists include, but are not limited to, NN703, hexarelin, MK-0677, SM-130686, CP424 391, L-692,429 and L-163, 255.

5HT2c agonists useful in the present disclosure include: U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457. Specific 5HT2c agonists useful in this disclosure include, but are not limited to, BVT933, DPCA37215, 1K264, PNU 22394, WAY161503, R-1065, and YM 348.

Mc4r agonists useful in the present disclosure include: PCT Application Nos. WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02111715, WO 02/12178, WO 02/15909, WO 02/068387, WO 02/068388, WO 02/067869, WO 03/007949, and WO 03/009847. Specific Mc4r agonists useful in the present disclosure include CIR86036 (Chiron), ME-10142, and ME-10145 (Melacure).

Monoamine reuptake inhibitors useful in the present disclosure include: PCT Application Nos. WO 01/27068, and WO 01/62341. Specific monoamine reuptake inhibitors useful in the present disclosure include, but are not limited to, sibutramine (Meridia O/Reductil®) disclosed in U.S. Pat. Nos. 4,746,680, 4,806,570, and 5,436,272, and U.S. Patent Publication No. 2002/0006964.

Serotonin reuptake inhibitors, and releasers, useful in the present disclosure include: dexfenfluramine, fluoxetine, and other serotonin reuptake inhibitors, including, but not limited to, those in U.S. Pat. No. 6,365,633, and PCT Patent Application Nos. WO 01/27060, and WO 01/162341.

11 β HSD-1 inhibitor useful in the present disclosure include, but are not limited to, BVT 3498, BVT 2733, and those compounds disclosed in WO 01/90091, WO 01/90090, WO 01/90092. Uncoupling Protein (UCP-1, UCP-2, and UCP-3) activators useful in the present disclosure include: PCT Patent Application No. WO 99/00123. Specific uncoupling protein (UCP-1, UCP-2, and UCP-3) activators useful in the present disclosure include, but are not limited to, phytanic acid, 4-[(E)-2-(5,6,7,8-tetrahydro-5,5,8,8-tetramethyl-2-napthalenyl)-1-propenyl]benzoic acid (TTNPB), and retinoic acid.

β3 adrenergic receptor (β3) agonists useful in the present disclosure include: U.S. Pat. Nos. 5,705,515 and 5,451,677 and PCT Patent Application Nos. WO 01/74782, and WO 02/32897. Specific P agonists useful in the present disclosure include, but are not limited to, AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A.

Thyroid hormone β agonists useful in the present disclosure include: PCT Application No. WO 02/15845 and Japanese Patent Application No. JP 2000256190. Specific thyroid hormone β agonists useful in the present disclosure include, but are not limited to, KB-2611 (KaroBioBMS). Specific fatty acid synthase (PAS) inhibitors useful in the present disclosure, include, but are not limited to, Cerulenin and $C_{75}$. Specific phosphodieterase (PDE) inhibitors useful in the present disclosure, include, but are not limited to, theophylline, pentoxifylline, zaprinast, sildenafil, arninone, milrinone, cilostamide, rolipram, and cilomilast.

Lipase inhibitors useful in the present disclosure include, but are not limited to, those disclosed in PCT Application No. WO 01/77094, and U.S. Pat. Nos. 4,598,089, 4,452,813, 5,512,565, 5,391,571, 5,602,151, 4,405,644, 4,189,438, and 4,242,453. Specific lipase inhibitors useful in the present disclosure include, but are not limited to, tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267.

Examples of HMG-CoA reductase inhibitors include, but are not limited to, lovastatin, simvastatin, pravastatin and fluvastatin. Examples of HMG-CoA synthase inhibitors are the beta-lactone derivatives disclosed in U.S. Pat. Nos. 4,806,564, 4,816,477, 4,847,271, and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Examples of squalene epoxidase inhibitors are disclosed in European Patent Publication EP 0 318 860 and in Japanese Patent Publication J02 169-571A. Examples of LDL-receptor gene inducer molecules are disclosed in U.S. Pat. No. 5,182,298 filed Mar. 18, 1991. Other cholesterol lowering agents that may be administered include niacin, probucol, fibric acids (i.e., clofibrate and gemfibrozil), and LDL-receptor gene inducers.

Examples of PARP inhibitors include, but are not limited to, iodonitocoumarin, 5-iodo-6-nitrocoumarin, 3,4-dihydro-5-methyl-isoquinolinone, 4-amino-1,8-naphthalimide, 3-methoxybenzamide, 8-hydroxy-2-methyl-3-hydro-quinazolin-4-one, 2-{3-[4-(4-fluorophenyl)-3,6-dihydro-1(2h)-pyridinyl]propyl}-8-methyl-4(3h)-quinazolinone, 5-fluoro-1-[4-(4-phenyl-3,6-dihydropyridin-1(butyl]quinazoline-2,4 (1h,3h)-dione, 3-(4-chlorophenyl) quinoxaline-5-carboxamide, 2-(3'-methoxyphenyl)benzimidazole-4-carboxam, benzamide, 3-aminobenzamide, 3-aminophtalhydrazide, and 1,5-dihydroxyisoquinoline.

The above-mentioned compounds, which can be used in combination with a compound of Formula (I) or (II), or a pharmaceutically acceptable salt thereof, can be prepared and administered as described in the art such as in the documents cited above.

The above compounds are only illustrative of the ACMSD inhibitors, anti-diabetic agents, anti-obesity agents, cholesterol lower agent, compounds that boost $NAD^+$ levels, compounds that inhibit $NAD^+$ consumption that can be used in the compositions of the present disclosure. As this listing of compounds is not meant to be comprehensive, the methods of the present disclosure may employ any anti-obesity agent and any anti-diabetic agent, and are not limited to any particular structural class of compounds.

As used herein, "combination therapy" includes the administration of a compound of the present disclosure, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, a cooperative, e.g., synergistic, effect and/or a pharmacokinetic or pharmacodynamic co-action, or any combination thereof, resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present disclosure.

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

Biological Assays and Animals Studies
Method of Screening ACMSD1 Inhibition

The activity of compounds as inhibitors of ACMSD1 is determined in a spectrophotometrical in vitro assay. The pre-assay mixture is incubated and a compound of Formula (I) or (II), or a pharmaceutically acceptable salt thereof, and ACMSD1 solution is then added. The effect of ACMS concentration on the enzyme activity is investigated by varying 3-hydroxyanthranilic acid (3OH-HA) concentration in the pre-assay mixture. Kinetic parameters are calculated from the initial velocity data using a Lineweaver-Burk plot.

Cellular Assay Methods

The mouse hepatocytes cell lines are grown and plated. The cells are maintained in culture at 37° C. and once the cells are attached, different concentrations of a compound of Formula (I) or (II), or a pharmaceutically acceptable salt thereof, or DMSO are added. Primary hepatocytes are harvested about 24 hrs later.

Determination of ACMSD-1 Modulation in HEK293T Cells.

HEK293T cells are seeded and transfected to transiently express ACMSD. The cells are then stimulated with different concentrations of a compound of Formula (I) or (II), and then lysed to measure the ACMSD activity in a spectrophotometrical in vitro assay. The amount of the whole protein content in cell lysates is detected by Bradford analysis and used to get the specificity activity of the enzyme normalized in all samples.

Determination of NAD$^+$ Content in Human Primary Hepatocytes

Primary hepatocytes are treated with different concentrations of a compound of Formula (I) or (II), or a pharmaceutically acceptable salt thereof, or MEHP (control) after seeding. The compound is replaced every 24 hours, and then cells are directly harvested and lysed to detect NAD$^+$ content through LC MS/MS (liquid chromatography mass spectrometry/mass spectroscopy).

Modulation of SOD2 Activity in AML12 Cells and Murine Primary Hepatocytes

Primary hepatocytes or AML-12 cells are lysed and total protein concentration is determined using the Bradford assay. SOD2 activity is determined at indicated times after treatment with a compound of Formula (I) or (II), or a pharmaceutically acceptable salt thereof, using a SOD Assay Kit. Absorbance is determined and results are expressed in U/ml/mg of protein according to the standard curve and measured protein concentration.

Determination of NAD$^+$ Content in Murine Primary Hepatocytes

NAD$^+$ is extracted using acidic extraction method and samples are collected and homogenized. After insoluble protein parts are pelleted, the samples are separated by high-performance liquid chromatography (HPLC) and analyzed by mass-spectrometry. The proteins in the pellet are quantified by Bradford assay and are used for normalization.

RNA Preparation and RT-qPCR Analysis of ACMSD and SIRT1-Regulated Genes in Cells Cells (AML-12, Hepa-1.6, HEK-293, primary human and murine hepatocytes) are treated with different concentrations of a compound of Formula (I) or (II), or a pharmaceutically acceptable salt thereof and the gene expression of ACMSD, Pgc1a, Sod1, and Sod2 (MnSOD) is determined using RT-qPCR. Total RNA is extracted from cells and the extracted RNA is treated with DNase and used for reverse transcription (RT).

Modulation of Caspase 3/7 Activity in MDCK Cells

MDCK cells are cultured in base medium to a final concentration of 10%. Cells are plated into 96 wells and 24 hours after cell plating the medium is changed with fresh medium supplemented with 1% FBS. Cisplatin is then used to induce cell injury. Different concentrations of Formula (I) or (II), or a pharmaceutically acceptable salt thereof (in DMSO) are added in combination with cisplatin or prior to adding cisplatin. Caspase 3/7 activity (Promega) is determined according to standard procedures using a luminescent signal readout on a plate reader. Each experiment/condition is performed in triplicate. Caspase activity is analyzed as percentage effect normalized to the cisplatin alone and vehicle treated cells.

Cytotoxicity and hERG Screening

HePG2 and AML-12 cells are seeded and a dose-response of the compound is performed at various concentrations. Cells are stimulated and the supernatant is used to perform LDH release as a measure of necrosis while the cells are lysed to detect ATP levels for determining cell viability.

The Predictor hERG assay kit is stably transfected with hERG potassium channel and a high-affinity red fluorescent hERG channel ligand and is used for the determination of hERG channel affinity binding of compounds of Formula (I) or (II), or a pharmaceutically acceptable salt thereof. Compounds that bind to the hERG channel protein (competitors) are identified by their ability to displace the tracer which results in a lower fluorescence polarization.

C. elegans Experiments—ACMSD1 Silencing, Lifespan Assays, Mobility Assessment and GFP Quantification ACMSD1 silencing: Bacterial feeding RNAi experiments to determine the effects of downregulation or silencing of acmsd-1 on gene expression and survival are carried out in the nematode Caenorhabditis elegans (C. elegans). The clones used for the bacterial feeding experiments are acmsd-1, SIR-2.1 and DAF-16. Total RNA is extracted from cells and the extracted RNA is treated with DNase, and used for reverse transcription (RT).

Worms are grown on NGM agar plates additionally containing Carbenicillin and IPTG and seeded with bacterial cultures. After RNAi treatment, worms are transferred to plates containing paraquat and seeded with RNAi bacteria. Control animals are grown on RNAi bacteria containing an empty vector (control) and then transferred to plates containing paraquat and seeded with RNAi bacteria. Quantification of gene expression of sod-3 at mRNA levels and protein levels using RT-qPCR and survival analyses are performed. The movement of worms is recorded at days 1, 3, and 5 of adulthood.

Anti-Diabetic Effects Studies in C57BL/6J and KK-Ay Mice

Mice are fed with regular chow or a high fat diet (HFD). A compound of Formula (I), or a pharmaceutically acceptable salt thereof, is dosed daily and blood and tissues are harvested for RNA isolation, lipid measurements and histology. Oxygen consumption is measured and histological analysis and transmission electron microscopy are performed. An oral glucose tolerance test and an intraperitoneal insulin tolerance test are also performed to quantify glucose and to measure plasma insulin concentrations.

Anti-Diabetic and Anti-Obesity Studies in db/db Mice with LepR Mutation

Animals are fed a high-fat diet (HFD). For subchronic intervention, the animals are treated once/day with a compound of Formula (I) or (II), or a pharmaceutically acceptable salt thereof, for 14 days. Blood samples are collected and glucose concentrations of each blood sample are determined. For acute intervention, initial blood samples are collected and then compounds of Formula (I) or (II), or a pharmaceutically acceptable salt thereof, are administered. Diet-access is then restricted, and a second blood sample is collected. The mice are subjected to an oral glucose tolerance test and blood glucose concentrations are determined.

For the euglycemic-hyperinsulinemic clamps assay, the animals receive a primed-continuous [3-$^3$H]glucose infusion and a blood sample is then collected to determine plasma insulin, glucose and [3-$^3$H]glucose concentrations and to calculate basal endogenous glucose appearance rates. The mice then receive vehicle or a compound of Formula (I) or (II), or a pharmaceutically acceptable salt thereof, via gavage. Subsequently, the animals receive a [3-$^3$H]glucose infusion containing insulin causing a moderate net-increase in plasma insulin concentrations. Blood glucose concentrations are measured and target glycemia is established by adjusting the rate of glucose infusion. 2-deoxy-D-[1-$^{14}$C] glucose is then given intravenously and blood samples are collected. The mice are then sacrificed. Gastrocnemius muscle and epidydimal adipose tissue are collected and plasma [$^3$H]- and [$^{14}$C]-radioactivity is determined in deproteinized plasma.

Body weights are assessed and brown adipose tissue (BAT) and gonadal white adipose tissue (WAT) are dissected and weighed. Volume oxygen (VO$_2$) and volume carbon dioxide production (VCO$_2$) are measured and are reported as average VO$_2$ per hour normalized to body weight (mL/h/kg). Activity counts by infrared beam interruptions and food intake are simultaneously measured.

Non-Alcoholic Fatty Liver Disease (NAFLD) and Non-Alcoholic Steatohepatitis (NASH) Studies in Male C57BL/6J Mice Mice are fed a 'Western' HF-HSD (high fat-high sucrose diet) or normal chow diet (NCD) as control. The animals are then treated with a compound of Formula (I) or (II), or a pharmaceutically acceptable salt thereof, for 4, 12 or 20 weeks, and then sacrificed. Body weight and food intake are monitored weekly and total fat mass is analysed. An intraperitoneal glucose tolerance test (IPGTT) is also performed and tail vein glucose levels are measured after glucose administration. Insulin resistance is calculated using the Homeostasis Model of Insulin Resistance. The mice are then sacrificed by blood sampling via cardiac puncture. Plasma is obtained and tissues were collected together with the plasma for further biochemical and molecular analyses or for histological analysis.

Non-Alcoholic Fatty Liver Disease (NAFLD) and Non-Alcoholic Steatohepatitis (NASH) Studies in Methionine and Choline Deficient Mice Mice weighing 25 g are either fed a methionine- and choline-deficient diet (MCD to induce NASH) or chow diet (as a control). Animal experiments and evaluation of NAFLD and NASH are conducted as described above in for C57BL/6J mice fed the high fat and high sucrose diet.

Atherosclerosis Studies in High Cholesterol Fed LDL-R Knockout Mice

LDL-R knockout (KO) mice are sacrificed about 12 weeks after the initiation of the atherogenic diet, after which the heart and aorta are perfused with PBS and subsequently fixed. Atherosclerosis and biochemistry parameters are measured with the appropriate commercially available kits. For the in vivo lipopoly saccharide (LPS) study, mice are intraperitoneally injected with LPS, and blood is taken from the tail vein. TNFα levels are quantified with a Mouse TNFα ELISA assay. Blood cell counts are determined.

Inherited Mitochondrial Disease Studies in Sco2$^{KO/KI}$ Mice

Compounds of Formula (I) or (II), or a pharmaceutically acceptable salt thereof, are dissolved in water and added to a standard powder diet at the appropriate concentration. The diet supply is changed every three days and administered ad libitum for one month. Tissues are collected for histological analysis. For the muscle quadriceps samples, the spectrophotometric activity of cI, cII, cIII, and cIV, as well as CS, is measured. NAD$^+$ is extracted from tissues using acidic and alkaline extraction methods, respectively, and analysed with mass spectrometry.

Inherited Mitochondrial Disease Studies in Deletor Mice

Deletor and WT male mice are administered either chow diet (CD) or a compound of Formula (I) or (II), or a pharmaceutically acceptable salt thereof, admixed with the CD. The mice are regularly monitored for weight, food consumption, and physical endurance and their exercise capability is measured. Oxygen consumption and carbon dioxide production, as well as spontaneous moving and feeding activities, are recorded. Tissue sections are collected and prepared from the quadriceps, liver, and BAT. Frozen sections from quadriceps are assayed for in situ histochemical COX and succinate dehydrogenase (SDH) activities, crista content in both BAT and muscle is determined from electron micrographs and skeletal muscle samples are analysed for citrate synthase activity.

Kidney Disease Studies

C57BL/6J WT mice are fed a standard commercial diet and divided into four groups: control; cisplatin; a compound of Formula (I) or (II), or a pharmaceutically acceptable salt thereof, alone. The mice are sacrificed and tissue samples and serum are collected. Serum creatinine and BUN levels are measured and the proinflammatory cytokines TNF-αt, IL-1b, and IL-6 from serum or homogenates from kidney tissue are quantified. Mouse kidneys are collected and stained for analysis. Tubular damage is examined and scored based on the percentage of cortical tubular necrosis. Neutrophil infiltration is quantitatively assessed on stained tissue by counting the number of neutrophils per high-power field.

Alternatively, C57BL/6J WT mice are numbered and kept in acclimatization for a period and then randomized into different treatment groups based on their body weight. Different groups are maintained on a specified diet for a period of time. Body weight measurements are taken and food consumption is evaluated. Blood is collected by retro-orbital puncture under mild anesthesia and used for analysis of basal blood urea nitrogen levels (BUN).

Mice are anesthetized and placed on a surgical platform. Both kidneys are exposed through incisions and renal pedicles are occluded using vascular clamps. The clamp is then removed and the surgical site is sutured. The sham-operated group is subjected to similar surgical procedures, except that the occluding clamp is not applied. Animals are monitored until recovery from anesthesia and returned to their home cage. Animals are observed every day for general clinical signs and symptoms and mortality.

One day prior to termination, animals are individually housed in metabolic cages and urine is collected for estimation of urea, creatinine, sodium and potassium. Blood is also collected by retro orbital puncture under mild anesthesia and plasma is used for analysis of blood urea nitrogen levels (BUN) and serum creatinine. Animals are then euthanized and organs are collected. One kidney is fixed and the other is flash frozen and used for the estimation of lipid peroxidation, GSH, MPO and SOD levels.

Ischemia Reperfusion-Induced Acute Kidney Injury Studies

CD-1 (ICR) mice are treated with a compound of Formula (I) or (II), or a pharmaceutically acceptable salt thereof, by oral gavage once per day. CD-1 mice are divided into four groups: (1) young mice with sham injury; (2) young mice with ischemic/reperfusion (I/R) injury; (3) adult mice with sham injury; and (4) adult mice with I/R injury. An additional 27 adult mice are randomized into two groups: mice receiving a compound of Formula (I) or (II), or a pharmaceutically acceptable salt thereof, and mice receiving the vehicle as a control. The serum creatinine level is measured and BUN measurements are recorded. Renal tissue is then evaluated and tubular injury is scored.

Cisplatin-Induced Acute Kidney Injury Studies

C57BL6 mice are treated with compounds of Formula (I) or (II), or a pharmaceutically acceptable salt thereof by oral gavage once per day. The animals are allowed to recover, and they are sacrificed 48, 72, and 96 hrs post cisplatin injection.

The serum creatinine level is measured as a primary endpoint. Tubular injury is scored on a scale of 0-4 on the basis of the percentage of tubules with necrosis, dilatation, or cell swelling: 0, less than 5%; 1, 5-25%; 2, 25-50%; 3, 50-75%; and 4, over 75%. All high-power fields (×400) in the cortex and outer medulla are evaluated by a pathologist in a blinded manner.

Effects on Sepsis-Induced Acute Kidney Injury

C57BL6 mice (12-15 weeks old). are treated with compounds of Formula (I) or (II), or a pharmaceutically acceptable salt thereof, via IP injection following Cecal ligation and puncture induced Sepsis.

Blood and kidney tissues are collected at the time of sacrificing for measurement of primary and secondary endpoints. Primary endpoint (at 48 hrs):serum creatinine. Secondary endpoints (at 48 hours) include: Macrophage phenotype marker (IF stain), Plasma NGAL, Plasma and kidney markers of inflammation (IL-6, IL-18, TNF), and Kidney Injury markers (KIM-1, NGAL, TIMP2 and IGFBP7). Addition endpoints include; cell death (IF: Annexin V and Propidium Iodide; Caspase 3/7), autophagy, biogenesis (PGC-1α, mitochondrial DNA), OXPHOS (Complex I, III, IV activity), Sirt1 and Sirt3 expression, AMPK (Total, P-AMPK, P-ACC, and HIF-1α.

Histological analysis is performed with H&E and PAS staining using standard protocols. Images are collected and analyzed using a light microscope (IX71, Olympus, Tokyo, Japan) with DP analyzer software (DP70-BSW, Tokyo, Japan). Tubular damage in PAS-stained kidney sections is scored based on the percentage of cortical tubular necrosis: 0=normal, 1=1-10, 2=11-25, 3=26-45, 4=46-75, and 5=76-100%. tubular injury score will be used to evaluate protection against kidney damage.

Determination of the Effects on FoxO1 Phosphorylation Levels

AML-12 cells are treated with different concentrations of a compound of Formula (I) or (II), or a pharmaceutically acceptable salt thereof. Cells are then lysed, and analyzed by SDS-PAGE/western blot. Blocking and antibody incubations are then done and each protein present is detected with its specific antibody.

Inhibitory Effect

The present disclosure also relates to a compound of Formula (I) or (II), or a pharmaceutically acceptable salt thereof, as defined herein, in a method for inhibiting the activity of ACMSD. The method includes contacting a cell with a compound of Formula (I) or (II), or a pharmaceutically acceptable salt thereof. In a related embodiment, the method further provides that the compound is present in an amount effective to produce a concentration sufficient to selectively inhibit ACMSD in the cell.

Thus, preferably in an assay for ACMSD inhibition (i.e., an ACMSD assay described herein, e.g., Biological Example 1, or an ACMSD assays known in the literature), the preferred compounds of Formula (I) or (II), or a pharmaceutically acceptable salt thereof, are compounds capable of reducing or preferably inhibiting ACMSD and increasing $NAD^+$ levels and/or activating SIRTs and the downstream targets of SIRTs, such as PGC-1α, FoxO1 and/or SOD. Preferably, said inhibition is determined as the $IC_{50}$ of said compound of Formula (I) or (II), or a pharmaceutically acceptable salt thereof, with respect to said ACMSD inhibition assay. Preferred compounds of Formula (I) or (II), or a pharmaceutically acceptable salt thereof, have an $IC_{50}$ at or below 1 μM, more preferably less than 300 nM, for example less than 100 nM, such as less than 50 nM with respect to inhibition of ACMSD.

Exemplary Embodiments

Some embodiments of this disclosure are Embodiment I, as follows:

Embodiment I-1. A compound represented by Formula (I):

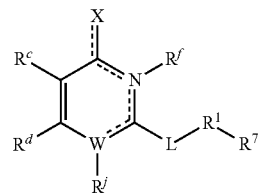

or a pharmaceutically acceptable salt or tautomer thereof, wherein:
X is H, S, $SR^2$, $NR^2$, $NR^2R^{2'}$, O, OH, $OR^h$, F, Br, or Cl;
W is N or C;
(i) when W is N, then:
L is —$(C(R^5)_2)_m CH=CH(C(R^5)_2)_p$—,

—$(C(R^5)_2)_m Y^1(C(R^5)_2)_p$—, —$(C(R^5)_2)_m Y^1(C(R^5)_2)_p$-cyclopropyl-, —$(C(R^5)_2)_m Y^1 CH=CH$—, —$(C(R^5)_2)_m NR^3 C=(O)(C(R^5)_2)_p$—, —$(C(R^5)_2)_m$phenyl$(C(R^5)_2)_p$—, —$(C(R^5)_2)_m$pyridinyl $(C(R^5)_2)_p$—, or —$(C(R^5)_2)_m$thiophenyl$(C(R^5)_2)_p$—;
(ii) when W is C, then:
L is —$(C(R^5)_2)_m CH=CH(C(R^5)_2)_p$—, —$(C(R^5)_2)_o$—, —$(C(R^5)_2)_m Y^1(C(R^5)_2)_p$—,

—$(C(R^5)_2)_m Y^1 CH=CH$—, —$(C(R^5)_2)_m C=(O)(CH_2)_p$—, —$(C(R^5)_2)_m C=(O)O(C(R^5)_2)_p$—, —$(C(R^5)_2)_m C=(O)NR^3(C(R^5)_2)_p$—, —$(C(R^5)_2)_m NR^3 C=(O)(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—;
$Y^1$ is O, $NR^4$, or $S(O)_q$;
each $Y^2$ is independently O, NH or S;
$R^1$ is absent or $C_6$-$C_{10}$ arylene or heteroarylene, wherein the heteroarylene comprises one or two 5- to 7-membered rings and 1-4 heteroatoms selected from N, O and S, and wherein the $C_6$-$C_{10}$ arylene or heteroarylene are optionally substituted with one to two $R^e$;
$R^2$ is H or $C_1$-$C_4$ alkyl;
$R^{2'}$ is H, $C_1$-$C_4$ alkyl, or $C_3$-$C_7$ cycloalkyl; or
$R^2$ and $R^{2'}$ together with the nitrogen atom to which they are attached form a 3- to 7-membered heterocycloalkyl ring comprising 1-3 additional heteroatoms selected from N, O and S;
$R^3$ is H or $C_1$-$C_4$ alkyl;
$R^4$ is H or $C_1$-$C_4$ alkyl;
each $R^5$ is independently at each occurrence H or $C_1$-$C_4$ alkyl;
each $R^6$ is independently at each occurrence H or $C_1$-$C_4$ alkyl;
$R^7$ is H, A, B, or C;
A is —$(C(R^6)_2)_r CO_2 R^x$, —$Y^2(C(R^6)_2)_r CO_2 R^x$, —$(CH_2)_r$tetrazole, —$(CH_2)_r$oxadiazolone, —$(CH_2)_r$tetrazolone, —$(CH_2)_r$thiadiazolol, —$(CH_2)_r$isoxazol-3-ol, —$(CH_2)_r P(O)(OH)OR^x$, —$(CH_2)_r S(O)_2 OH$, —$(CH_2)_r C(O)NHCN$, or —(CH$_2$)$_r$C(O)NHS(O)$_2$alkyl, wherein —(CH$_2$)$_r$tetrazole, —(CH$_2$)$_r$oxadiazolone, —(CH$_2$)$_r$tetrazolone, —(CH$_2$)$_r$thiadiazolol, —(CH$_2$)$_r$ isoxazol-3-ol are optionally substituted with C$_1$-C$_6$ alkyl;

B is —(C(R$^6$)$_2$)$_r$S(O)$_2$OC$_1$-C$_4$ alkyl, —O(C(R$^6$)$_2$)$_r$S(O)$_2$OC$_1$-C$_4$ alkyl, —Y$^2$(C(R$^6$)$_2$)$_r$C(O)NR$^g$R$^{g'}$, —Y$^2$(C(R$^6$)$_2$)$_r$S(O)$_2$NR$^g$R$^{g'}$, —(CH$_2$)$_r$C(O)NR$^g$R$^{g'}$, —(CH$_2$)$_r$S(O)$_2$NR$^g$R$^{g'}$, —(CH$_2$)$_r$C(O)NHS(O)$_2$NR$^g$R$^{g'}$, —(C(R$^6$)$_2$)$_r$CO$_2$R, —(C(R$^6$)$_2$)$_r$NH$_2$CO$_2$R$^x$, —(C(R$^6$)$_2$)$_r$P(O)(OR$^x$)$_2$, —O(C(R$^6$)$_2$)$_r$P(O)(OR$^x$)$_2$, —(C(R$^6$)$_2$)$_r$S(O)$_2$OH, —O(C(R$^6$)$_2$)$_r$S(O)$_2$OH, —(C(R$^6$)$_2$)$_r$P(O)$_2$OR$^x$, or —O(C(R$^6$)$_2$)$_r$P(O)$_2$OR$^x$;

C is —(CH$_2$)$_r$CN, —(CH$_2$)$_s$OH, halogen, —(C(R$^6$)$_2$)$_r$C$_6$-C$_{10}$ aryl, —(C(R$^6$)$_2$)$_r$S—C$_6$-C$_{10}$ aryl, —(C(R$^6$)$_2$)$_r$heteroaryl, —O(C(R$^6$)$_2$)$_r$heteroaryl, —O(C(R$^6$)$_2$)$_r$heterocycloalkyl, —O(C(R$^6$)$_2$)$_r$OH, —OR$^y$, —(C(R$^6$)$_2$)$_r$C(O)NHCN, —CH=CHCO$_2$R$^x$, or —(C(R$^6$)$_2$)$_r$C(O)NHS(O)$_2$C$_1$-C$_4$ alkyl, wherein the aryl and heteroaryl are substituted with one to three substituents each independently selected from C$_1$-C$_6$ alkyl, C$_1$-C$_6$ haloalkyl, halogen, and OH, and wherein the heterocycloalkyl is substituted with one to two =O or =S;

R$^c$ is H, C$_1$-C$_6$ alkyl, C$_1$-C$_6$ haloalkyl, halogen, —CN, —OR$^x$, or —CO$_2$R$^x$;

R$^d$ is methyl, CF$_3$, CR$^f$F$_2$, —(C(R$^6$)$_2$)$_r$C$_6$-C$_{10}$ aryl, —(C(R$^6$)$_2$)$_r$-5- or 6-membered heteroaryl, —(C(R$^6$)$_2$)$_r$-5- or 6-membered cycloalkyl, optionally substituted C$_6$-C$_{10}$ aryl, optionally substituted 5- or 6-membered heteroaryl, or optionally substituted 5- or 6-membered cycloalkyl;

each R$^e$ is independently at each occurrence C$_1$-C$_6$ alkyl, C$_2$-C$_6$ alkenyl, C$_2$-C$_6$ alkynyl, halogen, C$_1$-C$_6$ haloalkyl, —NHR$^z$, —OH, or —CN;

R$^f$ is absent, H, or methyl;

R$^g$ is H, C$_1$-C$_6$ alkyl, OH, —S(O)$_2$(C$_1$-C$_6$ alkyl), or S(O)$_2$N(C$_1$-C$_6$ alkyl)$_2$;

R$^{g'}$ is H, C$_1$-C$_6$ alkyl, C$_3$-C$_7$ cycloalkyl, 4- to 7-membered heterocycloalkyl ring comprising 1-3 heteroatoms selected from N, O and S, C$_6$-C$_{10}$ aryl, or 5- to 7-membered heteroaryl comprising 1-3 heteroatoms selected from N, O and S, wherein the alkyl is optionally substituted with one or more substituents independently selected from halogen and —OH, and wherein the cycloalkyl, heterocycloalkyl, aryl and heteroaryl are optionally substituted with one or more substituents independently selected from C$_1$-C$_6$ alkyl, halogen, and —OH;

R$^h$ is H, C$_1$-C$_4$ alkyl, or 3- to 7-membered heterocycloalkyl ring comprising 1-3 heteroatoms selected from N, O and S, wherein the alkyl is optionally substituted with one or more substituents each independently selected from NH$_2$, C$_1$-C$_4$ alkylamino, C$_1$-C$_4$ dialkylamino, and C(O)NH$_2$; and wherein the heterocycloalkyl is optionally substituted with one or more substituents each independently selected from C$_1$-C$_6$ alkyl and C$_1$-C$_6$ haloalkyl;

R$^i$ is (i) —(CH$_2$)$_s$OC(O)C$_1$-C$_6$ alkyl, wherein the alkyl is substituted with one or more NH$_2$; (ii) (CH$_2$CH$_2$O)$_n$CH$_2$CH$_2$OH; or (iii) C$_1$-C$_6$ alkyl substituted with one or more substituents each independently selected from OH and 4- to 7-membered heterocycloalkyl comprising 1 to 3 heteroatoms selected from O, N, or S;

R$^j$ is absent, H, C$_1$-C$_6$ alkyl, or —CN;

each R$^x$ is independently at each occurrence H, C$_1$-C$_6$ alkyl, or C$_6$-C$_{10}$ aryl;

each R$^y$ and R$^z$ is independently H, C$_1$-C$_6$ alkyl, or C$_1$-C$_6$ haloalkyl;

each m, p, q, r, and t is independently 0, 1 or 2;

n is 0, 1, 2, or 3;

s is 1 or 2;

o is 0, 1, 2, 3, or 4; and

=== represents a single bond or a double bond; and provided that when X is O; R$^f$ is H; W is C; R$^j$ is —CN; L is —SCH$_2$—; R$^1$ is phenylene or pyridine; then R$^7$ is not —COOH;

when X is O; R$^f$ is H; W is C; R$^j$ is —CN; L is —SCH$_2$—; R$^1$ is phenylene or pyridine; and R$^7$ is tetrazole; then R$^c$ is not H;

when X is O; R$^f$ is H; W is C; R$^j$ is —CN; L is —S—C(R$^5$)$_2$ or —SCH$_2$CH$_2$—; R$^1$ is absent; then R$^7$ is not COOH or tetrazole;

when X is O, R$^f$ is H; W is N; R$^j$ is absent; R$^d$ is methyl, optionally substituted 5- to 10-membered aryl, optionally substituted 5- or 6-membered heteroaryl, or optionally substituted 5- or 6-membered cycloalkyl; L is —SCH$_2$— or —OCH$_2$—; and R$^1$ is phenylene; then R$^7$ is not —COOH, —CH$_2$COOH, and when X is O, R$^f$ is H, W is N, R$^j$ is absent, L is —NHCH$_2$—, —CH$_2$NH—, or —NH—C(O)—, and R$^1$ is phenylene, then R$^d$ is not phenyl.

Embodiment I-2. The compound of Embodiment I-1, wherein X is O, OH, OR$^h$, F, Br, or Cl.

Embodiment I-3. The compound of Embodiment I-1, wherein X is H, S, SR$^2$, NR$^2$, or NR$^2$R$^2$.

Embodiment I-4. The compound of any one of Embodiments I-1 to I-3, wherein R is absent.

Embodiment I-5. The compound of any one of Embodiments I-1 to I-3, wherein R$^f$ is H or methyl.

Embodiment I-6. The compound of any one of Embodiments I-1 to I-5, wherein W is N.

Embodiment I-7. The compound of Embodiment I-6, wherein R$^j$ is absent.

Embodiment I-8. The compound of any one Embodiments I-1 to I-5, wherein W is C.

Embodiment I-9. The compound of Embodiment I-8, wherein R$^j$ is H, C$_1$-C$_6$ alkyl, or —CN.

Embodiment I-10. The compound of Embodiment I-8 or I-9, wherein R$^j$ is —CN.

Embodiment I-11. The compound of any one of Embodiments I-1 to I-10, wherein R$^c$ is C$_1$-C$_6$ alkyl, —CN, or halogen.

Embodiment I-12. The compound of any one of Embodiments I-1 to I-11, wherein R$^c$ is —CN or halogen.

Embodiment I-13. The compound of any one of Embodiments I-1 to I-12, wherein R$^c$ is —CN.

Embodiment I-14. The compound of any one of Embodiments I-1 to I-13, wherein R$^d$ is methyl.

Embodiment I-15. The compound of any one of Embodiments I-1 to I-13, wherein R$^d$ is optionally substituted 5- to 10-membered aryl.

Embodiment I-16. The compound of any one of Embodiments I-1 to I-13, wherein R$^d$ is optionally substituted 5- or 6-membered heteroaryl.

Embodiment I-17. The compound of any one of Embodiments I-1 to I-13, wherein R$^d$ is optionally substituted 5- or 6-membered cycloalkyl.

Embodiment I-18. The compound of any one of Embodiments I-1 to I-13, wherein R$^d$ is methyl, cyclohexyl, pyridinyl, thiazolyl, phenyl, or thienyl.

I-19. The compound of any one of Embodiments I-1 to I-13, wherein R$^d$ is methyl, cyclohexyl, pyridinyl, thiazolyl, thienyl, or optionally substituted phenyl.

Embodiment I-20. The compound of any one of Embodiments I-1 to I-13, wherein R$^d$ is methyl.

Embodiment I-21. The compound of any one of Embodiments I-1 to I-13, wherein R$^d$ is —CF$_3$.

Embodiment I-22. The compound of any one of Embodiments I-1 to I-13, wherein R$^d$ is CR$^f$F$_2$.

Embodiment I-23. The compound of any one of Embodiments I-1 to I-13, wherein R$^d$ is —(C(R$^6$)$_2$)$_r$C$_6$-C$_{10}$ aryl, —(C(R$^6$)$_2$)$_r$-5- or 6-membered heteroaryl, —(C(R$^6$)$_2$)$_r$-5- or 6-membered cycloalkyl.

Embodiment I-24. The compound of any one of Embodiments I-1 to I-13, wherein R$^d$ is —(C(R$^6$)$_2$)$_r$C$_6$-C$_{10}$ aryl.

Embodiment I-25. The compound of any one of Embodiments I-1 to I-24, wherein L is —(C(R$^5$)$_2$)$_m$Y$^1$(C(R$^5$)$_2$)$_p$—.

Embodiment I-26. The compound of Embodiment I-25, wherein Y$^1$ is S.

Embodiment I-27. The compound of any one of Embodiments I-1 to I-24, wherein L is —(C(R$^5$)$_2$)$_m$NR$^3$C=(O)(C(R$^5$)$_2$)$_p$— or —(C(R$^5$)$_2$)$_m$Y$^1$(C(R$^5$)$_2$)$_p$-cyclopropyl-.

Embodiment I-28. The compound of any one of Embodiments I-1 to I-27, wherein R$^1$ is C$_6$-C$_{10}$ arylene.

Embodiment I-29. The compound of any one of Embodiments I-1 to I-27, wherein R$^1$ is heteroarylene.

Embodiment I-30. The compound of any one of Embodiments I-1 to I-27, wherein R$^1$ is absent.

Embodiment I-31. The compound of any one of Embodiments I-1 to I-30, wherein R$^7$ is A.

Embodiment I-32. The compound of Embodiment I-31, wherein A is —(C(R$^6$)$_2$)$_r$CO$_2$R$^x$ or —(CH$_2$)$_r$tetrazole, wherein the —(CH$_2$)$_r$tetrazole is optionally substituted with C$_1$-C$_6$ alkyl.

Embodiment I-33. The compound of any one of Embodiments I-1 to I-30, wherein R$^7$ is B.

Embodiment I-34. The compound of Embodiment I-31, wherein B is —(CH$_2$)$_r$C(O)NR$^g$R$^{g'}$, or —(CH$_2$)$_r$S(O)$_2$NR$^g$R$^{g'}$, Embodiment I-35. The compound of any one of Embodiments I-1 to I-30, wherein R$^7$ is C.

Embodiment I-36. The compound of Embodiment I-31, wherein C is —(CH$_2$)$_r$CN, —(CH$_2$)$_s$OH, or —(C(R$^6$)$_2$)$_r$C$_6$-C$_{10}$ aryl, wherein the aryl is substituted with one to three substituents each independently selected from C$_1$-C$_6$ alkyl, C$_1$-C$_6$ haloalkyl, halogen, and OH.

Embodiment I-37. A compound, or a pharmaceutically acceptable salt or tautomer thereof, selected from the group consisting of:

| Cpd No. | Structure |
|---|---|
| I-1 | 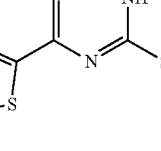 |
| I-2 | 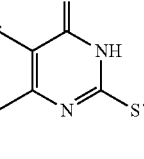 |
| I-3 | 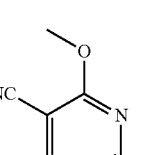 |
| I-4 | 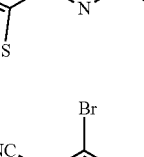 |
| I-5 | 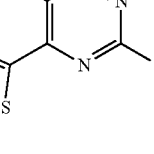 |
| I-6 | 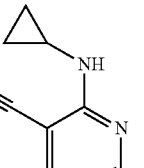 |
| I-7 | 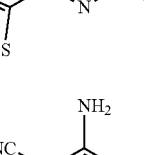 |
| I-8 | 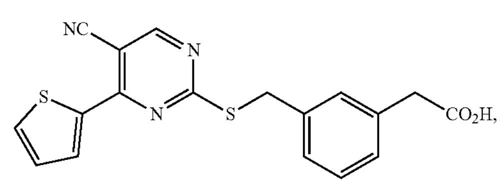 [SMILES: N#Cc1cnc(SCc2cccc(CC(=O)O)c2)nc1-c1cccs1] |

| Cpd No. | Structure |
|---|---|
| I-9 | 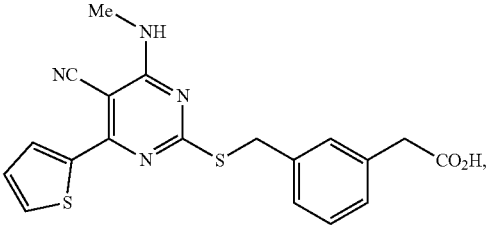 [SMILES: CNc1nc(SCc2cccc(CC(=O)O)c2)nc(-c2cccs2)c1C#N] |
| I-10 | 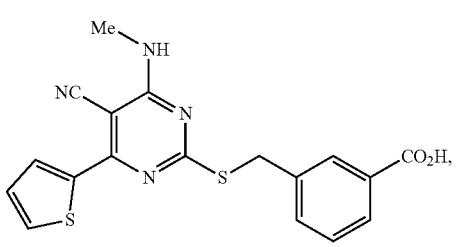 [SMILES: CNc1nc(SCc2cccc(C(=O)O)c2)nc(-c2cccs2)c1C#N] |
| I-11 | 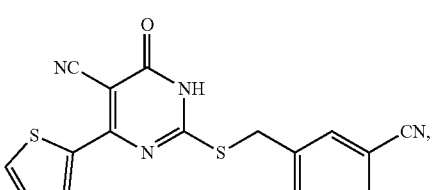 |
| I-12 | 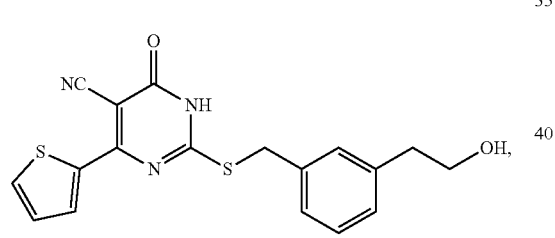 |
| I-13 | 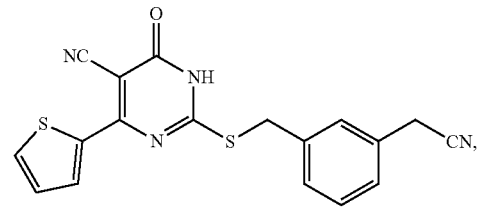 [SMILES: N#CCc1cccc(CSc2nc(-c3cccs3)c(C#N)c(=O)[nH]2)c1] |
| I-14 | 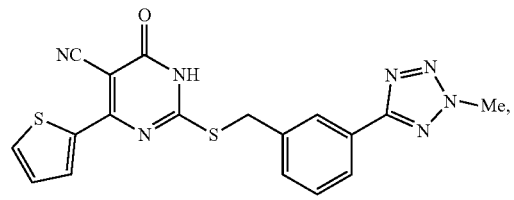 [SMILES: Cn1nnc(-c2cccc(CSc3nc(-c4cccs4)c(C#N)c(=O)[nH]3)c2)n1] |
| I-15 | 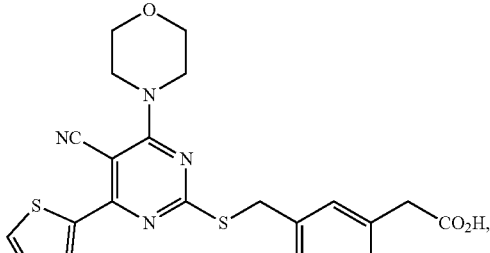 |
| I-16 | 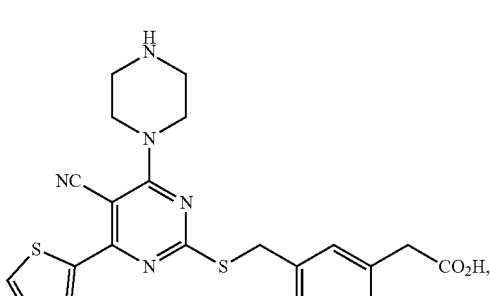 |
| I-17 | 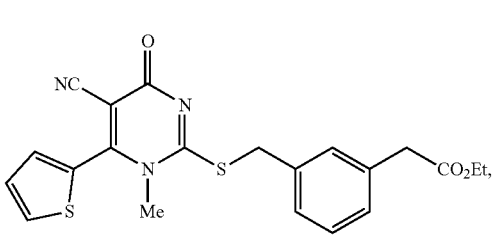 [SMILES: CCOC(=O)Cc1cccc(CSc2nc(=O)c(C#N)c(-c3cccs3)n2C)c1] |
| I-18 | 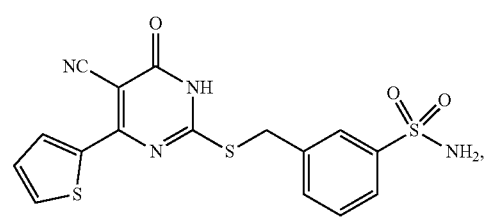 [SMILES: N#Cc1c(-c2cccs2)nc(SCc2cccc(S(N)(=O)=O)c2)[nH]c1=O] |
| I-19 | 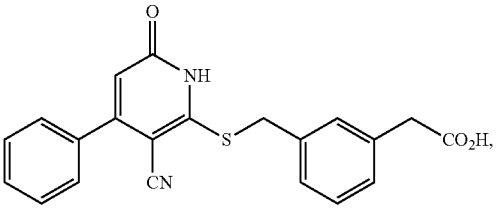 [SMILES: N#Cc1c(-c2ccccc2)cc(=O)[nH]c1SCc1cccc(CC(=O)O)c1] |
| I-20 | 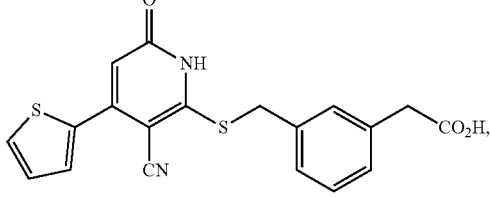 |

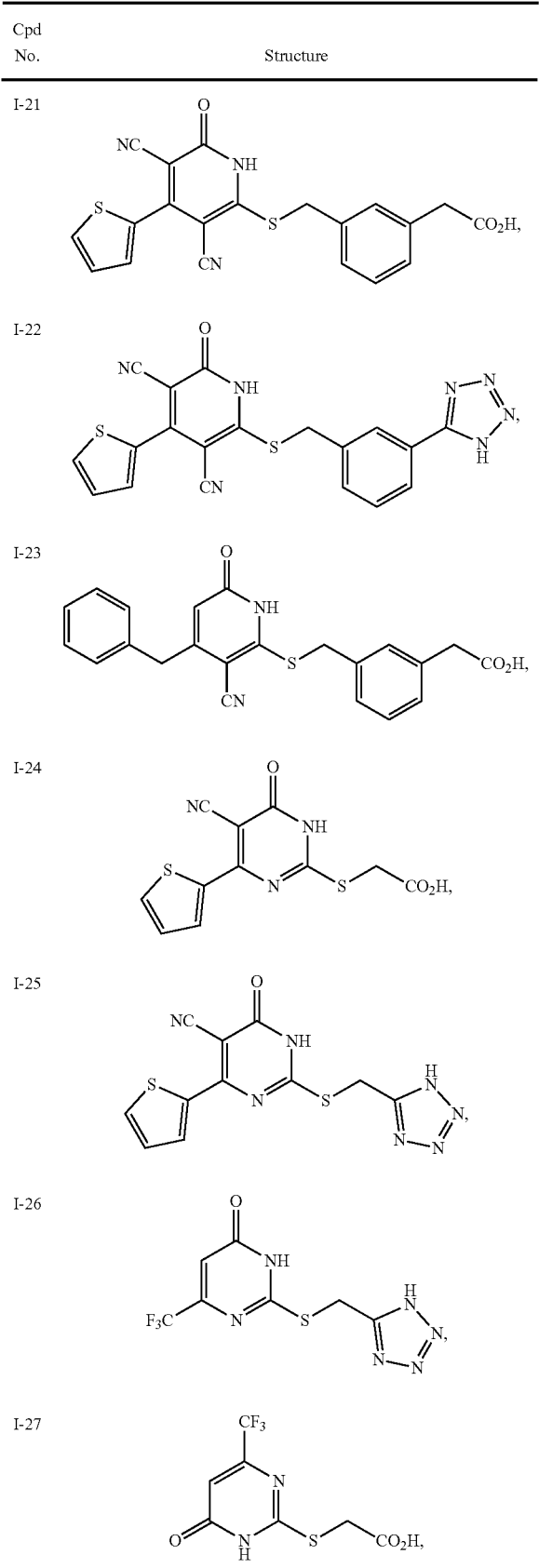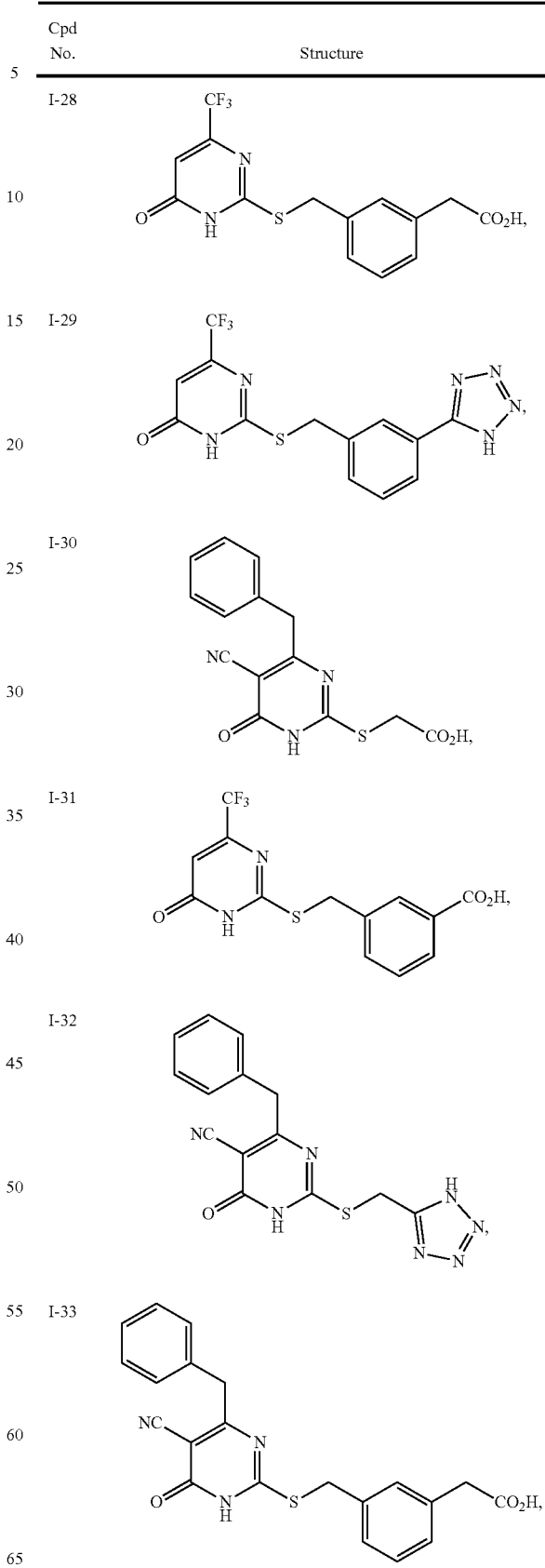

| Cpd No. | Structure |
|---|---|
| I-34 | 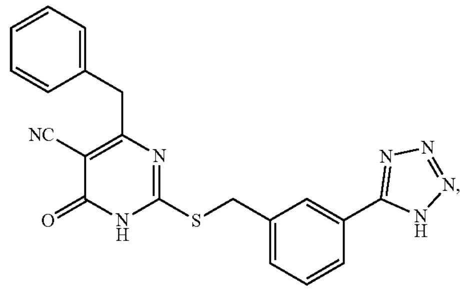 [SMILES: N#Cc1c(Cc2ccccc2)nc(SCc2cccc(-c3nnn[nH]3)c2)[nH]c1=O] |
| I-35 | 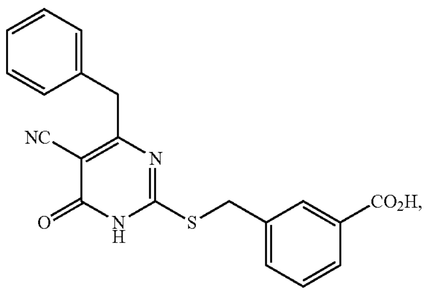 |
| I-36 | 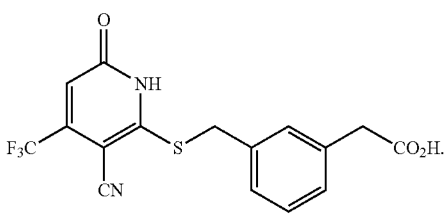 [SMILES: N#Cc1c(C(F)(F)F)cc(=O)[nH]c1SCc1cccc(CC(=O)O)c1] |
Embodiment I-38. A compound, or a pharmaceutically acceptable salt or tautomer thereof, selected from the group consisting of:
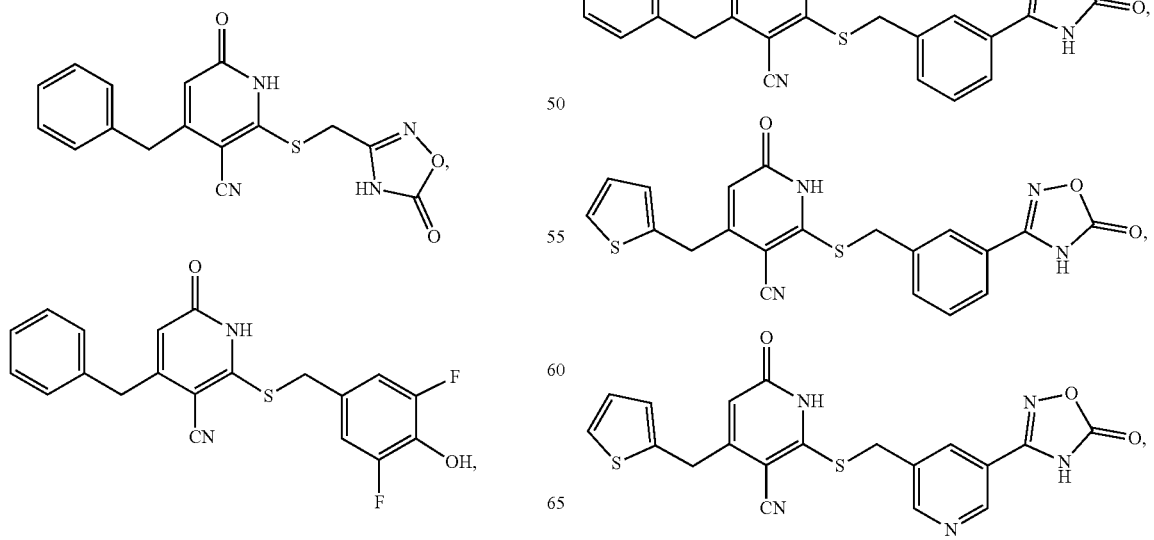

91
-continued
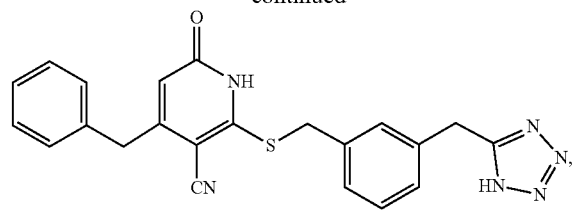
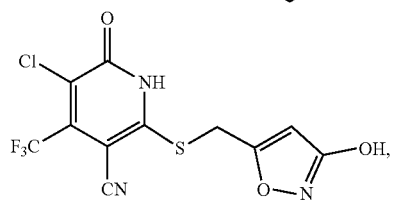
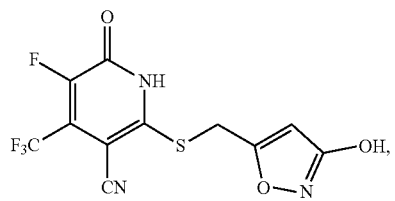
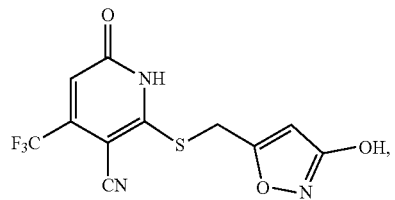
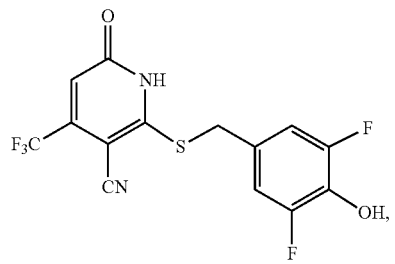
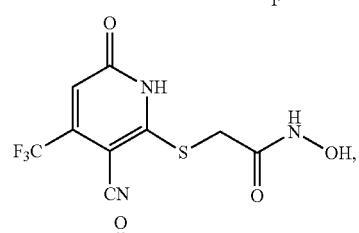
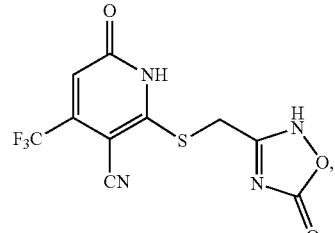
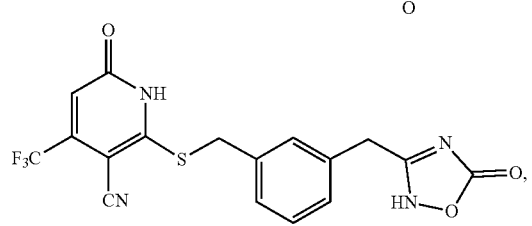
92
-continued
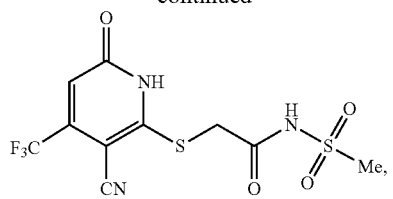
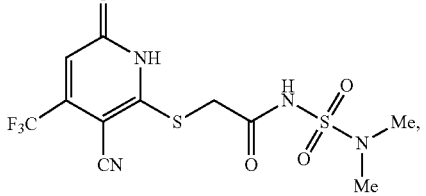
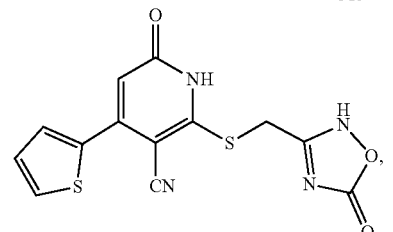
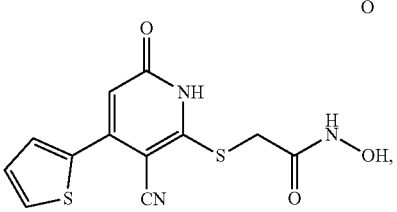
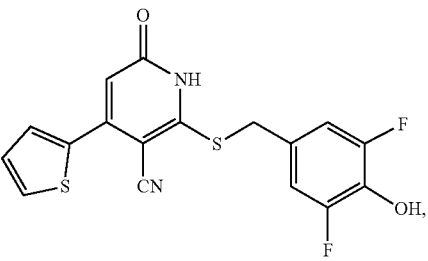
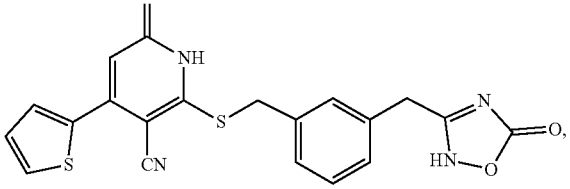
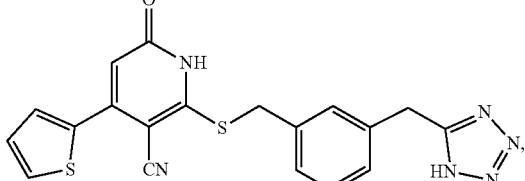
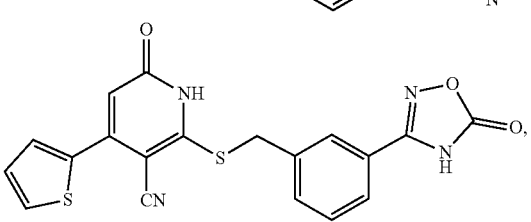

93
-continued
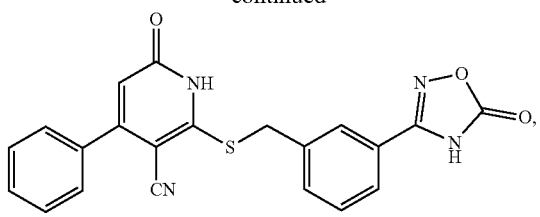
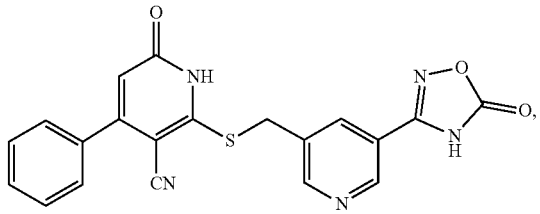
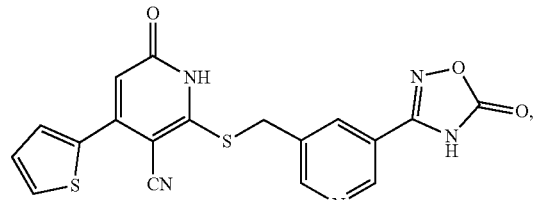
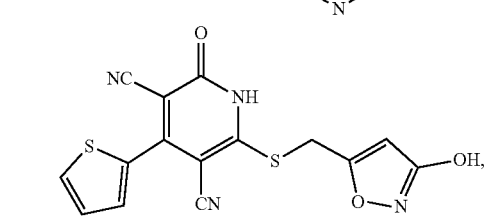
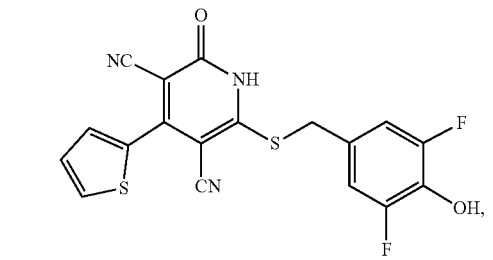
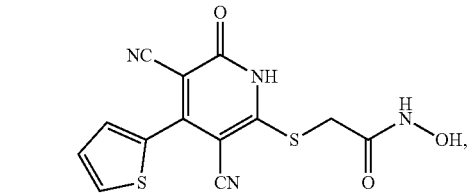
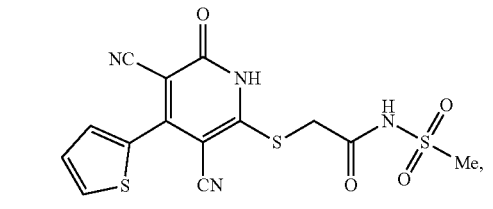
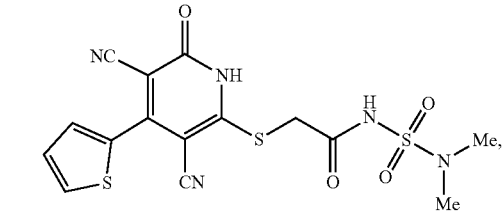
94
-continued
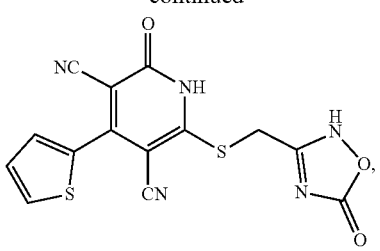
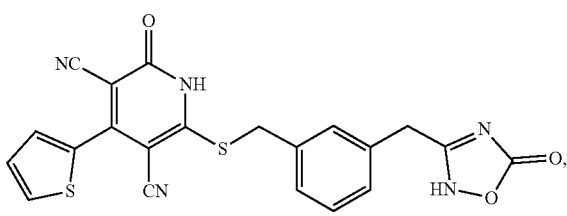
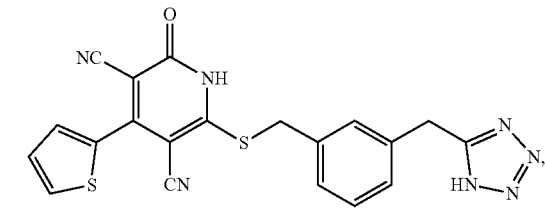
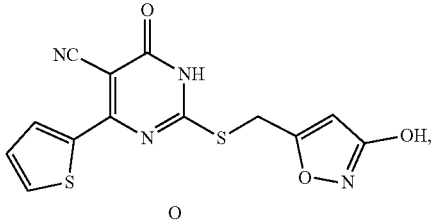
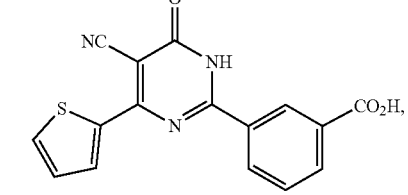
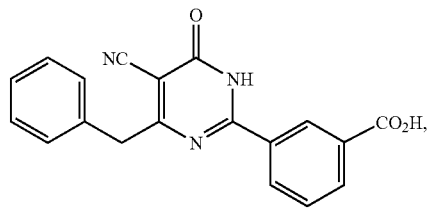
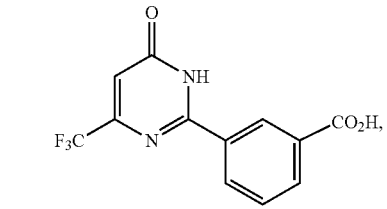
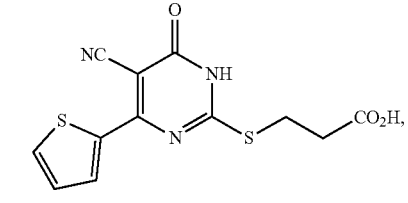

-continued

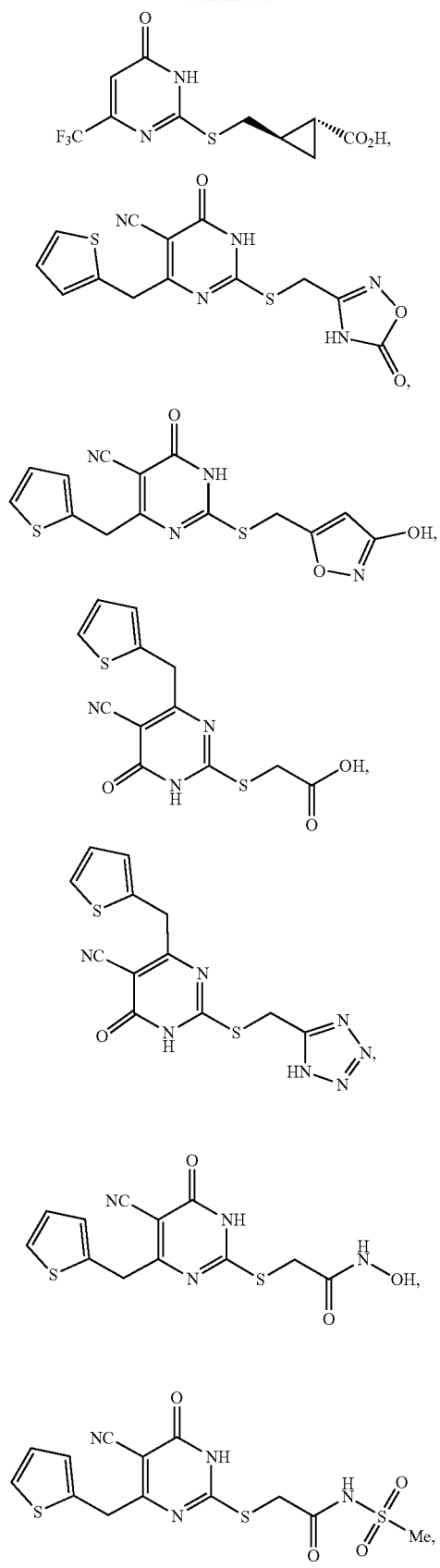
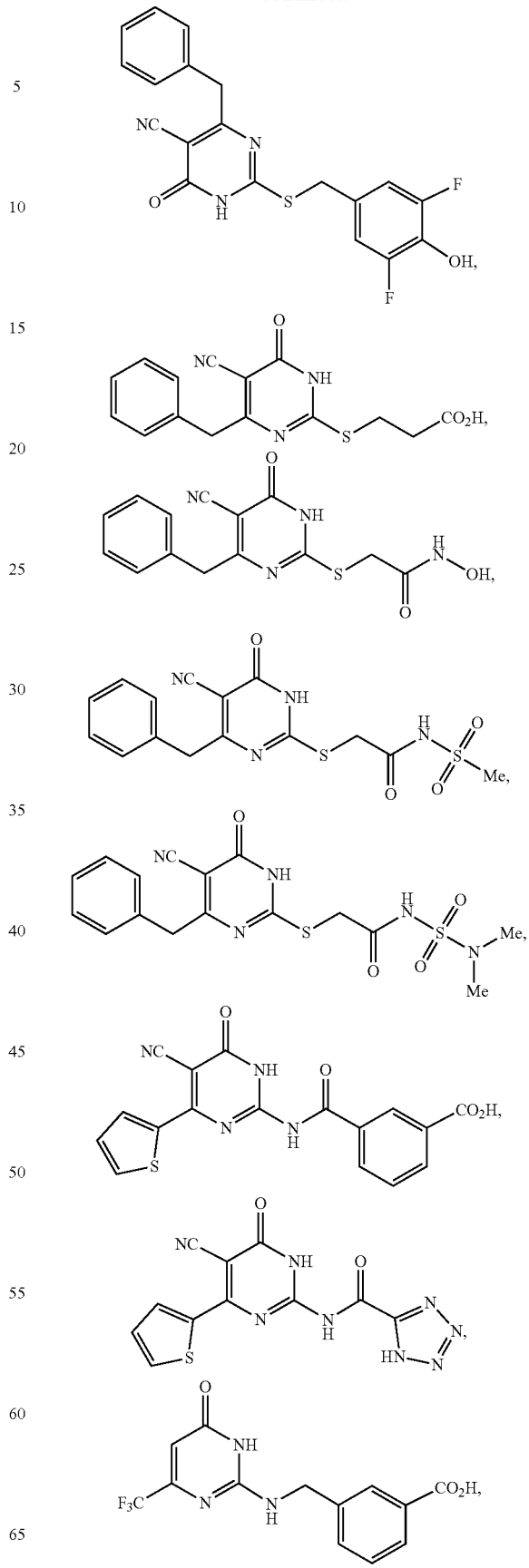

-continued

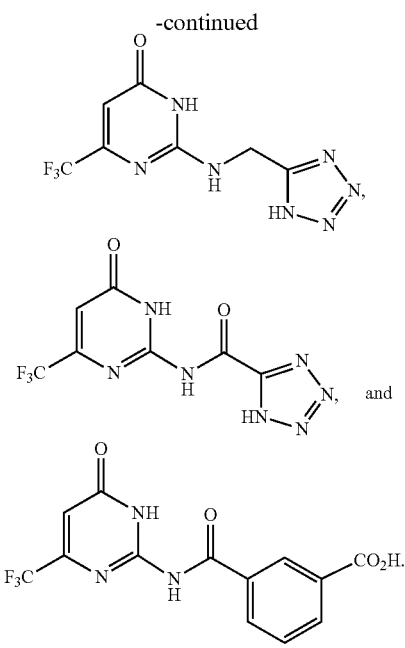

Embodiment I-39. A pharmaceutical composition comprising a compound of any one of Embodiments I-1 to I-38, or a pharmaceutically acceptable salt thereof, and at least one of a pharmaceutically acceptable carrier, diluent, or excipient.

Embodiment I-40. The pharmaceutical composition according to Embodiment I-39, which comprises one or more further therapeutic agents.

Embodiment I-41. A method of treating, preventing, or reducing the risk of a disease or disorder inhibited by α-amino-β-carboxymuconate-ε-semialdehyde decarboxylase (ACMSD) comprising administering to the subject suffering from or susceptible to developing the disease or disorder a therapeutically effective amount of one or more compounds of any one of Embodiments I-1 to I-38, or a pharmaceutically acceptable salt thereof.

Embodiment I-42. A method of treating, preventing, or reducing the risk of a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of any one of Embodiments I-1 to I-38, or a pharmaceutically acceptable salt thereof.

Embodiment I-43. The method of any one of Embodiments I-41 to I-42, wherein the disease is chronic liver disease selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

Embodiment I-44. A method of treating a disorder associated with mitochondrial dysfunction comprising administering to the subject suffering from or susceptible to developing a metabolic disorder a therapeutically effective amount of one or more compounds of any one of Embodiments I-1 to I-38, or a pharmaceutically acceptable salt thereof, that increases intracellular nicotinamide adenine dinucleotide (NAD$^+$).

Embodiment I-45. The method of Embodiment I-44, wherein said disorder associated with mitochondrial dysfunction is an inherited mitochondrial disease, a common metabolic disorder, a neurodegenerative disease, an aging related disorder, a kidney disorder, or a chronic inflammatory disease.

Embodiment I-46. The method of Embodiment I-45, wherein the common metabolic disorder is obesity or type II diabetes.

Embodiment I-47. A method of promoting oxidative metabolism comprising administering to the subject suffering from or susceptible to developing a metabolic disorder a therapeutically effective amount of one or more compounds of any one of Embodiments I-1 to I-38, or a pharmaceutically acceptable salt thereof, that increases intracellular nicotinamide adenine dinucleotide (NAD$^+$).

Embodiment I-48. A compound of any of Embodiments I-1 to I-38, or a pharmaceutically acceptable salt thereof, for use as a medicament.

Embodiment I-49. A compound of any of Embodiments I-1 to I-38, or a pharmaceutically acceptable salt thereof, for use in treating, preventing, or reducing the risk of a disease or disorder associated with reduced nicotinamide adenine dinucleotide (NAD$^+$) levels.

Embodiment I-50. A compound of any of Embodiments I-1 to I-38, or a pharmaceutically acceptable salt thereof, for use in for treating, preventing, or reducing the risk of a disorder associated with mitochondrial dysfunction.

Embodiment I-51. A compound of any of Embodiments I-1 to I-38, or a pharmaceutically acceptable salt thereof, for use in promoting oxidative metabolism.

Embodiment I-52. Use of a compound of any of Embodiments I-1 to I-38, or a pharmaceutically acceptable salt thereof, for treating, preventing, or reducing the risk of a disease or disorder associated with α-amino-β-carboxymuconate-ε-semialdehyde decarboxylase (ACMSD) dysfunction.

Embodiment I-53. Use of a compound of any of Embodiments I-1 to I-38, or a pharmaceutically acceptable salt thereof, for treating, preventing, or reducing the risk of a disease or disorder associated with reduced nicotinamide adenine dinucleotide (NAD$^+$) levels.

Embodiment I-54. Use of a compound of any of Embodiments I-1 to I-38, or a pharmaceutically acceptable salt thereof, for treating, preventing, or reducing the risk of a disorder associated with mitochondrial dysfunction.

Embodiment I-55. Use of a compound of any of Embodiments I-1 to I-38, or a pharmaceutically acceptable salt thereof, for promoting oxidative metabolism.

Embodiment I-56. Use of a compound of any of Embodiments I-1 to I-38, or a pharmaceutically acceptable salt thereof, in the manufacture of a medicament for treating, preventing, or reducing the risk of a disease or disorder associated with α-amino-β-carboxymuconate-ε-semialdehyde decarboxylase (ACMSD) dysfunction.

Embodiment I-57. Use of a compound of any of Embodiments I-1 to I-38, or a pharmaceutically acceptable salt thereof, in the manufacture of a medicament for treating, preventing, or reducing the risk of a disease or disorder associated with reduced nicotinamide adenine dinucleotide (NAD⁺) levels.

Embodiment I-58. Use of a compound of any of Embodiments I-1 to I-38, or a pharmaceutically acceptable salt thereof, in the manufacture of a medicament for treating, preventing, or reducing the risk of a disorder associated with mitochondrial dysfunction.

Embodiment I-59. Use of a compound of any of Embodiments I-1 to I-38, or a pharmaceutically acceptable salt thereof, in the manufacture of a medicament for promoting oxidative metabolism.

Embodiment I-60. A method of treating, preventing, or reducing the risk of a disease or disorder inhibited by α-amino-β-carboxymuconate-ε-semialdehyde decarboxylase (ACMSD) comprising administering to the subject suffering from or susceptible to developing the disease or disorder a therapeutically effective amount of a pharmaceutical composition of Embodiment I-39.

Embodiment I-61. A method of treating, preventing, or reducing the risk of a disease or disorder associated with reduced nicotinamide adenine dinucleotide (NAD⁺) levels comprising administering to the subject suffering from or susceptible to developing a disease or disorder associated with reduced NAD⁺ levels a therapeutically effective amount of a pharmaceutical composition of Embodiment I-39.

Embodiment I-62. The method of any one of Embodiments I-60 to I-61, wherein the disease is chronic liver disease selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

Embodiment I-63. A method of treating a disorder associated with mitochondrial dysfunction comprising administering to the subject suffering from or susceptible to developing a metabolic disorder a therapeutically effective amount of a pharmaceutical composition of Embodiment I-39.

Embodiment I-64. The method of Embodiment I-63, wherein said disorder associated with mitochondrial dysfunction is an inherited mitochondrial disease, a common metabolic disorder, a neurodegenerative disease, an aging related disorder, a kidney disorder, or a chronic inflammatory disease.

Embodiment I-65. The method of claim 64, wherein the common metabolic disorder is obesity or type II diabetes.

Embodiment I-66. A method of promoting oxidative metabolism comprising administering to the subject suffering from or susceptible to developing a metabolic disorder a therapeutically effective amount of a pharmaceutical composition of Embodiment I-39.

Embodiment I-67. A pharmaceutical composition of Embodiment I-39 for use as a medicament.

Embodiment I-68. A pharmaceutical composition of Embodiment I-39 for use in treating, preventing, or reducing the risk of a disease or disorder associated with reduced nicotinamide adenine dinucleotide (NAD⁺) levels.

Embodiment I-69. A pharmaceutical composition of Embodiment I-39 for use in for treating, preventing, or reducing the risk of a disorder associated with mitochondrial dysfunction.

Embodiment I-70. A pharmaceutical composition of Embodiment I-39 for use in promoting oxidative metabolism.

Embodiment I-71. Use of pharmaceutical composition of Embodiment I-39 for treating, preventing, or reducing the risk of a disease or disorder associated with α-amino-β-carboxymuconate-ε-semialdehyde decarboxylase (ACMSD) dysfunction.

Embodiment I-72. Use of a pharmaceutical composition of Embodiment I-39 for treating, preventing, or reducing the risk of a disease or disorder associated with reduced nicotinamide adenine dinucleotide (NAD⁺) levels.

Embodiment I-73. Use of pharmaceutical composition of Embodiment I-39 for treating, preventing, or reducing the risk of a disorder associated with mitochondrial dysfunction.

Embodiment I-74. Use pharmaceutical composition of Embodiment I-39 for promoting oxidative metabolism.

Embodiment I-75. Use of pharmaceutical composition of Embodiment I-39 in the manufacture of a medicament for treating, preventing, or reducing the risk of a disease or disorder associated with α-amino-β-carboxymuconate-ε-semialdehyde decarboxylase (ACMSD) dysfunction.

Embodiment I-76. Use of pharmaceutical composition of Embodiment I-39 in the manufacture of a medicament for treating, preventing, or reducing the risk of a disease or disorder associated with reduced nicotinamide adenine dinucleotide (NAD⁺) levels.

Embodiment I-77. Use of pharmaceutical composition of Embodiment I-39 in the manufacture of a medicament for treating, preventing, or reducing the risk of a disorder associated with mitochondrial dysfunction.

Embodiment I-78. Use of pharmaceutical composition of Embodiment I-39 in the manufacture of a medicament for promoting oxidative metabolism.

Embodiment II-1. A compound represented by Formula (II):

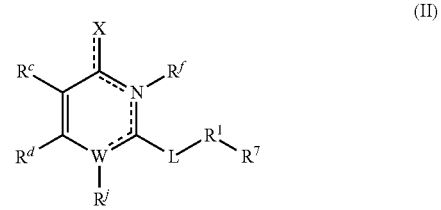

or a pharmaceutically acceptable salt or tautomer thereof, wherein:

X is H, S, $SR^2$, $NR^2$, $NR^2R^{2'}$, O, OH, $OR^h$, F, Br, or Cl;

W is N or C;

(i) when W is N, then: L is —$(C(R^5)_2)_m$CH=CH$(C(R^5)_2)_p$—,

—$(C(R^5)_2)_m Y^1 (C(R^5)_2)_p$—, —$(C(R^5)_2)_m Y^1 (C(R^5)_2)_p$-cyclopropyl-, —$(C(R^5)_2)_m Y^1$CH=CH—, —(C(R$^5$)$_2$)$_m$NR$^3$C═(O)(C(R$^5$)$_2$)$_p$—, —(C(R$^5$)$_2$)$_m$phenyl(C(R$^5$)$_2$)$_p$—, —(C(R$^5$)$_2$)$_m$pyridinyl(C(R$^5$)$_2$)$_p$—, or —(C(R$^5$)$_2$)$_m$thiophenyl(C(R$^5$)$_2$)$_p$—;

(ii) when W is C, then: L is —(C(R$^5$)$_2$)$_m$CH═CH(C(R$^5$)$_2$)$_p$—, —(C(R$^5$)$_2$)$_o$—, —(C(R)$_2$)$_m$Y$^1$(C(R$^5$)$_2$)$_p$—,

,

—(C(R)$_2$)$_m$ Y$^1$CH═CH—, —(C(R$^5$)$_2$)$_m$C═(O)(CH$_2$)$_p$—, —(C(R$^5$)$_2$)$_m$C═(O)O(C(R$^5$)$_2$)$_p$—, —(C(R$^5$)$_2$)$_m$C═(O)NR$^3$(C(R$^5$)$_2$)$_p$—, —(C(R$^5$)$_2$)$_m$NR$^3$C═(O)(C(R$^5$)$_2$)$_p$—, —(C(R$^5$)$_2$)$_m$phenyl(C(R$^5$)$_2$)$_p$—, —(C(R$^5$)$_2$)$_m$pyridinyl(C(R$^5$)$_2$)$_p$—, or —(C(R$^5$)$_2$)$_m$thiophenyl(C(R$^5$)$_2$)$_p$—;

Y$^1$ is O, NR$^4$, or S(O)$_q$;

each Y$^2$ is independently O, NH or S;

R$^1$ is absent, $C_6$-$C_{10}$ arylene, heteroarylene, or $C_3$-$C_8$cycloalkylene, wherein the heteroarylene comprises one or two 5- to 7-membered rings and 1-4 heteroatoms selected from N, O and S, and wherein the $C_6$-$C_{10}$ arylene, heteroarylene, and $C_3$-$C_8$cycloalkylene are optionally substituted with one to two R$^e$;

R$^2$ is H or $C_1$-$C_4$ alkyl;

R$^{2'}$ is H, $C_1$-$C_4$ alkyl, or $C_3$-$C_7$ cycloalkyl; or

R$^2$ and R$^{2'}$ together with the nitrogen atom to which they are attached form a 3- to 7-membered heterocycloalkyl ring comprising 1-3 additional heteroatoms selected from N, O and S;

R$^3$ is H or $C_1$-$C_4$ alkyl;

R$^4$ is H or $C_1$-$C_4$ alkyl;

each R$^5$ is independently at each occurrence H or $C_1$-$C_4$ alkyl;

each R$^6$ is independently at each occurrence H or $C_1$-$C_4$ alkyl;

R$^7$ is H, A, B, or C;

A is —(C(R$^6$)$_2$)$_r$CO$_2$R$^x$, —Y$^2$(C(R$^6$)$_2$)$_r$CO$_2$R$^x$, —(C(R$^6$)$_2$)$_r$tetrazole, —(C(R$^6$)$_2$)$_r$oxadiazolone, —(C(R$^6$)$_2$)$_r$tetrazolone, —(C(R$^6$)$_2$)$_r$thiadiazolol, —(C(R$^6$)$_2$)$_r$ isoxazol-3-ol, —(C(R$^6$)$_2$)$_r$P(O)(OH)OR$^x$, —(C(R$^6$)$_2$)$_r$S(O)$_2$OH, —(C(R$^6$)$_2$)$_r$C(O)NHCN, or —(C(R$^6$)$_2$)$_r$C(O)NHS(O)$_2$alkyl, wherein —(C(R$^6$)$_2$)$_r$ tetrazole, —(C(R$^6$)$_2$)$_r$oxadiazolone, —(C(R$^6$)$_2$)$_r$tetrazolone, —(C(R$^6$)$_2$)$_r$thiadiazolol, —(C(R$^6$)$_2$)$_r$ isoxazol-3-ol are optionally substituted with $C_1$-$C_6$ alkyl, B is —(C(R$^6$)$_2$)$_r$S(O)$_2$OC$_1$-$C_4$ alkyl, —O(C(R$^6$)$_2$)$_r$S(O)$_2$OC$_1$-$C_4$ alkyl, —Y$^2$(C(R$^6$)$_2$)$_r$C(O)NR$^g$R$^{g'}$, —Y$^2$(C(R$^6$)$_2$)$_r$S(O)$_2$NR$^g$R$^{g'}$, —(C(R$^6$)$_2$)$_r$C(O)NR$^g$R$^{g'}$, —(C(R$^6$)$_2$)$_r$S(O)$_2$NR$^g$R$^{g'}$, —(C(R$^6$)$_2$)$_r$C(O)NHS(O)$_2$NR$^g$R$^{g'}$, —(C(R$^6$)$_2$)$_r$CO$_2$R', —(C(R$^6$)2)$_r$NH$_2$CO$_2$R$^x$, —(C(R$^6$)$_2$)$_r$P(O)(OR$^x$)$_2$, —O(C(R$^6$)$_2$)$_r$P(O)(OR$^x$)$_2$, —(C(R$^6$)$_2$)$_r$S(O)$_2$OH, —O(C(R$^6$)$_2$)$_r$S(O)$_2$OH, —(C(R$^6$)$_2$)$_r$P(O)$_2$OR$^x$, or —O(C(R$^6$)$_2$)$_r$P(O)$_2$OR$^x$, C is —(CH$_2$)$_r$CN, —(CH$_2$)$_s$OH, halogen, —(C(R$^6$)$_2$)$_r$C$_6$-$C_{10}$ aryl, —(C(R$^6$)$_2$)$_r$S—$C_6$-$C_{10}$ aryl, —(C(R$^6$)$_2$)$_r$heteroaryl, —O(C(R$^6$)$_2$)$_r$heteroaryl, —O(C(R$^6$)$_2$)$_r$heterocycloalkyl, —O(C(R$^6$)$_2$)$_r$OH, —OR$^y$, —(C(R$^6$)$_2$)$_r$C(O)NHCN, —CH═CHCO$_2$R$^x$, or —(C(R$^6$)$_2$)$_r$C(O)NHS(O)$_2$C$_1$-$C_4$ alkyl, wherein the aryl and heteroaryl are substituted with one to three substituents each independently selected from $C_1$-$C_6$ alkyl, $C_1$-$C_6$ haloalkyl, halogen, and OH, and wherein the heterocycloalkyl is substituted with one to two ═O or ═S;

R$^c$ is H, $C_1$-$C_6$ alkyl, $C_1$-$C_6$ haloalkyl, halogen, —CN, —OR$^x$, or —CO$_2$R$^x$;

R$^d$ is methyl, CF$_3$, CR$^f$F$_2$, —(C(R$^6$)$_2$)$_t$C$_6$-$C_{10}$ aryl, —(C(R$^6$)$_2$)$_t$-5- or 6-membered heteroaryl, —(C(R$^6$)$_2$)$_t$-5- or 6-membered cycloalkyl, optionally substituted $C_6$-$C_{10}$ aryl, optionally substituted 5- or 6-membered heteroaryl, or optionally substituted 5- or 6-membered cycloalkyl;

each R$^e$ is independently at each occurrence $C_1$-$C_6$ alkyl, $C_2$-$C_6$ alkenyl, $C_2$-$C_6$ alkynyl, halogen, $C_1$-$C_6$ haloalkyl, —NHR$^z$, —OH, or —CN;

R$^f$ is absent, H, or methyl;

R$^g$ is H, $C_1$-$C_6$ alkyl, OH, —S(O)$_2$(C$_1$-$C_6$ alkyl), or S(O)$_2$N(C$_1$-$C_6$ alkyl)$_2$;

R$^{g'}$ is H, $C_1$-$C_6$ alkyl, $C_3$-$C_7$ cycloalkyl, 4- to 7-membered heterocycloalkyl ring comprising 1-3 heteroatoms selected from N, O and S, $C_6$-$C_{10}$ aryl, or 5- to 7-membered heteroaryl comprising 1-3 heteroatoms selected from N, O and S, wherein the alkyl is optionally substituted with one or more substituents independently selected from halogen and —OH, and wherein the cycloalkyl, heterocycloalkyl, aryl and heteroaryl are optionally substituted with one or more substituents independently selected from $C_1$-$C_6$ alkyl, halogen, and —OH;

R$^h$ is H, $C_1$-$C_4$ alkyl, or 3- to 7-membered heterocycloalkyl ring comprising 1-3 heteroatoms selected from N, O and S, wherein the alkyl is optionally substituted with one or more substituents each independently selected from NH$_2$, $C_1$-$C_4$ alkylamino, $C_1$-$C_4$ dialkylamino, and C(O)NH$_2$; and wherein the heterocycloalkyl is optionally substituted with one or more substituents each independently selected from $C_1$-$C_6$ alkyl and $C_1$-$C_6$ haloalkyl;

R$^i$ is (i) —(CH$_2$)$_s$OC(O)C$_1$-$C_6$ alkyl, wherein the alkyl is substituted with one or more NH$_2$; (ii) (CH$_2$CH$_2$O)$_n$CH$_2$CH$_2$OH; or (iii) $C_1$-$C_6$ alkyl substituted with one or more substituents each independently selected from OH and 4- to 7-membered heterocycloalkyl comprising 1 to 3 heteroatoms selected from O, N, or S;

R$^j$ is absent, H, $C_1$-$C_6$ alkyl, or —CN;

each R$^x$ is independently at each occurrence H, $C_1$-$C_6$ alkyl, or $C_6$-$C_{10}$ aryl;

each R$^y$ and R$^z$ is independently H, $C_1$-$C_6$ alkyl, or $C_1$-$C_6$ haloalkyl;

each m, p, q, r, and t is independently 0, 1 or 2;

n is 0, 1, 2, or 3;

s is 1 or 2;

o is 0, 1, 2, 3, or 4; and

═══ represents a single bond or a double bond; and provided that when X is O; R$^f$ is H; W is C; R is —CN; L is —SCH$_2$—; R$^1$ is phenylene or pyridine; then R$^7$ is not —COOH;

when X is O; R$^f$ is H; W is C; R is —CN; L is —SCH$_2$—; R$^1$ is phenylene or pyridine; and R$^7$ is tetrazole; then R$^c$ is not H;

when X is O; R$^f$ is H; W is C; R$^j$ is —CN; L is —S—C(R$^5$)$_2$ or —SCH$_2$CH$_2$—; R$^1$ is absent; then R$^7$ is not COOH or tetrazole;

when X is O, R$^f$ is H; W is N; R$^j$ is absent; R$^d$ is methyl, optionally substituted 5- to 10-membered aryl, optionally substituted 5- or 6-membered heteroaryl, or optionally substituted 5- or 6-membered cycloalkyl; L is —SCH$_2$— or —OCH$_2$—; and R$^1$ is phenylene; then R$^7$ is not —COOH, —CH$_2$COOH,

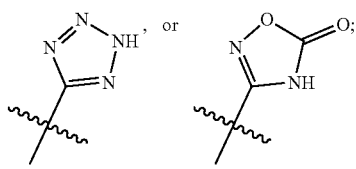 [SMILES: *c1nn[nH]n1 ; *c1noc(=O)[nH]1]

and when X is O, $R^f$ is H, W is N, $R^j$ is absent, L is —NHCH₂—, —CH₂NH—, or —NH—C(O)—, and $R^1$ is phenylene, then $R^d$ is not phenyl.

Embodiment II-2. A compound represented by Formula (I):

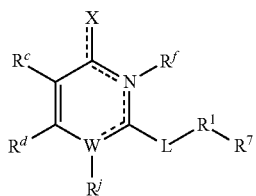

or a pharmaceutically acceptable salt or tautomer thereof, wherein:

X is H, S, $SR^2$, $NR^2$, $NR^2R^{2'}$, O, OH, $OR^h$, F, Br, or Cl;
W is N or C;
(i) when W is N, then:
L is —$(C(R^5)_2)_m$CH=CH$(C(R^5)_2)_p$—,

—$(C(R^5)_2)_m Y^1 (C(R^5)_2)_p$—, —$(C(R^5)_2)_m Y^1 (C(R^5)_2)_p$-cyclopropyl-, —$(C(R^5)_2)_m Y^1$CH=CH—, —$(C(R^5)_2)_m NR^3$C=(O)$(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—;
(ii) when W is C, then:
L is —$(C(R^5)_2)_m$CH=CH$(C(R^5)_2)_p$—, —$(C(R^5)_2)_o$—, —$(C(R^5)_2)_m Y^1 (C(R^5)_2)_p$—,

—$(C(R^5)_2)_m Y^1$CH=CH—, —$(C(R^5)_2)_m$C=(O)(CH₂)_p—, —$(C(R^5)_2)_m$C=(O)O$(C(R^5)_2)_p$—, —$(C(R^5)_2)_m$C=(O)$NR^3(C(R^5)_2)_p$—, —$(C(R^5)_2)_m NR^3$C=(O)$(C(R^5)_2)_p$—, —$(C(R^5)_2)_m$phenyl$(C(R^5)_2)_p$—, —$(C(R^5)_2)_m$pyridinyl$(C(R^5)_2)_p$—, or —$(C(R^5)_2)_m$thiophenyl$(C(R^5)_2)_p$—;
$Y^1$ is O, $NR^4$, or $S(O)_q$;
each $Y^2$ is independently O, NH or S;
$R^1$ is absent or $C_6$-$C_{10}$ arylene or heteroarylene, wherein the heteroarylene comprises one or two 5- to 7-membered rings and 1-4 heteroatoms selected from N, O and S, and wherein the $C_6$-$C_{10}$ arylene or heteroarylene are optionally substituted with one to two $R^e$;
$R^2$ is H or $C_1$-$C_4$ alkyl;
$R^{2'}$ is H, $C_1$-$C_4$ alkyl, or $C_3$-$C_7$ cycloalkyl; or $R^2$ and $R^{2'}$ together with the nitrogen atom to which they are attached form a 3- to 7-membered heterocycloalkyl ring comprising 1-3 additional heteroatoms selected from N, O and S;
$R^3$ is H or $C_1$-$C_4$ alkyl;
$R^4$ is H or $C_1$-$C_4$ alkyl;
each $R^5$ is independently at each occurrence H or $C_1$-$C_4$ alkyl;
each $R^6$ is independently at each occurrence H or $C_1$-$C_4$ alkyl;
$R^7$ is H, A, B, or C;
A is —$(C(R^6)_2)_r CO_2 R^x$, —$Y^2(C(R^6)_2)_r CO_2 R^x$, —(CH₂)_r tetrazole, —(CH₂)_r oxadiazolone, —(CH₂)_r tetrazolone, —(CH₂)_r thiadiazolol, —(CH₂)_r isoxazol-3-ol, —(CH₂)_r P(O)(OH)$OR^x$, —(CH₂)_r S(O)₂OH, —(CH₂)_r C(O)NHCN, or —(CH₂)_r C(O)NHS(O)₂alkyl, wherein —(CH₂)_r tetrazole, —(CH₂)_r oxadiazolone, —(CH₂)_r tetrazolone, —(CH₂)_r thiadiazolol, —(CH₂)_r isoxazol-3-ol are optionally substituted with $C_1$-$C_6$ alkyl,
B is —$(C(R^6)_2)_r S(O)_2 OC_1$-$C_4$ alkyl, —$O(C(R^6)_2)_r S(O)_2 OC_1$-$C_4$ alkyl, —$Y^2(C(R^6)_2)_r C(O)NR^g R^{g'}$, —$Y^2(C(R^6)_2)_r S(O)_2 NR^g R^{g'}$, —(CH₂)_r C(O)$NR^g R^{g'}$, —(CH₂)_r S(O)₂$NR^g R^{g'}$, —(CH₂)_r C(O)NHS(O)₂$NR^g R^{g'}$, —$(C(R^6)_2)_r CO_2 R$, —$(C(R^6)_2)_r NH_2 CO_2 R^x$, —$(C(R^6)_2)_r P(O)(OR^x)_2$, —$O(C(R^6)_2)_r P(O)(OR^x)_2$, —$(C(R^6)_2)_r S(O)_2 OH$, —$O(C(R^6)_2)_r S(O)_2 OH$, —$(C(R^6)_2)_r P(O)_2 OR^x$, or —$O(C(R^6)_2)_r P(O)_2 OR^x$,
C is —(CH₂)_s CN, —(CH₂)_s OH, halogen, —$(C(R^6)_2)_r C_6$-$C_{10}$ aryl, —$(C(R^6)_2)_r S$—$C_6$-$C_{10}$ aryl, —$(C(R^6)_2)_r$heteroaryl, —$O(C(R^6)_2)_r$heteroaryl, —$O(C(R^6)_2)_r$heterocycloalkyl, —$O(C(R^6)_2)_r OH$, —$OR^y$, —$(C(R^6)_2)_r C(O)NHCN$, —CH=CHCO₂$R^x$, or —$(C(R^6)_2)_r C(O)NHS(O)_2 C_1$-$C_4$ alkyl, wherein the aryl and heteroaryl are substituted with one to three substituents each independently selected from $C_1$-$C_6$ alkyl, $C_1$-$C_6$ haloalkyl, halogen, and OH, and wherein the heterocycloalkyl is substituted with one to two =O or =S;
$R^c$ is H, $C_1$-$C_6$ alkyl, $C_1$-$C_6$ haloalkyl, halogen, —CN, —$OR^x$, or —$CO_2 R^x$;
$R^d$ is methyl, $CF_3$, $CR^f F_2$, —$(C(R^6)_2)_r C_6$-$C_{10}$ aryl, —$(C(R^6)_2)_r$-5- or 6-membered heteroaryl, —$(C(R^6)_2)_r$-5- or 6-membered cycloalkyl, optionally substituted $C_6$-$C_{10}$ aryl, optionally substituted 5- or 6-membered heteroaryl, or optionally substituted 5- or 6-membered cycloalkyl;
each $R^e$ is independently at each occurrence $C_1$-$C_6$ alkyl, $C_2$-$C_6$ alkenyl, $C_2$-$C_6$ alkynyl, halogen, $C_1$-$C_6$ haloalkyl, —$NHR^z$, —OH, or —CN;
$R^f$ is absent, H, or methyl;
$R^g$ is H, $C_1$-$C_6$ alkyl, OH, —S(O)₂($C_1$-$C_6$ alkyl), or S(O)₂N($C_1$-$C_6$ alkyl)₂;
$R^{g'}$ is H, $C_1$-$C_6$ alkyl, $C_3$-$C_7$ cycloalkyl, 4- to 7-membered heterocycloalkyl ring comprising 1-3 heteroatoms selected from N, O and S, $C_6$-$C_{10}$ aryl, or 5- to 7-membered heteroaryl comprising 1-3 heteroatoms selected from N, O and S, wherein the alkyl is optionally substituted with one or more substituents independently selected from halogen and —OH, and wherein the cycloalkyl, heterocycloalkyl, aryl and heteroaryl are optionally substituted with one or more substituents independently selected from $C_1$-$C_6$ alkyl, halogen, and —OH;
$R^h$ is H, $C_1$-$C_4$ alkyl, or 3- to 7-membered heterocycloalkyl ring comprising 1-3 heteroatoms selected from N, O and S, wherein the alkyl is optionally substituted with one or more substituents each independently selected from NH₂, $C_1$-$C_4$ alkylamino, $C_1$-$C_4$ dialkylamino, and C(O)NH$_2$; and wherein the heterocycloalkyl is optionally substituted with one or more substituents each independently selected from C$_1$-C$_6$ alkyl and C$_1$-C$_6$ haloalkyl;

R$^i$ is (i) —(CH$_2$)$_s$OC(O)C$_1$-C$_6$ alkyl, wherein the alkyl is substituted with one or more NH$_2$; (ii) (CH$_2$CH$_2$O)$_n$CH$_2$CH$_2$OH; or (iii) C$_1$-C$_6$ alkyl substituted with one or more substituents each independently selected from OH and 4- to 7-membered heterocycloalkyl comprising 1 to 3 heteroatoms selected from O, N, or S;

R$^j$ is absent, H, C$_1$-C$_6$ alkyl, or —CN;

each R$^x$ is independently at each occurrence H, C$_1$-C$_6$ alkyl, or C$_6$-C$_{10}$ aryl;

each R$^y$ and R$^z$ is independently H, C$_1$-C$_6$ alkyl, or C$_1$-C$_6$ haloalkyl;

each m, p, q, r, and t is independently 0, 1 or 2;

n is 0, 1, 2, or 3;

s is 1 or 2;

o is 0, 1, 2, 3, or 4; and

=== represents a single bond or a double bond; and provided that when X is O; R$^f$ is H; W is C; R$^j$ is —CN; L is —SCH$_2$—; R$^1$ is phenylene or pyridine; then R$^7$ is not —COOH;

when X is O; R$^f$ is H; W is C; R$^j$ is —CN; L is —SCH$_2$—; R$^1$ is phenylene or pyridine; and R$^7$ is tetrazole; then R is not H;

when X is O; R$^f$ is H; W is C; R$^j$ is —CN; L is —S—C(R$^5$)$_2$ or —SCH$_2$CH$_2$—; R$^1$ is absent; then R$^7$ is not COOH or tetrazole;

when X is O, R$^f$ is H; W is N; R$^j$ is absent; R$^d$ is methyl, optionally substituted 5- to 10-membered aryl, optionally substituted 5- or 6-membered heteroaryl, or optionally substituted 5- or 6-membered cycloalkyl; L is —SCH$_2$— or —OCH$_2$—; and R$^1$ is phenylene; then R$^7$ is not —COOH, —CH$_2$COOH,

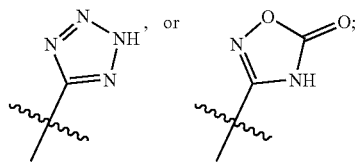 [SMILES: *c1nn[nH]n1 ; *c1noc(=O)[nH]1]

and when X is O, R$^f$ is H, W is N, R$^j$ is absent, L is —NHCH$_2$—, —CH$_2$NH—, or —NH—C(O)—, and R$^1$ is phenylene, then R$^d$ is not phenyl.

Embodiment II-3. The compound of Embodiment II-1 or II-2, wherein X is O, OH, OR$^h$, F, Br, or Cl.

Embodiment II-4. The compound of Embodiment II-1 or II-2, wherein X is H, S, SR$^2$, NR$^2$, or NR$^2$R$^2$.

Embodiment II-5. The compound of any one of Embodiments II-1 to II-4, wherein R$^f$ is absent.

Embodiment II-6. The compound of any one of Embodiments II-1 to II-4, wherein R$^f$ is H or methyl.

Embodiment II-7. The compound of any one of Embodiments II-1 to II-6, wherein W is N.

Embodiment II-8. The compound of Embodiment II-7, wherein R$^j$ is absent.

Embodiment II-9. The compound of any one Embodiments II-1 to II-6, wherein W is C.

Embodiment II-10. The compound of Embodiment II-9, wherein R$^j$ is H, C$_1$-C$_6$ alkyl, or —CN.

Embodiment II-11. The compound of Embodiments II-9 or II-10, wherein R$^j$ is —CN.

Embodiment II-12. The compound of any one of Embodiments II-1 to II-11, wherein R$^c$ is C$_1$-C$_6$ alkyl, —CN, or halogen.

Embodiment II-13. The compound of any one of Embodiments II-1 to II-12, wherein R$^c$ is —CN or halogen.

Embodiment II-14. The compound of any one of Embodiments II-1 to II-12, wherein R is —CN.

Embodiment II-15. The compound of any one of Embodiments II-1 to II-14, wherein R$^d$ is methyl.

Embodiment II-16. The compound of any one of Embodiments II-1 to II-14, wherein R$^d$ is optionally substituted 5- to 10-membered aryl.

Embodiment II-17. The compound of any one of Embodiments II-1 to II-14, wherein R$^d$ is optionally substituted 5- or 6-membered heteroaryl.

Embodiment II-18. The compound of any one of Embodiments II-1 to II-14, wherein R$^d$ is optionally substituted 5- or 6-membered cycloalkyl.

Embodiment II-19. The compound of any one of Embodiments II-1 to II-14, wherein R$^d$ is methyl, cyclohexyl, pyridinyl, thiazolyl, phenyl, or thienyl.

Embodiment II-20. The compound of any one of Embodiments II-1 to II-14, wherein R$^d$ is methyl, cyclohexyl, pyridinyl, thiazolyl, thienyl, or optionally substituted phenyl.

Embodiment II-21. The compound of any one of Embodiments II-1 to II-14, wherein R$^d$ is methyl.

Embodiment II-22. The compound of any one of Embodiments II-1 to II-14, wherein R$^d$ is —CF$_3$.

Embodiment II-23. The compound of any one of Embodiments II-1 to II-14, wherein R$^d$ is CR$^f$F$_2$.

Embodiment II-24. The compound of any one of Embodiments II-1 to II-14, wherein R$^d$ is —(C(R$^6$)$_2$)$_r$C$_6$-C$_{10}$ aryl, —(C(R$^6$)$_2$)$_r$-5- or 6-membered heteroaryl, —(C(R$^6$)$_2$)$_r$-5- or 6-membered cycloalkyl.

Embodiment II-25. The compound of any one of Embodiments II-1 to II-14, wherein R$^d$ is —(C(R$^6$)$_2$)$_r$C$_6$-C$_{10}$ aryl.

Embodiment II-26. The compound of any one of Embodiments II-1 to II-25, wherein L is —(C(R$^5$)$_2$)$_m$Y$^1$(C(R$^5$)$_2$)$_p$—.

Embodiment II-27. The compound of Embodiment II-26, wherein Y$^1$ is S.

Embodiment II-28. The compound of any one of Embodiments II-1 to II-25, wherein L is —(C(R$^5$)$_2$)$_m$NR$^3$C=(O)(C(R$^5$)$_2$)$_p$— or —(C(R$^5$)$_2$)$_m$Y$^1$(C(R$^5$)$_2$)$_p$-cyclopropyl-.

Embodiment II-29. The compound of any one of Embodiments II-1 to II-28, wherein R$^1$ is C$_6$-C$_{10}$ arylene.

Embodiment II-30. The compound of any one of Embodiments II-1 to II-28, wherein R$^1$ is heteroarylene.

Embodiment II-31. The compound of any one of Embodiments II-1 to II-28, wherein R$^1$ is absent.

Embodiment II-32. The compound of any one of Embodiments II-1 to II-31, wherein R$^7$ is A.

Embodiment II-33. The compound of Embodiment II-32, wherein A is —(C(R$^6$)$_2$)$_r$CO$_2$R$^x$ or —(CH$_2$)$_t$tetrazole, wherein the —(CH$_2$)$_t$tetrazole is optionally substituted with C$_1$-C$_6$ alkyl.

Embodiment II-34. The compound of any one of Embodiments II-1 to II-31, wherein R$^7$ is B.

Embodiment II-35. The compound of Embodiment II-32, wherein B is —(CH$_2$)$_r$C(O)NR$^g$R$^{g'}$, or —(CH$_2$)$_r$S(O)$_2$NR$^g$R$^{g'}$, Embodiment II-36. The compound of any one of Embodiments II-1 to II-31, wherein R$^7$ is C.

Embodiment II-37. The compound of Embodiment II-32, wherein C is —(CH$_2$)$_r$CN, —(CH$_2$)$_s$OH, or —(C(R$^6$)$_2$)$_r$C$_6$-C$_{10}$ aryl, wherein the aryl is substituted with one to three substituents each independently selected from $C_1$-$C_6$ alkyl, $C_1$-$C_6$ haloalkyl, halogen, and OH.

Embodiment II-38. A compound, or a pharmaceutically acceptable salt or tautomer thereof, selected from the group consisting of:

| Cpd No. | Structure |
|---|---|
| I-1 | |
| I-2 | |
| I-3 | |
| I-4 | |
| I-5 | |
| I-6 | |
| I-7 | 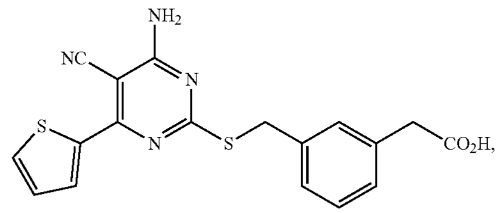 [SMILES: N#Cc1c(N)nc(SCc2cccc(CC(=O)O)c2)nc1-c1cccs1] |
| I-8 | 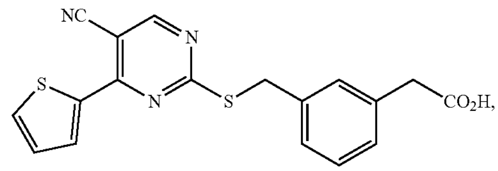 [SMILES: N#Cc1cnc(SCc2cccc(CC(=O)O)c2)nc1-c1cccs1] |
| I-9 | 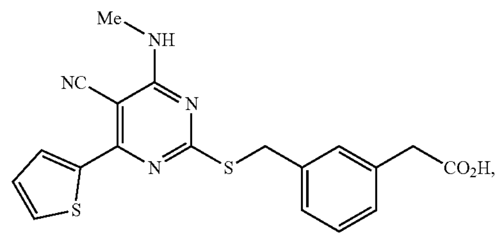 [SMILES: CNc1nc(SCc2cccc(CC(=O)O)c2)nc(-c2cccs2)c1C#N] |
| I-10 | 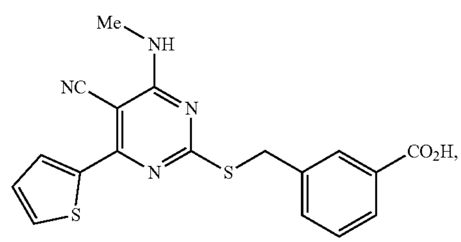 [SMILES: CNc1nc(SCc2cccc(C(=O)O)c2)nc(-c2cccs2)c1C#N] |
| I-11 | 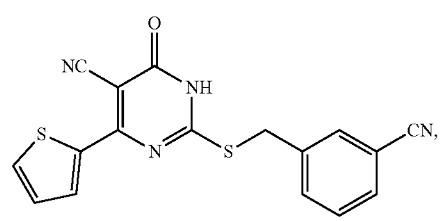 [SMILES: N#Cc1cccc(CSc2nc(-c3cccs3)c(C#N)c(=O)[nH]2)c1] |
| I-12 | 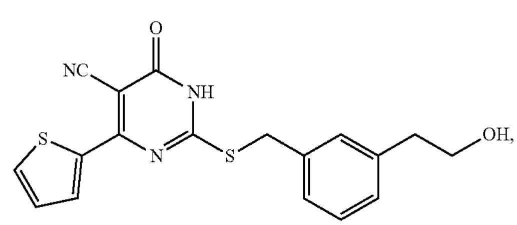 [SMILES: N#Cc1c(-c2cccs2)nc(SCc2cccc(CCO)c2)[nH]c1=O] |
| I-13 | 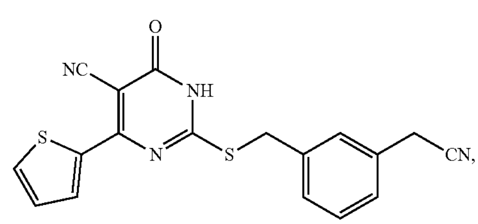 [SMILES: N#CCc1cccc(CSc2nc(-c3cccs3)c(C#N)c(=O)[nH]2)c1] |

| Cpd No. | Structure |
|---|---|
| I-14 | 5-cyano-6-(thiophen-2-yl)-2-((3-(2-methyl-2H-tetrazol-5-yl)benzyl)thio)pyrimidin-4(3H)-one |
| I-15 | 2-(3-(((5-cyano-6-morpholino-4-(thiophen-2-yl)pyrimidin-2-yl)thio)methyl)phenyl)acetic acid |
| I-16 | 2-(3-(((5-cyano-6-(piperazin-1-yl)-4-(thiophen-2-yl)pyrimidin-2-yl)thio)methyl)phenyl)acetic acid |
| I-17 | ethyl 2-(3-(((5-cyano-1-methyl-6-oxo-4-(thiophen-2-yl)-1,6-dihydropyrimidin-2-yl)thio)methyl)phenyl)acetate |
| I-18 | 3-(((5-cyano-6-oxo-4-(thiophen-2-yl)-1,6-dihydropyrimidin-2-yl)thio)methyl)benzenesulfonamide |
| I-19 | 2-(3-(((3-cyano-6-oxo-4-phenyl-1,6-dihydropyridin-2-yl)thio)methyl)phenyl)acetic acid |
| I-20 | 2-(3-(((3-cyano-6-oxo-4-(thiophen-2-yl)-1,6-dihydropyridin-2-yl)thio)methyl)phenyl)acetic acid |
| I-21 | 2-(3-(((3,5-dicyano-6-oxo-4-(thiophen-2-yl)-1,6-dihydropyridin-2-yl)thio)methyl)phenyl)acetic acid |
| I-22 | 6-(((3-(1H-tetrazol-5-yl)benzyl)thio)-2-oxo-4-(thiophen-2-yl)-1,2-dihydropyridine-3,5-dicarbonitrile |
| I-23 | 2-(3-(((4-benzyl-3-cyano-6-oxo-1,6-dihydropyridin-2-yl)thio)methyl)phenyl)acetic acid |
| I-24 | 2-((5-cyano-6-oxo-4-(thiophen-2-yl)-1,6-dihydropyrimidin-2-yl)thio)acetic acid |
| I-25 | 2-(((1H-tetrazol-5-yl)methyl)thio)-6-oxo-4-(thiophen-2-yl)-1,6-dihydropyrimidine-5-carbonitrile |
| I-26 | 2-(((1H-tetrazol-5-yl)methyl)thio)-6-(trifluoromethyl)pyrimidin-4(3H)-one |

| Cpd No. | Structure |
|---|---|
| I-27 | 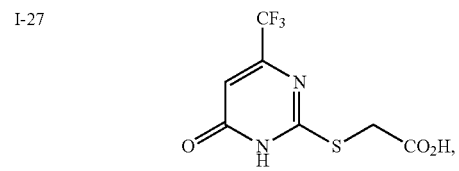 |
| I-28 | 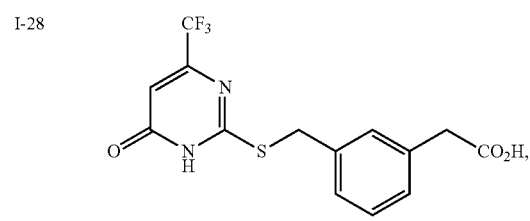 |
| I-29 | 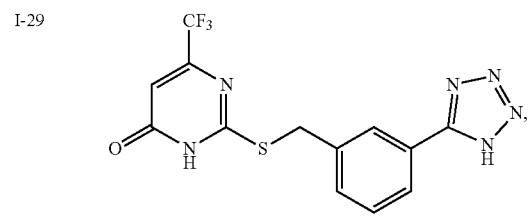 |
| I-30 | 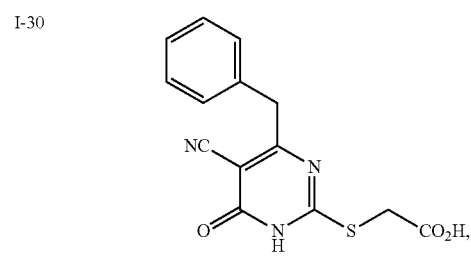 |
| I-31 | 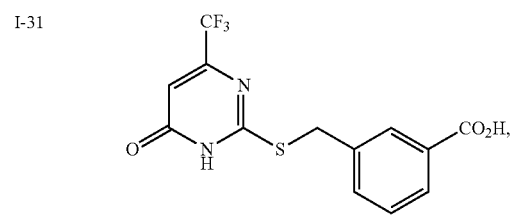 |
| I-32 | 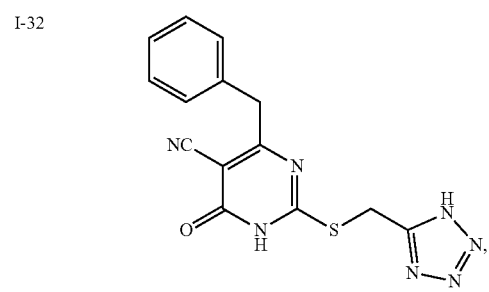 |
| Cpd No. | Structure |
|---|---|
| I-33 | 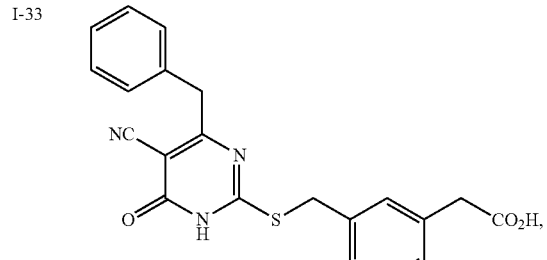 |
| I-34 | 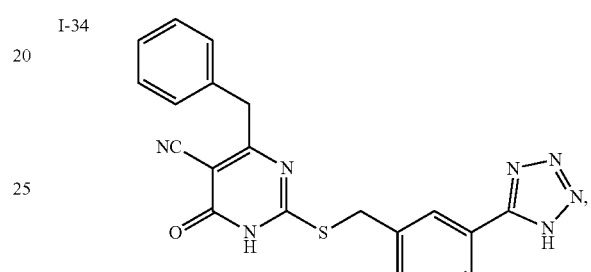 |
| I-35 | 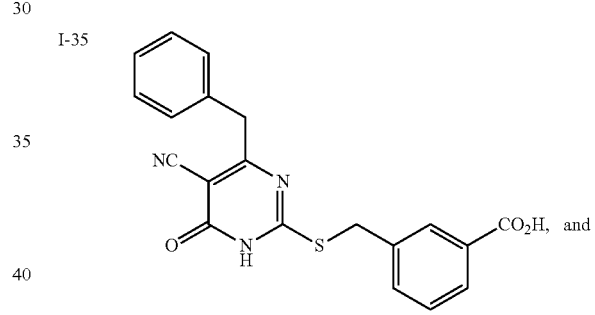 |
| I-36 | 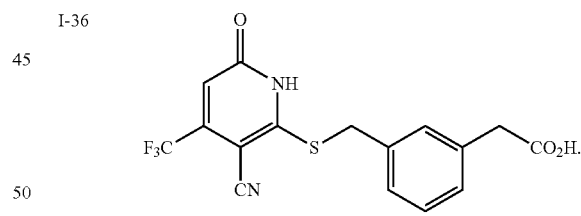 |
Embodiment II-39. A compound, or a pharmaceutically acceptable salt or tautomer thereof, selected from the group consisting of:
I-37
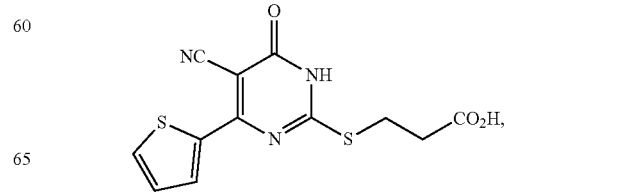

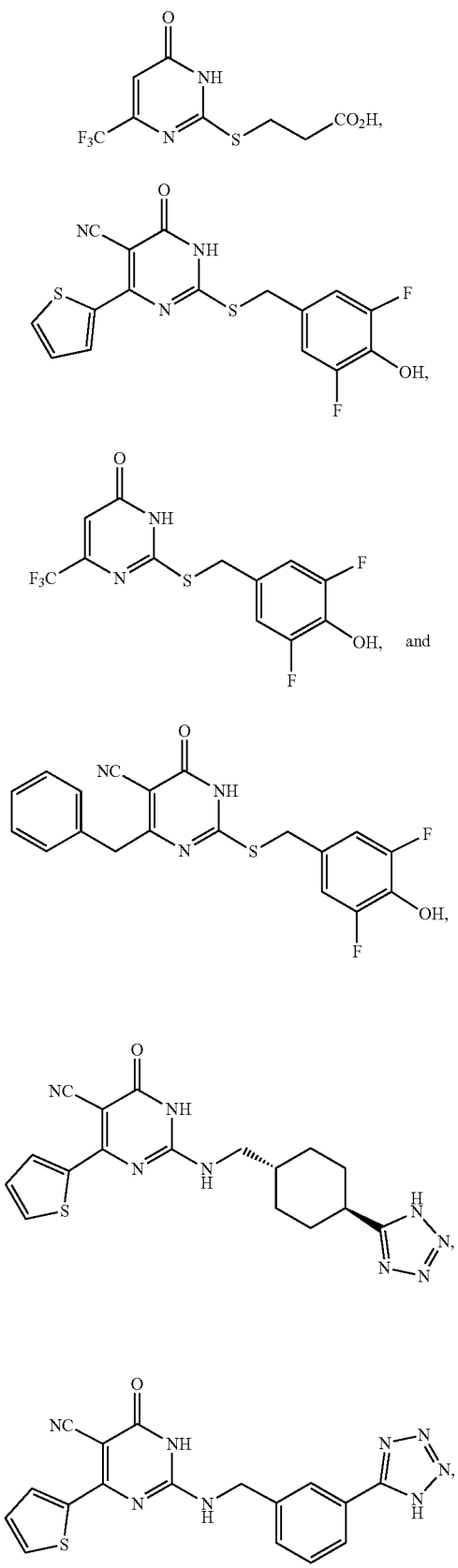
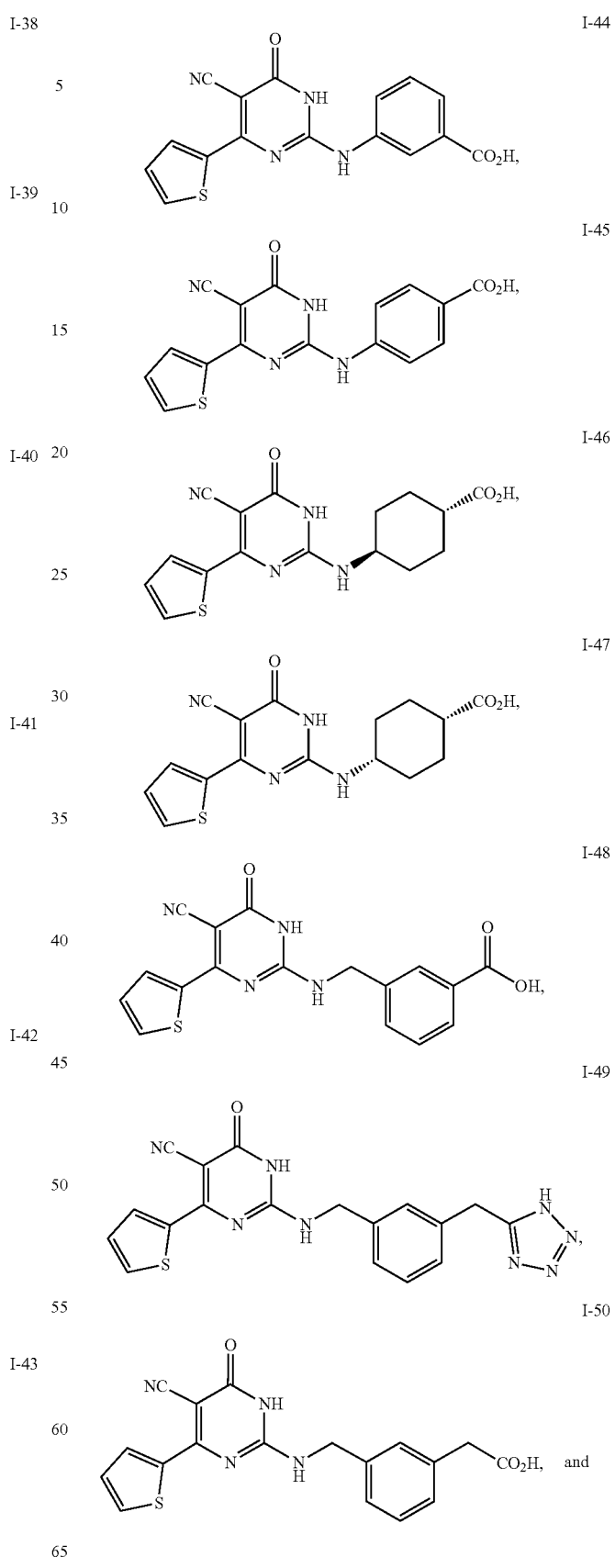

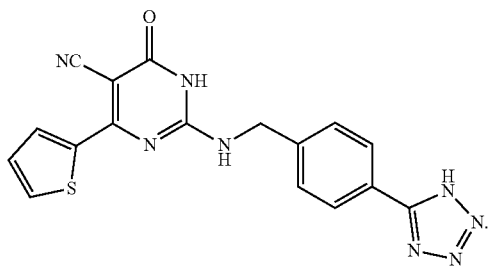
I-51
Embodiment II-40. A compound, or a pharmaceutically acceptable salt or tautomer thereof, selected from the group consisting of:
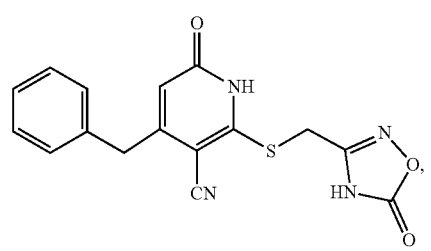 [SMILES: N#Cc1c(Cc2ccccc2)cc(=O)[nH]c1SCc1noc(=O)[nH]1]
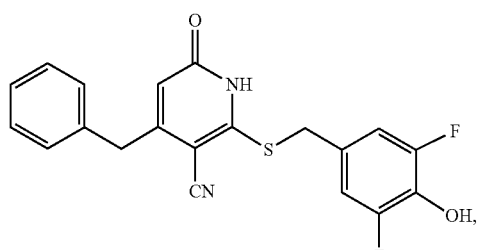
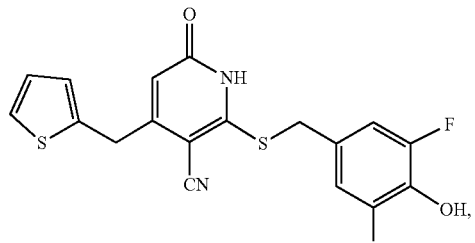
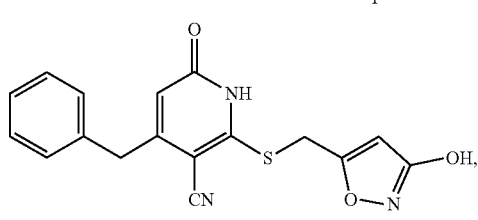
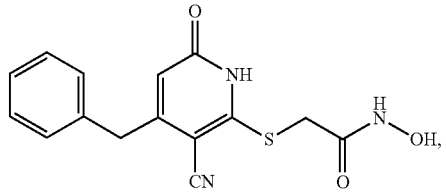
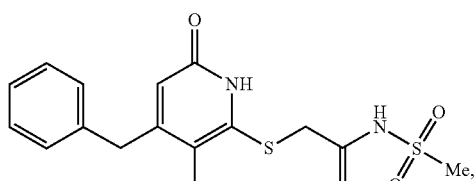
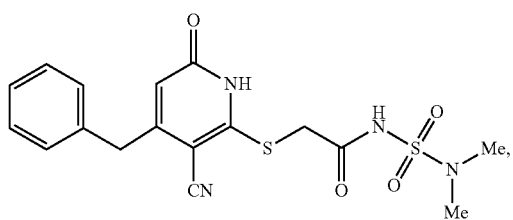
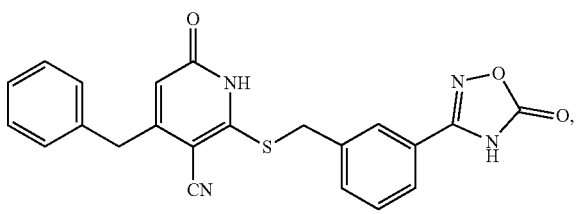
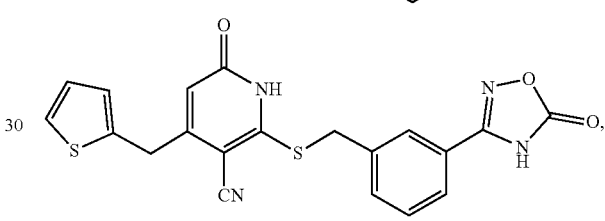
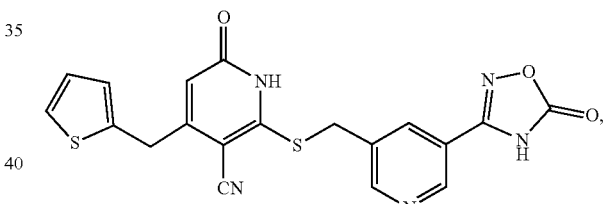
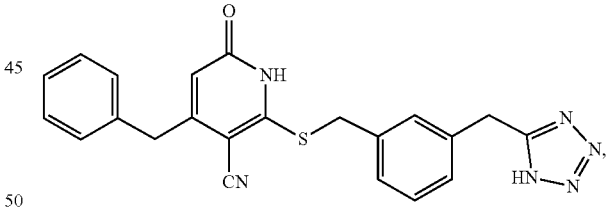
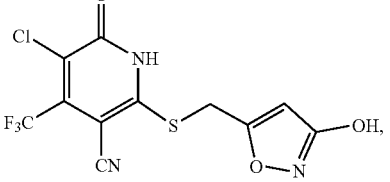
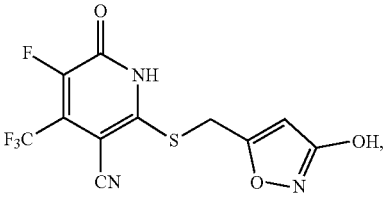

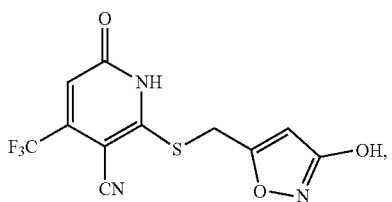
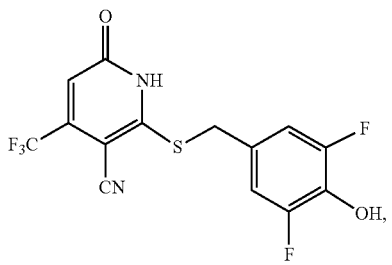
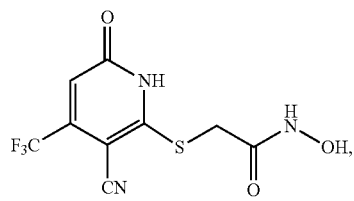
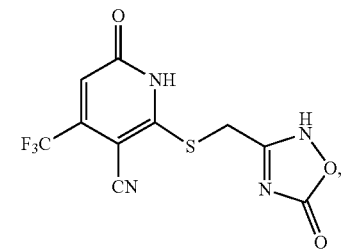
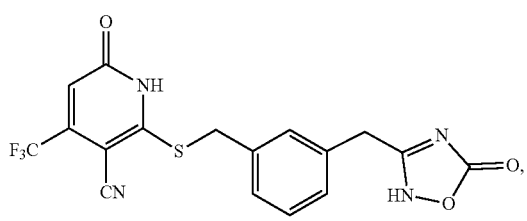
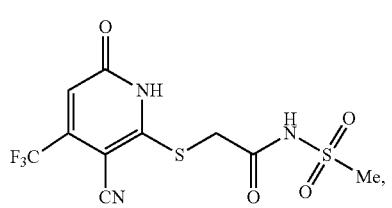
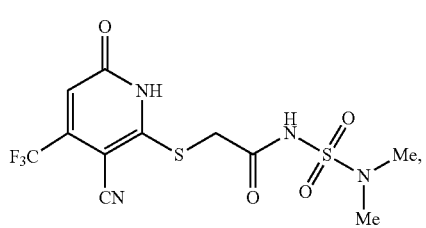
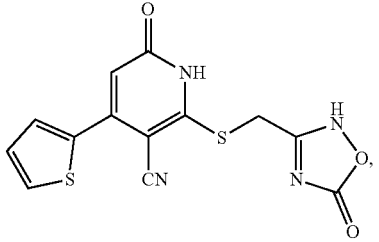
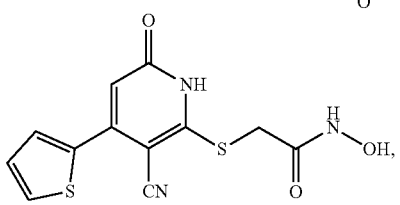
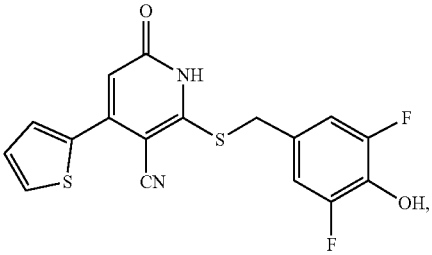
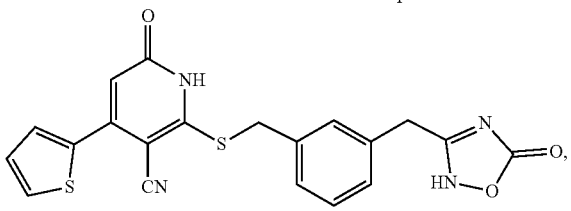
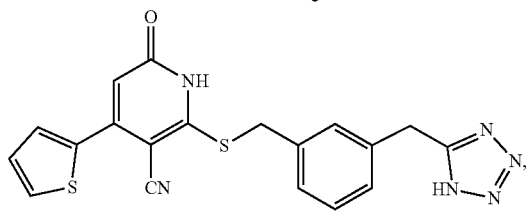
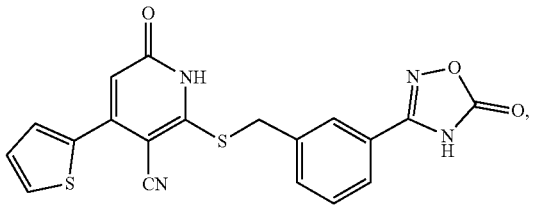
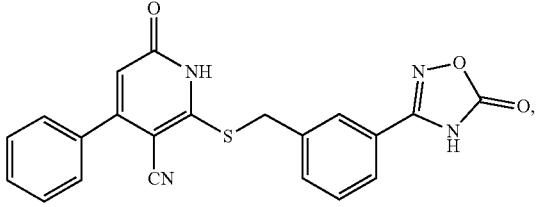
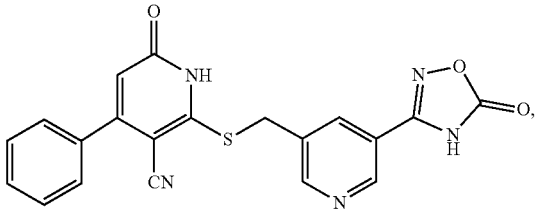

121
-continued
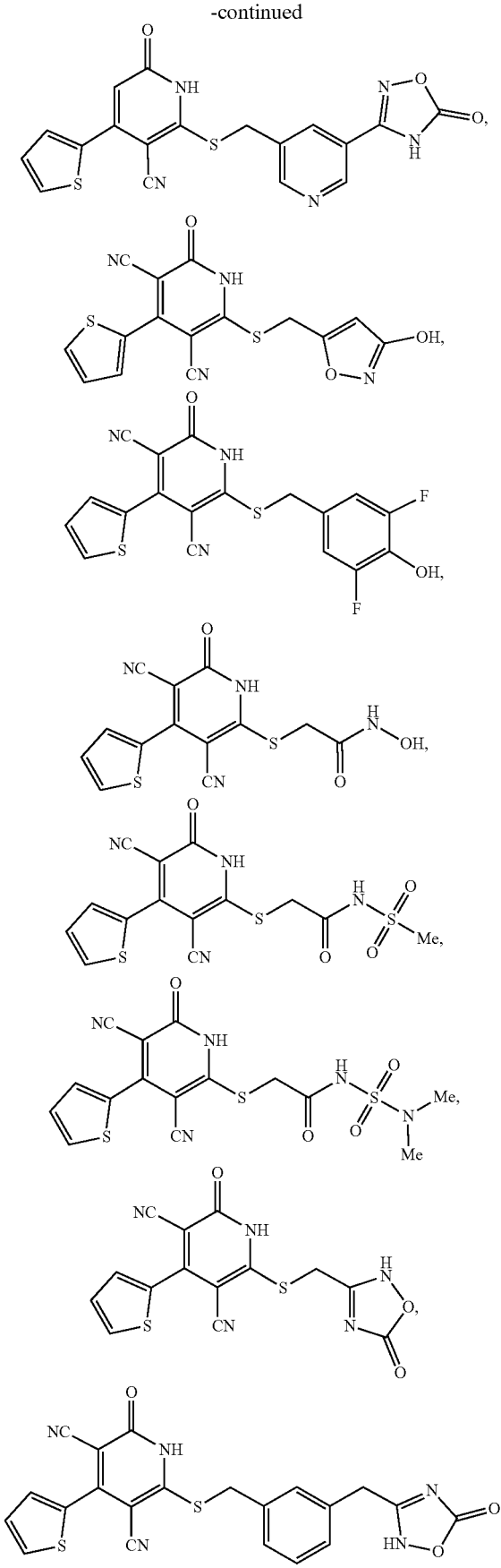
122
-continued
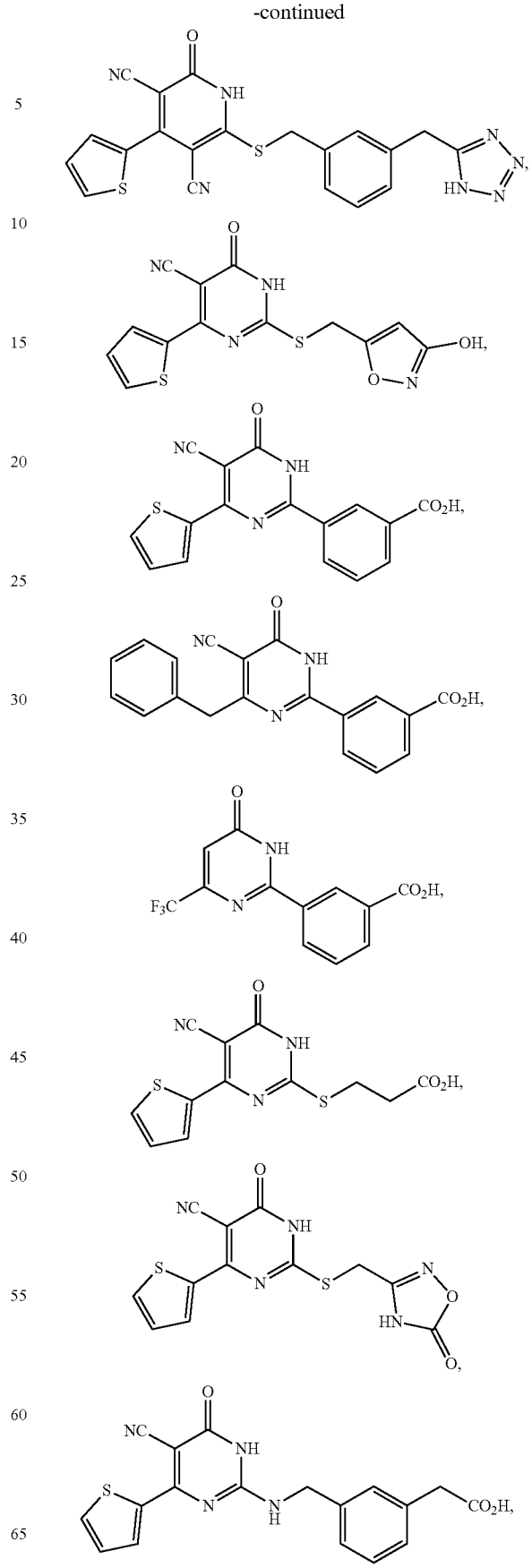

-continued
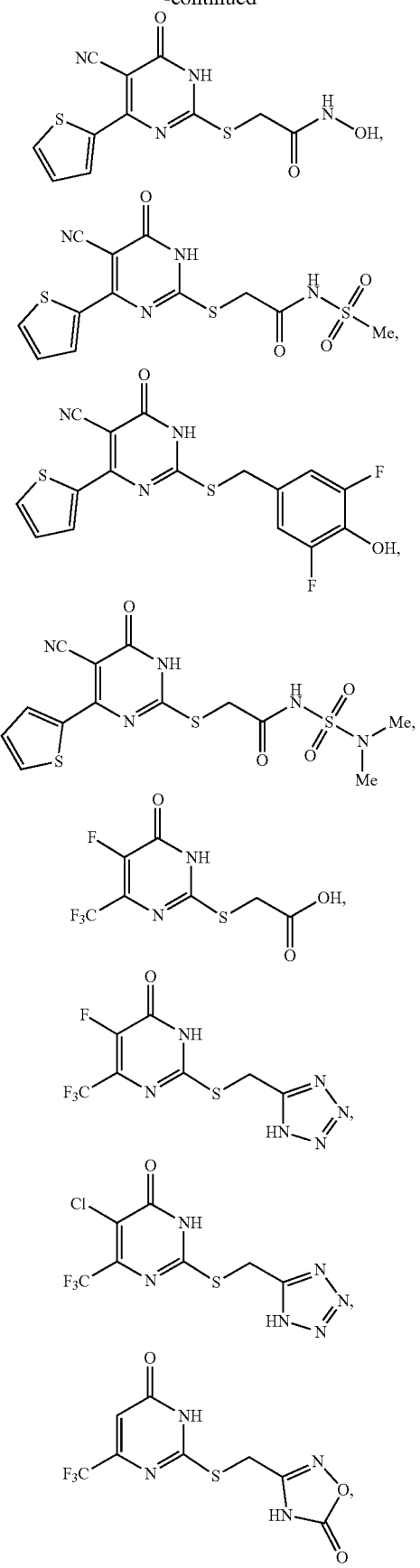
-continued
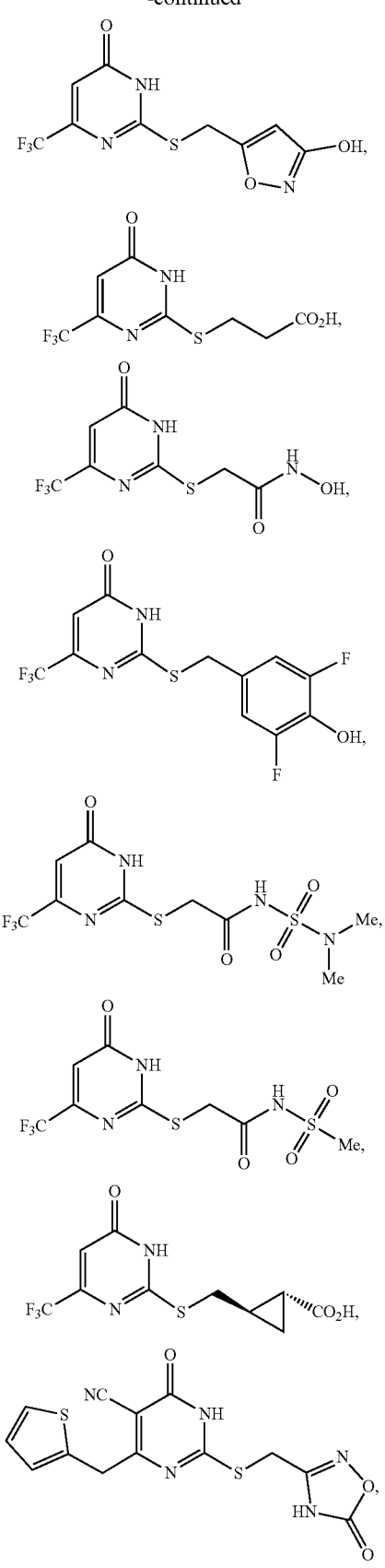

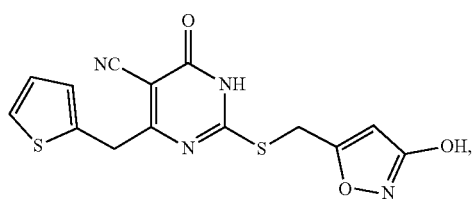
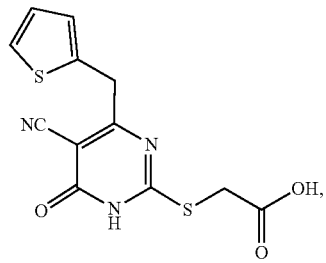
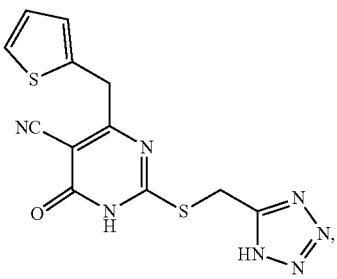
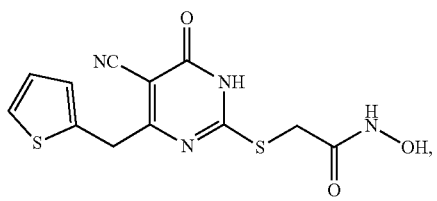
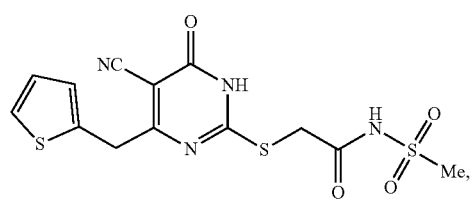
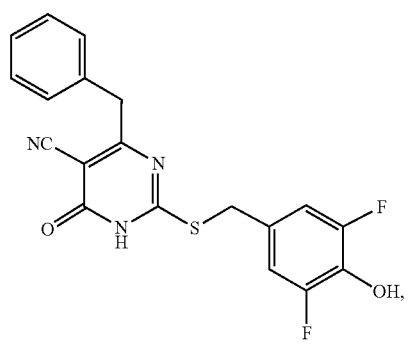
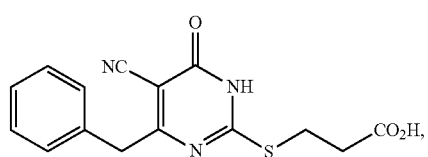
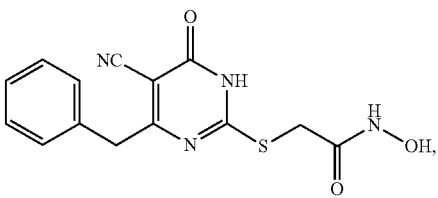
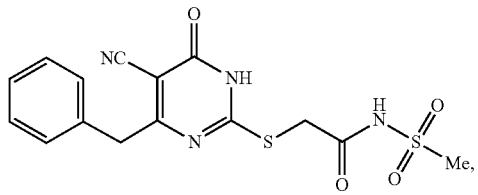
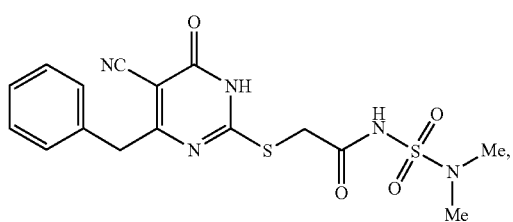
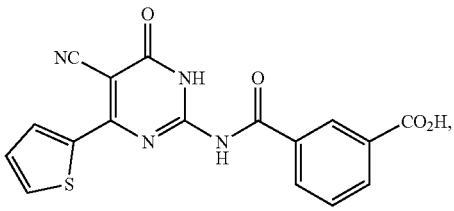
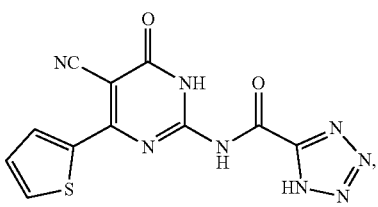
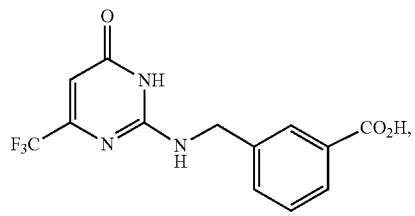
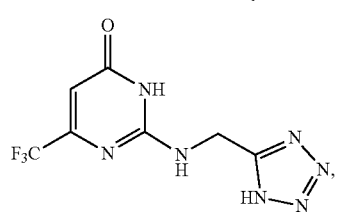
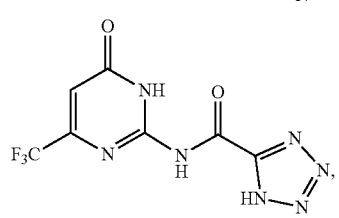

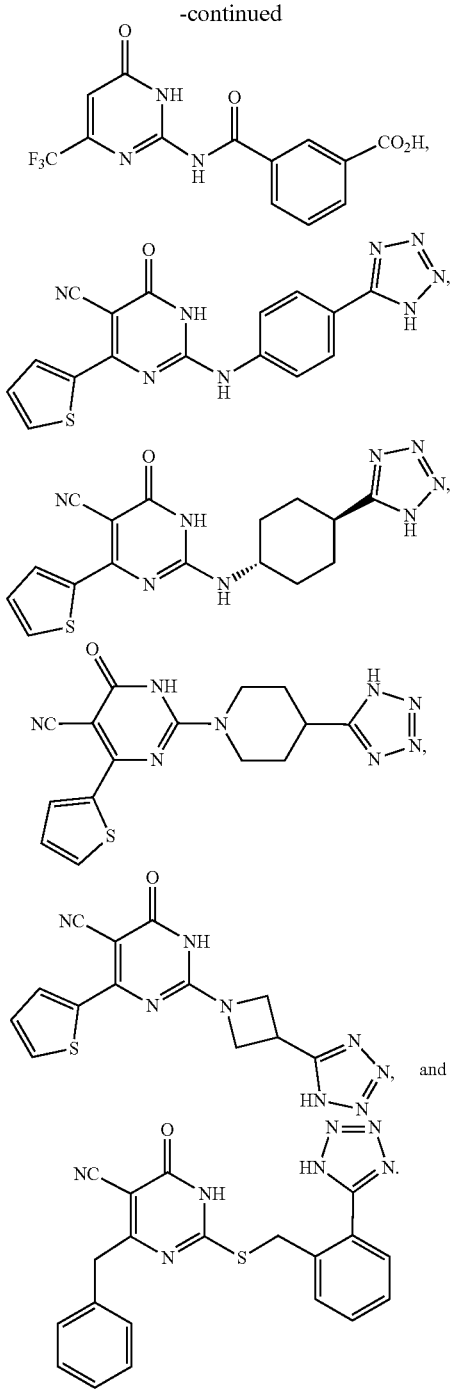

Embodiment II-41. A pharmaceutical composition comprising a compound of any one of Embodiments II-1 to II-40, or a pharmaceutically acceptable salt thereof, and at least one of a pharmaceutically acceptable carrier, diluent, or excipient.

Embodiment II-42. The pharmaceutical composition according to Embodiment II-41, which comprises one or more further therapeutic agents.

Embodiment II-43. A method of treating, preventing, or reducing the risk of a disease or disorder inhibited by α-amino-β-carboxymuconate-ε-semialdehyde decarboxylase (ACMSD) comprising administering to the subject suffering from or susceptible to developing the disease or disorder a therapeutically effective amount of one or more compounds of any one of Embodiments II-1 to II-40, or a pharmaceutically acceptable salt thereof.

Embodiment II-44. A method of treating, preventing, or reducing the risk of a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of one or more compounds of any one of Embodiments II-1 to II-40, or a pharmaceutically acceptable salt thereof.

Embodiment II-45. The method of any one of Embodiments II-43 to II-44, wherein the disease is chronic liver disease selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

Embodiment II-46. A method of treating a disorder associated with mitochondrial dysfunction comprising administering to the subject suffering from or susceptible to developing a metabolic disorder a therapeutically effective amount of one or more compounds of any one of Embodiments II-1 to II-40, or a pharmaceutically acceptable salt thereof, that increases intracellular nicotinamide adenine dinucleotide (NAD$^+$).

Embodiment II-47. The method of Embodiment II-46, wherein said disorder associated with mitochondrial dysfunction is an inherited mitochondrial disease, a common metabolic disorder, a neurodegenerative disease, an aging related disorder, a kidney disorder, or a chronic inflammatory disease.

Embodiment II-48. The method of Embodiment II-47, wherein the common metabolic disorder is obesity or type II diabetes.

Embodiment II-49. A method of promoting oxidative metabolism comprising administering to the subject suffering from or susceptible to developing a metabolic disorder a therapeutically effective amount of one or more compounds of any one of Embodiments II-1 to II-40, or a pharmaceutically acceptable salt thereof, that increases intracellular nicotinamide adenine dinucleotide (NAD$^+$).

Embodiment II-50. A compound of any of Embodiments II-1 to II-40, or a pharmaceutically acceptable salt thereof, for use as a medicament.

Embodiment II-51. A compound of any of Embodiments II-1 to II-40, or a pharmaceutically acceptable salt thereof, for use in treating, preventing, or reducing the risk of a disease or disorder associated with reduced nicotinamide adenine dinucleotide (NAD$^+$) levels.

Embodiment II-52. A compound of any of Embodiments II-1 to II-40, or a pharmaceutically acceptable salt thereof, for use in for treating, preventing, or reducing the risk of a disorder associated with mitochondrial dysfunction.

Embodiment II-53. A compound of any of Embodiments II-1 to II-40, or a pharmaceutically acceptable salt thereof, for use in promoting oxidative metabolism.

Embodiment II-54. Use of a compound of any of Embodiments II-1 to II-40, or a pharmaceutically acceptable salt thereof, for treating, preventing, or reducing the risk of a disease or disorder associated with α-amino-β-carboxymuconate-ε-semialdehyde decarboxylase (ACMSD) dysfunction.

Embodiment II-55. Use of a compound of any of Embodiments II-1 to II-40, or a pharmaceutically acceptable salt thereof, for treating, preventing, or reducing the risk of a disease or disorder associated with reduced nicotinamide adenine dinucleotide (NAD$^+$) levels.

Embodiment II-56. Use of a compound of any of Embodiments II-1 to II-40, or a pharmaceutically acceptable salt thereof, for treating, preventing, or reducing the risk of a disorder associated with mitochondrial dysfunction.

Embodiment II-57. Use of a compound of any of Embodiments II-1 to II-40, or a pharmaceutically acceptable salt thereof, for promoting oxidative metabolism.

Embodiment II-58. Use of a compound of any of Embodiments II-1 to II-40, or a pharmaceutically acceptable salt thereof, in the manufacture of a medicament for treating, preventing, or reducing the risk of a disease or disorder associated with α-amino-β-carboxymuconate-ε-semialdehyde decarboxylase (ACMSD) dysfunction.

Embodiment II-59. Use of a compound of any of Embodiments II-1 to II-40, or a pharmaceutically acceptable salt thereof, in the manufacture of a medicament for treating, preventing, or reducing the risk of a disease or disorder associated with reduced nicotinamide adenine dinucleotide (NAD$^+$) levels.

Embodiment II-60. Use of a compound of any of Embodiments II-1 to II-40, or a pharmaceutically acceptable salt thereof, in the manufacture of a medicament for treating, preventing, or reducing the risk of a disorder associated with mitochondrial dysfunction.

Embodiment II-61. Use of a compound of any of Embodiments II-1 to II-40, or a pharmaceutically acceptable salt thereof, in the manufacture of a medicament for promoting oxidative metabolism.

Embodiment II-62. A method of treating, preventing, or reducing the risk of a disease or disorder inhibited by α-amino-β-carboxymuconate-ε-semialdehyde decarboxylase (ACMSD) comprising administering to the subject suffering from or susceptible to developing the disease or disorder a therapeutically effective amount of a pharmaceutical composition of Embodiment II-41.

Embodiment II-63. A method of treating, preventing, or reducing the risk of a disease or disorder associated with reduced nicotinamide adenine dinucleotide (NAD$^+$) levels comprising administering to the subject suffering from or susceptible to developing a disease or disorder associated with reduced NAD$^+$ levels a therapeutically effective amount of a pharmaceutical composition of Embodiment II-41.

Embodiment II-64. The method of any one of Embodiments II-62 to II-63, wherein the disease is chronic liver disease selected from primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

Embodiment II-65. A method of treating a disorder associated with mitochondrial dysfunction comprising administering to the subject suffering from or susceptible to developing a metabolic disorder a therapeutically effective amount of a pharmaceutical composition of Embodiment II-41.

Embodiment II-66. The method of Embodiment II-65, wherein said disorder associated with mitochondrial dysfunction is an inherited mitochondrial disease, a common metabolic disorder, a neurodegenerative disease, an aging related disorder, a kidney disorder, or a chronic inflammatory disease.

Embodiment II-67. The method of Embodiment II-66, wherein the common metabolic disorder is obesity or type II diabetes.

Embodiment II-68. A method of promoting oxidative metabolism comprising administering to the subject suffering from or susceptible to developing a metabolic disorder a therapeutically effective amount of a pharmaceutical composition of Embodiment II-41.

Embodiment II-69. A pharmaceutical composition of Embodiment II-41 for use as a medicament.

Embodiment II-70. A pharmaceutical composition of Embodiment II-41 for use in treating, preventing, or reducing the risk of a disease or disorder associated with reduced nicotinamide adenine dinucleotide (NAD$^+$) levels.

Embodiment II-71. A pharmaceutical composition of Embodiment II-41 for use in for treating, preventing, or reducing the risk of a disorder associated with mitochondrial dysfunction.

Embodiment II-72. A pharmaceutical composition of Embodiment II-41 for use in promoting oxidative metabolism.

Embodiment II-73. Use of pharmaceutical composition of Embodiment II-41 for treating, preventing, or reducing the risk of a disease or disorder associated with α-amino-β-carboxymuconate-ε-semialdehyde decarboxylase (ACMSD) dysfunction.

Embodiment II-74. Use of a pharmaceutical composition of Embodiment II-41 for treating, preventing, or reducing the risk of a disease or disorder associated with reduced nicotinamide adenine dinucleotide (NAD$^+$) levels.

Embodiment II-75. Use of pharmaceutical composition of Embodiment II-41 for treating, preventing, or reducing the risk of a disorder associated with mitochondrial dysfunction.

Embodiment II-76. Use pharmaceutical composition of Embodiment II-41 for promoting oxidative metabolism.

Embodiment II-77. Use of pharmaceutical composition of Embodiment II-41 in the manufacture of a medicament for treating, preventing, or reducing the risk of a disease or disorder associated with α-amino-β-carboxymuconate-ε-semialdehyde decarboxylase (ACMSD) dysfunction.

Embodiment II-78. Use of pharmaceutical composition of Embodiment II-41 in the manufacture of a medicament for treating, preventing, or reducing the risk of a disease or disorder associated with reduced nicotinamide adenine dinucleotide (NAD$^+$) levels.

Embodiment II-79. Use of pharmaceutical composition of Embodiment II-41 in the manufacture of a medicament for treating, preventing, or reducing the risk of a disorder associated with mitochondrial dysfunction.

Embodiment II-80. Use of pharmaceutical composition of Embodiment II-41 in the manufacture of a medicament for promoting oxidative metabolism.

EXAMPLES

All percentages and ratios used herein, unless otherwise indicated, are by weight. Other features and advantages of the present disclosure will become apparent from the different examples. The provided examples illustrate different components and methodology useful in practicing the present disclosure. Generally speaking, the disclosure extends to any novel one, or any novel combination, of the features disclosed in this specification (including the accompanying claims and drawings). The examples do not limit the claimed disclosure. Thus, features, integers, characteristics, compounds or chemical moieties described in conjunction with a particular aspect, embodiment or example of the disclosure are to be understood to be applicable to any other aspect, embodiment or example described herein, unless incompatible therewith. Based on the present disclosure the skilled artisan can identify and employ other components and methodology useful for practicing the present disclosure. Moreover, unless stated otherwise, any feature disclosed herein may be replaced by an alternative feature serving the same or a similar purpose.

The Disclosure will now be described by way of example only with reference to the Examples below:

Exemplification

Compound Preparation

General Methods and Materials

All chemicals were purchased from Sigma-Aldrich, Alfa Aesar. $^1$H NMR spectra were recorded at 200 and 400 MHz and $^{13}$C NMR spectra were recorded at 100.6 and 50.3 MHz by using deuterated solvents indicated below. TLC were performed on aluminium backed silica plates (silica gel 60 F254). All the reactions were performed under nitrogen atmosphere using distilled solvents. All tested compounds were found to have >95% purity determined by HPLC analysis. HPLC-grade water was obtained from a tandem Milli-Ro/Milli-Q apparatus. The analytical HPLC measurements were made on a Shimadzu LC-20AProminence equipped with a CBM-20A communication bus module, two LC-20AD dual piston pumps, a SPD-M20A photodiode array detector and a Rheodyne 7725i injector with a 20 µL stainless steel loop.

Abbreviations used in the following examples and elsewhere herein are:

Ac$_2$O acetic anhydride
AcOH acetic acid
AIBN Azobisisobutyronitrile
atm atmosphere
br broad
DIPEA N,N-diisopropylethylamine
DCM dichloromethane
DME dimethoxyethane
DMF N,N-dimethylformamide
DMSO dimethyl sulfoxide
BPO Dibenzoylperoxide
EDC N-(3-Dimethylaminopropyl)-N-ethylcarbodiimide hydrochloride
ESI electrospray ionization
EtOAc ethyl acetate
EtO$_2$ diethyl ether
EtOH ethanol
EtO$^-$Na$^+$ sodium ethoxide
Et$_3$NH$^+$Cl$^-$ triethylamine hydrochloride
h hour(s)
HPLC high-performance liquid chromatography
LCMS liquid chromatography-mass spectrometry
m multiplet
MeI methyl iodide
MeOH methanol
MHz megahertz
min minutes
MS molecular sieves
MTBE 2-methoxy-2-methylpropane
MW microwave
NBS N-bromosuccinamide
NMR nuclear magnetic resonance
PET petroleum ether
ppm parts per million
p-TSA para-toluenesulfonic acid
r.t. room temperature
TLC thin layer chromatography Example 1: Intermediate 1.4. 4-Oxo-6-thiophen-2-yl-2-thioxo-1,2,3,4-tetrahydro-pyrimidine-5-carbonitrile

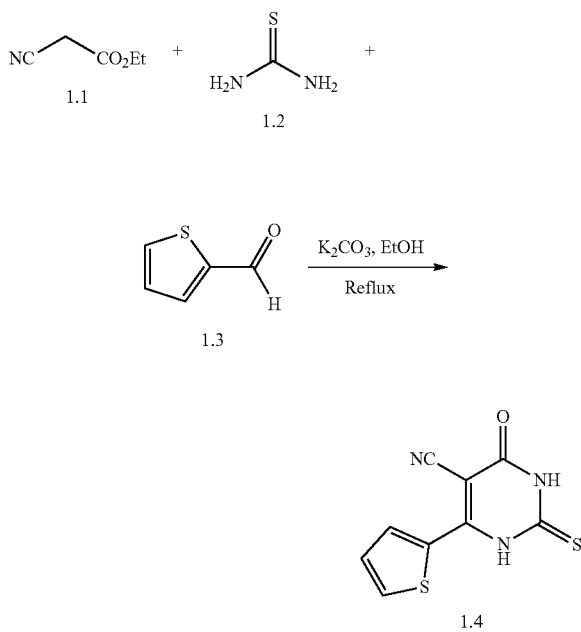

To a stirred solution of compound 1.1 (0.96 g, 8.8 mmol), 1.2 (672 mg, 8.8 mmol) and 1.3 (1 g, 0.83 mL) in ethanol (55 mL) was added K$_2$CO$_3$ (1.57 g, 11.44 mmol). Stirring was continued at reflux overnight. The yellowish solid formed was collected after cooling, taken up with hot water and filtered again. The aqueous phase was acidified to pH1, the precipitate was filtered and dried under reduced pressure. The title compound 1.4 was obtained as a yellowish solid (1 g, 4.25 mmol). Yield 49%. $^1$H NMR (200 MHz, DMSO-d$_6$) δ 7.22 (m, 1H), 7.68 (m, 1H), 7.85 (d, J=4.8 Hz, 1H), 8.05 (s, 1H).

Example 2: Intermediate 2.2. Sodium; 6-oxo-4-trifluoromethyl-1,6-dihydro-pyrimidine-2-thiolate

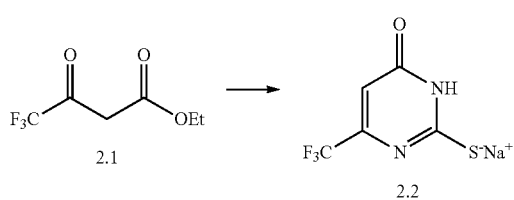

Sodium (0.35 g, 16.29 mmol) was dissolved in abs. EtOH (25 mL) under N$_2$ atmosphere. To the resulting solution ethyl trifluoroacetoacetate 2.1 (1.59 mL, 10.86 mmol) and thiourea 1.2 (0.91 g, 11.94 g) were added. The mixture was stirred and refluxed for 4 h. Once cooled at room temperature the obtained precipitate was collected by filtration under vacuum and washed with cold EtOH (2×5 mL), to afford (1.34 g, 6.14 mmol) of intermediate 2.2. Yield 38%. MS-ESI (−) m/z: 194.8 [M−H].

Example 3: Intermediate 3.3. 2-Mercapto-6-oxo-4-phenyl-1,6-dihydro-pyridine-3-carbonitrile

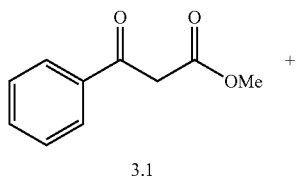

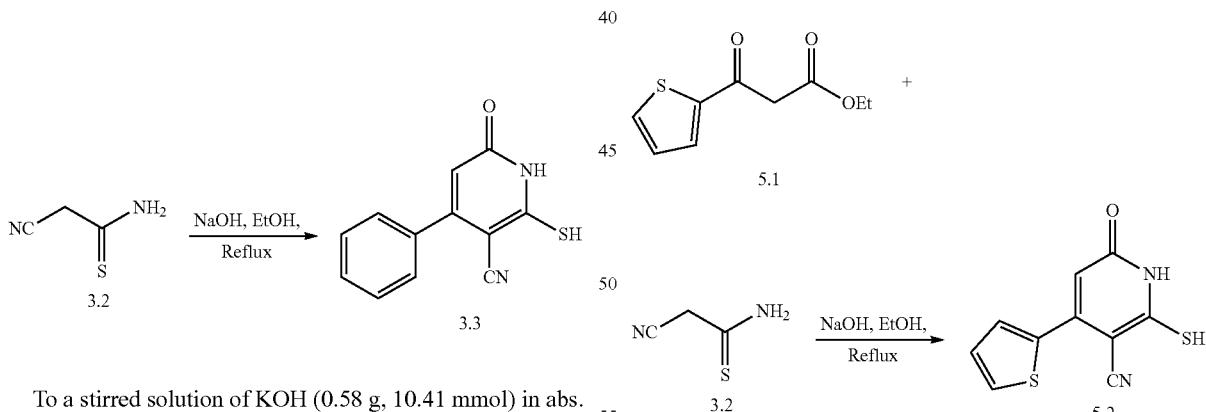

To a stirred solution of KOH (0.58 g, 10.41 mmol) in abs. EtOH (20 mL), ethyl 3-oxo-3-phenyl-propionate 3.1 (1.80 mL, 10.41 mmol) and 2-cyanothioacetamide 3.2 (1.04 g, 10.41 mmol) were added, and the resulting mixture was stirred and refluxed for 3 hours. Then it was cooled at room temperature and concentrated under reduced pressure. The crude was poured in H$_2$O (20 mL) and washed with AcOEt (2×15 mL). The organic phase was acidified un to pH=2 by adding aq. HCl 37%, and the resulting precipitate was collected by filtration under vacuum and washed with H$_2$O (2×5 mL). The solid was then titered with AcMe, to give intermediate 3.3 (0.49 g, 2.14 mmol) as a yellowish solid. Yield 21%. MS-ESI(−) m/z: 227.3 [M−H]$^-$

Example 4: Intermediate 4.2. 4-Benzyl-2-mercapto-6-oxo-1,6-dihydro-pyrimidine-5-carbonitrile

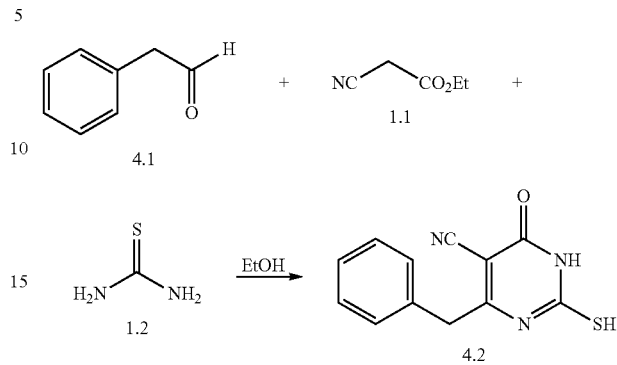

To a solution of phenyl acetaldehyde 4.1 (1.5 g, 16.65 mmol), ethylcyanoacetate 1.1 (1.41 g, 16.65 mmol) and thiourea 1.2 (950 mg, 16.65 mmol) in EtOH (35 mL) was added K$_2$CO$_3$ (2.2 g, 21.6 mmol). Stirring was continued at reflux 16 h. The mixture was cooled to r.t. The white solid was collected, dissolved in water. The pH was adjusted to 3 by the addition of 3N HCl. The aqueous phase was extracted with EtOAc (3×50 mL). The combined organic phase was washed with brine and dried over anhydrous Na$_2$SO$_4$. The title intermediate 4.2 (800 mg, 3.28 mmol) was obtained as a light yellow solid. Yield: 20%. $^1$H NMR (200 MHz, DMSO-d$_6$) δ 3.93 (s, 2H), 7.26-7.41 (m, 5H), 13.15 (brs, 1H).

Example 5: Intermediate 5.2. 2-Mercapto-6-oxo-4-thiophen-2-yl-1,6-dihydro-pyridine-3-carbonitrile To a stirred solution of KOH (0.28 g, 5.04 mmol) in abs. EtOH (10 mL), ethyl 3-oxo-3-thiophen-2-yl-propionate 5.1 (0.77 mL, 5.04 mmol) and 2-cyanothioacetamide 3.2 (0.50 g, 5.04 mmol) were added, and the resulting mixture was stirred at reflux for 8 hours. Then it was cooled at room temperature and the precipitate formed was collected by filtration under vacuum and washed with EtOH (2×5 mL), to give intermediate 5.2 (0.17 g, 0.72) as a yellowish solid. Yield 12%. MS-ESI(−) m/z: 233.3 [M−H]$^-$.

135

Example 6: Intermediate 6.4. 6-Mercapto-2-oxo-4-thiophen-2-yl-1,2-dihydro-pyridine-3,5-dicarbonitrile

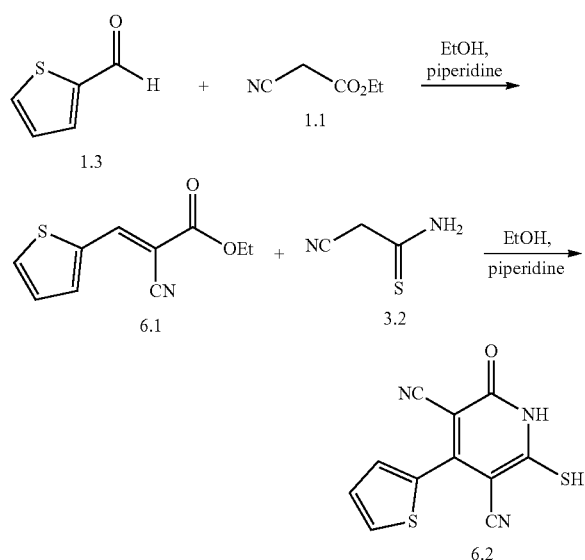

Step 1: 2-Cyano-3-thiophen-2-yl-acrylic acid ethyl ester (6.1)

To a solution of thiophene-2-carboxaldehyde 1.3 (1 g, 8.9 mmol), ethylcyanoacetate 1.1 (0.94 mL, 8.9 mmol) in EtOH (20 mL) was added piperidine (3 drops). Stirring was continued ar r.t. 16 h. The solvent was removed under vacuo. The crude was taken up with water, extracted with EtOAc (3×50 mL). The organic phase was collected, washed with brine and dried over anhydrous $Na_2SO_4$. The title intermediate 6.1 (1.3 g, 6.27 mmol) was obtained as a white solid. Yield 70%.

Step 2: 6-Mercapto-2-oxo-4-thiophen-2-yl-1,2-dihydro-pyridine-3,5-dicarbonitrile (6.2)

To a solution of intermediate 6.1 (1.2 g, 5.79 mmol) in EtOH (15 mL) was added piperidine (4 drops). Stirring was continued at reflux 16 h. Upon cooling a red precipitate was formed. The precipitate was collected, washed with cold EtOH, and dried under vacuo. The title intermediate 6.2 (640 mg, 2.46 mmol) as a red powder. Yield 42%. $^1$H NMR (200 MHz, DMSO-$d_6$) δ 7.24-7.27 (m, 1H), 7.53-7.55 (m, 1H), 7.94-7.95 (m, 1H), 13.0 (brs, 1H).

Example 7: Intermediate 7.1. Potassium; 3-cyano-6-oxo-4-trifluoromethyl-1,6-dihydro-pyridine-2-thiolate

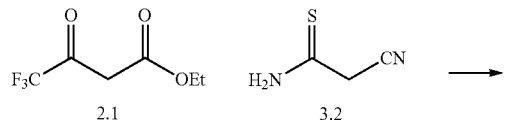

136

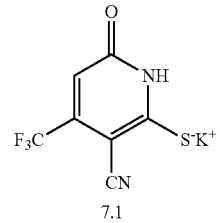

To a stirred solution of KOH (0.91 g, 16.29 mmol) in abs. EtOH (32 mL), ethyl trifluoroacetoacetate 2.1 (2.38 mL, 16.29 mmol) and 2-cyanothioacetamide 3.2 (1.63 g, 16.29 mmol) were added, and the resulting mixture was stirred and refluxed for 7 hours. Then it was cooled at room temperature and left to stand overnight. The copious precipitate thus formed was collected by filtration under vacuum and washed with EtOH (2×5 mL), to give intermediate 7.1 (2.01 g, 7.78 mmol) as a white solid. Yield 48%. MS-ESI(−) m/z: 218.9 [M−H]$^−$

Example 8: Intermediate 8.3. (3-Bromomethyl-phenyl)-acetic acid ethyl ester

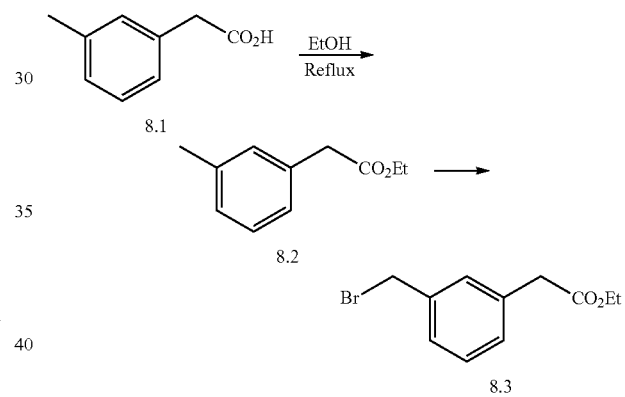

Step 1: m-Tolyl-acetic acid ethyl ester (8.2)

To a solution of 8.1 (15 g, 99.88 mmol) in EtOH (absolute) (400 mL) was added HCl (conc.) (0.3 mL, 9.9 mmol) and stirring was continued at reflux for 4 h. The volatiles were removed under reduced pressure. The crude was taken up with DCM (200 mL) dried over $Na_2SO_4$ and evaporated under reduced pressure. The title compound 8.2 was obtained as a colorless oil (17 g, 95.39 mmol). Yield 96%. $^1$H NMR (200 MHz, CDCl$_3$) δ 1.28 (t, J=7.1 Hz, 3H), 2.37 (s, 2H), 3.6 (s, 2H), 4.18 (q, J=7.11 Hz, 2H), 7.20-7.35 (m, 4H). GC/MS m/z 178.1 (M+).

Step 2: (3-Bromomethyl-phenyl)-acetic acid ethyl ester (8.3)

NBS (10.1 g, 58.9 mmol) and BPO (70%) (68 mg, 0.28 mmol) were added to a solution of intermediate 8.2 (10 g, 56.11 mmol) in CH$_3$CN (300 mL). Stirring was continued at reflux for 4 h. The volatile were removed under reduced pressure. The crude residue was partitioned between EtOAc (300 mL) and a saturated NaHCO$_3$ aqueous solution (300 mL). The organic phase was collected and dried over Na₂SO₄. The crude product was purified by flash chromatography (dry load) eluting with PET/Et₂O from 2% to 4% for product. The title compound 8.3 (10 g, 38.89 mmol) was obtained as a yellowish oil. Yield 66%. ¹H NMR (200 MHz, CDCl₃) δ 1.27 (t, J=7.1 Hz, 3H), 3.62 (s, 2H), 4.17 (q, J=7.13 Hz, 2H), 4.50 (s, 2H), 7.09-7.13 (m, 3H), 7.21-7.28 (m, 1H).

Example 9: Intermediate 9.3.
3-Bromomethyl-benzamide

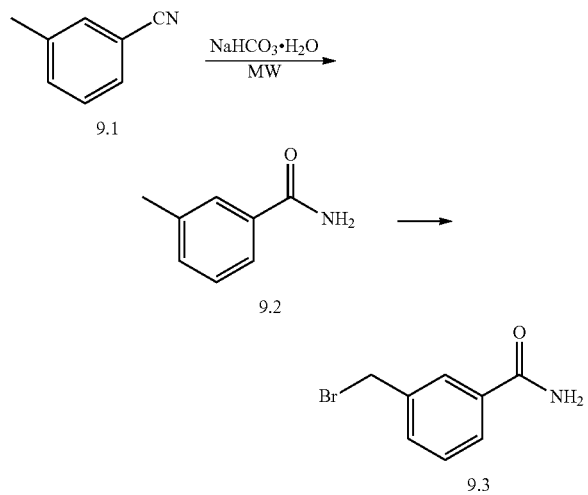

Step 1: 3-Methyl-benzamide (9.2)

A solution of compound 9.1 (1.54 mL, 12.8 mmol) and K₂CO₃ (707 mg, 5.12 mmol) in H₂O (5 mL) was heated under microwave irradiation at 130° C., 200 psi, 200 W for 20 minutes. Upon cooling, the resulting white precipitate was collected and dried under reduced pressure to afford the title compound 9.2 as white crystals (870 mg, 6.4 mmol). Yield 50%. GC-MS (m/z) 135.1 (M+).

Step 2: 3-Bromomethyl-benzamide (9.3)

NBS (434.6 mg, 2.4 mmol) and BPO (70%) (8 mg, 0.022 mmol) were added to a solution of intermediate 9.2 (300 mg, 2.22 mmol) in CH₃CN (20 mL). Stirring was continued at reflux for 4 h. The volatile were removed under reduced pressure. The crude product was partitioned between EtOAc (300 mL) and a saturated NaHCO₃ aqueous solution (300 mL). The organic phase was collected and dried over Na₂SO₄. The title compound 9.3 (250 mg, 1.16 mmol) was obtained as a yellowish solid. Yield 53%.

Example 10: Intermediate 10.4. 3'-Bromomethyl-3,5-difluoro-4-methoxy-biphenyl

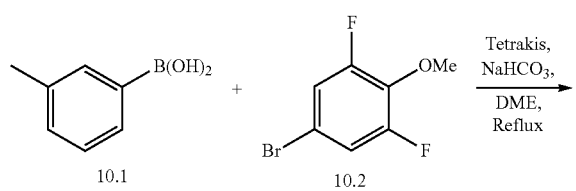

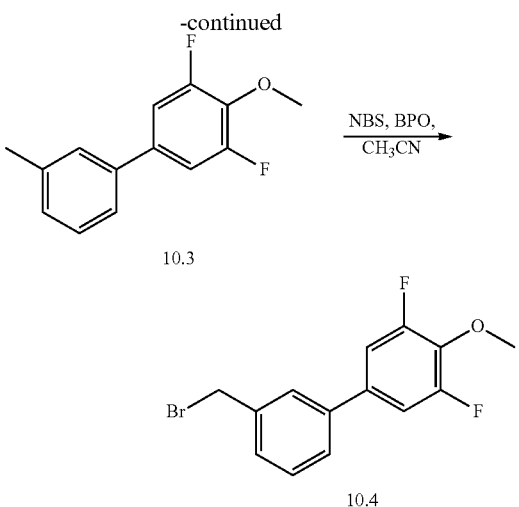

Step 1: 3,5-Difluoro-4-methoxy-3'-methyl-biphenyl (10.3)

To a solution of compound 10.1 (0.18 mL, 1.33 mmol) in DME (15 mL) was added palladium tetrakis (50 mg, 0.039 mmol). Stirring was continued at r.t. for 5 min. m-Tolyl boronic acid 10.2 (202 mg, 1.35 mmol) and K₂CO₃ (745 mg, 3.56 mmol) were added in turn. Stirring was continued at reflux for 4 h. The solvent was removed under reduced pressure. The crude residue was taken up in water and extracted with DCM (3×20 ml). The organic phase was washed with brine, dried over Na₂SO₄, filtered and concentrated under reduced pressure. Pure title compound 10.3 (282 mg, 1.22 mmol) was obtained as a colorless oil and it was used for the next step without further purification. Yield 91%. ¹H NMR (400 MHz, CDCl₃) δ 2.43 (s, 3H), 4.04 (s, 3H), 7.14 (d, J=9.3, 2H), 7.32-7.33 (m, 4H).

Step 2: 3'-Bromomethyl-3,5-difluoro-4-methoxy-biphenyl (10.4)

To a solution of the intermediate 10.3 (260 mg, 1.1 mmol) in CH₃CN (15 mL) was added BPO (4 mg, 0.0055 mmol) and NBS (210 mg, 1.22 mmol). Stirring was continued at reflux overnight. The solvent was removed under reduced pressure. The reaction partitioned between NaHCO₃₍ₛₛ₎ and DCM. The organic phase was washed with brine and dried over Na₂SO₄. The crude was purified by flash chromatography, eluting with PET/Et₂O affording the title compound 10.4 (250 mg, 0.77 mmol) as a yellow oil. Yield 72%. ¹H NMR (400 MHz, CDCl₃) δ 4.06 (d, J=3.7 Hz, 3H), 4.55 (s, 2H), 7.14 (d, J=6.2 Hz, 1H), 7.16 (d, J=6.1 Hz, 1H), 7.41-7.47 (m, 3H), 7.54 (s, 1H).

Example 11: Intermediate 11.2.
(3-Bromomethyl-phenyl)-acetic acid

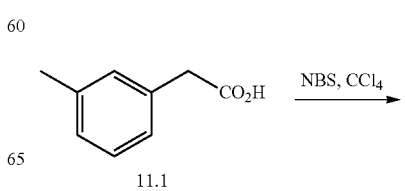

-continued

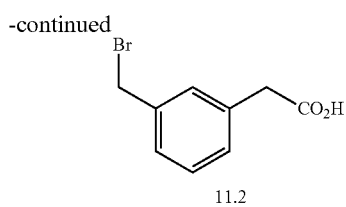

11.2

To a suspension of compound 11.1 (750 mg, 5 mmol) in CCl$_4$ (15 mL) was added AIBN (41 mg, 0.25 mmol) and NBS (933.7 mg, 5.24 mmol). Stirring was continued at reflux overnight. The solvent was removed under reduced pressure. The reaction was taken up with water, extracted with EtOAc (3×20 mL) washed with brine, and dried over Na$_2$SO$_4$. The crude was purified by flash chromatography, eluting with CH$_2$Cl$_2$/MeOH (3% for product) affording the title intermediate 11.2 (800 mg, 3.49 mmol) as a white solid. Yield 70%. GC/MS (m/z) 227.9 (M+).

Example 12: Intermediate 12.2. [3-(4-Chloro-5-cyano-6-thiophen-2-yl-pyrimidin-2-ylsulfanylmethyl)-phenyl]-acetic acid

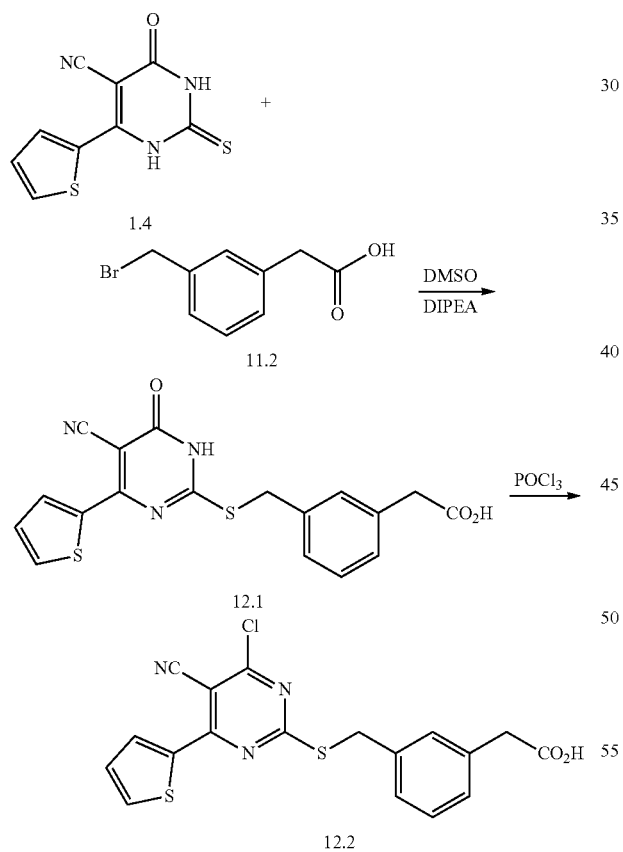

Step 1: [3-(5-Cyano-6-oxo-4-thiophen-2-yl-1,6-dihydro-pyrimidin-2-ylsulfanylmethyl)-phenyl]-acetic acid (12.1)

To a stirred suspension of intermediate 1.4 (500 mg, 2.12 mmol) and DIPEA (0.4 mL, 2.12 mmol) in DMSO (5 mL) was added intermediate 11.2 (487 mg, 2.12 mmol). Stirring was continued overnight at room temperature. The crude reaction mixture was poured into water and the resulting aqueous mixture was washed with EtOAc, acidified to pH 3, and extracted with EtOAc (3×50 mL). The title intermediate 12.1 was obtained (200 mg, 0.52 mmol) as a pure yellowish solid after flash chromatography purification eluting with CH$_2$Cl$_2$/MeOH (10% for product) and shredding with a mixture of EtO$_2$/Acetone. Yield 25%. $^1$H NMR (400 MHz, DMSO-d$_6$) δ 3.49 (s, 2H), 4.53 (s, 2H), 7.16 (d, J=6.8 Hz, 1H), 7.26 (t, J=7.2 Hz, 1H), 7.36 (m, 3H), 8.05 (d, J=4.4 Hz, 1H), 8.27 (s, 1H), 12.13 (s, 1H); $^{13}$C NMR (100 MHz, DMSO-d$_6$) δ 34.3, 40.9, 88.5, 116.8, 127.6, 128.9, 129.1, 129.8, 130.4, 131.9, 135.2, 135.8, 137.0, 139.9, 159.1, 161.6, 165.7, 172.9. HPLC 95.8%.

Step 2: [3-(4-Chloro-5-cyano-6-thiophen-2-yl-pyrimidin-2-ylsulfanylmethyl)-phenyl]-acetic acid (12.2)

A mixture of intermediate 12.1 (300 mg, 0.78 mmol) and POCl$_3$ (6 ml) were heated at 80° C. 4 h. The crude reaction mixture was then poured in ice. The resulting yellow precipitate was collected and dried under reduced pressure affording the title intermediate 12.2 (250 mg, 0.62 mmol) as a yellowish solid. Yield 79%. $^1$H NMR (400 MHz, DMSO-d$_6$) δ 3.53 (s, 2H), 4.50 (s, 2H), 7.16 (d, J=7.5 Hz, 1H), 7.27 (t, J=7.4 Hz, 1H), 7.36-7.39 (m, 3H), 8.13 (d, J=4.9 Hz, 1H), 8.3 (d, J=3.9 Hz, 1H), 12.25 (brs, 1H). $^{13}$C NMR (100 MHz, DMSO-d$_6$) δ 35.1, 40.9, 97.7, 115.5, 127.6, 128.8, 129, 130.2, 130.4, 133.3, 135.7, 136, 137, 138.6, 160.3, 163.2, 172.9, 174.

Example 13: Intermediate 13.3. [3-(4-Chloro-5-cyano-6-thiophen-2-yl-pyrimidin-2-ylsulfanylmethyl)-benzoic acid

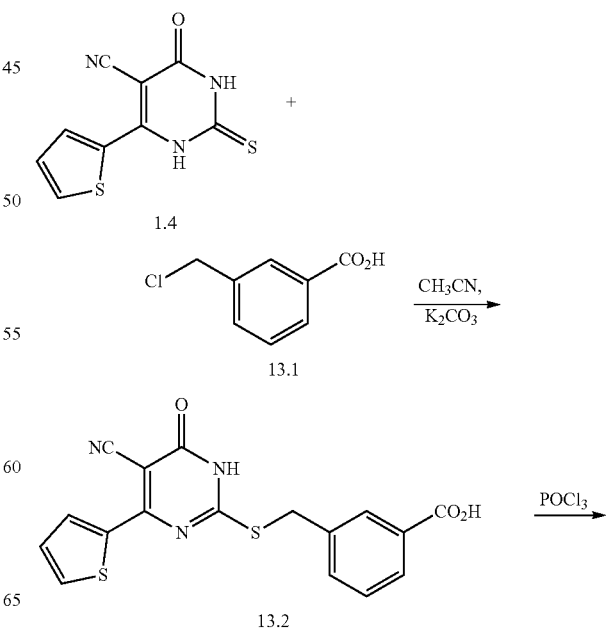

141

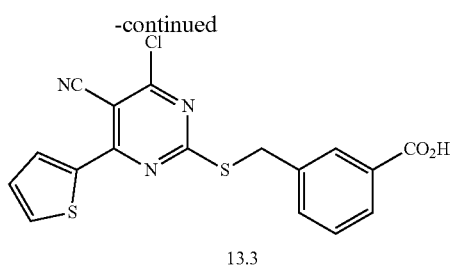

13.3

Step 1: 3-(5-Cyano-6-oxo-4-thiophen-2-yl-1,6-di-hydro-pyrimidin-2-ylsulfanylmethyl)-benzoic acid (13.2)

To a stirred suspension of intermediate 1.4 (250 mg, 1.06 mmol) and K$_2$CO$_3$ (440 mg, 3.18 mmol) in CH$_3$CN (15 mL) was added 3-(chloromethyl)benzoic acid 13.1 (180 mg, 1.06 mmol). Stirring was continued overnight at reflux. The volatiles were then removed under reduced pressure. The crude product was taken up in water, washed with EtOAc, acidified to pH 1, and extracted with EtOAc (3×50 mL). Shredding with hot acetone afforded the title intermediate 13.2 (45 mg, 0.12 mmol) as a yellowish solid. Yield 12%. $^1$H NMR (400 MHz, DMSO-d$_6$) δ 4.62 (s, 2H), 7.33 (t, J=4.3 Hz, 1H), 7.44 (t, J=7.6 Hz, 1H), 7.72 (d, J=7.5 Hz, 1H), 7.82 (d, J=7.5 Hz, 1H), 8.05 (m, 2H), 8.26 (d, J=3.8 Hz, 1H), 12.99 (s, 1H); $^{13}$C NMR (100 MHz, DMSO) δ 33.9, 88.7, 116.5, 128.8, 129.3, 129.9, 130.2, 131.5, 132.1, 133.7, 135.4, 137.9, 139.7, 159.0, 161.2, 165.3, 167.4. HPLC: 97.2%

Step 2: 3-(4-Chloro-5-cyano-6-thiophen-2-yl-pyrimidin-2-ylsulfanylmethyl)-benzoic acid (13.3)

A mixture of intermediate 13.2 (300 mg, 0.81 mmol) and POCl$_3$ (6 ml) were heated at 80° C. for 4 h. The reaction mixture was then poured into ice. The resulting yellow precipitate was collected and purified by flash chromatography eluting with DCM/MeOH (3% for product) to provide intermediate 13.3 (120 mg, 0.3 mmol) as a yellowish solid. Yield 79%. $^{13}$C NMR (100 MHz, DMSO-d$_6$) δ 33.8, 88.7, 116.5, 128.8, 129.3, 129.9, 130.2, 131.4, 132.1, 133.7, 135.5, 137.9, 139.6, 159, 161.1, 165.2, 167.3;

Example 14: Intermediate 14.2. 3-Bromomethyl-benzonitrile

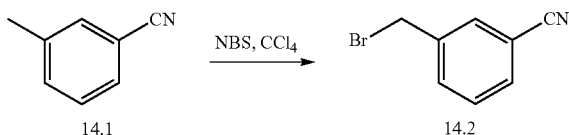

To a solution of compound 14.1 (2 mL, 17.07 mmol) in CCl$_4$ was added a mixture of NBS (2.9 g, 17.1 mmol) and BPO (16 mg, 0.06 mmol). Stirring was continued at reflux for 16 h and the reaction was then allowed to warm to rt. The resulting solid was collected, washed with CCl$_4$, and dried under reduced pressure. The title compound 14.2 was obtained as a white solid (2.84 g, 14.5 mmol). Yield 85%. GC-) 196.9 (M+).

142

Example 15: Intermediate 15.1. 2-(3-Bromomethyl-phenyl)-ethanol

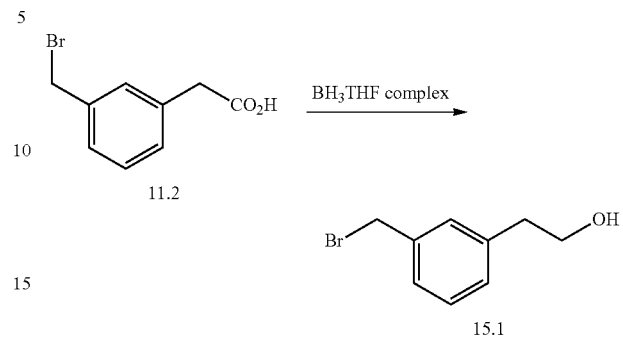

To a solution of intermediate 11.2 (500 mg, 2.17 mmol) in THF (10 mL) at 0° C. was added BH$_3$-THF (1M in THF, 2.8 mL) dropwise. The mixture was stirred at 0° C. for 1 h and then at r.t. for 12 h. The mixture was diluted with THF/H$_2$O (1:1 v:v, 15 mL) and washed with saturated aq. K$_2$CO$_3$. The phases were separated and the aqueous layer was extracted with EtOAc (3×20 mL). The combined organic phase was washed with brine and dried over Na$_2$SO$_4$. Flash chromatography purification of the crude product (eluting with DCM/MeOH) afforded the title intermediate 15.1 (400 mg, 1.85 mmol) as a white solid. Yield 85%. GC/MS (m/z) 214 (M+).

Example 16: Intermediate 16.2. 2 (3-Bromomethyl-phenyl)-acetonitrile

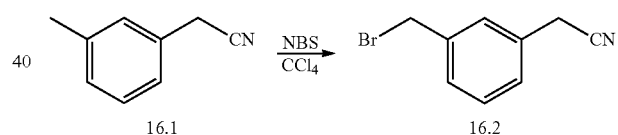

NBS (338 mg, 1.9 mmol) and BPO (70%) (28.7 mg, 0.11 mmol) were added to a solution of intermediate 16.1 (0.5 mL, 2.37 mmol) in CH$_3$CN (15 mL). Stirring was continued at reflux for 4 h. The volatiles were removed under reduced pressure. The crude product was partitioned between EtOAc (100 mL) and a saturated NaHCO$_3$ aqueous solution (100 mL). The organic phase was collected and dried over Na$_2$SO$_4$. The title compound 16.2 (250 mg, 1.18 mmol) was obtained as a yellowish solid after flash chromatography purification (eluting with PET/EtOAc). Yield 50%.

Example 17: Intermediate 17.3. 5-(3-Bromomethyl-phenyl)-2-methyl-2H-tetrazole

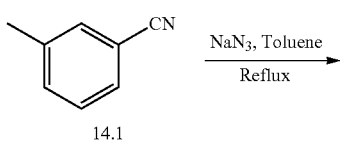

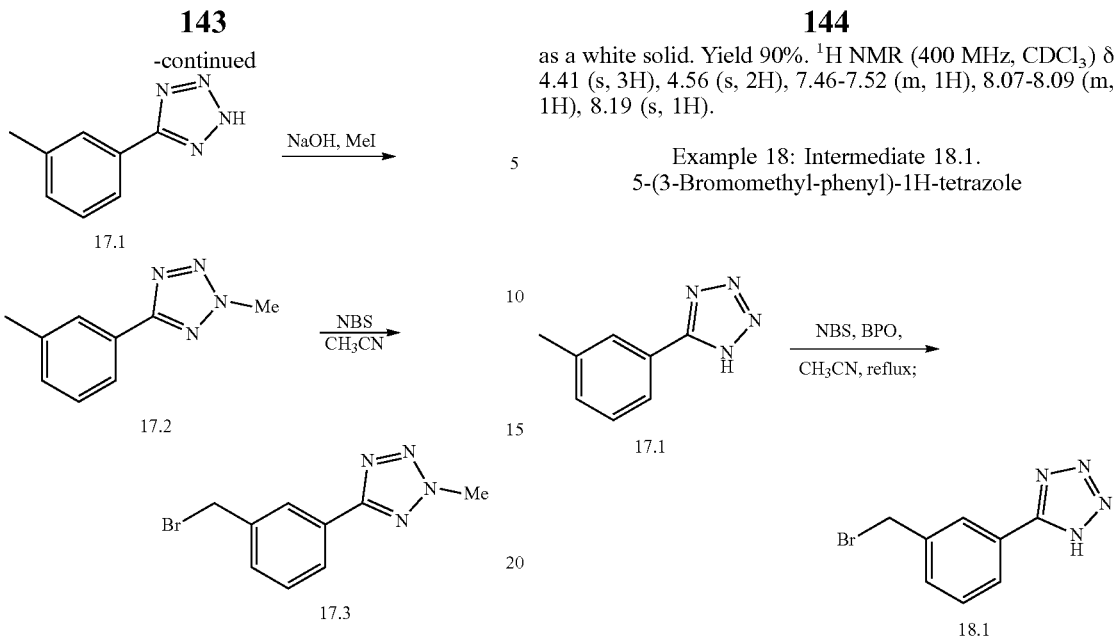

Step 1: 5-m-Tolyl-2H-tetrazole (17.1)

A mixture of compound 14.1 (1.02 mL, 8.54 mmol), NaN$_3$ (832 mg, 12.8 mmol) and Et$_3$N·HCl (1.76 g, 12.8 mmol) in toluene (20 mL) was heated at reflux for 4 h. The solvent was then removed under reduced pressure. The crude product was poured into water and the resulting aqueous solution was acidified to pH 1 with 3N HCl and extracted with EtOAc (3×20 mL). The organic phase was washed with brine, dried over Na$_2$SO$_4$, and concentrated under reduced pressure. The title compound 17.1 (1.22 g, 7.6 mmol) was obtained as a white solid. Yield 89%. $^1$H NMR (200 MHz, DMSO-d$_6$) δ 2.39 (s, 3H), 7.39 (m, 1H), 7.48 (t, J=7.58 Hz, 1H), 7.80 (s, 1H), 7.85 (m, 1H); GC/MS (m/z) 160.1 (M+).

Step 2: 2-Methyl-5-m-tolyl-2H-tetrazole (17.2)

To a solution of intermediate 17.1 (1 g, 6.2 mmol) in water (5 mL) and NaOH (500 mg, 12.5 mmol) was added a solution of MeI (0.38 mL, 6.1 mmol) in acetone (10 mL). Stirring was continued at reflux for 6 h. The solvent was then removed under reduced pressure and the resulting residue was taken up in EtOAc and H$_2$O. The organic layer was separated, dried over Na$_2$SO$_4$ and evaporated to dryness in vacuo. Purification of the crude product afforded the title intermediate 17.2 (500 mg, 2.87 mmol) as a white solid. Yield 46%. $^1$H NMR (400 MHz, CDCl$_3$) δ 4.37 (s, 3H), 7.26-7.39 (m, 1H), 7.35-7.39 (m, 1H), 7.91-7.96 (m, 2H).

Step 3: 5-(3-Bromomethyl-phenyl)-2-methyl-2H-tetrazole (17.3)

To a suspension of compound 17.2 (200 mg, 1.15 mmol) in CH$_3$CN (15 mL) was added BPO (21 mg, 0.057 mmol) and NBS (163.5 mg, 0.92 mmol). Stirring was continued at 92° C. overnight. The solvent was removed under reduced pressure. The reaction mixture was taken up in water, extracted with EtOAc (3×20 mL), washed with brine, and dried over Na$_2$SO$_4$. The crude product was purified by flash chromatography eluting with CH$_2$Cl$_2$/MeOH (7% for product) to afford the title compound 17.3 (261 mg, 1.03 mmol) as a white solid. Yield 90%. $^1$H NMR (400 MHz, CDCl$_3$) δ 4.41 (s, 3H), 4.56 (s, 2H), 7.46-7.52 (m, 1H), 8.07-8.09 (m, 1H), 8.19 (s, 1H).

Example 18: Intermediate 18.1. 5-(3-Bromomethyl-phenyl)-1H-tetrazole

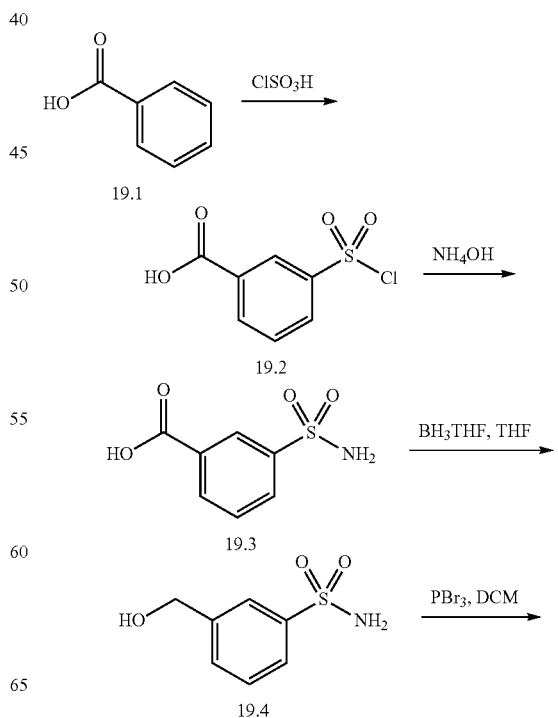

To a suspension of compound 17.1 (300 mg, 1.87 mmol) in CH$_3$CN (15 mL) was added AIBN (31 mg, 0.18 mmol) and NBS (333 mg, 1.87 mmol). Stirring was continued at reflux overnight. The solvent was removed under reduced pressure. The reaction was taken up with water, extracted with EtOAc (3×20 mL) washed with brine, and dried over Na$_2$SO$_4$. The crude was purified by flash chromatography, eluting with CH$_2$Cl$_2$/MeOH (7% for product) affording the title compound 18.1 (150 mg, 0.62 mmol) as a light yellow solid. Yield 34%.

Example 19: Intermediate 19.5. 3-Bromomethyl-benzenesulfonamide

-continued

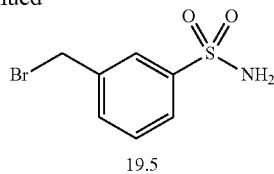

19.5

Step 1: 3-Chlorosulfonyl-benzoic acid (19.2)

A mixture of compound 19.1 (1 g, 8.13 mmol) and chlorosulfonic acid (4 mL) was stirred at 125° C. for 2 h. The mixture was poured into ice water dropwise. The resulting solid was collected, solubilized in EtOAc, and washed with water (3×20 mL). The organic layer was dried over $Na_2SO_4$ and evaporated under reduced pressure. The title intermediate 19.2 (1.19 g, 5.39 mmol) was obtained as a white solid. Yield 65%. $^1$H NMR (400 MHz, DMSO-$d_6$) δ 7.45 (t, J=7.69 Hz, 1H), 7.65 (d, J=7.8 Hz, 1H), 7.86 (d, J=7.6 Hz, 1H), 8.1 (s, 1H), 13.9 (brs, 1H).

Step 2: 3-Sulfamoyl-benzoic acid (19.3)

To a cold solution of 25% $NH_4OH$ (10 mL) was added portionwise intermediate 19.2 (1.10 g, 5.39 mmol). Stirring was continued at rt for 2 h and the resulting mixture was concentrated. The crude product was suspended in water (4 mL) and 37% HCl solution was then added dropwise to the mixture. The resulting precipitate was collected and dried under reduced pressure to afford the title intermediate 19.3 (943 mg, 4.6 mmol) as a white solid. Yield 87%. $^1$H NMR (400 MHz, DMSO-$d_6$) δ 7.50 (brs, 2H), 7.71 (t, J=7.78 Hz, 1H), 8.04 (d, J=7.8 Hz, 1H), 8.13 (d, J=7.7 Hz, 1H), 8.38 (s, 1H), 13.4 (brs, 1H).

Step 3: 3-Hydroxymethyl-benzenesulfonamide (19.4)

To a stirred solution of intermediate 19.3 (940 mg, 4.67 mmol) was added dropwise at 0° C. $BH_3$-THF complex (14 mL, 14.01 mmol) and stirring was continued for 4 h at rt. The reaction mixture was then cooled to 0° C., and quenched by the dropwise addition of MeOH. After 15 min, a 3N solution of HCl (37 mL) was added to the mixture and the volatiles were removed under reduced pressure. The aqueous phase was extracted with EtOAc (3×20 mL). The combined organic phase was washed with brine and dried over $Na_2SO_4$ to afford the title intermediate 19.4 (785 mg, 4.2 mmol) as a colorless oil. Yield 89%. $^1$H NMR (400 MHz, DMSO-$d_6$) δ 4.51 (s, 2H), 7.34 (s, 2H), 7.5 (d, J=5 Hz, 2H), 7.68 (t, J=5.2 Hz, 1H), 7.8 (s, 1H).

Step 4: 3-Bromomethyl-benzenesulfonamide (19.5)

To a stirred suspension of intermediate 19.4 (200 mg, 1.07 mmol) in DCM (3.5 mL) was added $PBr_3$ and stirring was continued at 20° C. for 16 h. Water was then added carefully to the mixture and the phases were separated. The aqueous phase was extracted with DCM (2×20 mL). The combined organic layers were washed with brine and dried over $Na_2SO_4$ to afford the title intermediate 19.5 (120 mg, 0.47 mmol) as a colorless oil. Yield 45%. $^1$H NMR (400 MHz, $CDCl_3$) δ 4.53 (s, 2H), 7.54 (t, J=10.7 Hz, 1H), 7.69 (d, J=7.6 Hz, 1H), 7.88 (d, J=7.8 Hz, 1H), 7.97 (s, 1H).

Example 20: Intermediate 20.2. 4-Benzyl-2-mercapto-6-oxo-1,6-dihydro-pyridine-3-carbonitrile

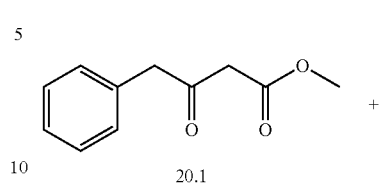

20.1

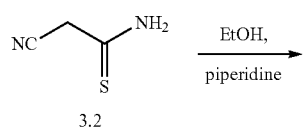

3.2

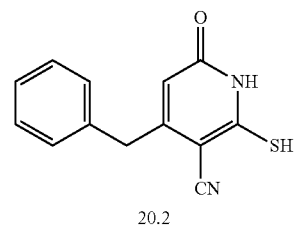

20.2

To a solution of intermediate 20.1 (1.2 g, 6.24 mmol) and potassium tert butoxide (764 mg, 6.24 mmol) in DMF (15 mL) was added compound 3.2 (31 mg, 0.18 mmol). Stirring was continued at 85° C. overnight. The reaction was poured water, The pH was acidified to 5 by the addition of AcOH followed by washing with EtOAc (3×20 mL). Then, pH was brought to 3 by the addition of 3N HCl solution. The aqueous phase was extracted with EtOAc (3×30 mL). The organic phase was washed with brine and dried over anhydrous $Na_2SO_4$. The title compound (600 mg, 2.47 mmol) was obtained as light yellow solid. Yield 40%. $^1$H NMR (400 MHz, DMSO-$d_6$) δ 3.63 (s, 2H), 5.81 (s, 1H), 7.17-7.36 (m, 5H), 13.1 (brs, 1H).

Example 21: [3-(5-Cyano-6-oxo-4-thiophen-2-yl-1,6-dihydro-pyrimidin-2-ylsulfanylmethyl)-phenyl]-acetic acid ethyl ester (Compound I-1)

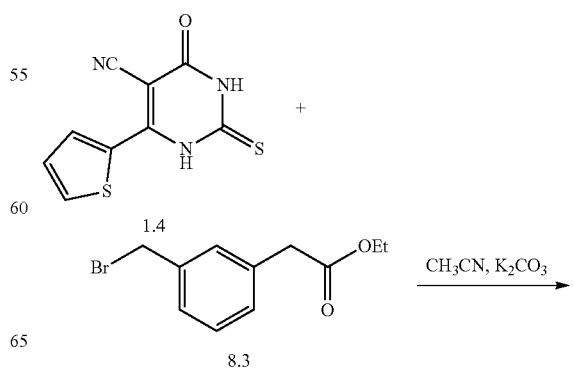

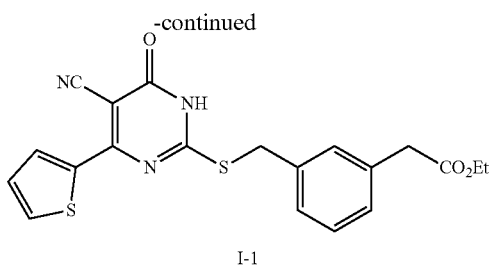

I-1

To a stirred suspension of intermediate 1.4 (2.13 g, 9.1 mmol) and K₂CO₃ (1.88 g, 13.6 mmol) in CH₃CN (80 mL) was added intermediate 8.3 (2.45 g, 9.52 mmol) and stirring was continued at a gentle reflux for 16 h. The solvent was then removed under reduced pressure. The crude product was taken up in water and the resulting aqueous solution was neutralized with 3N HCl solution. The resulting pale yellow solid was collected, washed with ice cold water, and dried under reduced pressure. The title compound I-1 (3.1 g, 7.46 mmol) was obtained as a grey solid after trituration with Et₂O. Yield 82%. ¹H NMR (400 MHz, DMSO-d₆) δ 1.15 (d, J=7.03 Hz, 3H), 3.62 (s, 2H), 4.03 (q, J=7.16 Hz, 2H), 4.55 (s, 2H), 7.17 (d, J=7.1 Hz, 1H), 7.28 (t, J=7.7 Hz, 1H), 7.38 (m, 3H), 8.1 (d, J=4.7 Hz, 1H), 8.29 (d, J=3.35 Hz, 1H). ¹³C NMR (100 MHz, DMSO-d₆) δ 14.4, 34.2, 60.7, 88.6, 116.6, 127.8, 129.1, 129.1, 129.9, 130.3, 132.1, 135.2, 135.5, 137.1, 139.7, 159.1, 161.1, 165.3, 171.4. HPLC>97.9%.

Example 22: 3-(5-Cyano-6-oxo-4-thiophen-2-yl-1,6-dihydro-pyrimidin-2-ylsulfanylmethyl)-benzamide (Compound I-2)

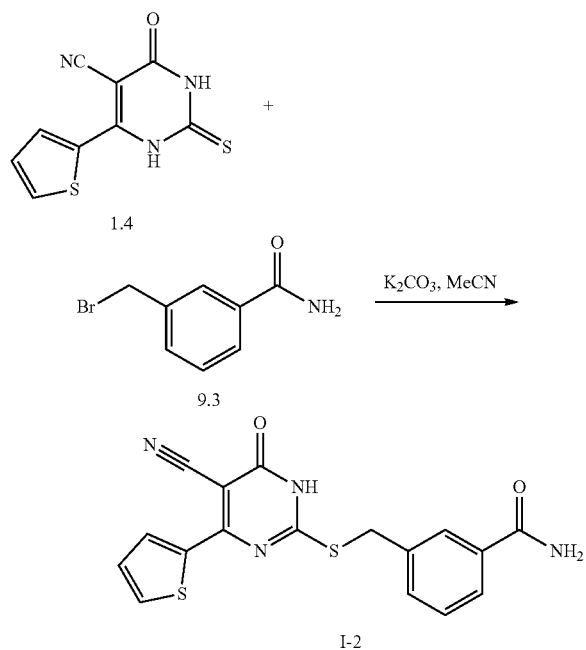

To a stirred suspension of intermediate 1.4 (182 mg, 0.78 mmol) and intermediate 9.3 (200 mg, 0.65 mmol) in CH₃CN (20 mL) was added K₂CO₃ (119 mg, 0.86 mmol) and stirring was continued at a gentle reflux for 16 h. The volatiles were removed under reduced pressure. The crude product was taken up in water, and the resulting aqueous mixture was acidified to pH 3 with a 3N HCl solution and extracted with EtOAc (3×20 mL). The combined organic phases were washed with brine and dried over Na₂SO₄ to afford the title compound I-2 (120 mg, 0.24 mmol) as a yellowish solid after trituration with hot Et₂O. Yield 42%. ¹H NMR (400 MHz, DMSO-d₆) δ 4.61 (s, 2H), 7.3 (m, 1H), 7.41 (m, 2H), 7.63 (d, J=7.12 Hz, 1H), 7.76 (d, J=7.3 Hz, 1H), 7.97 (s, 2H), 8.01 (d, J=4.47 Hz, 1H), 8.3 (d, J=2.8 Hz, 1H). ¹³C NMR (100 MHz, DMSO-d₆) δ 34.5, 88.1, 117.1, 127.3, 129.1, 129.3, 130.4, 132.5, 132.5, 135.5, 135.9, 137.7, 140.2, 159.4, 161.6, 165.7, 168.4. HPLC>94.2%.

Example 23: 2-({[3-(3,5-difluoro-4-hydroxyphenyl)phenyl]methyl}sulfanyl)-6-oxo-4-(thiophen-2-yl)-1,6-dihydropyrimidine-5-carbonitrile (Compound I-3)

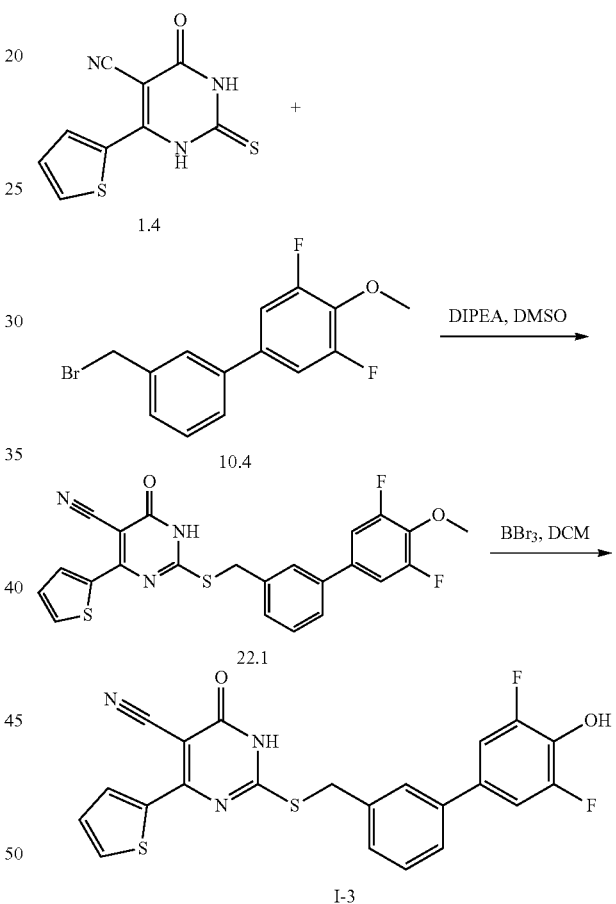

Step 1: 2-({[3-(3,5-difluoro-4-hydroxyphenyl)phenyl]methyl}sulfanyl)-6-oxo-4-(thiophen-2-yl)-1,6-dihydropyrimidine-5-carbonitrile (22.1)

To a stirred solution of intermediate 1.4 (152 mg, 0.65 mmol) and intermediate 10.4 (250 mg, 0.77 mmol) in DMSO (6 mL) was added DIPEA (0.13 mL, 0.72 mmol) and stirring was continued at rt for 4 h. The crude mixture was poured into water and the resulting aqueous mixture was washed with EtOAc, acidified to pH 3, and extracted with EtOAc (3×50 mL). The combined organic phases were washed with brine and dried over Na₂SO₄ to afford intermediate 22.1 (180 mg, 0.0.38 mmol) as a pale yellow powder after flash chromatography purification eluting with CH$_2$Cl$_2$/MeOH (4% for product). Yield 55%. $^1$H NMR (400 MHz, DMSO-d$_6$) δ 3.93 (s, 3H), 4.60 (s, 2H), 7.34-7.43 (m, 4H), 7.5 (d, J=4.3 Hz, 1H), 7.60 (d, J=7.5 Hz, 1H), 7.84 (s, 1H), 8.0 (d, J=4.9 Hz, 1H), 8.29 (d, J=4.9 Hz, 1H), 13.9 (brs, 1H).

Step 2: 2-({[3-(3,5-difluoro-4-hydroxyphenyl)phenyl]methyl}sulfanyl)-6-oxo-4-(thiophen-2-yl)-1,6-dihydropyrimidine-5-carbonitrile (Compound I-3)

To a stirred suspension of intermediate 22.1 (170 mg, 0.36 mmol) in DCM (25 mL) was added a 1M solution of BBr$_3$ in DCM (0.72 mL, 0.72 mmol) and stirring was continued at reflux for 16 h. The reaction mixture was quenched by the addition of MeOH and the volatiles were removed under reduced pressure. The crude product was purified by flash chromatography eluting with DCM/MeOH (5% for product). The title compound I-3 (90 mg, 0.2 mmol) was obtained as a white solid after trituration with hot Et$_2$O. Yield 42%. $^1$H NMR (400 MHz, DMSO) δ 4.59 (s, 3H), 7.31 (d, J=9.1 Hz, 2H), 7.36 (m, 1H), 7.39 (d, J=7.6 Hz, 1H), 7.45 (d, J=7.7 Hz, 1H), 7.56 (d, J=7.5 Hz, 1H), 7.81 (s, 1H), 8.07 (d, J=5 Hz, 1H), 8.3 (d, J=3.8 Hz, 1H), 10.34 (s, 1H). $^{13}$C NMR (100 MHz, DMSO-d$_6$) δ 88.7, 110.3 ($^2$J$^{CF}$=15.1 Hz), 110.3 ($^2$J$^{CF}$=15.5 Hz), 125.8, 127.4, 128.5, 129.7, 130, 130.5, 132.1, 133.5 ($^3$J$_{CF}$=16 Hz), 133.7 ($^3$J$^{CF}$=16 Hz), 135.3, 138.1, 138.4, 139.7, 152.9 ($^1$J$^{CF}$=239.9 Hz), 153.01 ($^1$J$^{CF}$=240.1 MHz), 159.0, 161.3, 165.5. HPLC: 98.4%.

Example 24: [3-(5-Cyano-4-methoxy-6-thiophen-2-yl-pyrimidin-2-ylsulfanylmethyl)-phenyl]-acetic acid (Compound I-4)

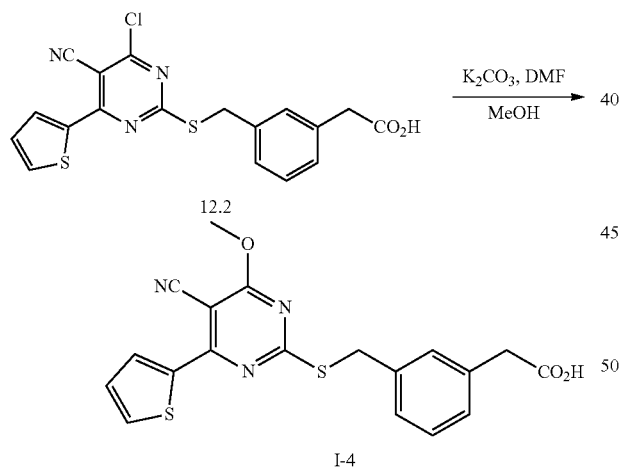

To a stirred solution of intermediate 12.2 (80 mg, 0.19 mmol) and MeOH (0.04 mL, 0.95 mmol) in DMF (3 mL) was added K$_2$CO$_3$ (60 mg, 0.43 mmol) and stirring was continued at rt for 16 h. The reaction mixture was poured into water and the resulting aqueous mixture was extracted with EtOAc (3×20 mL). The combined organic phase was washed with brine and dried over Na$_2$SO$_4$. Flash chromatography purification of the crude product (eluting with DCM/MeOH, 1.5% for product) afforded the title compound I-4 (45 mg, 0.11 mmol) as a white solid. Yield 58%; $^1$H NMR (400 MHz, DMSO-d$_6$) δ 3.56 (s, 3H), 3.66 (s, 2H), 4.54 (s, 2H), 7.17 (d, J=7.2 Hz, 1H), 7.27 (t, J=7.6 Hz, 1H), 7.33-7.38 (m, 3H), 8.07 (d, J=4.8 Hz, 1H), 8.28 (d, J=3.6 Hz, 1H). $^{13}$C NMR (100 MHz, DMSO-d$_6$) δ 34.2, 40.3, 52.1, 88.5, 116.6, 127.8, 129, 129.1, 129.8, 130.3, 132, 135.1, 135.3, 137.1, 139.8, 159.1, 161.4, 165.5, 171.8. HPLC>97.1%.

Example 25: [3-(4-Bromo-5-cyano-6-thiophen-2-yl-pyrimidin-2-ylsulfanylmethyl)-phenyl]-acetic acid (Compound I-5)

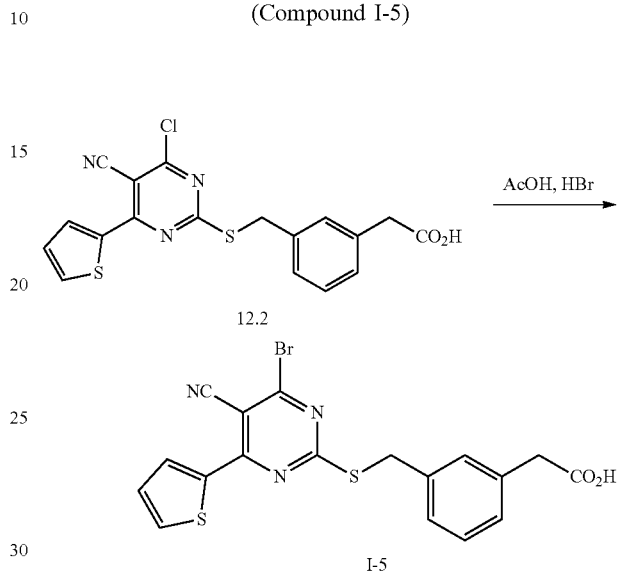

To a stirred solution of intermediate 12.2 (30 mg, 0.051 mmol) in AcOH (3.0 mL) was added HBr (36% solution in AcOH, 0.17 mL, 1.029 mmol) and the resulting mixture was stirred at 60° C. for 72 h. The reaction mixture was then diluted with DCM (10 mL), washed with H$_2$O (3×10 mL), brine (10 mL), dried over Na$_2$SO$_4$ and concentrated under reduced pressure. The crude product was purified by flash chromatography (DCM/MeOH/AcOH, from 99:1:0.1 92:8:0.1) to afford the title compound I-5 (17 mg, 0.038 mmol) as a yellow solid. Yield 75%. MS/MS ESI (+): 447.8, 401.9, 338.3. $^1$H-NMR (CDCl$_3$, 400 MHz) δ: 3.63 (s, 2H), 4.45 (s, 2H), 7.21 (m, 1H), 7.31 (m, 2H), 7.39 (m, 2H), 7.70 (brs, 1H), 8.45 (brs, 1H). $^{13}$C-NMR (CDCl$_3$, 100 MHz) δ: 29.3, 40.7, 100.1, 116.0, 127.9, 128.7, 128.9, 129.4, 130.1, 133.1, 133.6, 134.6, 136.6, 138.7, 155.8, 159.7, 174.3, 177.1. HPLC>95%.

Example 26: [3-(5-Cyano-4-cyclopropylamino-6-thiophen-2-yl-pyrimidin-2-ylsulfanylmethyl)-phenyl]-acetic acid (Compound I-6)

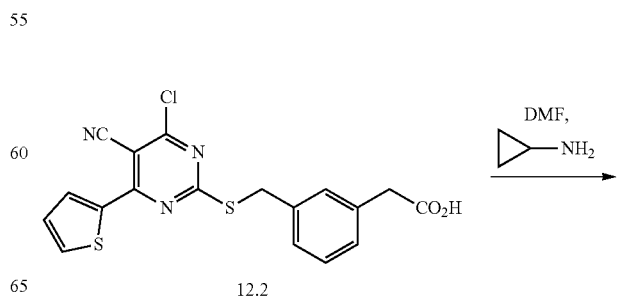

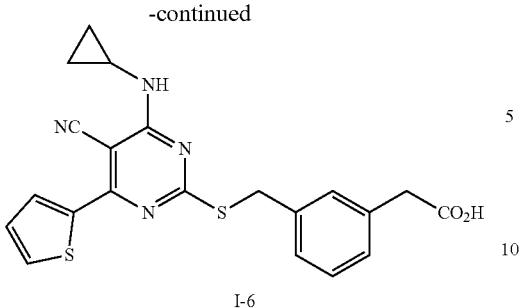

I-6

To a stirred solution of intermediate 12.2 (200 mg, 0.49 mmol) in DMF (3 mL) was added cyclopropylamine (0.037 mL, 0.55 mmol) and stirring was continued at r.t. for 16 h. The reaction mixture was quenched with brine, poured into water, and the resulting aqueous mixture was extracted with EtOAc (3×20 mL). The combined organic phases were washed with brine and dried over $Na_2SO_4$. The title compound I-6 (80 mg, 0.2 mmol) was obtained as a white solid after shredding with $Et_2O$. Yield 39%. $^1$H NMR (400 MHz, DMSO-$d_6$) δ 0.73 (m, 4H), 2.95 (m, 1H), 3.53 (s, 2H), 4.45 (s, 2H), 7.13 (d, J=7.4 Hz, 1H), 7.23-7.29 (m, 2H), 7.33-7.35 (m, 2H), 7.93 (d, J=4.9 Hz, 1H), 8.18 (d, J=3.2 Hz, 1H), 8.21 (s, 1H), 12.3 (s, 1H). $^{13}$C NMR (100 MHz, DMSO-$d_6$) δ 6.6, 6.6, 25, 34.3, 40.8, 79.7, 116.7, 127.3, 128.5, 128.6, 129.2, 130.1, 130.7, 133.2, 135.4, 138.3, 140.1, 158.7, 162.8, 172.8, 172.8. HPLC>99.3%.

Example 27: [3-(4-Amino-5-cyano-6-thiophen-2-yl-pyrimidin-2-ylsulfanylmethyl)-phenyl]-acetic acid (Compound I-7)

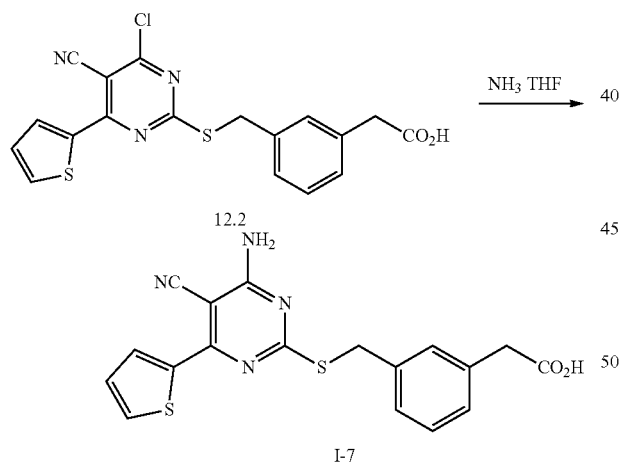

[3-(4-Cloro-5-cyano-6-thiophen-2-yl-pyrimidin-2-ylsulfanylmethyl)-phenyl]-acetic acid (12.2) (100 mg, 0.248 mmol) was dissolved in $NH_3$ 0.4 M in THF (18 mL, 7.466 mmol) and the resulting opalescent solution was stirred at room temperature for 72 hours. Then the mixture was poured in AcOEt (15 ml), washed with HCl 3 M (5 mL), aq. $NaHCO_3$ss (10 mL), brine (10 mL) dried over $Na_2SO_4$ and concentrated under reduced pressure. The crude was purified by flash chromatography ($CH_2Cl_2$/MeOH/AcOH, from 99:1:0.1 90:10:0.1) to afford the title compound I-7 (86 mg, 0.22 mmol) as a white solid. Yield 94%; MS/MS ESI (+): 382.9. $^1$H NMR (400 MHz, DMSO-$d_6$) δ 3.53 (s, 2H), 4.39 (s, 2H), 7.13 (d, J=7.3 Hz, 1H), 7.24 (t, J=7.1 Hz, 1H), 7.29 (m, 1H), 7.35 (m, 2H), 7.8 (brs, 1H), 7.94 (d, J=4.3 Hz, 1H), 8.20 (m, 1H), 12.32 (brs, 1H). $^{13}$C NMR (100 MHz, DMSO-$d_6$) δ 34.3, 40.9, 78.9, 116.9, 127.6, 128.6, 128.7, 129.3, 130.4, 130.8, 133.4, 135.5, 138.3, 140.4, 159.1, 163.7, 173. HPLC>97.9%.

Example 28: [3-(5-Cyano-6-thiophen-2-yl-pyrimidin-2-ylsulfanylmethyl)-phenyl]-acetic acid (Compound I-8)

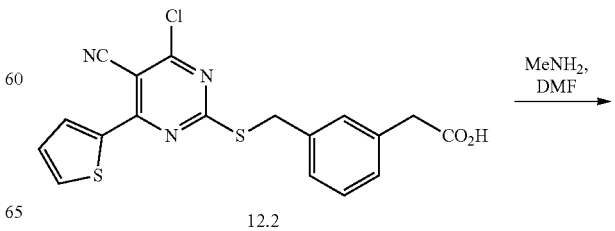

I-8

$Et_3N$ (0.15 mL, 1.119 mmol) was added to a stirred solution of intermediate 12.2 (150 mg, 0.373 mmol) in THF (3.7 mL). The resulting solution was continuously hydrogenated for 12 h using the Thales Nano H-Cub Hydrogenator (Cartridge: Pd/C 10%, $H_2$ Pressure: 8 bar, temperature: 40° C., transporting solvent: THF, flowrate: 1.0 mL/min). The resulting reaction mixture (about 5 mL) was diluted with EtOAc (15 mL), washed with 3M HCl (5 mL) and brine (10 mL), dried over $Na_2SO_4$, filtered, and concentrated under reduced pressure. The crude product was purified by reverse-phase flash chromatography (column: RP-18, eluting with $H_2O$/MeOH 80/20 to 10/90) to give the title compound I-8 as a white powder. Yield 34%. MS/MS ESI (+): 368.1. $^1$H-NMR (DMSO-$d_6$, 400 MHz) δ: 3.60 (s, 2H), 4.45 (s, 2H), 7.15 (m, 1H), 7.25 (m, 1H), 7.36 (m, 4H), 8.06 (br-s, 1H), 8.30 (ps-s, 1H), 9.03 (s, 1H).

Example 29: [3-(5-Cyano-4-methylamino-6-thiophen-2-yl-pyrimidin-2-ylsulfanylmethyl)-phenyl]-acetic acid (Compound I-9)

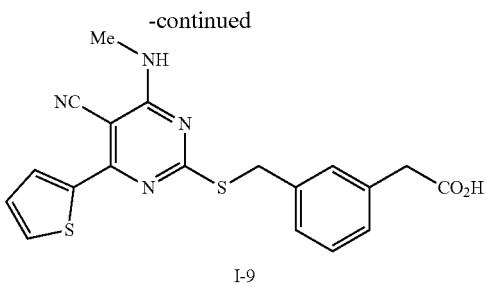

I-9

To a stirred solution of intermediate 12.2 (100 mg, 0.25 mmol) in DMF (3 mL) was added a 33% solution of MeNH$_2$ (0.03 mL, 0.27 mmol) in ethanol and stirring was continued at rt for 16 h. The reaction mixture was quenched with brine, poured into water, acidified to pH 6 by the addition of a 3M HCl solution, and then extracted with EtOAc (3×20 mL). The combined organic phase was washed with brine and dried over Na$_2$SO$_4$ to afford the title compound I-9 (80 mg, 0.2 mmol) as a white solid. Yield 80%. $^1$H NMR (400 MHz, DMSO-d$_6$) δ 2.93 (d, J=4.5 Hz, 3H), 3.53 (s, 2H), 2.92 (s, 2H), 7.13 (d, J=7.6 Hz, 1H), 7.24 (d, J=7.5 Hz, 1H), 7.27-7.29 (m, 1H), 7.33 (m, 2H), 7.94 (d, J=5.1 Hz, 1H), 8.1 (q, J=4.5 Hz, 1H), 8.18 (d, J=3.8 Hz, 1H), 12.33 (s, 1H). $^{13}$C NMR (100 MHz, DMSO-d$_6$) δ 28.6, 34.5, 40.9, 79.6, 116.9, 127.4, 128.6, 128.7, 129.3, 130.2, 130.7, 133.3, 135.5, 138.3, 140.3, 158.5, 161.9, 172.9, 173.1. HPLC>98.1%.

Example 30: 3-(5-Cyano-4-methylamino-6-thiophen-2-yl-pyrimidin-2-ylsulfanylmethyl)-benzoic acid (Compound I-10)

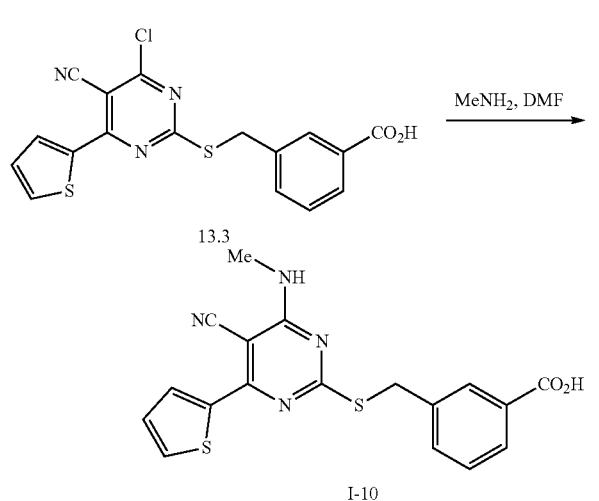

To a stirred solution of intermediate 13.3 (90 mg, 0.23 mmol) in DMF (3 mL) was added a 33% solution of MeNH$_2$ (0.03 mL, 0.25 mmol) in ethanol and stirring was continued at rt for 16 h. The reaction mixture was quenched with brine, poured into water, acidified to pH 6 by the addition of a 3M HCl solution, and then extracted with EtOAc (3×20 mL). The combined organic phase was washed with brine and dried over Na$_2$SO$_4$. The crude product was purified by flash chromatography eluting with DCM/MeOH (4% for product) to afford the title compound I-10 (45 mg, 0.12 mmol) as a white solid. Yield 51%. $^1$H NMR (400 MHz, DMSO-d$_6$) δ 2.94 (d, J=4.4 Hz, 3H), 4.49 (s, 2H), 7.28 (t, J=4.4 Hz, 1H), 7.44 (t, J=7.7 Hz, 1H), 7.70 (d, J=7.5 Hz, 1H), 7.81 (d, J=7.7 Hz, 1H), 7.92 (d, J=5. Hz, 1H), 8.04 (q, J=4.5 Hz, 1H), 8.06 (s, 1H)), 8.18 (d, J=3.8 Hz, 1H), 12.92 (s, 1H). $^{13}$C NMR (100 MHz, DMSO-d$_6$) δ 28.6, 34.2, 79.8, 116.8, 128.3, 129.1, 129.2, 130, 130.7, 131.3, 133.3, 133.5, 139.3, 140.2, 158.5, 161.9, 167.4, 172.9. HPLC>95.1%.

Example 31: 2-(3-Cyano-benzylsulfanyl)-6-oxo-4-thiophen-2-yl-1,6-dihydro-pyrimidine-5-carbonitrile (Compound I-11)

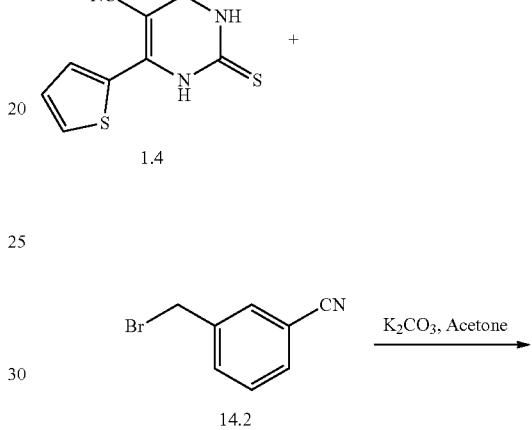

To a stirred solution of intermediate 1.4 (200 mg, 0.85 mmol) and K$_2$CO$_3$ (133 mg, 0.93 mmoL) in acetone (20 mL) was added intermediate 14.2 (133 mg, 0.93 mmol) and stirring was continued at rt for 16 h. The solvent was then removed under reduced pressure. The resulting mixture was poured into water, acidified to pH 6 by the addition of a 3M HCl solution, and then extracted with EtOAc (3×20 mL). The combined organic phase was washed with brine and dried over Na$_2$SO$_4$. The crude product was purified by flash chromatography eluting with DCM/MeOH to provide the title compound I-11 (50 mg, 0.17 mmol) as a white solid. Yield 17%. $^1$H NMR (400 MHz, DMSO-d$_6$) δ 4.60 (s, 2H), 7.35 (d, J=4.8 Hz, 1H), 7.54 (t, J=7.8 Hz, 1H), 7.74 (d, J=7.7 Hz, 1H), 7.83 (d, J=7.9 Hz, 1H), 7.96 (s, 1H), 8.1 (d, J=5.02 Hz, 1H), 8.27 (d, J=3.9 Hz, 1H), 13.80 (brs, 1H). $^{13}$C NMR (100 MHz, DMSO-d$_6$) δ 33.2, 88.8, 111.8, 116.5, 118.9, 130, 130.2, 131.6, 132.1, 132.8, 134.1, 135.4, 139.3, 139.6, 159, 161.2, 165.1. HPLC>99.1%.

Example 32: 2-[3-(2-Hydroxy-ethyl)-benzylsulfanyl]-6-oxo-4-thiophen-2-yl-1,6-dihydropyrimidine-5-carbonitrile (Compound I-12)

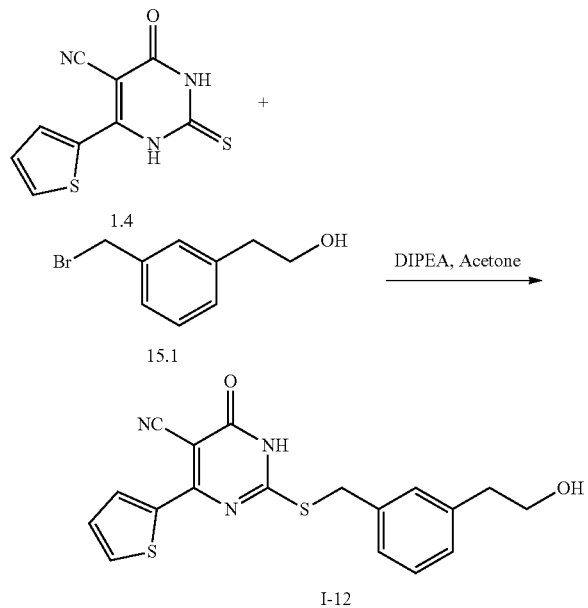

To a stirred solution of intermediate 1.4 (200 mg, 0.85 mmol) and DIPEA (0.16 mL, 0.93 mmol) in acetone (15 mL) was added intermediate 15.1 (201 mg, 0.93 mmol) and stirring was continued at rt for 16 h. The solvent was then removed under reduced pressure. The resulting mixture was poured into water, acidified to pH 6 by the addition of a 3M HCl solution, and then extracted with EtOAc (3×20 mL). The combined organic phase was washed with brine and dried over Na$_2$SO$_4$. The crude product was purified by flash chromatography eluting with DCM/MeOH to provide the title compound I-12 (120 mg, 0.32 mmol) as a white solid. Yield 38%. $^1$H NMR (400 MHz, DMSO-d$_6$) δ 2.47, (t, J=8.35 Hz, 2H), 2.67 (t, J=7.01 Hz, 2H), 4.48 (s, 2H), 4.51 (brs, 1H), 7.11 (d, J=7.5 Hz, 1H), 7.22 (t, J=7.5 Hz, 1H), 7.29 (d, J=7.7 Hz, 1H), 7.32-7.36 (m, 2H), 8.06 (d, J=4.9 Hz, 1H), 8.27 (d, J=3.9 Hz, 1H), 13.80 (brs, 1H). $^{13}$C NMR (100 MHz, DMSO-d$_6$) δ 34.3, 62.3, 62.3, 88.3, 116.9, 126.8, 128.5, 128.8, 129.8, 129.9, 131.8, 135.1, 136.9, 139.9, 140.3, 159, 162, 165.9. HPLC>96.1%.

Example 33: 2-(3-Cyanomethyl-benzylsulfanyl)-6-oxo-4-thiophen-2-yl-1,6-dihydro-pyrimidine-5-carbonitrile (Compound I-13)

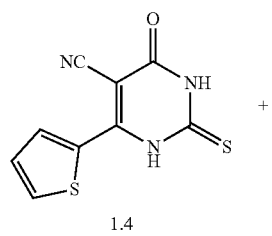

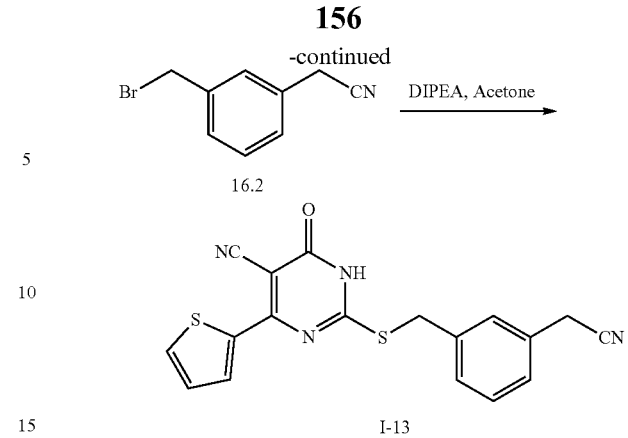

To a stirred solution of intermediate 1.4 (200 mg, 0.85 mmol) and DIPEA (0.2 mL, 0.94 mmol) in acetone (20 mL) was added intermediate 16.2 (196 mg, 0.94 mmol) and stirring was continued at rt for 16 h. The solvent was then removed under reduced pressure. The resulting mixture was poured into water, acidified to pH 6 by the addition of a 3M HCl solution, and then extracted with EtOAc (3×20 mL). The combined organic phase was washed with brine and dried over Na$_2$SO$_4$. The crude product was purified by flash chromatography eluting with DCM/MeOH (2.5% for product) to provide the title compound I-13 (300 mg, 0.82 mmol) as a yellow solid. Yield 96%. $^1$H NMR (400 MHz, DMSO-d$_6$) δ 4.01 (s, 2H), 4.52 (s, 2H), 7.24 (d, J=7.49 Hz, 1H), 7.31-7.36 (m, 2H), 7.43-7.45 (m, 2H), 8.0 (d, J=5 Hz, 1H), 8.23 (d, J=3.8 Hz, 1H), 13.80 (brs, 1H). $^{13}$C NMR (100 MHz, DMSO-d$_6$) δ 22.6, 33.9, 87.9, 117.5, 119.5, 127.5, 128.5, 128.9, 129.6, 129.6, 131.3, 131.9, 134.5, 138.6, 140.3, 159.1, 164.1, 166.7. HPLC>97.7%.

Example 34: 2-[3-(2-Methyl-2H-tetrazol-5-yl)-benzylsulfanyl]-6-oxo-4-thiophen-2-yl-1,6-dihydro-pyrimidine-5-carbonitrile (Compound I-14)

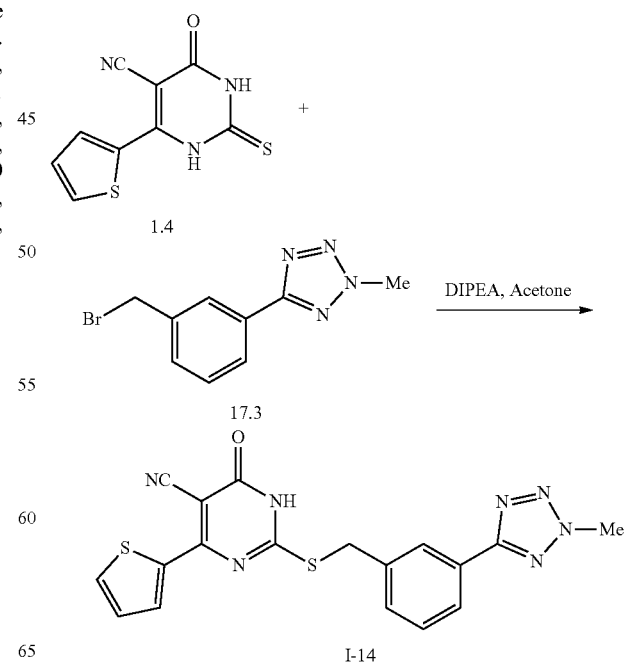

To a stirred solution of intermediate 1.4 (200 mg, 0.85 mmol) and DIPEA (0.17 mL, 0.93 mmoL) in acetone (15 mL) was added intermediate 17.3 (236 mg, 0.93 mmol) and stirring was continued at rt for 16 h. The solvent was then removed under reduced pressure. The resulting solid was collected and dried under reduced pressure to give the title compound I-14 (200 mg, 0.49 mmol) as a yellowish solid. Yield 58%. $^1$H NMR (400 MHz, DMSO-$d_6$) δ 4.40 (s, 3H), 4.66 (s, 2H), 7.35 (m, 1H), 7.51 (t, J=7.5 Hz, 1H), 7.66 (d, J=6.9 Hz, 1H), 7.94 (d, J=7.2 Hz, 1H), 8.08 (d, J=4.1 Hz, 1H), 8.21 (s, 1H), 8.28 (s, 1H), 13.80 (s, 1H). $^{13}$C NMR (100 MHz, DMSO-$d_6$) δ 33.9, 40.5, 88.7, 116.5, 125.7, 127.2, 127.5, 129.9, 130, 131.3, 132.1, 135.4, 138.6, 139.7, 159.1, 161.1, 164.2, 165.2. HPLC>99.3%.

Example 35: [3-(5-Cyano-4-morpholin-4-yl-6-thiophen-2-yl-pyrimidin-2-ylsulfanylmethyl)-phenyl]-acetic acid (Compound I-15)

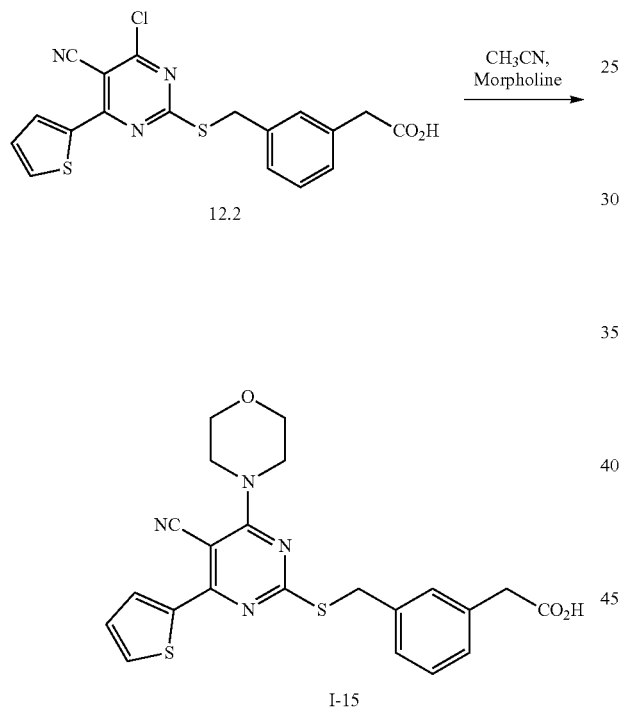

To a stirred suspension of intermediate 12.2 (100 mg, 0.25 mmol) in CH$_3$CN (10 mL) was added morpholine (0.023 mL, 0.27 mmol) and stirring was continued at rt for 16 h. The solvent was then removed under reduced pressure. The crude product was taken up in water, and the resulting aqueous mixture was extracted with EtOAc (3×20 mL). The combined organic phase was washed with brine and dried over Na$_2$SO$_4$ to provide the title compound I-15 (80 mg, 0.18 mmol) as a white solid. Yield 71%. $^1$H NMR (400 MHz, CDCl$_3$) δ 3.60 (s, 2H), 3.79 (m, 4H), 3.93 (m, 4H) 4.41 (s, 2H), 7.17-7.20 (m, 2H), 7.27-7.36 (m, 2H), 7.37 (d, J=8.23 Hz, 2H), 7.61 (d, J=5.1 Hz, 1H), 8.32 (d, J=3.5 Hz, 1H). $^{13}$C NMR (100 MHz, CDCl$_3$) δ 35.1, 40.6, 47.7, 47.7, 66.5, 66.6, 80.6, 118.4, 127.7, 128.3, 128.6, 128.8, 129.7, 131.7, 132.4, 133.5, 137.6, 139.9, 161.6, 162.9, 172.6, 176.3. HPLC>98.1%.

Example 36: [3-(5-Cyano-4-piperazin-1-yl-6-thiophen-2-yl-pyrimidin-2-ylsulfanylmethyl)-phenyl]-acetic acid (Compound I-16)

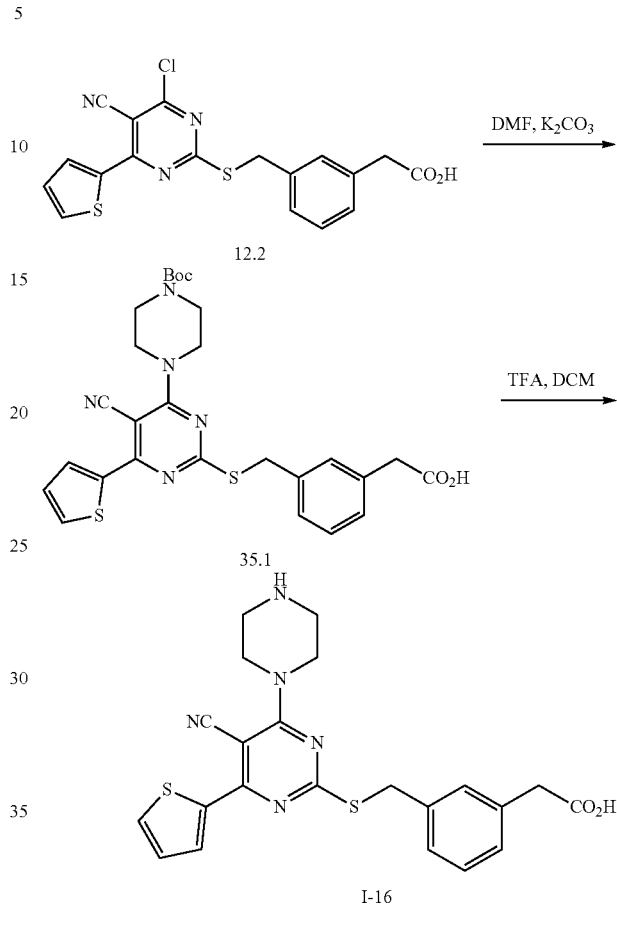

Step 1. 4-[2-(3-Carboxymethyl-benzylsulfanyl)-5-cyano-6-thiophen-2-yl-pyrimidin-4-yl]-piperazine-1-carboxylic acid tert-butyl ester (36.1)

To a stirred suspension of intermediate 12.2 (250 mg, 0.62 mmol) and K$_2$CO$_3$ (128 mg, 0.93 mmol) in DMF (4 mL) was added 1-boc-piperazine (127 mg, 0.68 mmol) and stirring was continued at rt for 16 h. The solvent was then removed under reduced pressure. The resulting mixture was taken up in water, and the aqeuous mixture was extracted with EtOAc (3×20 mL). The combined organic phase was washed with brine and dried over Na$_2$SO$_4$. The crude product was purified by flash chromatography eluting with DCM/MeOH (4% for product) to provide the title intermediate 35.1 (60 mg, 0.11 mmol) as a yellowish solid. Yield 18%.

Step 2. [3-(5-Cyano-4-piperazin-1-yl-6-thiophen-2-yl-pyrimidin-2-ylsulfanylmethyl)-phenyl]-acetic acid (I-16)

To a stirred solution of intermediate 35.1 (65 mg, 0.12 mmol) in DCM (15 mL) was added TFA (0.28 mL, 3.6 mmol) and stirring was continued at rt for 16 h. The solvent was then removed under reduced pressure. The crude mixture was taken up in water, and the resulting aqueous mixture was extracted with EtOAc (3×20 mL). The combined organic phase was washed with brine and dried over Na₂SO₄. The title compound I-16 (20 mg, 0.044 mmol) was obtained as a white solid after shredding with hot Et₂O. Yield 37%. ¹H NMR (400 MHz, DMSO-d₆) δ 2.83 (m, 4H), 3.51 (s, 2H), 3.81 (m, 4H), 4.39 (s, 3H), 7.13 (d, J=7.03 Hz, 1H), 7.24-7.33 (m, 4H), 7.95 (d, J=4.4 Hz, 1H), 8.20 (d, J=2.8 Hz, 1H). ¹³C NMR (100 MHz, DMSO-d₆) δ 34.6, 41.2, 45.5, 45.5, 48.4, 48.4, 118.7, 127.2, 128.6, 128.7, 129.2, 130.1, 131.8, 133.7, 135.8, 138.1, 140.1, 161.5, 162.4, 172, 173.1. HPLC>90.9%.

Example 37. [3-(5-Cyano-1-methyl-4-oxo-6-thiophen-2-yl-1,4-dihydro-pyrimidin-2-ylsulfanylmethyl)-phenyl]-acetic acid ethyl ester (Compound I-17)

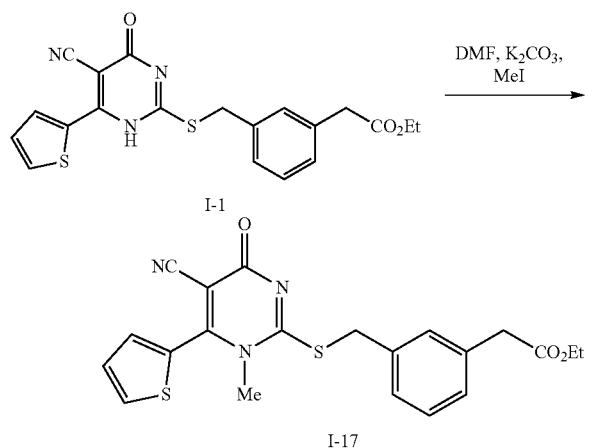

To a stirred suspension of compound I-1 (300 mg, 0.73 mmol) and K₂CO₃ (151 mg, 1.09 mmol) in DMF (15 mL) was added MeI (0.047 mL, 0.77 mmol) dropwise and stirring was continued at rt for 16 h. The resulting mixture was poured into water, and then extracted with EtOAc (3×20 mL). The combined organic phase was washed with brine and dried over Na₂SO₄ to provide the title compound I-17 (298 mg, 0.7 mmol) as a yellowish solid. Yield 96%. ¹H NMR (400 MHz, DMSO-d₆) δ 0.14 (t, J=7.12 Hz, 3H), 3.41 (s, 3H), 3.62 (s, 2H), 4.03 (q, J=7.1 Hz, 2H), 4.64 (s, 2H), 7.19 (d, J=7.6 Hz, 1H), 7.27-7.31 (m, 1H), 7.35 (t, J=4.1 Hz, 1H), 7.40 (m, 2H), 8.08 (d, J=4.9 Hz, 1H), 8.28 (d, J=3.8 Hz, 1H). ¹³C NMR (100 MHz, DMSO-d₆) δ 14.4, 31.1, 36.1, 40.5, 60.6, 87.5, 116.5, 127.9, 129.1, 129.2, 130, 130.4, 132.1, 135.3, 135.4, 136.2, 139.5, 157.1, 160.1, 166.4, 171.3. HPLC>95.1%.

Example 38. 3-(5-Cyano-6-oxo-4-thiophen-2-yl-1,6-dihydro-pyrimidin-2-ylsulfanylmethyl)-benzenesulfonamide (Compound I-18)

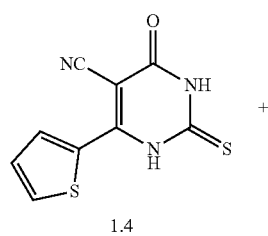

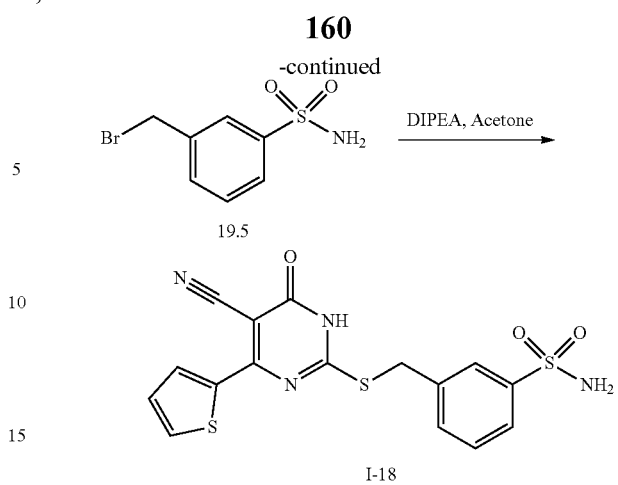

To a stirred solution of intermediate 1.4 (107 mg, 0.45 mmol) and DIPEA (0.08 mL, 0.49 mmoL) in acetone (15 mL) was added intermediate 19.5 (125 mg, 0.49 mmol) and stirring was continued at rt for 16 h. The solvent was then removed under reduced pressure. The crude mixture was taken up in water, and then extracted with EtOAc (3×20 mL). The combined organic phase was washed with brine and dried over Na₂SO₄. The title compound I-18 (50 mg, 0.12 mmol) was obtained as a yellowish solid after trituration with hot Et₂O. Yield 28%. ¹H NMR (400 MHz, DMSO-d₆) δ 4.65 (s, 2H), 7.34 (t, J=4.6 Hz, 1H), 7.40 (s, 2H), 7.52 (t, J=7.6 Hz, 1H), 7.72 (t, J=6.1 Hz, 2H), 7.94 (s, 1H), 8.06 (d, J=4.8 Hz, 1H), 8.27 (d, J=3.6 Hz, 1H), 13.8 (s, 1H). ¹³C NMR (100 MHz, DMSO-d₆) δ 33.7, 88.6, 116.6, 125.2, 126.1, 129.7, 129.9, 132, 132.5, 135.4, 138.4, 139.7, 144.8, 159.1, 161.4, 165.3. HPLC>95.1%.

Example 39: [3-(3-Cyano-6-oxo-4-phenyl-1,6-dihydro-pyridin-2-ylsulfanylmethyl)-phenyl]-acetic acid (Compound I-19)

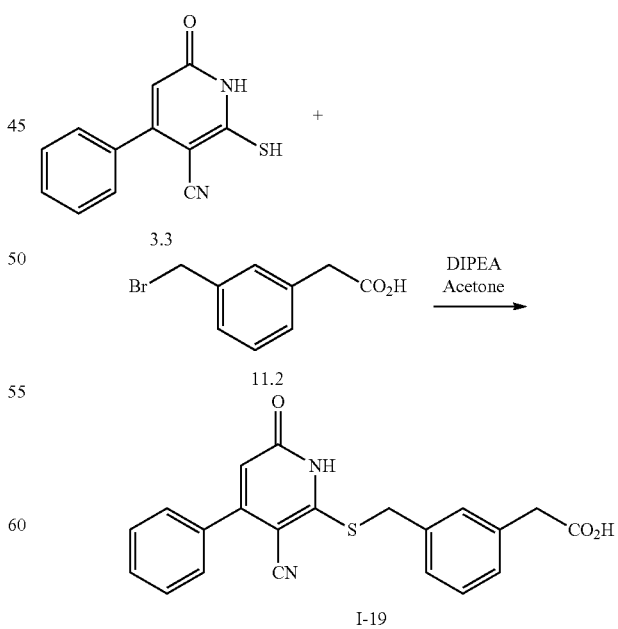

To a stirred suspension of intermediate 3.3 (100 mg, 0.44 mmol) and DIPEA (0.09 mL, 0.53 mmol) in acetone (15 mL) was added intermediate 11.2 (94 mg, 0.44 mmol). Stirring was continued overnight at rt. The mixture was diluted with crushed ice and water. pH was adjusted to 5 by the addition of AcOH. The precipitate was collected, washed with cold water and dried under vacuo. Compound I-19 (60 mg, 0.16 mmol) was obtained as a brownish powder. Yield 37%. $^1$H NMR (400 MHz, DMSO-$d_6$) δ 3.55 (s, 2H), 4.5 (s, 2H), 6.51 (s, 1H), 7.16 (d, J=7.4 Hz, 1H), 7.27 (t, J=7.7 Hz, 1H), 7.37 (m, 2H), 7.51-7.53 (m, 3H), 7.55-7.56 (m, 2H), 12.17 (brs, 2H); $^{13}$C NMR (100 MHz, DMSO-$d_6$) δ 33.5, 40.6, 95.9, 108, 116.2, 127.6, 128.3, 128.3, 128.5, 128.5, 128.9, 128.9, 130, 130.3, 135.4, 135.9, 137.5, 155.9, 162.1, 164.9, 172.7; HPLC: 96.88%.

Example 40: [3-(3-Cyano-6-oxo-4-thiophen-2-yl-1,6-dihydro-pyridin-2-ylsulfanylmethyl)-phenyl]-acetic acid (Compound I-20)

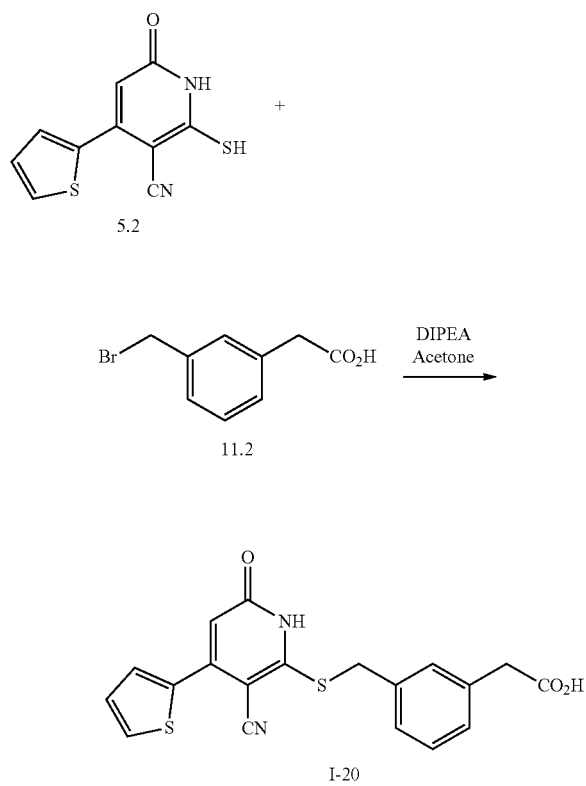

To a stirred suspension of intermediate 5.2 (153 mg, 0.56 mmol) and DIPEA (0.12 mL, 0.67 mmol) in DMSO/acetone (15/4 mL) was added intermediate 11.2 (121 mg, 0.56 mmol). Stirring was continued overnight at room temperature. The mixture was diluted with crushed ice and water. The pH was adjusted to 5 by the addition of AcOH. The precipitate was collected washed with cold water and dried under vacuo. Compound I-20 (90 mg, 0.22 mmol) was obtained as a brownish powder. Yield 42%. $^1$H NMR (400 MHz, DMSO-$d_6$) δ 3.55 (s, 2H), 4.51 (s, 2H), 6.62 (s, 1H), 7.15 (d, J=7.4 Hz, 1H), 7.24-7.28 (m, 2H), 7.35 (d, J=6.4 Hz, 2H), 7.75 (d, J=3.5 Hz, 1H), 7.85 (d, J=4.9 Hz, 1H), 12.1 (brs, 1H); $^{13}$C NMR (100 MHz, DMSO-$d_6$) δ 33.6, 40.6, 93.8, 104.5, 116.5, 127.6, 128.6, 128.6, 128.7, 128.7, 129.5, 130.3, 130.3, 135.4, 136.6, 137.4, 147.4, 165.1, 172.7; HPLC: 96.5%.

Example 41: [3-(3,5-Dicyano-6-oxo-4-thiophen-2-yl-1,6-dihydro-pyridin-2-ylsulfanylmethyl)-phenyl]-acetic acid (Compound I-21)

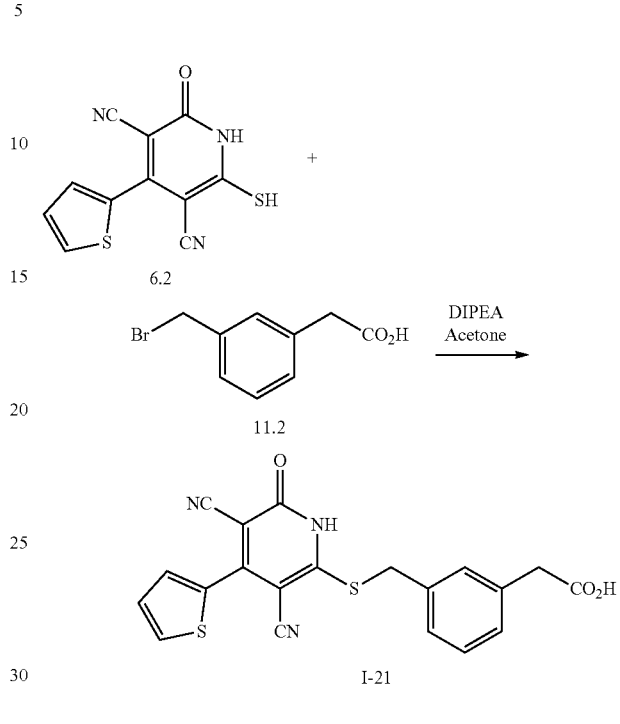

To a stirred solution of intermediate 6.2 (200 mg, 0.77 mmol) and DIPEA (0.16 mL, 0.92 mmol) in acetone (15 mL) was added intermediate 11.2 (165 mg, 0.77 mmol). Stirring was continued overnight at room temperature. The mixture was diluted with crushed ice and water. The pH was adjusted to 5 by the addition of AcOH. The precipitate was collected washed with cold water and dried under vacuo. Compound I-21 (110 mg, 0.27 mmol) was obtained as a brownish powder. Yield 35%. $^1$H NMR (400 MHz, DMSO-$d_6$) δ 3.56 (s, 2H), 4.48 (s, 2H), 7.63 (d, J=7.6 Hz, 1H), 7.24-7.28 (m, 2H), 7.38-7.40 (m, 2H), 7.54 (dd, J=1.1 Hz, J=3.6 Hz, 1H), 7.93 (dd, J=1.1 Hz, J=5 Hz, 1H), 8.12 (brs, 1H), 12.29 (brs, 1H); $^{13}$C NMR (100 MHz, DMSO-$d_6$) δ 33.3, 40.6, 85.8, 93.1, 115.5, 127.8, 128, 128, 128.6, 130.5, 130.9, 131.4, 131.4, 132.9, 135.3, 137.4, 150.8, 159.8, 166.9, 172.8; HPLC: 97.5%.

Example 42: 2-Oxo-6-[3-(1H-tetrazol-5-yl)-benzylsulfanyl]-4-thiophen-2-yl-1,2-dihydro-pyridine-3,5-dicarbonitrile (Compound I-22)

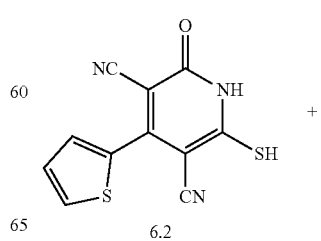

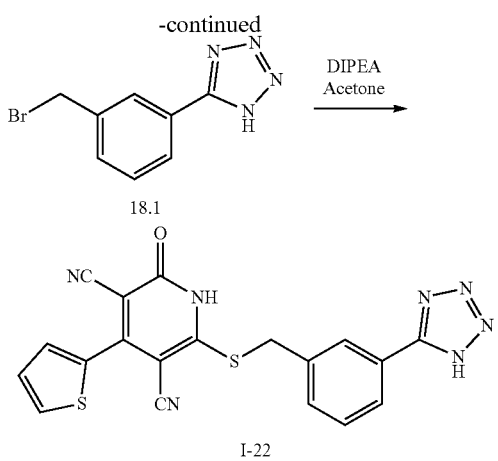

To a stirred solution of intermediate 6.2 (150 mg, 0.57 mmol) and DIPEA (0.18 mL, 0.68 mmol) in acetone (15 mL) was added intermediate 18.1 (138 mg, 0.57 mmol). Stirring was continued overnight at room temperature. The mixture was diluted with crushed ice and water. pH was adjusted to 5 by the addition of AcOH. The precipitate was collected washed with cold water and dried under vacuo. Compound I-22 (90 mg, 0.27 mmol) was obtained as a yellowish powder. Yield 38%. $^1$H NMR (400 MHz, DMSO-$d_6$) δ 4.6 (s, 2H), 7.26 (dd, J=5.0 Hz, J=3.6 Hz, 1H), 7.54-7.56 (m, 2H), 7.76 (d, J=7.7 Hz, 1H), 7.90-7.94 (m, 2H), 8.1 (s, 1H); $^{13}$C NMR (100 MHz, DMSO-$d_6$) δ 33.2, 86.2, 93.4, 115.7, 124.9, 126.2, 128.1, 128.2, 129.8, 131.2, 131.6, 131.6, 132.5, 133, 139.5, 151.1, 155.8, 160.1, 166.8; HPLC: 96.7%

Example 43: [3-(4-Benzyl-3-cyano-6-oxo-1,6-dihydro-pyridin-2-ylsulfanylmethyl)-phenyl]-acetic acid (Compound I-23)

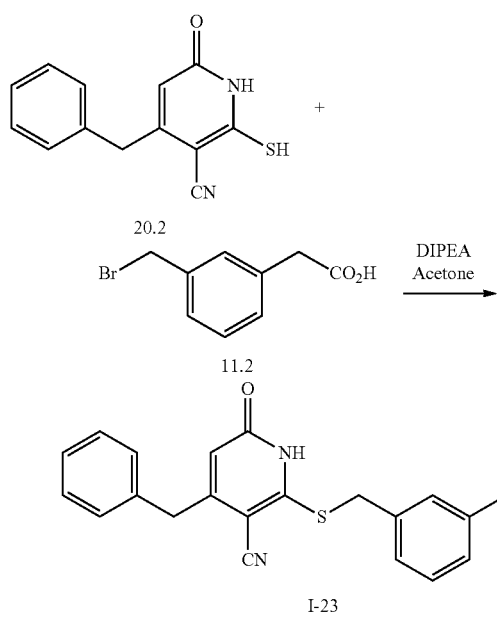

To a stirred solution of intermediate 20.2 (154 mg, 0.63 mmol) and DIPEA (0.12 mL, 0.7 mmol) in acetone (15 mL) was added intermediate 11.2 (150 mg, 0.7 mmol). Stirring was continued overnight at room temperature. The mixture was diluted with crushed ice and water. pH was adjusted to 5 by the addition of AcOH. The precipitate was collected washed with cold water and dried under vacuo. Compound I-23 (100 mg, 0.25 mmol) was obtained as a yellowish powder. Yield 40%). $^1$H NMR (400 MHz, DMSO-$d_6$) δ 3.37 (s, 2H), 3.98 (s, 2H), 4.48 (s, 2H), 6.34 (s, 1H), 7.13-7.32 (m, 9H), 12.1 (brs, 1H); HPLC: 98.5%.

Example 44: (5-Cyano-6-oxo-4-thiophen-2-yl-1,6-dihydro-pyrimidin-2-ylsulfanyl)-acetic acid (Compound I-24)

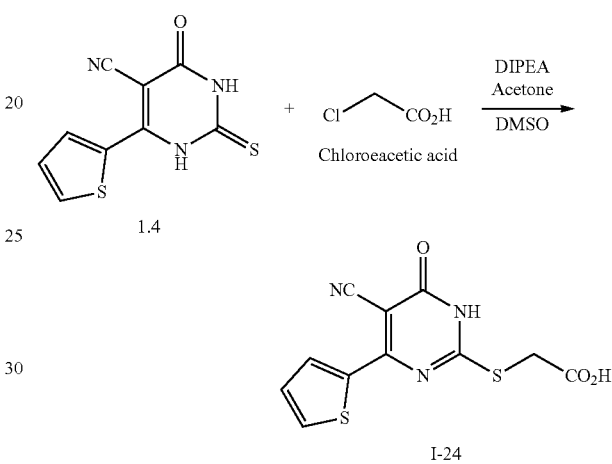

To a stirred solution of intermediate 1.4 (200 mg, 0.85 mmol) and DIPEA (0.18 mL, 1.02 mmol) in acetone/DMSO (20:2 mL) was added chloroacetic acid (80 mg, 0.85 mmol). Stirring was continued overnight at room temperature. Additional 0.3 equivalents of DIPEA and of chloroacetic acid were then added to complete the reaction. The mixture was diluted with crushed ice and water. pH was adjusted to 3 by the addition of 3N HCl. The precipitate was collected and purified by reverse flash chromatography, eluting with $H_2O$/MeOH from 10 to 80%. Compound I-24 (210 mg, 0.71 mmol) was obtained as a yellowish powder. Yield 83%. $^1$H NMR (400 MHz, DMSO-$d_6$) δ 4.0 (s, 2H), 7.33 (t, J=4.7 Hz, 1H), 8.1 (d, J=4.9 Hz, 1H), 8.25 (d, J=3.8 Hz, 1H), 12.8 (brs, 1H); $^{13}$C NMR (100 MHz, DMSO-$d_6$) δ 33.4, 88.5, 116.5, 129.8, 132.3, 135.6, 139.5, 159, 161.1, 165.2, 169.3; HPLC: 99.6%.

Example 45: 6-Oxo-2-(1H-tetrazol-5-ylmethylsulfanyl)-4-thiophen-2-yl-1,6-dihydro-pyrimidine-5-carbonitrile (Compound I-25)

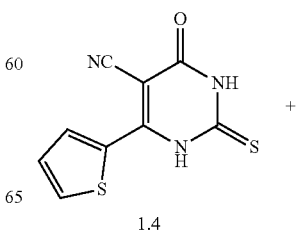

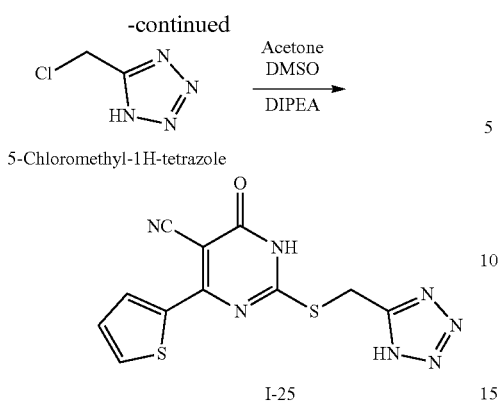

To a stirred solution of intermediate 1.4 (200 mg, 0.85 mmol) and DIPEA (0.18 mL, 1.02 mmol) in acetone/DMSO (20:2 mL) was added intermediate 5-chloromethyl-1H-tetrazole (101 mg, 0.85 mmol). Stirring was continued overnight at room temperature. Additional 0.3 equivalents of DIPEA and of 5-chloromethyl-1H-tetrazole were then added to complete the reaction. The mixture was diluted with crushed ice and water. pH was adjusted to 3 by the addition of 3N HCl. The precipitate was collected and purified by reverse flash chromatography, eluting with $H_2O$/MeOH from 10 to 80%. Compound I-25 (120 mg, 0.37 mmol) was obtained as a yellowish powder. Yield 44%. $^1$H NMR (400 MHz, DMSO-$d_6$) δ 4.82 (s, 2H), 7.31 (t, J=4.2 Hz, 1H), 8.0 (d, J=4.9 Hz, 1H), 8.22 (d, J=3.8 Hz, 1H); $^{13}$C NMR (100 MHz, DMSO-$d_6$) δ 23.6, 88.7, 116.4, 129.9, 132.2, 135.6, 139.4, 157.1, 159.0, 161.4, 164.4; HPLC: 94.6%.

Example 46: 2-(1H-Tetrazol-5-ylmethylsulfanyl)-6-trifluoromethyl-3H-pyrimidin-4-one (Compound I-26)

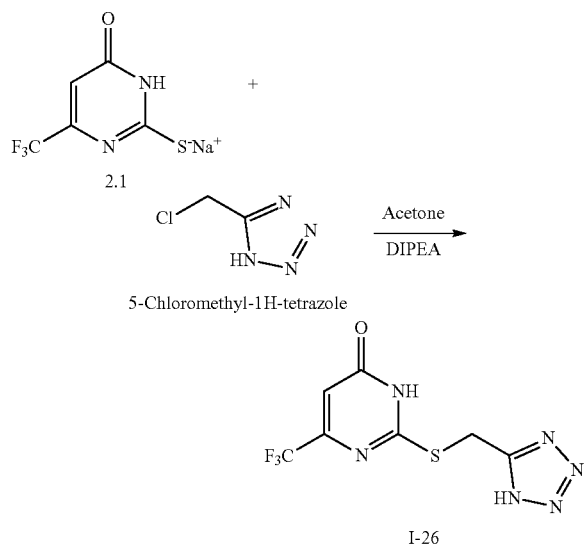

To a stirred solution of intermediate 2.1 (100 mg, 0.56 mmol) and DIPEA (0.13 mL, 0.73 mmol) in acetone (5 mL) was added 5-chloromethyl-1H-tetrazole (87 mg, 0.73 mmol). Stirring was continued overnight at room temperature. The mixture was diluted with crushed ice and water. pH was adjusted to 3 by the addition of 3N HCl. The aqueous phase was extracted with EtOAc (3×20 mL). The combined organic phase was washed with brine and dried over $Na_2SO_4$. Compound I-26 (60 mg, 0.19 mmol) was obtained as a white powder. Yield 35%. $^1$H NMR (400 MHz, DMSO-$d_6$) δ 4.69 (s, 2H), 6.67 (s, 1H), 15.1 (brs, 1H); $^{13}$C NMR (100 MHz, DMSO-$d_6$) δ 23.1, 107.7, 120.6 (q, $J^{CF}$=2.7 Hz), 152, 154.3, 163.9, 164.8; HPLC: 97.9%

Example 47: (6-Oxo-4-trifluoromethyl-1,6-dihydro-pyrimidin-2-ylsulfanyl)-acetic acid (Compound I-27)

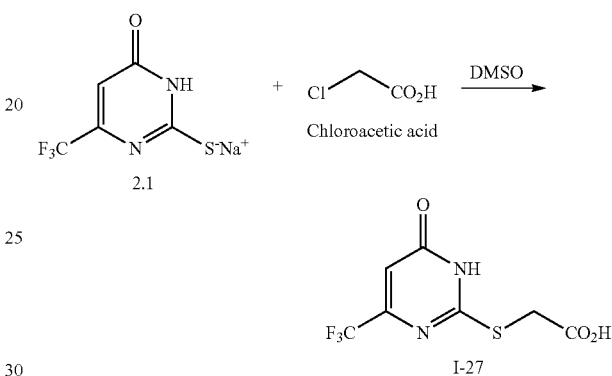

To a stirred solution of intermediate 2.1 (200 mg, 0.85 mmol) and DIPEA (0.16 mL, 0.94 mmol) in DMSO (5 mL) was added chloroacetic acid (89 mg, 0.94 mmol). Stirring was continued overnight at rt. The mixture was diluted with crushed ice and water. pH was adjusted to 3 by the addition of 3N HCl. The aqueous phase was extracted with EtOAc (3×20 mL). The combined organic phase was washed with brine and dried over $Na_2SO_4$. The crude of reaction was purified by reverse flash chromatography eluting with $H_2O$/MeOH from 5 to 65% for product. Compound I-27 (125 mg, 0.49 mmol) was obtained as a white powder. Yield 58%. $^1$H NMR (400 MHz, DMSO-$d_6$) δ 3.96 (s, 2H), 6.63 (s, 1H); $^{13}$C NMR (100 MHz, DMSO-$d_6$) δ 33.1, 108, 120.6 (q, $J_{CF}$=2.7 Hz), 163.1, 165.4, 169.5; HPLC: 95.9%.

Example 48: [3-(6-Oxo-4-trifluoromethyl-1,6-dihydro-pyrimidin-2-ylsulfanylmethyl)-phenyl]-acetic acid (Compound I-28)

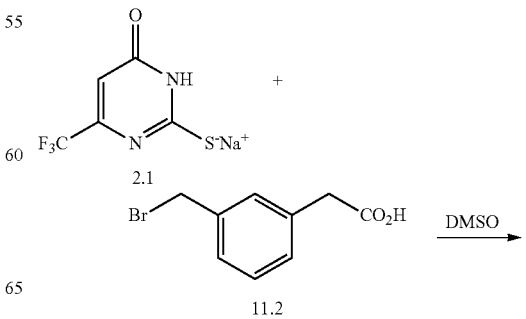

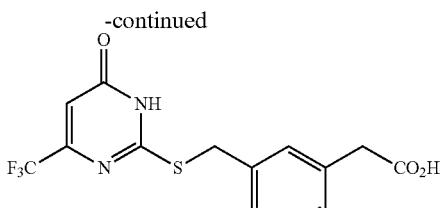

To a stirred solution of intermediate 2.1 (150 mg, 0.64 mmol) and DIPEA (0.12 mL, 0.71 mmol) in DMSO (5 mL) was added intermediate 11.2 (152 mg, 0.71 mmol). Stirring was continued overnight at rt. The mixture was diluted with crushed ice and water. pH was adjusted to 3 by the addition of 3N HCl. The aqueous phase was extracted with EtOAc (3×20 mL). The combined organic phase was washed with brine and dried over $Na_2SO_4$. The crude of reaction was purified by reverse flash chromatography eluting with $H_2O$/MeOH from 5 to 80% for product. Compound I-28 (100 mg, 0.29 mmol) was obtained as a white powder. Yield 45%. $^1$H NMR (400 MHz, DMSO-$d_6$) δ 3.54 (s, 2H), 4.52 (s, 2H), 6.87 (s, 1H), 7.16 (d, J=7.3 Hz, 1H), 7.26 (t, J=7.4 Hz, 1H), 7.33-7.35 (m, 2H), 12.18 (brs, 1H); HPLC: 98.1%.

Example 49: 2-[3-(1H-Tetrazol-5-yl)-benzylsulfanyl]-6-trifluoromethyl-3H-pyrimidin-4-one (Compound I-29)

To a stirred solution of intermediate 2.1 (150 mg, 0.64 mmol) and DIPEA (0.12 mL, 0.71 mmol) in DMSO (5 mL) was added intermediate 18.1 (152 mg, 0.64 mmol). Stirring was continued overnight at rt. The mixture was diluted with crushed ice and water. pH was adjusted to 3 by the addition of 3N HCl. The white solid was collected and characterized as the title compound. Compound I-29 (160 mg, 0.45 mmol) was obtained as a white powder. Yield 70%. $^1$H NMR (400 MHz, DMSO-$d_6$) δ 4.50 (s, 2H), 6.63 (s, 1H), 7.54 (t, J=7.7 Hz, 1H), 7.64 (d, J=7.5 Hz, 1H), 7.9 (d, J=7.6 Hz, 1H), 8.13 (s, 1H), 13.3 (brs, 1H); HPLC: 95.2%.

Example 50: (4-Benzyl-5-cyano-6-oxo-1,6-dihydropyrimidin-2-ylsulfanyl)-acetic acid (Compound I-30)

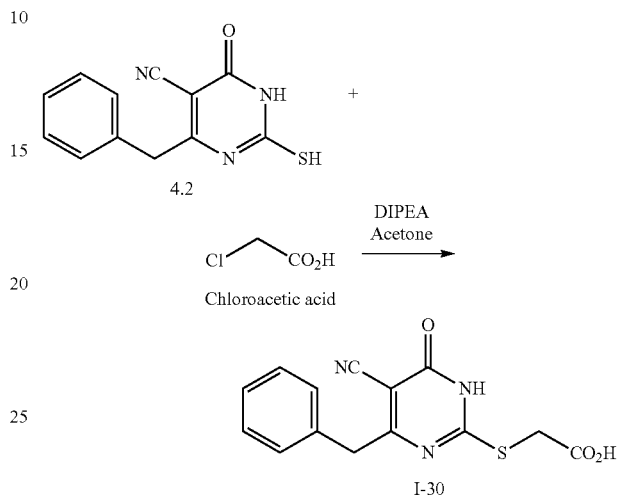

To a stirred solution of intermediate 4.2 (110 mg, 0.45 mmol) and DIPEA (0.086 mL, 0.5 mmol) in acetone (10 mL) was added chloroacetic acid (43 mg, 0.45 mmol). Stirring was continued overnight reflux. The mixture cooled to rt and it was diluted with crushed ice and water. pH was adjusted to 3 by the addition of 3N HC. The aqueous phase was extracted with EtOAc (3×20 mL). The combined organic phase was washed with brine and dried over $Na_2SO_4$. The crude of reaction was purified by reverse phase flash chromatography eluting with $H_2O$/MeOH from 5 to 80% for product. Compound I-30 (95 mg, 0.32 mmol) was obtained as a white powder. Yield 69%. $^1$H NMR (400 MHz, DMSO-$d_6$) δ 3.92 (s, 2H), 4.0 (s, 2H), 7.24-7.28 (m, 1H), 7.31-7.32 (4H); $^{13}$C NMR (100 MHz, DMSO-$d_6$) δ 33.4, 42.6, 95.0, 115.4, 127.4, 129, 129, 129.3, 129.3, 136.4, 160.7, 166.3, 169.4, 169.4; HPLC: 98.9%.

Example 51: 3-(6-Oxo-4-trifluoromethyl-1,6-dihydro-pyrimidin-2-ylsulfanylmethyl)-benzoic acid (Compound I-31)

-continued

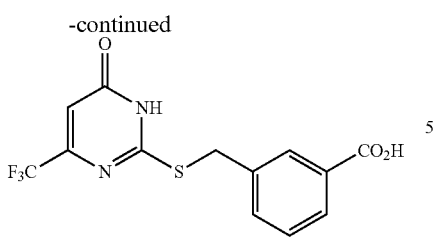

I-31

To a stirred solution of intermediate 2.1 (200 mg, 0.92 mmol) and DIPEA (0.19 mL, 1.1 mmol) in DMSO (5 mL) was added 3(2-chloromethyl) benzoic acid 13.1 (170 mg, 1 mmol). Stirring was continued overnight at rt. The mixture was diluted with crushed ice and water. pH was adjusted to 3 by the addition of 3N HCl. The white precipitate was collected and dried under vacuo. The crude was purified by reverse phase chromatography, eluting with $H_2O$/MeOH. from 4 to 80%. Compound I-31 (120 mg, 0.36 mmol) was obtained as a white powder. Yield 40%. $^1$H NMR (400 MHz, DMSO-$d_6$) δ 2.5 (s, 2H), 4.45 (s, 2H), 6.61 (s, 1H), 7.42 (t, J=7.6 Hz, 1H), 7.48 (d, J=7.4 Hz, 1H), 7.81 (d, J=7.58 Hz, 1H), 8.02 (s, 1H), 13.12 (brs, 1H); $^{13}$C NMR (100 MHz, DMSO-$d_6$) δ 33.8, 107.7, 120.6 (q, $J_{CF}$=2.7 Hz), 128.6, 128.9, 130.4, 131.3, 134, 138.3, 150, 163, 165, 167.4; HPLC: 98.8%.

Example 52: 3-(6-Oxo-4-trifluoromethyl-1,6-dihydro-pyrimidin-2-ylsulfanylmethyl)-benzoic acid (Compound I-32)

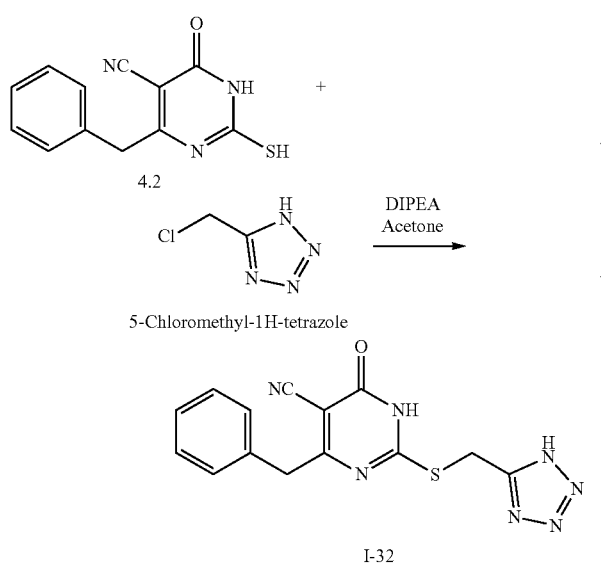

I-32

To a stirred solution of intermediate 4.2 (200 mg, 0.92 mmol) and DIPEA (0.16 mL, 0.9 mmol) in acetone (10 mL) was added 5 chloromethyl-1H-tetrazole (97 mg, 0.82 mmol). Stirring was continued overnight at reflux. The mixture was diluted with crushed ice and water. pH was adjusted to 3 by the addition of 3N HCl. The mixture was extracted with EtOAc (3×30 mL). The combined organic phase was washed with brine and dried over $Na_2SO_4$. Compound I-32 (58 mg, 0.18 mmol) was obtained as a white powder after purification by reverse phase flash chromatography, eluting with $H_2O$/MeOH from 5 to 80%. Yield 20%. $^1$H NMR (400 MHz, DMSO-$d_6$) δ 3.90 (s, 2H), 4.74 (s, 2H), 7.13-7.21 (m, 5H); HPLC: 98.9%.

Example 53: [3-(4-Benzyl-5-cyano-6-oxo-1,6-dihydro-pyrimidin-2-ylsulfanylmethyl)-phenyl]-acetic acid (Compound I-33)

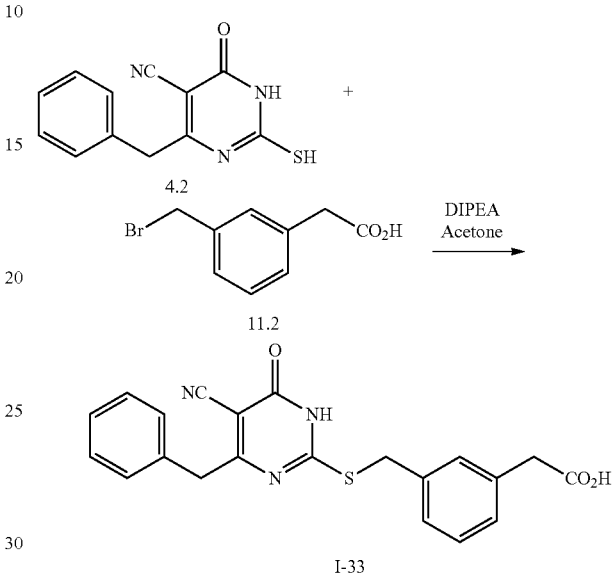

I-33

To a stirred solution of intermediate 4.2 (150 mg, 0.62 mmol) and DIPEA (0.12 mL, 0.68 mmol) in acetone (10 mL) was added intermediate 11.2 (146 mg, 0.68 mmol). Stirring was continued overnight reflux. The mixture cooled to rt and it was diluted with crushed ice and water. pH was adjusted to 5 by the addition of AcOH. The precipitate was collected and dried under vacuo. The title compound I-33 (80 mg, 0.2 mmol) was obtained as a white solid. Yield: 33%. $^1$H NMR (400 MHz, DMSO-$d_6$) δ 3.5 (s, 2H), 4.0 (s, 2H), 4.37 (s, 2H), 7.12-7.32 (m, 9H); $^{13}$C NMR (100 MHz, DMSO-$d_6$) δ 34.2, 42.6, 54.1, 95.2, 116, 127.5, 127.8, 128.9, 129, 129.1, 129.1, 129.6, 129.6, 130.4, 135.7, 136.8, 137.5, 161, 166.7, 172.6, 173.1; HPLC: 90.2%

Example 54: 4-Benzyl-6-oxo-2-[3-(1H-tetrazol-5-yl)-benzylsulfanyl]-1,6-dihydro-pyrimidine-5 carbonitrile (Compound I-34)

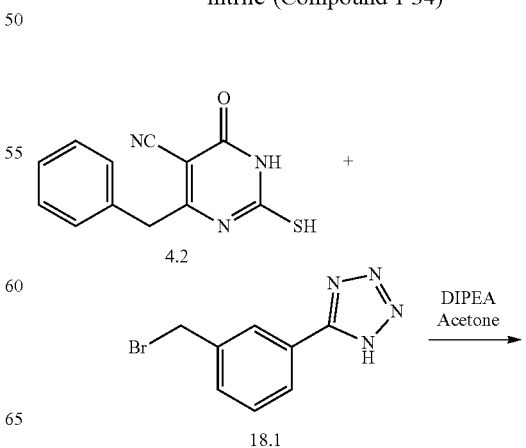

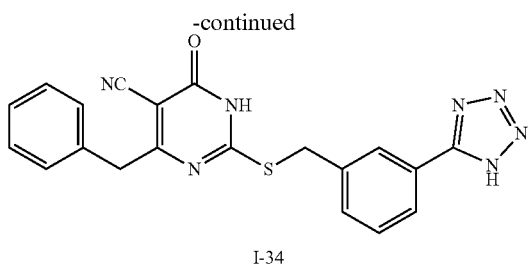

I-34

To a stirred solution of intermediate 4.2 (150 mg, 0.62 mmol) and DIPEA (0.12 mL, 0.68 mmol) in acetone (10 mL) was added intermediate 18.1 (162 mg, 0.68 mmol). Stirring was continued overnight reflux. The mixture cooled to rt and it was diluted with crushed ice and water. pH was adjusted to 5 by the addition of AcOH. The precipitate was collected and dried under vacuo. The crude was suspended in water, acidified to pH 3 by the addition of 3N HCl solution and extracted with EtOAc, (3×20 mL). The combined organic phase was washed with brine and dried over $Na_2SO_4$. The title compound I-34 (125 mg, 0.31 mmol) was obtained as a light yellow solid. Yield: 50%. $^1$H NMR (400 MHz, DMSO-$d_6$) δ 4.0 (s, 2H), 4.51 (s, 2H), 7.17-7.28 (m, 5H), 7.41-7.47 (2H), 7.90 (d, J=6.82 Hz, 1H), 8.06 (s, 2H); $^{13}$C NMR (100 MHz, DMSO-$d_6$) δ 33.7, 42.5, 95.5, 115.5, 124.7, 126.2, 127.3, 128.8, 128.9, 128.9, 129.4, 129.4, 129.9, 132.1, 136.5, 139, 158, 160.6, 166.2, 172.7; HPLC: 93%.

Example 55: 3-(4-Benzyl-5-cyano-6-oxo-1,6-dihydro-pyrimidin-2-ylsulfanylmethyl)-benzoic acid (Compound I-35)

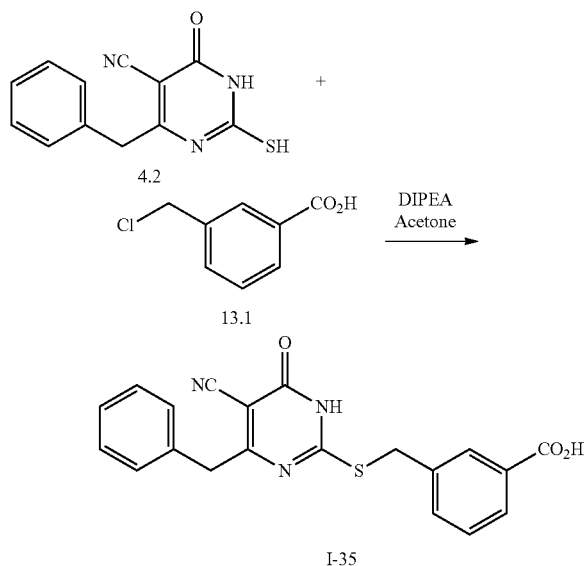

To a stirred solution of intermediate 4.2 (150 mg, 0.62 mmol) and DIPEA (0.14 mL, 0.82 mmol) in acetone (10 mL) was added 3(2-chloromethyl) benzoic acid 13.1 (116 mg, 0.68 mmol). Stirring was continued overnight at r.t. The mixture cooled to rt and it was diluted with crushed ice and water. pH was adjusted to 3 by the addition of 3N HCl. The precipitate was collected and dried under vacuo. The title compound I-35 (160 mg, 0.42 mmol) was obtained as a light yellow solid. Yield: 68%. $^1$H NMR (400 MHz, DMSO-$d_6$) δ 4.0 (s, 2H), 4.46 (s, 2H), 7.25-7.36 (m, 5H), 7.44 (d, J=7.3 Hz, 1H), 7.81 (d, J=7.6 Hz, 1H), 8.0 (s, 1H), 13.1 (brs, 1H); $^{13}$C NMR (100 MHz, DMSO-$d_6$) δ 33.7, 42.5, 95.5, 115.5, 127.4, 128.6, 129, 129, 129.1, 129.4, 129.4, 130.3, 131.2, 133.8, 136.5, 138.1, 160.5, 166.2, 167.4, 172.7; HPLC: 98%. HPLC: 98%.

Example 56: [3-(3-cyano-6-oxo-4-trifluoromethyl-1,6-dihydro-pyridin-2-ylsulfanylmethyl)-phenyl]-acetic acid (Compound I-36)

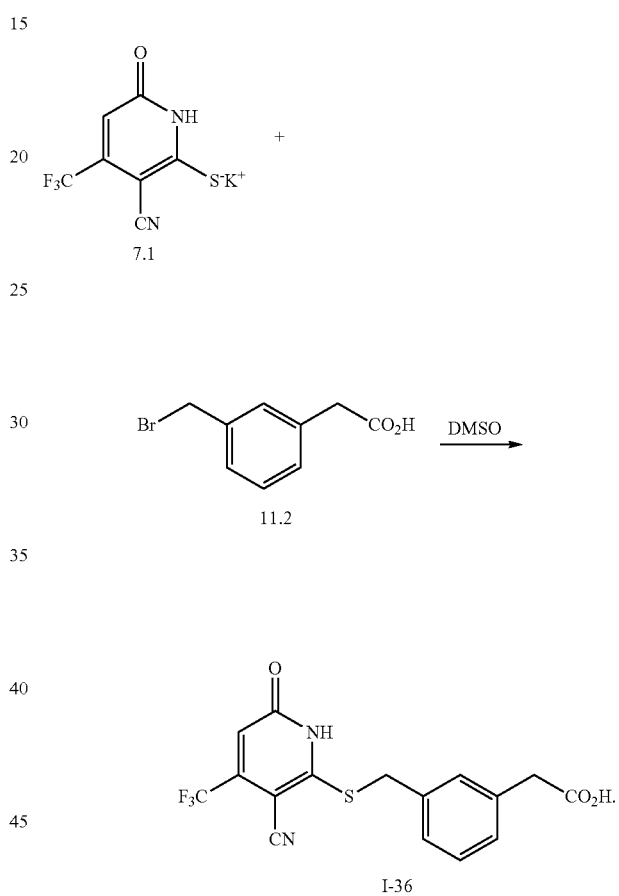

To a stirred solution of intermediate 7.1 (164 mg, 0.63 mmol) and DIPEA (0.12 mL, 0.71 mmol) in DMSO (5 mL) was added intermediate 11.2 (150 mg, 0.71 mmol). Stirring was continued overnight at r.t. The mixture was diluted with crushed ice and water. pH was adjusted to 3 by the addition of 3N HCl followed by extraction with EtOAc, (3×20 mL). The combined organic phase was washed with brine, dried over $Na_2SO_4$. The crude was purified by reverse phase chromatography eluting with $H_2O$/MeOH from 8% to 40% for product. The title compound I-36 (85 mg, 0.23 mmol) was obtained as a white powder. Yield: 37%. $^1$H NMR (400 MHz, DMSO-$d_6$) δ 3.55 (s, 2H), 4.53 (s, 2H), 6.87 (s, 1H), 7.16 (m, 1H), 7.26 (m, 1H), 7.35 (m, 2H), 12.2 (brs, 1H). $^{13}$C NMR (100 MHz, DMSO-$d_6$) δ 34.1, 40.8, 91.5, 105.3, 113.8, 121.5 (q, JCF=2.7 Hz), 127.8, 128.8, 129, 130.6, 135.7, 137.1, 142 (q, JCF=0.3 Hz), 164.6, 165.6, 173; HPLC: 97.8%.

Example 57: [3-(5-Cyano-6-oxo-4-thiophen-2-yl-1,6-dihydro-pyrimidin-2-ylsulfanyl)-propionic acid (Compound I-37)

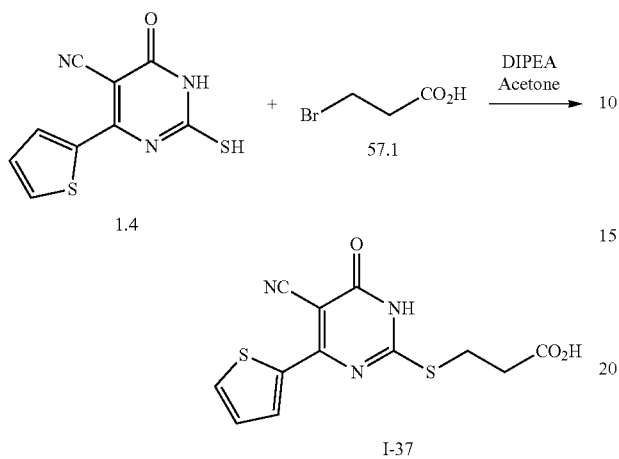

To a stirred solution of intermediate 1.4 (200 mg, 0.84 mmol) and DIPEA (0.16 mL, 0.93 mmol) in acetone (10 mL) was added 3-bromo-propionic acid (57.1) (142 mg, 0.93 mmol). Stirring was continued overnight at rt. The mixture was then diluted with crushed ice and water and the pH was adjusted to 3 by the addition of 3N HCl. The resulting precipitate was collected and dried under vacuo. The title compound I-37 (180 mg, 0.58 mmol) was obtained as a light yellow solid. Yield: 69%. $^1$H NMR (400 MHz, DMSO-d$_6$) δ2.75-2.80 (m, 2H), 3.34-3.39 (m, 2H), 7.32-7.36 (m, 1H), 8.0-8.24 (m, 1H), 8.24-8.27 (m, 1H), 12.18 (brs, 1H), 13.72 (brs, 1H); $^{13}$C NMR (100 MHz, DMSO-d$_6$) δ 26.2, 33.8, 40.7, 88.4, 1116.6, 130.1, 131.9, 135.4, 139.9, 158.9, 161.1, 165.6, 173.1; HPLC: 96.6%.

Example 58: 3-(6-Oxo-4-trifluoromethyl-1,6-dihydro-pyrimidin-2-ylsulfanyl)-propionic acid (Compound I-38)

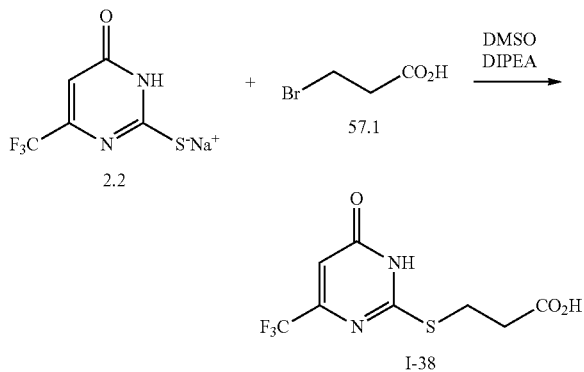

To a stirred solution of intermediate 2.2 (150 mg, 0.69 mmol) and DIPEA (0.13 mL, 0.75 mmol) in DMSO (5 mL) was added 3-bromo-propionic acid (57.1) (115 mg, 0.75 mmol). Stirring was continued overnight at rt. The mixture was diluted with crushed ice and water and the pH was adjusted to 3 by the addition of 3N HCl. The aqueous phase was extracted with EtOAc (3×20 mL). The combined organic phase was washed with brine, and dried over Na$_2$SO$_4$. The title compound I-38 (65 mg, 0.24 mmol) was obtained as a white powder. Yield: 35%. $^1$H NMR (400 MHz, DMSO-d$_6$) δ2.69 (t, J=6.68 Hz, 2H), 3.27 (t, J=6.7 Hz, 2H), 6.61 (s, 1H), 12.9 (brs, 2H); HPLC: 98.8%.

Example 59: 2-(3,5-Difluoro-4-hydroxy-benzylsulfanyl)-6-oxo-4-thiophen-2-yl-1,6-dihydro-pyrimidine-5-carbonitrile (Compound I-39)

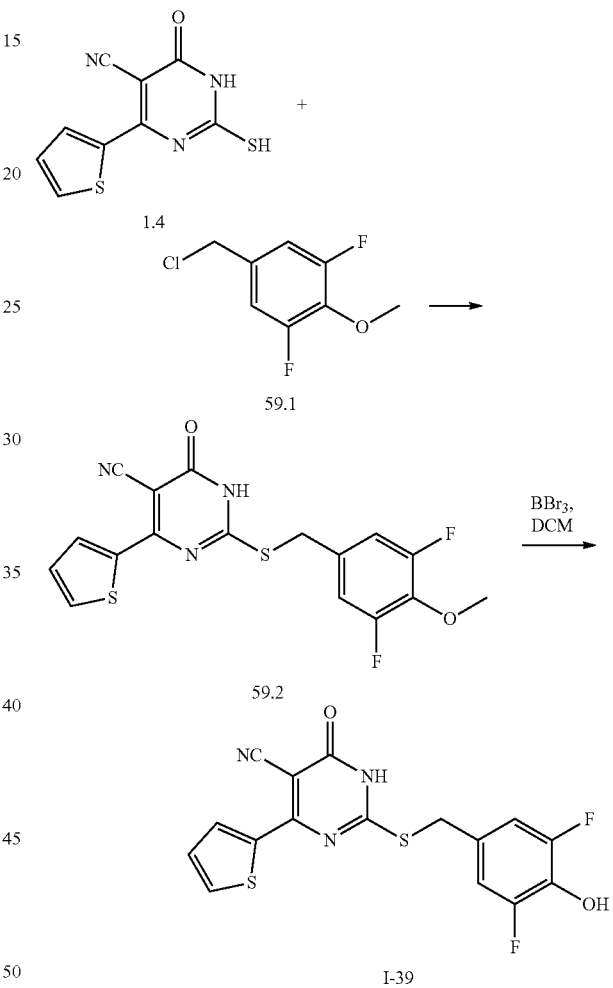

Step 2: 2-(3,5-Difluoro-4-hydroxy-benzylsulfanyl)-6-oxo-4-thiophen-2-yl-1,6-dihydro-pyrimidine-5-carbonitrile (I-39)

To a stirred suspension of intermediate 59.2 (160 mg, 0.41 mmol) in DCM (10 mL) was added at 0° C. a 1 M solution of BBr$_3$ in DCM (0.5 mL, 0.45 mmol). Stirring was continued at rt 16 h at rt. The reaction was quenched with MeOH and the solvents were removed under vacuo. The crude was purified by flash chromatography eluting with DCM/MeOH from 0 to 6% for product. The title compound I-39 (68 mg, 0.18 mmol) was obtained as a white powder after trituration with Et$_2$O. Yield: 44%. $^1$H NMR (400 MHz, DMSO-d$_6$) δ 4.47 (s, 2H), 7.17 (d, J=8.3 Hz, 2H), 7.36 (t, J=4.6 Hz, 1H), 8.28 (d, J=3.9 Hz, 1H), 10.25 (s, 1H), 13.9 (brs, 1H); $^{13}$C NMR (100 MHz, DMSO-d$_6$) δ 33.3, 88.7, 112.7 (d, J$_{CF}$=28.6 Hz), 112.9 (d, J$_{CF}$=28.6 Hz), 116.5, 127.8 (t, J$_{CF}$=32.8 Hz), 130, 132.1, 133.4 (t, J$_{CF}$=63.7 Hz), 135.4, 139.7, 151.0 (d, J$_{CF}$=28.9 Hz), 153.4 (d, J$_{CF}$=28.6 Hz), 158.9, 161.2, 165.2; HPLC: 95.7%.

Example 60: 2-(3,5-Difluoro-4-hydroxy-benzylsulfanyl)-6-trifluoromethyl-3H-pyrimidin-4-one (Compound I-40)

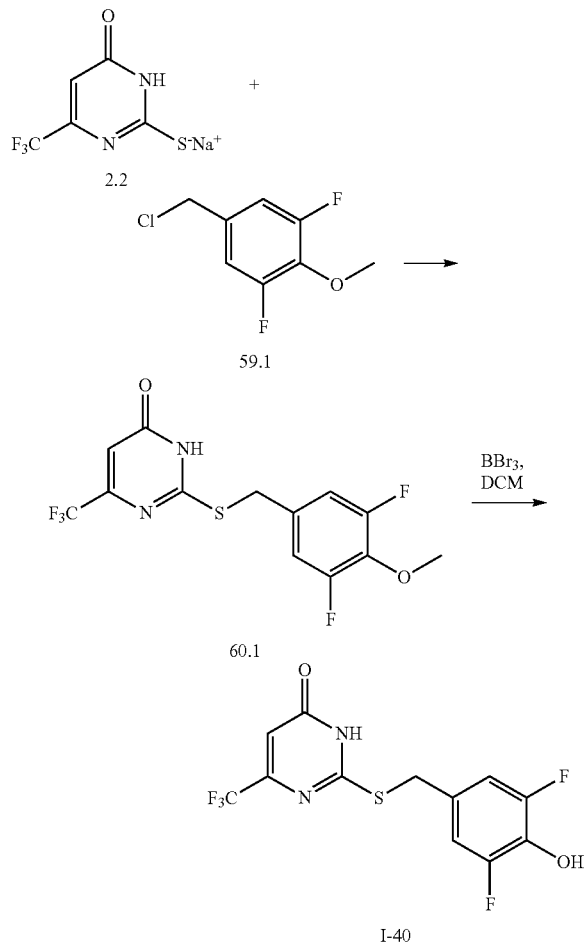

Step 1: 2-(3,5-Difluoro-4-methoxy-benzylsulfanyl)-6-trifluoromethyl-3H-pyrimidin-4-one (60.1)

Following the procedure of Example 59 (Step 1) and starting from intermediate 2.2 (200 mg, 0.91 mmol), 59.1 (211.8 mg, 1.1 mmol) and DIPEA (0.19 mL, 1.1 mmol) in DMSO (5 mL) the title intermediate 60.1 (200 mg, 0.56 mmol) was obtained as white powder. Yield 62%. $^1$H NMR (400 MHz, DMSO-d$_6$) δ 3.88 (s, 2H), 4.33 (s, 3H), 6.63 (s, 1H), 7.21 (d, J=9.2 Hz, 2H).

Step 2: 2-(3,5-Difluoro-4-hydroxy-benzylsulfanyl)-6-trifluoromethyl-3H-pyrimidin-4-one (I-40)

To a stirred suspension of intermediate 60.1 (190 mg, 0.54 mmol) in DCM (10 mL) was added at 0° C. a 1 M solution of BBr$_3$ in DCM (0.6 mL, 0.59 mmol). Stirring was continued at rt 16 h at rt. The reaction was quenched with MeOH. The solvents were removed under vacuo. The crude was purified by flash chromatography eluting with DCM/MeOH from 0 to 6% for product. The title compound I-40 (61 mg, 0.18 mmol) was obtained as a white powder after trituration with Et$_2$O. Yield: 33%. $^1$H NMR (400 MHz, DMSO-d$_6$) 4.29 (s, 2H), 6.63 (s, 1H), 7.11 (d, J=7.82 Hz, 2H), 10.19 (s, 1H), 13.15 (brs, 1H); $^{13}$C NMR (100 MHz, DMSO-d$_6$) δ 33.3, 113.1 (d, J$_{CF}$=28.2 Hz), 113.2 (d, J$_{CF}$=28.4 Hz), 119.6, 122.3, 128.2, 133.3 (t, J$_{CF}$=64.1 Hz), 150.9 (d, J$_{CF}$=28.3 Hz), 153.3 (d, J$_{CF}$=28.4 Hz); HPLC: 98.3%.

Example 61: 4-Benzyl-2-(3,5-difluoro-4-hydroxy-benzylsulfanyl)-6-oxo-1,6-dihydro-pyrimidine-5-carbonitrile (Compound I-41)

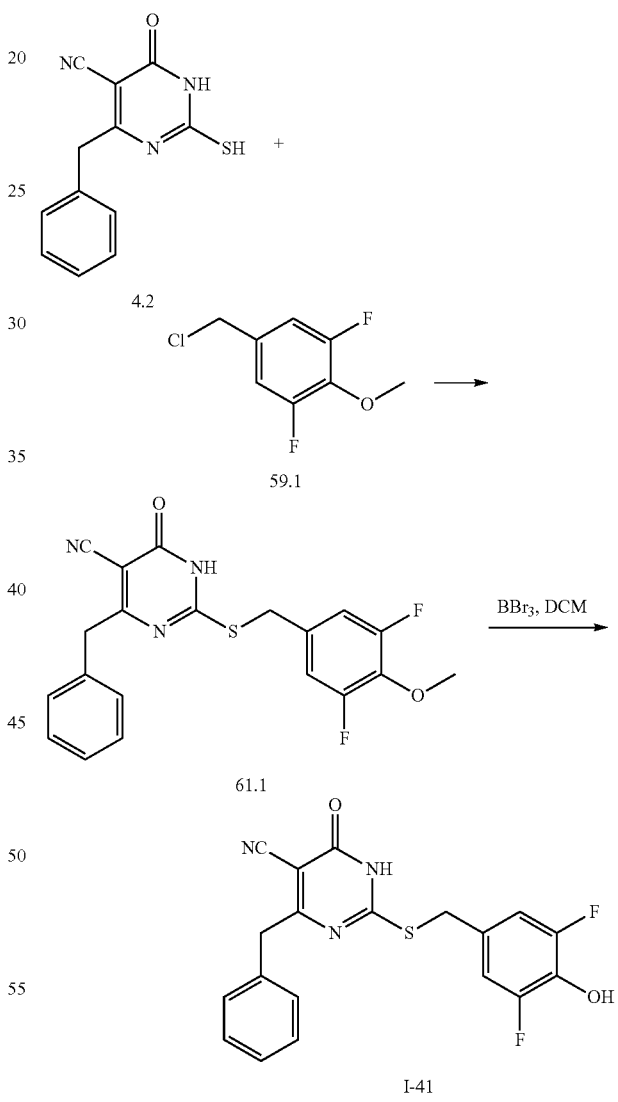

Step 1: 4-Benzyl-2-(3,5-difluoro-4-methoxy-benzylsulfanyl)-6-oxo-1,6-dihydro-pyrimidine-5-carbonitrile (61.1)

Following the procedure of Example 59 (Step 1) and starting from intermediate 4.2 (200 mg, 0.82 mmol), 59.1

(189.9 mg, 0.98 mmol) and DIPEA (0.17 mL, 0.98 mmol) in DMSO (5 mL) the title intermediate 60.1 (200 mg, 0.5 mmol) was obtained as white powder. Yield 61%. ¹H NMR (400 MHz, DMSO-d₆) δ 3.87 (s, 2H), 4.02 (s, 2H), 4.35 (s, 2H), 7.0 (d, J=8.9 Hz, 2H), 7.3 (m, 5H).

Step 2: 4-Benzyl-2-(3,5-difluoro-4-hydroxy-benzylsulfanyl)-6-oxo-1,6-dihydro-pyrimidine-5-carbonitrile (Compound I-41)

To a stirred suspension of intermediate 61.1 (190 mg, 0.54 mmol) in DCM (10 mL) was added at 0° C. a 1 M solution of BBr₃ in DCM (0.5 mL, 0.52 mmol). Stirring was continued at rt 16 h at rt. The reaction was quenched with MeOH. The solvents were removed under vacuo. The crude was purified by flash chromatography eluting with DCM/MeOH from 0 to 6% for product. The title compound I-41 (40 mg, 0.1 mmol) was obtained as a white powder after trituration with Et₂O. Yield: 22%. ¹H NMR (400 MHz, DMSO-d₆) 4.02 (s, 2H), 4.3 (s, 2H), 6.93 (d, J=7.6 Hz, 2H), 7.27 (m, 4H), 7.9 (brs, 1H), 10.2 (s, 1H), 13.92 (bras, 1H); HPLC 96.7%.

Example 62: 6-Oxo-2-{[4-(1H-tetrazol-5-yl)-cyclohexylmethyl]-amino}-4-thiophen-2-yl-1,6-dihydro-pyrimidine-5-carbonitrile (Compound I-42)

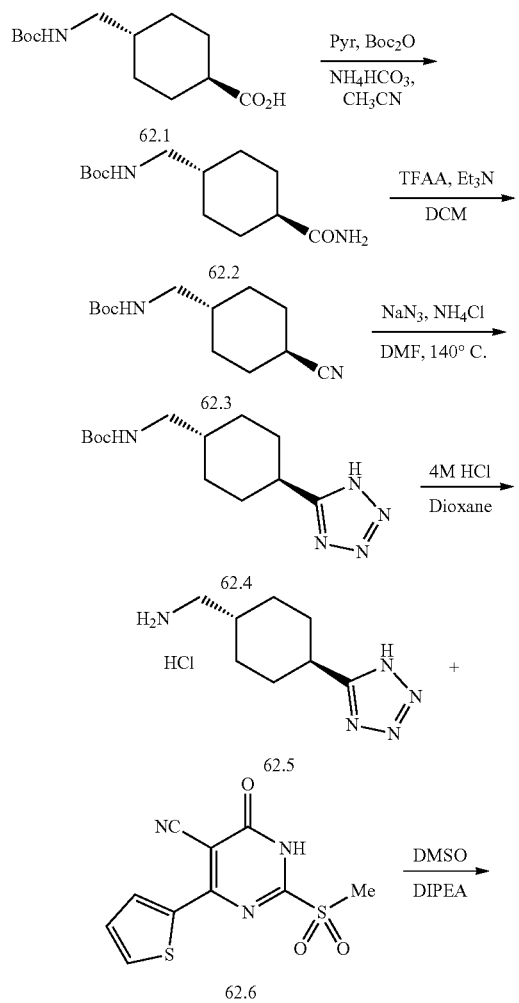

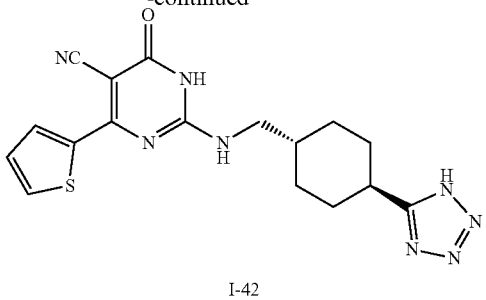

I-42

Step 1: (4-Carbamoyl-cyclohexylmethyl)-carbamic acid tert-butyl ester (62.2)

To a solution of the starting intermediate 62.1 (1.3 g, 5.1 mmol) in CH₃CN (20 mL) was added pyridine (0.45 mL, 5.55 mmol), Boc₂O (1.67 g, 7.65 mmol) and ammonium bicarbonate (605 mg, 7.65 mmol). Stirring was continued at rt 16 h. The crude was poured in water. The aqueous phase was extracted with EtOAc (3×20 mL). The combined organic phase was washed with brine, and dried over Na₂SO₄. The title compound 62.2 (1 g, 3.9 mmol) was obtained as a white powder. Yield: 76%. ¹H NMR (400 MHz, CDCl₃) δ 0.8 (q, J=2.6 Hz, 2H), 1.45 (s, 9H), 1.63 (s, 2H), 1.86 (d, J=13.3 Hz, 2H), 1.97 (d, J=13.4 Hz, 2H), 2.11 (t, J=3.4 Hz, 1H), 2.99 (m, 2H), 4.5 (s, 1H), 5.38 (m, 2H).

Step 2: (4-Cyano-cyclohexylmethyl)-carbamic acid tert-butyl ester (62.3)

A solution of the starting intermediate 62.2 (200 mg, 0.78 mmol) in DCM (10 ml) was added Et₃N (0.3 mL, 1.95 mmol). The mixture was cooled at 0° C. and TFAA (0.14 mL, 0.98 mmol) was added dropwise. Stirring was continued at rt 16 h. The reaction was poured in water, extracted with DCM (3×20 mL). The combined organic phase was washed with brine and were dried over Na₂SO₄ to give the title compound 62.3 (150 mg, 0.62 mmol) as yellow oil. Yield 84%. ¹H NMR (400 MHz, CDCl₃) δ 0.98-1 (m, 2H), 1.46 (s, 9H), 1.52 (m, 2H), 1.57-1.61 (m, 1H), 1.75-1.77 (m, 1H), 1.83-1.87 (m, 2H), 2.12-2.16 (m, 2H), 2.35-2.42 (m, 1H), 2.98 (t, J=6.4 Hz, 2H), 3.58 (d, J=6.8 Hz, 1H), 4.61 (brs, 1H).

Step 3: [4-(1H-Tetrazol-5-yl)-cyclohexylmethyl]-carbamic acid tert-butyl ester (62.4)

To a solution of the starting intermediate 62.3 (200 mg, 0.84 mmol) in DMF (3 mL) was sodium azide (164 mg, 2.52 mmol) and NH4Cl (135 mg, 2.52 mmol). Stirring was continued at 140° C. for 25 h. The crude was poured in water, acidified to pH3 by the addition of 3M HCl solution. The aqueous phase was extracted with EtOAc (3×20 mL). The combined organic phase was washed with brine and dried over Na₂SO₄. The title compound 62.4 (160 mg, 0.56 mmol) was obtained as a white powder. Yield: 67%. ¹H NMR (200 MHz, DMSO-d₆) δ 1.01 (t, J=6.8 Hz, 2H), 1.36-1.52 (m, 11H), 1.76 (d, J=11.7 Hz, 2H), 2.01 (d, J=11.0 Hz, 2H), 2.72-2.96 (m, 3H), 6.59-6.87 (m, 1H), 14.1 (brs, 1H).

Step 4: C-[4-(1H-Tetrazol-5-yl)-cyclohexyl]-methyl-amine (62.5)

To a solution of intermediate 62.4 (450 mg, 1.60 mmol) in dioxane (5 mL) was added a 4M solution of HCl in dioxane (13.2 mL). Stirring was continued at r.t 16 h. The solvent was removed under vacuo to give the title intermediate 62.5 (378 mg, 1.73 mmol) as a white powder chlorohydrate salt. Yield 95%. $^1$H NMR (200 MHz, DMSO-$d_6$) δ 1.0-1.14 (m, 2H), 1.46-1.52 (m, 3H), 1.84 (d, J=13.1 Hz, 2H), 2.01 (d, J=13.4 Hz, 2H), 2.64-2.70 (m, 2H), 2.93 (m, 1H), 8.05 (brs, 3H).

Step 5: 6-Oxo-2-{[4-(1H-tetrazol-5-yl)-cyclohexyl-methyl]-amino}-4-thiophen-2-yl-1,6-dihydro-pyrimidine-5-carbonitrile (Compound I-42)

To a stirred solution of intermediate 62.6 (250 mg, 0.88 mmol) in DMSO (5 mL) was added DIPEA (0.3 mL, 1.76 mmol) and intermediate 62.5 (211 mg, 0.97 mmol). Stirring was continued at 80° C. 4 h. The crude was poured in water, acidified to pH 3 and extracted with EtOAc (3×20 mL). The crude product from the reaction was purified by flash chromatography eluting with DCM/MeOH (6% for product). The title compound I-42 (24 mg, 0.06 mmol) was obtained as yellowish solid. Yield 7%. MS-ESI (−) m/z: 381.4 (M−H). HPLC: 88%

Example 63: Preparation of Intermediate 1b.3

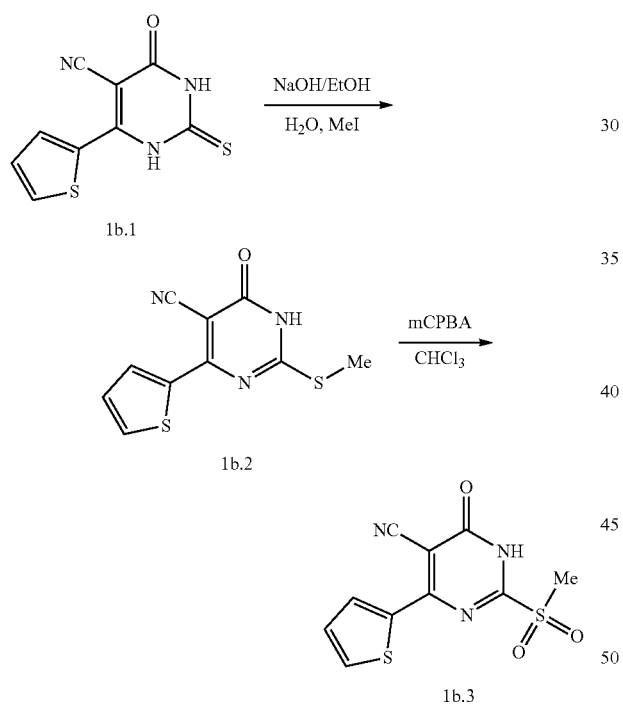

Step 1: Preparation of Intermediate 1b.2

To a stirred solution of compound 1b.1 (500 mg, 2.13 mmol), in a mixture of $H_2O$/EtOH (2 mL+4 mL) was added NaOH (85 mg, 2.13 mmol) and MeI (0.12 mL, 2.13 mmol). Stirring was continued at 60° C. for 30 minutes. The title compound 1b.2 was collected as yellow powder upon filtration from the reaction medium (491 mg, 4.9 mmol). Yield 92%.

Step 2: Preparation of Intermediate 1b.3

To a stirred solution of compound 1b.2 (200 mg, 0.8 mmol), in $CHCl_3$ (6 mL) was added mCPBA (207 mg, 1.2 mmol). Stirring was continued at rt for 16 h. The yellow solid was collected and washed with DCM and $Et_2O$. The title compound 1b.3 was obtained (190 mg, 0.67 mmol) as a pale yellow solid. Yield 84%.

Example 64: Preparation of Intermediate 2b.2

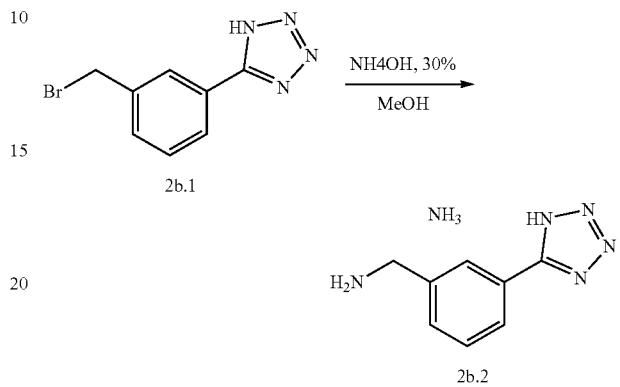

Step 1: Preparation of Intermediate 2b.2

To a solution of the starting intermediate 2b.1 (200 mg, 0.83 mmol) in MeOH (3 mL) was added a 30% ammonia solution in water (2 mL). Stirring was continued at rt for 24 h. The solvent was then removed under vacuo. The title intermediate 2b.2 (143 mg, 0.74 mmol) was obtained as yellowish powder without further purifications. Yield 90%.

Example 65: Preparation of Intermediate 3b.6

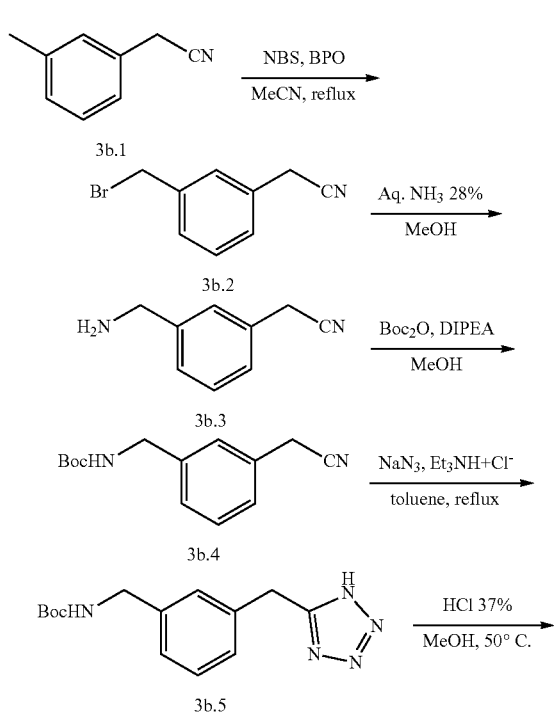

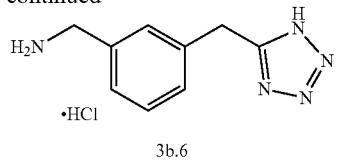

3b.6

Step 1: Preparation of Intermediate 3b.2

To a stirred and boiling solution of 3b.1 (1.00 g, 7.62 mmol) in MeCN (30 mL), a solution of NBS (1.42 g) and BPO 70% (13 mg, 0.04 mmol) in MeCN (10 mL) was added dropwise. After 30 min the mixture was slowly cooled to r.t. and poured in aq. $NaHCO_3$ ss (15 mL). The mixture was extracted with AcOEt (3×30 mL), washed with brine (50 mL), dried over $Na_2SO_4$, and concentrated under reduced pressure. The title intermediate 3b.2 was used directly (1.60 g) for the next step.

Step 2: Preparation of Intermediate 3b.3

A solution of intermediate 3b.2 (1.60 g, crude of previous step) in MeOH (15 mL) was treated with aq. $NH_3$ 28% (15 mL), and the resulting mixture was stirred for 16 h. Volatiles were removed under reduced pressure and the crude was poured in $H_2O$ (30 mL) and washed with AcOEt (3×30 mL). The aqueous phase was concentrated under reduced pressure. The title intermediate 3b.3 (1.17 g) was used as crude for the next step.

Step 3: Preparation of Intermediate 3b.4

A stirred suspension of intermediate 3b.3 (1.17 g, crude of previous step) in $CH_2Cl_2$ (30 mL), $Boc_2O$ (1.99 g, 9.14 mmol) and DIPEA (3.32 mL, 19.06 mmol) were added, and the mixture was reacted at r.t. for 2 h obtaining an opalescent solution. $H_2O$ (20 mL) was added, the two phases were separated and the organic one was washed with aq. citric acid 0.5 M (2×20 mL), $H_2O$ (20 mL), brine (20 mL), dried over $Na_2SO_4$ and concentrated under reduced pressure. The crude was purified by chromatographic purification (Petroleum ether/AcOEt from 9:1 to 7:3) to give the title intermediate 3b.4 as dense oil in 28% yield starting from 3.1. MS-ESI (+) m/z: 247.2 (M+H).

Step 4: Preparation of Intermediate 3b.5

A mixture of intermediate 3b.4 (525 mg, 2.13 mmol), sodium azide (415 mg, 6.39 mmol) and triethylammonium chloride (880 mg, 6.39 mmol) in toluene (40 mL) was stirred and refluxed for 18 h. Once cooled at r.t., aq. $NaHCO_3$ ss (15 mL) was added, and the mixture was vigorously stirred for 10 min. The two phases were separated and the organic one was extracted with $H_2O$ (3×30). All the aqueous phases were collected together and acidified up to pH=3 by adding citric acid 0.5 M. The resulting acid aqueous phase was extracted with $CH_2Cl_2$ (3×50 mL), washed with), brine (50 mL), dried over $Na_2SO_4$ and concentrated under reduced pressure. The title intermediate 3b.5 (214 mg, 0.74 mmol) was obtained as white solid. Yield: 35%. MS-ESI (−) m/z: 288.2 (M−H).

Step 5: Preparation of Intermediate 3b.6

Intermediate 3b.5 (205 mg, 0.71 mmol) was dissolved in MeOH (10 mL) and treated with HCl 37% (0.29 mL, 3.35 mmol) at 50° C. for 2 h. Volatiles were removed under reduced pressure, to afford intermediate 3b.6 in nearly quantitative yield as hydrochloride salt. MS-ESI (+) m/z: 190.3 (M+H); MS-ESI (−) m/z: 188.2 (M−H).

Example 66: Preparation of Intermediate 4b.4

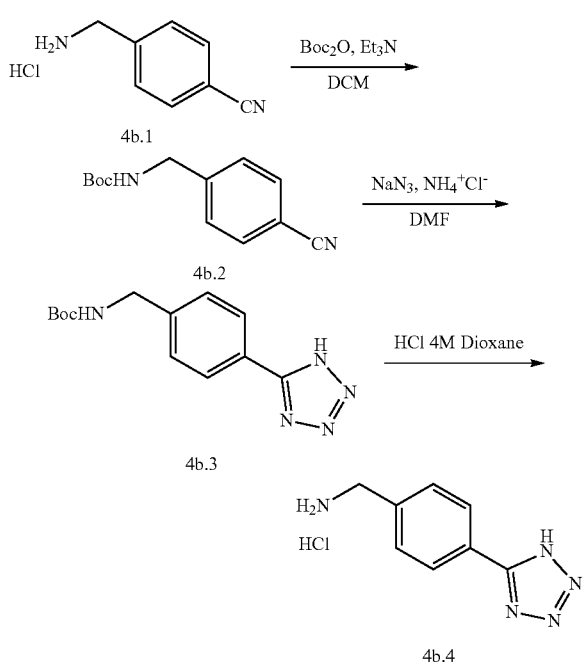

Step 1: Preparation of Intermediate 4b.2

To a solution of intermediate 4b.1 (2 g, 11.86 mmol) in DCM (20 mL) was added TEA (1.99 mL, 14.2 mmol) and $BOC_2O$ (2.717 g, 12.45 mmol). Stirring was continued at rt 5 h. The crude was poured in water and was extracted with DCM. The organic phase were washed with brine and dried over $Na_2SO_4$. The title intermediate 4b.2 (2 g, 8.61 mmol) was obtained as white solid. Yield 72%.

Step 2: Preparation of Intermediate 4b.3

To a solution of the starting intermediate 4b.2 (2 g, 7.26 mmol) in DMF (6 mL) was added $NaN_3$ (839 mg, 12.91 mmol) and ammonium chloride (689 mg, 12.91 mmol). Stirring was continued at 140° C. for 6 h. The crude was poured in water and brine followed by extraction with EtOAc at pH=3. The organic phase were dried over $Na_2SO_4$ and evaporated under vacuo. The title intermediate 4b.3 (2.2 g, 8.0 mmol) was obtained as white solid. Yield 93%.

Step 3: Preparation of Intermediate 4b.4

The starting intermediate 4b.3 (1.5 g, 5.48 mmol) was stirred overnight in a 4 M dioxane solution of HCl (10 mL). The solvent was removed under vacuo. The title intermediate 4b.4 (1.14 g, 5.38 mmol) was obtained as a white solid. Yield 98%.

Example 67: Preparation of Intermediate 5b.2

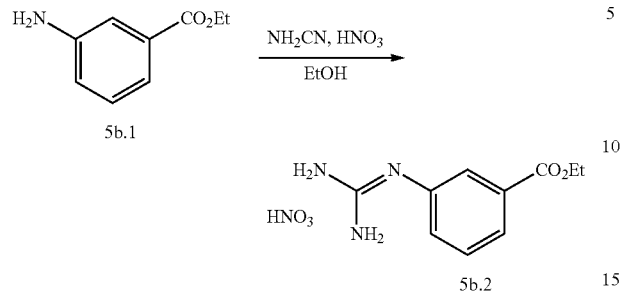

To a solution of intermediate 5b.1 (1 g, 6.1 mmol) in EtOH (10 mL) was added NH$_2$CN (0.7 mL, 9.1 mmol) and HNO$_3$ (0.25 mL, 6.1 mmol). Stirring was continued at reflux for 16 h. The mixture was cooled to 0° C. and was added of Et$_2$O. The white precipitate was collected. The title intermediate 5b.2 (1 g, 3.7 mmol) was thus obtained as white solid as HNO$_3$ salt. Yield 60%.

Example 68: Preparation of Intermediate 6b.2

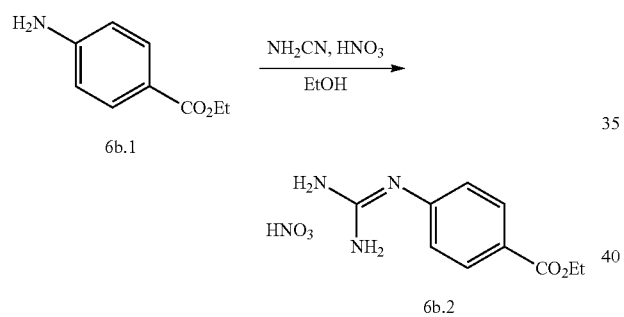

To a solution of intermediate 6b.1 (1 g, 6.1 mmol) in EtOH (10 mL) was added NH$_2$CN (0.7 mL, 9.1 mmol) and HNO$_3$ (0.25 mL, 6.1 mmol). Stirring was continued at reflux for 16 h. The mixture was cooled to 0° C. and was added of Et$_2$O. The white precipitate was collected. The title intermediate 6b.2 (1.2 g, 4.4 mmol) was obtained as yellowish solid as HNO$_3$ salt. Yield 72%.

Example 69: Preparation of Compound I-43

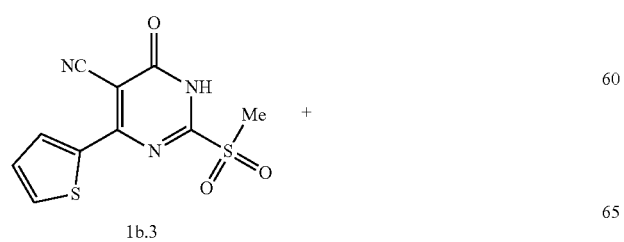

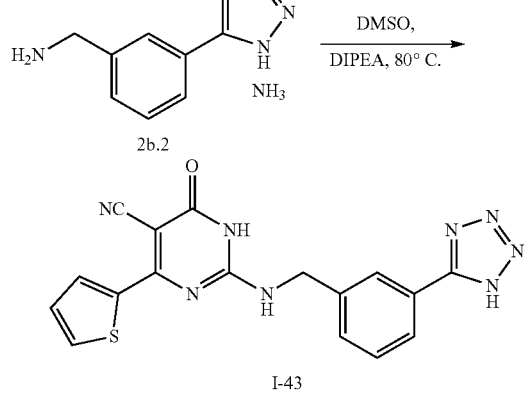

To a stirred suspension of intermediate 1b.3 (200 mg, 0.85 mmol) in DMSO (5 mL) was added DIPEA (0.29 mL, 1.7 mmol) and intermediate 2b.2 (164 mg, 0.94 mmol). Stirring was continued at 80° C. for 4 h. The crude was poured in water, acidified to pH 3 and extracted with EtOAc (3×20 mL). The crude of reaction was purified by flash chromatography eluting with DCM/MeOH (3% for product). The title compound I-43 (50 mg, 0.13 mmol) was obtained as yellowish solid. Yield 15%. $^1$H NMR (400 MHz, DMSOd$_6$) δ 4.69 (2H), 7.25 (m, 1H), 7.58 (m, 2H), 7.91 (m, 2H), 8.0 (s, 1H), 8.16 (m, 1H), 11.94 (brs, 1H); $^{13}$C NMR (100 MHz, DMSOd$_6$) δ 44.2, 81.8, 117.8, 124.6, 126.1, 126.3, 129.3, 129.9, 130.7, 130.9, 130.9, 133.9, 140.5, 141.1, 154.4, 161.6, 162.1. HPLC 96.3%.

Example 70: Preparation of Compound I-44

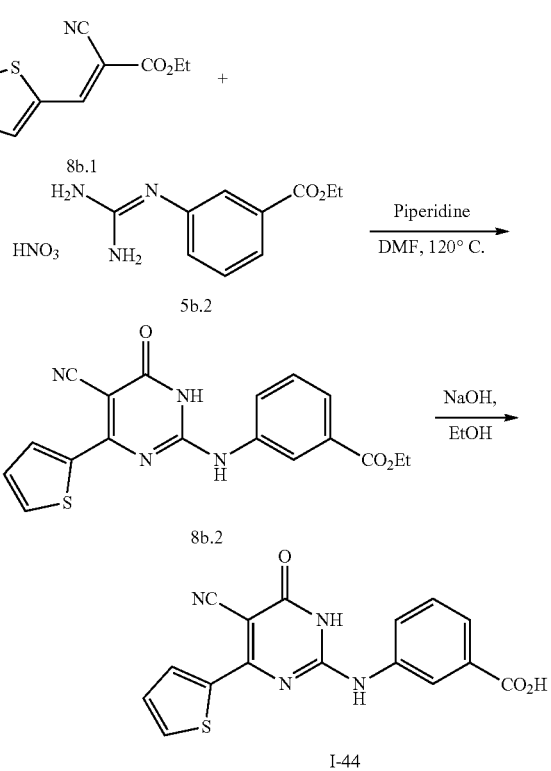

Step 1: Synthesis of Intermediate 8b.2

A solution of intermediate 8b.1 (195 mg, 0.72 mmol) and intermediate 5b.2 (150 mg, 0.72 mmol) in DMF (2 mL), was added of piperidine (0.14 mL, 1.45 mmol). The mixture was sealed in a Q-tube apparatus and heated at 120° C. 16 h. The mixture was cooled to rt, poured in water, extracted with EtOAc, and purified by flash chromatography eluting with DCM/MeOH (5% for product). The title intermediate 8b.2 (200 mg, 0.39 mmol) has been obtained as brownish powder. Yield 54%

Step 2: Synthesis of Compound I-54

To a solution of intermediate 8b.2 (150 mg, 0.41 mmol) in EtOH (10 mL) was added a 1 M solution of NaOH (1.2 mL). Stirring was continued at reflux gently for 16 h. The precipitate was collected by filtration and it was dissolved in water. The pH was adjusted to 3 by the addition of 3N HCl solution. The precipitate was collected and dried under vacuo to give the title compound I-44 (100 mg, 0.295 mmol) as a brown solid. Yield 72%. $^1$H NMR (400 MHz, DMSOd$_6$) δ 7.31 (t, J=4.22 Hz, 1H), 7.50 (t, J=7.8 Hz, 1H), 7.72 (d, J=7.48 Hz, 1H), 7.88 (d, J=7.4 Hz, 1H), 7.99 (d, J=4.7 Hz, 1H), 8.25 (m, 2H), 10.1 (s, 1H), 11.9 (brs, 1H); $^{13}$C NMR (100 MHz, DMSOd$_6$) δ 83.5, 117.4, 122.4, 125.3, 125.7, 129.5, 129.6, 131.2, 131.8, 134.3, 137.9, 140.8, 152.5, 161.4, 161.9, 167.3. HPLC: 98.4%

Example 71: Preparation of Compound I-45

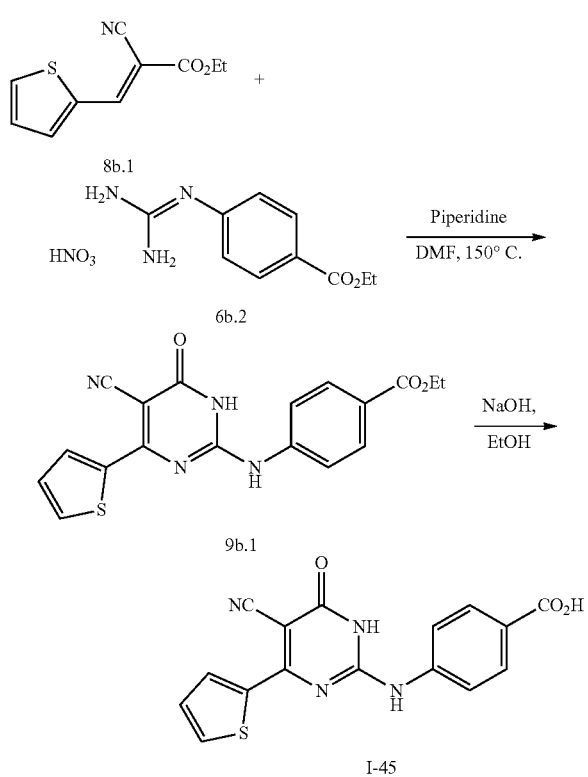

Step 1: Synthesis of Intermediate 9b.1

A solution of intermediate 8b.1 (990 mg, 0.72 mmol) and intermediate 6b.2 (1.18 g, 4.34 mmol) in DMF (10 mL), was added of piperidine (0.86 mL, 8.68 mmol). The mixture was heated at 150° C. for 16 h. The mixture was cooled to rt, poured in water, the pH was adjusted to 3 by the addition of HCl (3N). The solid was collected and washed with acetone. The title intermediate 9b.1 (250 mg, 0.68 mmol) has been obtained as grey powder. Yield 14%

Step 2: Synthesis of Compound I-45

To a solution of intermediate 9b.1 (150 mg, 0.41 mmol) in EtOH (10 mL) was added a 1 M solution of NaOH (1.2 mL). Stirring was continued at reflux gently 16 h. The solvent was removed under vacuo. The solid was suspended in EtOH (5 mL) sonicated and filtered. The sodium salt was dissolved in water and ice, pH was adjusted to 3 by the addition of 3N HCl solution. The gummy precipitate was collected and dried under vacuo to give the title compound I-45 (90 mg, 0.21 mmol) brown solid. Yield 65%. $^1$H NMR (400 MHz, DMSOd$_6$) δ 7.32 (d, J=4.1 Hz, 1H), 7.79 (d, J=8.6 Hz, 2H), 7.96 (d, J=8.6 Hz, 2H), 8.0 (d, J=4.9 Hz, 1H), 8.24 (d, J=3.8 Hz, 1H), 10.23 (s, 1H), 11.9 (brs, 1H); $^{13}$C NMR (100 MHz, DMSOd$_6$) δ 83.9, 117.2, 120.5, 120.5, 126.2, 129.7, 130.7, 130.7, 131.3, 134.5, 140.7, 141.9, 152.5, 161.3, 167.2; HPLC: 95.56%.

Example 72: Preparation of Compound I-46

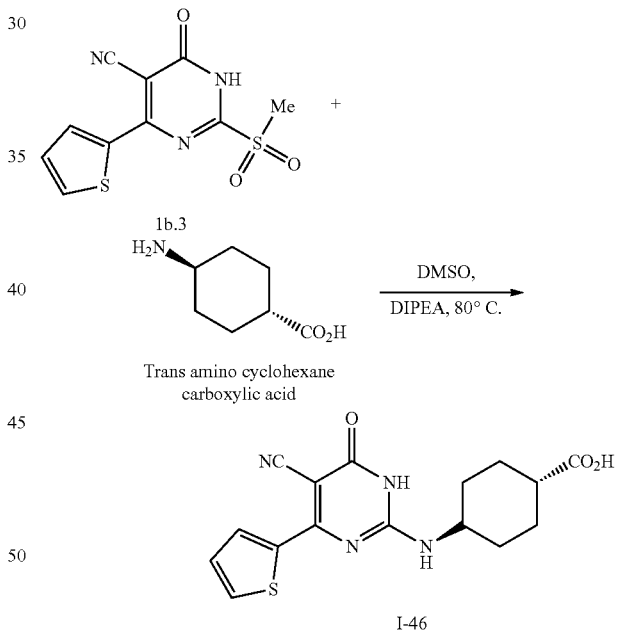

To a solution of intermediate 1b.3 (100 mg, 0.36 mmol) in DMSO (3 mL) was added 1,4-trans amino cyclohexane (51 mg, 0.36 mmol). Stirring was continued at 80° C. for 16 h. The mixture was poured in water, the pH was adjusted to 3 by the addition of HCl (3N solution). The gummy precipitate was collected and dried under vacuo. The crude was purified by flash chromatography eluting with DCM/MeOH 15% and acetone due to the low compound solubility. The title compound I-46 (40 mg, 0.12 mmol) was obtained as yellowish powder. Yield 32%. $^1$H NMR (200 MHz, DMSOd$_6$) δ 1.34 (m, 4H), 1.92 (m, 4H), 2.20 (brs, 1H), 3.73 (brs, 1H), 7.27 (t, J=4.2 Hz, 1H), 7.61 (s, 1H), 7.91 (d, J=4.9 Hz, 1H), 8.15 (m, 1H), 12.0 (brs, 1H). $^{13}$C NMR (100 MHz, DMSOd$_6$) δ 27.8, 27.8, 31.1, 31.1, 41.7, 41.7, 50.2, 81.05, 118.0, 129.4, 130.7, 133.9, 141.3, 153.9, 161.6, 176.8; HPLC: 96.3%.

Example 73: Preparation of Compound I-47

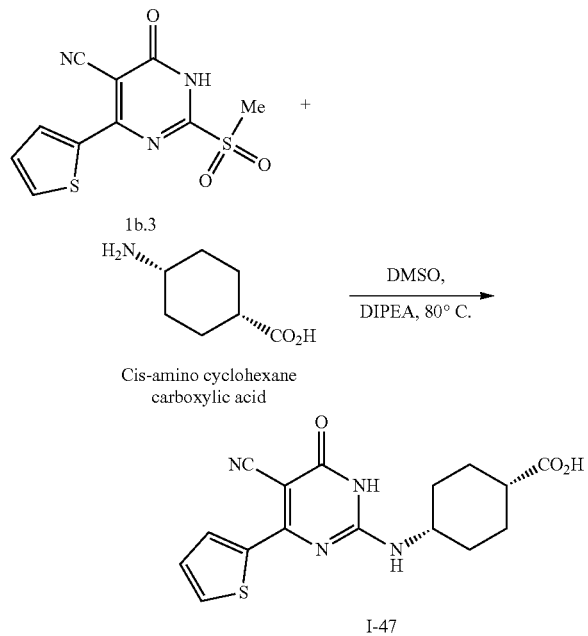

To a solution of intermediate 1b.3 (150 mg, 0.53 mmol) in DMSO (5 mL) was added 1,4-cis amino cyclohexane (76 mg, 0.53 mmol). Stirring was continued at 80° C. for 16 h. Ice was added to the mixture under stirring. The white solid was collected and then purified by flash chromatography, eluting with DCM/MeOH. The title compound I-47 (70 mg, 0.2 mmol) was obtained as white solid. Yield 38%. $^1$H NMR (400 MHz, DMSOd$_6$) δ 1.71 (m, 8H), 2.4 (brs, 1H), 4.05 (s, 1H), 7.28 (t, J=4.2 Hz, 1H), 7.3 (m, 1H), 7.93 (d, J=4.6 Hz, 1H), 8.18 (d, J=3.23 Hz, 1H), 10.9 (brs, 1H), 12.1 (brs, 1H); $^{13}$C NMR (100 MHz, DMSOd$_6$) δ 24.6, 28.8, 47.6, 48.9, 55.3, 55.3, 81.2, 117.8, 129.4, 130.8, 133.9, 141.2, 153.6, 161.6, 161.7, 176.5; HPLC: 98.51%.

Example 74: Preparation of Compound I-48

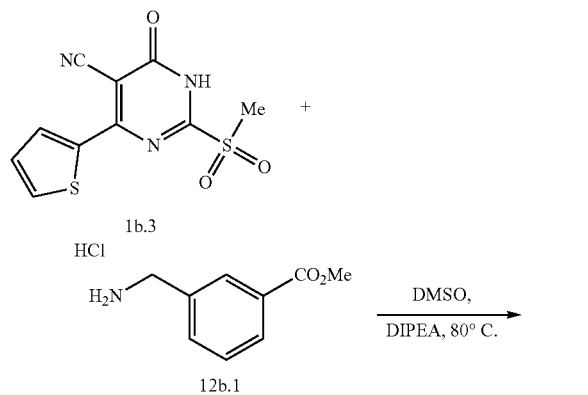

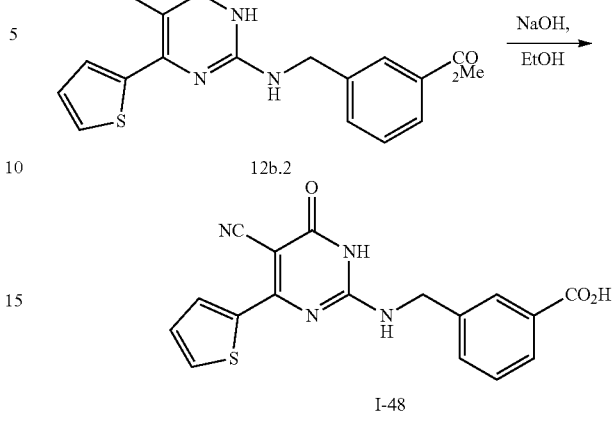

Step 1: Synthesis of Intermediate 12b.2

To a solution of the starting intermediate 1b.3 (400 mg, 1.42 mmol) in DMSO (5 mL) was added DIPEA (0.36 mL, 2.13 mmol) and intermediate 12b.1 (344 mg, 1.7 mmol). Stirring was continued at 80° C. for 16 h. The crude was poured in water. The solution was adjusted to pH3 by the addition of HCl (3N solution). The aqueous phase was extracted with EtOAc. The mixture was purified by flash chromatography, eluting with DCM/MeOH. The title intermediate 12b.2 (200 mg, 0.54 mmol) was obtained as yellowish powder. Yield 38%.

Step 2: Synthesis of Compound I-48

To a solution of intermediate 12b.2 (200 mg, 0.52 mmol) in MeOH (15 mL) was added a 1 M solution of NaOH (3 mL). Stirring was continued at reflux gently for 16 h. The solvent was removed under vacuo. The sodium salt was dissolved in water and ice, pH was adjusted to 3 by the addition of 3N HCl solution. The jelly precipitate was collected and dried under vacuo to give the title compound I-48 (150 mg, 0.42 mmol) as yellowish solid after trituration with Et$_2$O. Yield 82%. MS-ESI (+) m/z: 353.3 (M+H).

Example 75: Preparation of Compound I-49

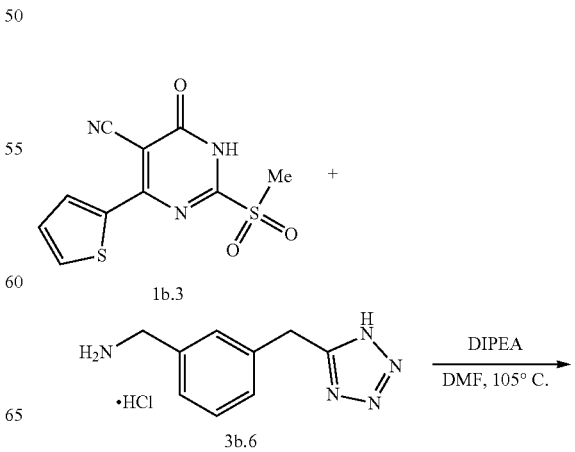

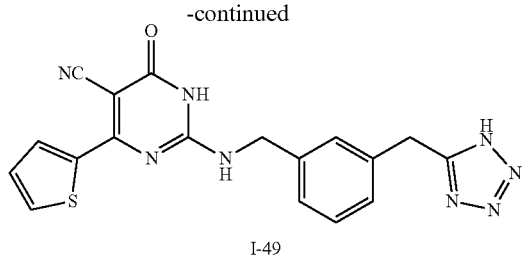

I-49

To a stirred solution of Intermediate 1b.3 (150 mg, 0.53 mmol) in DMF (10 mL), Intermediate 3b.6 (120 mg, 0.53 mmol) and DIPEA (0.46 mL, 2.65 mmol) were added, and the mixture was reacted at 105° C. for 6 h. Once cooled at r.t. it was poured in $H_2O$ (25 mL) and washed with $Et_2O$ (2×20 mL). HCl 3.0 M was added to the aqueous solution up to pH=1 and the mixture was extracted with $CH_2Cl_2$/MeOH 9:1 (vol/vol, 3×30 mL). The collected organic phases were concentrated under reduced pressure, and the crude was purified by RP-flash chromatography ($H_2O$/MeCN from 8:2 to 1:9). The collected impure compound (15 mg) was tritured with cold acetone, to afford 10 mg of pure Compound I-49 (Yield: 5%). MS-ESI (−) m/z: 389.4 (M−H). $^1$H NMR (400 MHz, DMSOd$_6$) δ 4.25 (s, 2H), 4.55 (d, J=4.74 Hz, 2H), 7.17 (s, 1H), 7.26 (m, 4H), 7.91 (d, J=4.8 Hz, 1H), 7.94 (brs, 1H), 8.16 (d, J=3.3 Hz, 1H); $^{13}$C NMR (100 MHz, DMSOd$_6$) δ 29.4, 44.3, 81.5, 117.9, 126.5, 127.9, 128.2, 129.1, 129.3, 130.8, 133.9, 136.8, 139.4, 141.1, 154.6, 155.8, 161.6, 162.4; HPLC: 99.5%.

Example 76: Preparation of Compound I-50

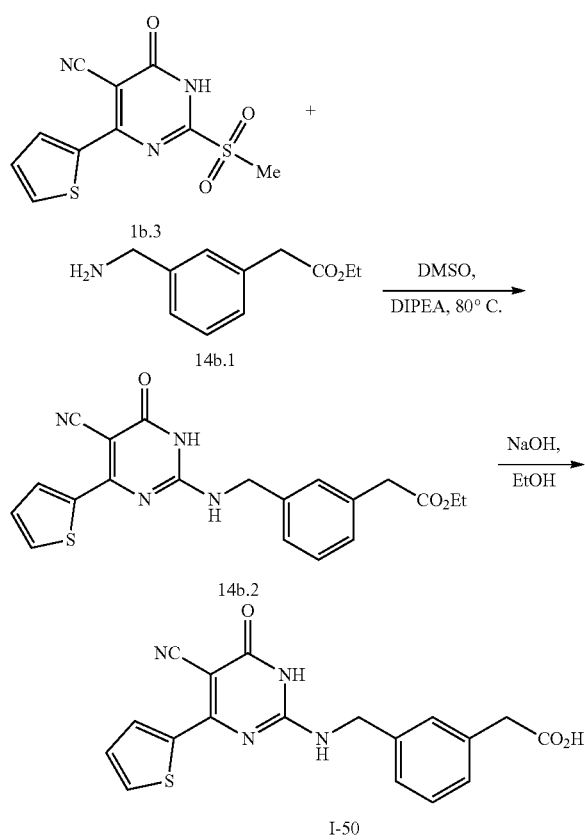

Step 1: Synthesis of Intermediate 14b.2

To a solution of intermediate 1b.3 (200 mg, 0.71 mmol) in DMSO (5 mL) was added DIPEA (0.18 mL, 1.07 mmol) and intermediate 14b.1 (164 mg, 0.85 mmol). Stirring was continued at 80° C. for 16 h. The mixture was poured in water and extracted with EtOAc (3×20 mL). The mixture was purified by flash chromatography eluting with DCM/MeOH 1.5% for product. The title intermediate 14b.2 (173 mg, 0.43 mmol) was obtained as yellow solid. Yield 62%. $^1$H NMR (400 MHz, DMSOd$_6$) δ 1.13 (t, J=7.1 Hz, 3H), 3.63 (s, 2H), 4.02 (q, J=7.0 Hz, 2H), 4.56 (d, J=5.8 Hz, 2H), 7.16 (m, 1H), 7.27 (m, 4H), 7.93 (m, 1H), 7.94 (d, J=4.0 Hz, 1H), 8.17 (d, J=3.8 Hz, 1H), 11.91 (brs, 1H).

Step 2: Synthesis of Compound I-50

To a solution of intermediate 14b.2 (165 mg, 0.42 mmol) in EtOH (6 mL) was added a 1 M solution of NaOH (1.3 mL). Stirring was continued at reflux gently 16 h. The mixture was cooled to room temperature and the precipitate was collected. The sodium salt was dissolved in water and ice, pH was adjusted to 1 by the addition of 3N HCl solution. The precipitate was collected and dried under vacuo to give the title compound I-50 (75 mg, 0.21 mmol) as white solid. Yield 49%. $^1$H NMR (400 MHz, DMSOd$_6$) δ 3.55 (s, 2H), 4.57 (d, J=5.8 Hz, 2H), 7.16 (m, 1H), 7.27 (m, 4H), 7.84 (m, 1H), 7.92 (d, J=4.5 Hz, 1H), 8.17 (d, J=3.7 Hz, 1H), 11.73 (brs, 1H), 12.49 (brs, 1H); $^{13}$C NMR (100 MHz, DMSOd$_6$) δ 41.0, 44.3, 81.6, 117.8, 126.3, 128.7, 129.1, 129.1, 129.3, 130.9, 134.0, 135.5, 138.8, 141.1, 154.3, 161.7, 161.9, 173.0; HPLC: 95.2%.

Example 77: Preparation of Compound I-51

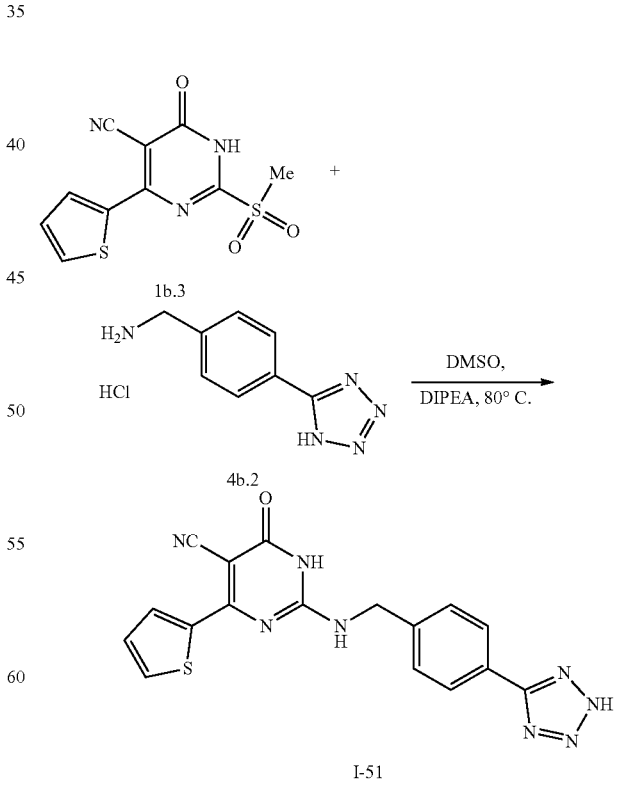

To a solution of intermediate 4b.2 (211.6 mg, 1 mmol) in DMSO (5 mL) was added DIPEA and stirring was continued at rt 10 minutes. Then a solution of compound 1b.3 in DMSO was added. Stirring was continued at 90° C. for 16 h. The crude was collected, dried and purified by flash chromatography eluting with DCM/MeOH-6% for product. The title compound I-51 was obtained (25 mg, 0.06 mmol) as yellow solid after trituration with EtOAc. Yield 7%. $^1$H NMR (400 MHz, DMSOd$_6$) δ 4.68 (d, J=5.7 Hz, 2H), 7.27 (t, J=4.1 Hz, 1H), 7.60 (d, J=7.7 Hz, 2H), 7.9 (d, J=4.9 Hz, 1H), 8.0 (d, J=7.7 Hz, 2H), 8.18 (d, J=3.6 Hz, 1H), 12.1 (brs, 1H); $^{13}$C NMR (100 MHz, DMSOd$_6$) δ 44.2, 53.9, 81.7, 117.8, 123.6, 127.4, 127.4, 128.7, 129.3, 130.9, 134.0, 141.0, 142.2, 154.5, 155.7, 161.6, 162.1; HPLC: 96.6%.

Biological Activity

Biological Example 1: Determination of ACMSD1 Inhibition

The activity of compounds 1-36 as inhibitors of ACMSD1 was determined by measuring the conversion of 3OH-Anthranilic Acid into product (i.e., ACMS) in a spectrophotometrical in vitro assay.

The pre-assay mixture consisting of 3-hydroxyanthranilic acid (3OH-HA), 3-hydroxyanthranilic acid, 3,4-diOxygenase (HAO), and a dialyzed crude extract of *E. coli* BL21 (DE3) cells expressing the recombinant enzyme, was incubated at 25° C. with monitoring of the increase in absorbance at 360 nm due to the formation of ACMS from 3OH-HA. After the reaction was completed within ~2 mins, an aliquot of ACMSD1 solution (prepared and purified from *Pichia pastoris* overexpressing the recombinant enzyme) was added, and the decrease in absorbance at 360 nm was followed at 15 second intervals. The effect of ACMS concentration on the enzyme activity was investigated by varying 3OH-HA concentration from 2 to 20 μM. Kinetic parameters were calculated from the initial velocity data by using the Lineweaver-Burk plot.

The rate of the decrease in absorbance caused by ACMSD1 was calculated by subtracting that of the control reaction mixture without ACMSD from that described above. One unit of ACMSD activity was indicated as the amount of enzyme that converts 1 mmol of ACMS per minute at 25° C. The absence or a reduction of ACMSD1 activity (e.g., by using ACMSD inhibitors) results in a slow ACMS-spontaneous degradation (i.e., cyclization to form quinolic acid).

The enzymatic activity was determined at a HAA concentration of 10 μM in the presence of the compounds in Table 1 below. The compounds were tested at the concentration of about 5 μM and 10 μM and the IC$_{50}$ was calculated for compounds showing inhibitory activity higher than 50%. The results are shown in Table 1. In Table 1, A is <0.1 μM; B is 0.1 to 1 μM; C is 1 to 10 μM; and D is >10 μM.

TABLE 1

| Cpd No. | Structure | Activity hACMSD IC$_{50}$ |
|---|---|---|
| I-1 | 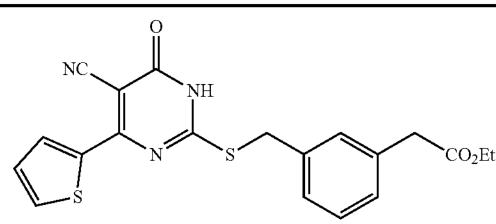 | C |
| I-2 | 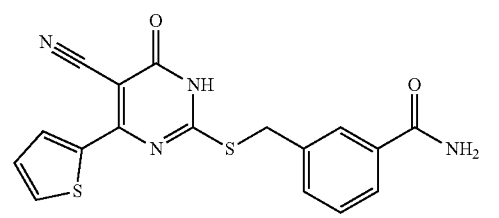 [SMILES: N#Cc1c(-c2cccs2)nc(SCc2cccc(C(N)=O)c2)[nH]c1=O] | B |
| I-3 | 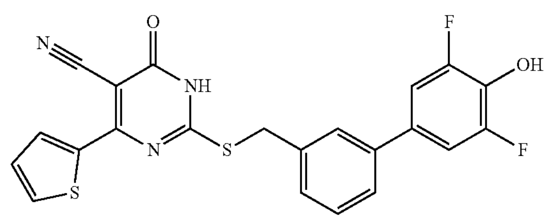 [SMILES: N#Cc1c(-c2cccs2)nc(SCc2cccc(-c3cc(F)c(O)c(F)c3)c2)[nH]c1=O] | A |
| I-4 | 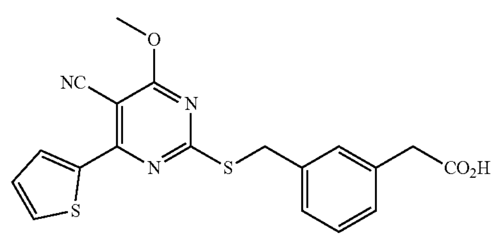 [SMILES: COc1nc(SCc2cccc(CC(=O)O)c2)nc(-c2cccs2)c1C#N] | C |

TABLE 1-continued

| Cpd No. | Structure | Activity hACMSD IC$_{50}$ |
|---|---|---|
| I-5 | 4-bromo-5-cyano-6-(thiophen-2-yl)pyrimidin-2-yl thioether with benzyl-CH$_2$CO$_2$H | B |
| I-6 | 4-(cyclopropylamino)-5-cyano-6-(thiophen-2-yl)pyrimidin-2-yl thioether with benzyl-CH$_2$CO$_2$H | C |
| I-7 | 4-amino-5-cyano-6-(thiophen-2-yl)pyrimidin-2-yl thioether with benzyl-CH$_2$CO$_2$H | B |
| I-8 | 5-cyano-4-(thiophen-2-yl)pyrimidin-2-yl thioether with benzyl-CH$_2$CO$_2$H | B |
| I-9 | 4-(methylamino)-5-cyano-6-(thiophen-2-yl)pyrimidin-2-yl thioether with benzyl-CH$_2$CO$_2$H | B |
| I-10 | 4-(methylamino)-5-cyano-6-(thiophen-2-yl)pyrimidin-2-yl thioether with benzyl-CO$_2$H | C |
| I-11 | 5-cyano-4-oxo-6-(thiophen-2-yl)-1H-pyrimidin-2-yl thioether with benzyl-CN | C |

TABLE 1-continued
| Cpd No. | Structure | Activity hACMSD IC$_{50}$ |
|---|---|---|
| I-12 | 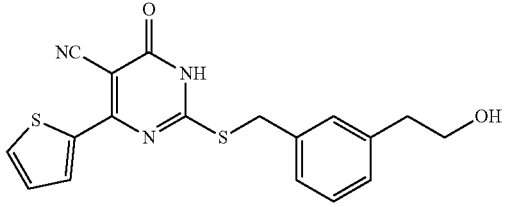 [SMILES: N#Cc1c(-c2cccs2)nc(SCc2cccc(CCO)c2)[nH]c1=O] | C |
| I-13 | 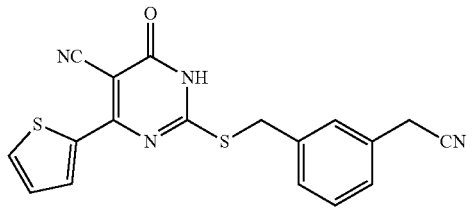 [SMILES: N#CCc1cccc(CSc2nc(-c3cccs3)c(C#N)c(=O)[nH]2)c1] | C |
| I-14 | 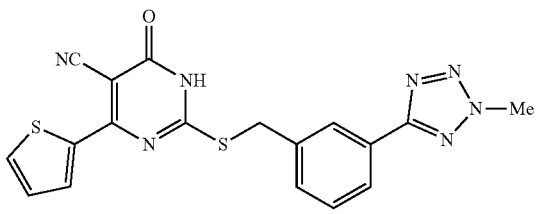 [SMILES: Cn1nnc(-c2cccc(CSc3nc(-c4cccs4)c(C#N)c(=O)[nH]3)c2)n1] | C |
| I-15 | 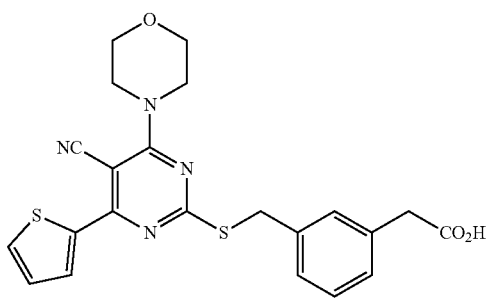 [SMILES: N#Cc1c(-c2cccs2)nc(SCc2cccc(CC(=O)O)c2)nc1N1CCOCC1] | C |
| I-16 | 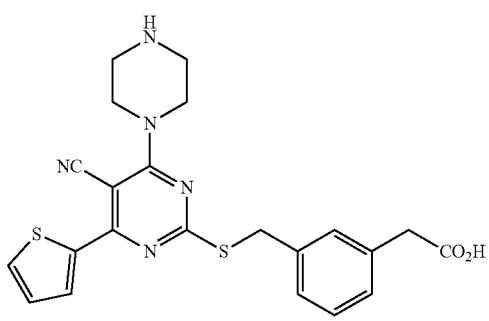 [SMILES: N#Cc1c(-c2cccs2)nc(SCc2cccc(CC(=O)O)c2)nc1N1CCNCC1] | D |
| I-17 | 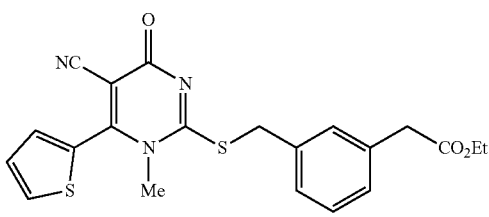 [SMILES: CCOC(=O)Cc1cccc(CSc2nc(=O)c(C#N)c(-c3cccs3)n2C)c1] | D |

TABLE 1-continued

| Cpd No. | Structure | Activity hACMSD IC$_{50}$ |
|---|---|---|
| I-18 | 5-cyano-6-(thiophen-2-yl)-2-{[(3-sulfamoylphenyl)methyl]sulfanyl}pyrimidin-4(1H)-one | B |
| I-19 | 2-({[3-(carboxymethyl)phenyl]methyl}sulfanyl)-3-cyano-6-oxo-4-phenyl-1,6-dihydropyridine | A |
| I-20 | 2-({[3-(carboxymethyl)phenyl]methyl}sulfanyl)-3-cyano-6-oxo-4-(thiophen-2-yl)-1,6-dihydropyridine | A |
| I-21 | 2-({[3-(carboxymethyl)phenyl]methyl}sulfanyl)-3,5-dicyano-6-oxo-4-(thiophen-2-yl)-1,6-dihydropyridine | A |
| I-22 | 3,5-dicyano-6-oxo-2-({[3-(1H-tetrazol-5-yl)phenyl]methyl}sulfanyl)-4-(thiophen-2-yl)-1,6-dihydropyridine | A |
| I-23 | 5-benzyl-2-({[3-(carboxymethyl)phenyl]methyl}sulfanyl)-3-cyano-6-oxo-1,6-dihydropyrimidine | C |
| I-24 | 2-[(carboxymethyl)sulfanyl]-5-cyano-6-(thiophen-2-yl)pyrimidin-4(1H)-one | C |

TABLE 1-continued

| Cpd No. | Structure | Activity hACMSD IC$_{50}$ |
|---|---|---|
| I-25 | 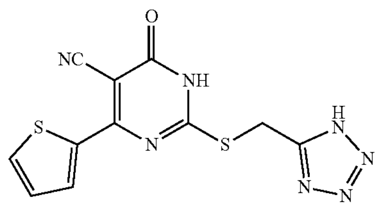 [SMILES: N#Cc1c(-c2cccs2)nc(SCc2nnn[nH]2)[nH]c1=O] | A |
| I-26 | 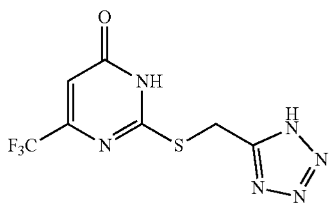 [SMILES: O=c1cc(C(F)(F)F)nc(SCc2nnn[nH]2)[nH]1] | A |
| I-27 | 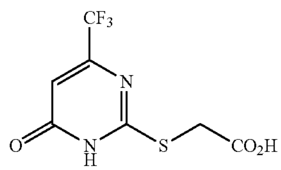 [SMILES: O=C(O)CSc1nc(C(F)(F)F)cc(=O)[nH]1] | B |
| I-28 | 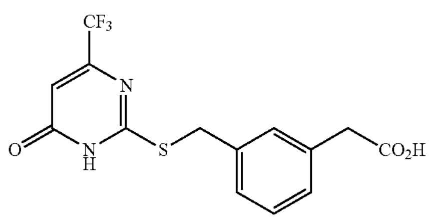 [SMILES: O=C(O)Cc1cccc(CSc2nc(C(F)(F)F)cc(=O)[nH]2)c1] | B |
| I-29 | 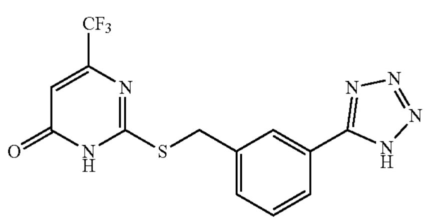 [SMILES: O=c1cc(C(F)(F)F)nc(SCc2cccc(-c3nnn[nH]3)c2)[nH]1] | A |
| I-30 | 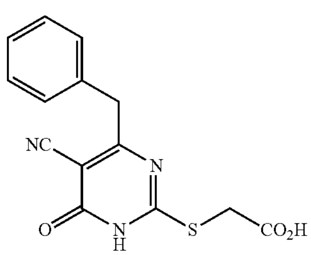 [SMILES: N#Cc1c(Cc2ccccc2)nc(SCC(=O)O)[nH]c1=O] | B |
| I-31 | 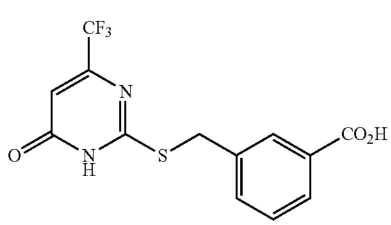 [SMILES: O=C(O)c1cccc(CSc2nc(C(F)(F)F)cc(=O)[nH]2)c1] | C |

TABLE 1-continued

| Cpd No. | Structure | Activity hACMSD IC$_{50}$ |
|---|---|---|
| I-32 | 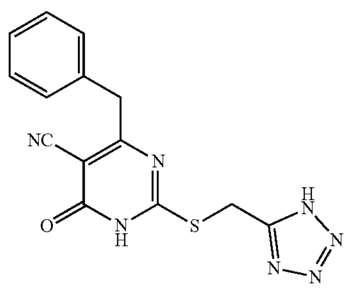 [SMILES: N#Cc1c(Cc2ccccc2)nc(SCc2nnn[nH]2)[nH]c1=O] | A |
| I-33 | 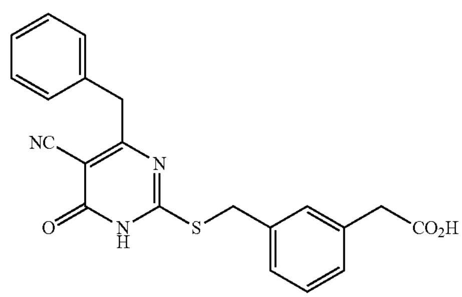 [SMILES: N#Cc1c(Cc2ccccc2)nc(SCc2cccc(CC(=O)O)c2)[nH]c1=O] | A |
| I-34 | 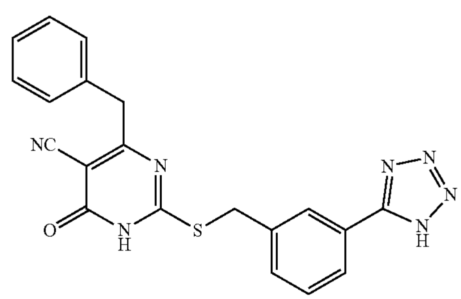 [SMILES: N#Cc1c(Cc2ccccc2)nc(SCc2cccc(-c3nnn[nH]3)c2)[nH]c1=O] | A |
| I-35 | 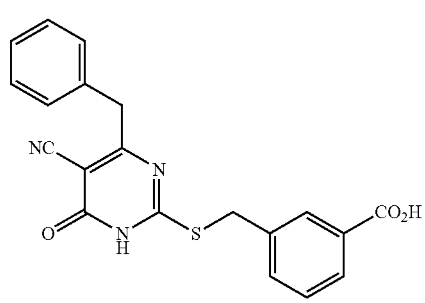 [SMILES: N#Cc1c(Cc2ccccc2)nc(SCc2cccc(C(=O)O)c2)[nH]c1=O] | B |
| I-36 | 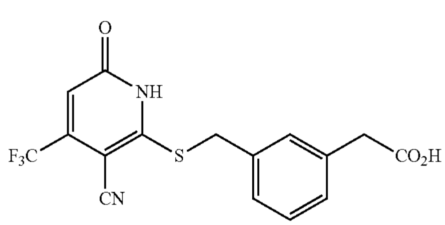 [SMILES: N#Cc1c(C(F)(F)F)cc(=O)[nH]c1SCc1cccc(CC(=O)O)c1] | B |

TABLE 1-continued

| Cpd No. | Structure | Activity hACMSD IC$_{50}$ |
|---|---|---|
| I-37 | 6-(thiophen-2-yl)-5-cyano-2-[(2-carboxyethyl)thio]-pyrimidin-4(3H)-one | C |
| I-38 | 6-(trifluoromethyl)-2-[(2-carboxyethyl)thio]-pyrimidin-4(3H)-one | n/a |
| I-39 | 6-(thiophen-2-yl)-5-cyano-2-[(3,5-difluoro-4-hydroxybenzyl)thio]-pyrimidin-4(3H)-one | C |
| I-40 | 6-(trifluoromethyl)-2-[(3,5-difluoro-4-hydroxybenzyl)thio]-pyrimidin-4(3H)-one | n/a |
| I-41 | 6-benzyl-5-cyano-2-[(3,5-difluoro-4-hydroxybenzyl)thio]-pyrimidin-4(3H)-one | C |
| I-42 | 6-(thiophen-2-yl)-5-cyano-2-{[(trans-4-(1H-tetrazol-5-yl)cyclohexyl)methyl]thio}-pyrimidin-4(3H)-one | n/a |

TABLE 1-continued
| Cpd No. | Structure | Activity hACMSD IC$_{50}$ |
|---|---|---|
| I-43 | 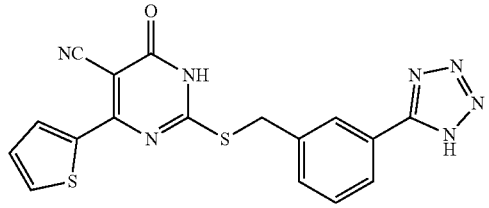 [SMILES: N#Cc1c(-c2cccs2)nc(SCc2cccc(-c3nnn[nH]3)c2)[nH]c1=O] | A |
| I-44 | 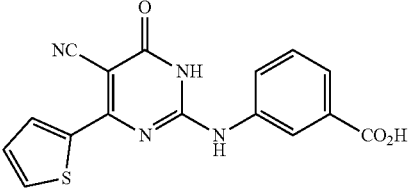 [SMILES: N#Cc1c(-c2cccs2)nc(Nc2cccc(C(=O)O)c2)[nH]c1=O] | n/a |
| I-45 | 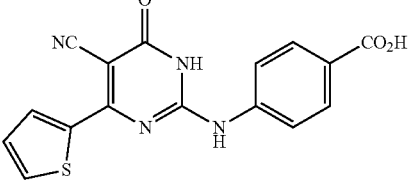 | n/a |
| I-46 | 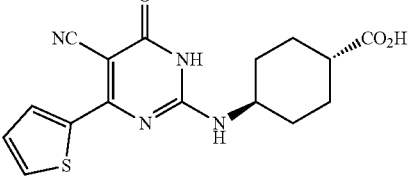 | D |
| I-47 | 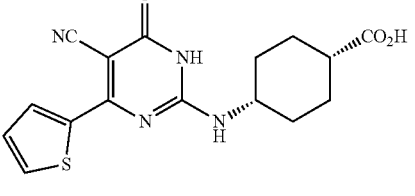 | n/a |
| I-48 | 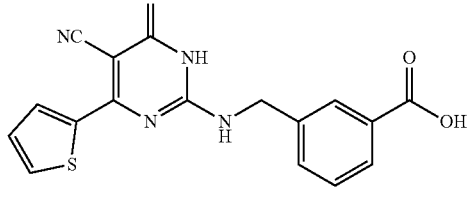 | C |
| I-49 | 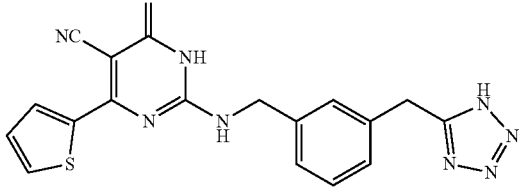 | A |

TABLE 1-continued

| Cpd No. | Structure | Activity hACMSD IC$_{50}$ |
|---|---|---|
| I-50 | [structure: 5-cyano-6-(thiophen-2-yl)-2-((3-(carboxymethyl)benzyl)amino)pyrimidin-4(3H)-one] | C |
| I-51 | [structure: 5-cyano-6-(thiophen-2-yl)-2-((4-(1H-tetrazol-5-yl)benzyl)amino)pyrimidin-4(3H)-one] | B |

Biological Example 2: Determination of ACMSD-1 Modulation in HEK293T Cells

HEK293T cells (ATCC) are seeded in six-well plates and transfected using Fugene HD to express transiently ACMSD. 24 hrs post transfection, the cells are stimulated for 48 hrs to 72 hrs with different concentrations of a compound of Formula (I) or a pharmaceutically acceptable salt thereof, and then lysed to measure the ACMSD activity, by measuring the conversion of 3OH-Anthranilic Acid into product (i.e. (α-amino-β-carboxymuconate-ε-semialdehyde, ACMS) in a spectrophotometrical in vitro assay. The amount of the whole protein content in cell lysates is detected by Bradford analysis. This value is used to get the specificity activity of the enzyme normalized in all samples (mU/ml or ΔE/Δt/mg of total protein).

ACMSD-1 enzyme is known to be expressed in liver, kidney and brain; available cell lines for these cell types were therefore tested to determine the expression levels of ACMSD. We determine whether ACMSD-1 is not expressed in transformed cell lines from liver and kidney, such as HepG2, HEK293T, Hep3B, etc. Transfection of ACMSD was performed to express the enzyme in different cellular backgrounds such as COS-7, HEK293T, and HepG2. The HEK293T cellular background proved to be the best system, with the highest protein production allowing robust measurement ACMSD1 enzyme activity. This is probably due to the better transfection efficacy observed in HEK293T.

Having determined the optimum stimulation time and transfection protocol cells are stimulated with different concentrations of a compound of Formula (I) or a pharmaceutically acceptable salt thereof (about 50 nM to about 5 uM).

Biological Example 3: Determination of NAD$^+$ Content in Human Primary Hepatocytes Treated with a Compound of the Disclosure The NAD$^+$ concentration or content is determined in human primary hepatocytes treated with a compound of Formula (I) or a pharmaceutically acceptable salt thereof. Vehicle (NT) was used as a control.

At least three experiments are run treating primary hepatocytes with different concentrations of a compound of Formula (I) or a pharmaceutically acceptable salt thereof, (0.5 μM and 5 μM) after 48 hrs from seeding. The compounds are replaced every 24 hrs, and then cells are directly harvested and lysed with ACN/H$_2$O (ratio 5:1). LCMS/MS is used to detect and measure NAD$^+$ concentration/content.

Biological Example 4: Determination of NAD$^+$ Content in Human Primary Hepatocytes Treated with a Compound of the Disclosure The NAD$^+$ concentration or content is determined in human primary hepatocytes treated with a compound of Formula (I) or a pharmaceutically acceptable salt thereof, and MEHP, a known ACMSD inhibitor. MEHP is used as a control.

At least three experiments are run treating primary hepatocytes with different concentrations of a compound of Formula (I) or a pharmaceutically acceptable salt thereof, (0.5 μM, 5 μM, and 50 μM) after 48 hrs from seeding. The compounds are replaced every 24 hrs, and then cells are directly harvested and lysed with ACN/H$_2$O (ratio 5:1). LCMS/MS is used to detect and measure NAD$^+$ concentration/content.

Biological Example 5: Modulation of SOD2 Activity in AML-12 Cells and Murine Primary Hepatocytes The modulation of SOD-2 activity in AML-12 cells and murine primary hepatocytes treated with a compound of Formula (I) or a pharmaceutically acceptable salt thereof, is measured.

The mouse hepatocytes cell line AML-12 (alpha mouse liver 12) is obtained from ATCC and grown at 37° C. in a humidified atmosphere of 5% CO$_2$/95% air in Dulbecco's Modified Eagle Medium/Nutrient Mixture F-12 (DMEM/F-12) supplemented with 0.005 mg/ml insulin, 0.005 mg/ml transferrin, 5 ng/ml selenium, 40 ng/ml dexamethasone and 1% gentamycin. ACMSD inhibitors are initially diluted from powder in DMSO to a stock concentration of 1 mM.

This stock is further diluted with water to a concentration of 100 μM which was used for the cell treatments.

Primary hepatocytes are prepared from 8-12-week-old C57BL/6J mice by collagenase perfusion method. Mouse livers are perfused with Hank's balanced salt solution (HBSS, KCl, 5.4 mM; $KH_2PO_4$, 0.45 mM; NaCl, 138 mM; $NaHCO_3$, 4.2 mM; $Na_2HPO_4$, 0.34 mM; glucose, 5.5 mM; HEPES, 1 M; EGTA, 50 mM; $CaCl_2$), 50 mM; pH 7.4). Livers are then washed at a rate of 5 ml/min through the portal vein. After washing, livers are perfused with collagenase (0.025%) solution. Cell viability is assessed by the trypan blue method. Isolated primary hepatocytes are plated with DMEM medium (Gibco) including 10% FCS, 10 units per ml penicillin and HEPES for buffering. The cells are maintained in culture at 37° C. in a humidified atmosphere of 5% $CO_2$/95% air. After 6-8 hrs of attachment, this medium is replaced with media containing different concentrations of an ACMSD inhibitor (i.e., compound of Formula (I) or a pharmaceutically acceptable salt thereof) or with the corresponding concentration of DMSO (as a control). Primary hepatocytes are harvested about 24 hrs later if not indicated differently.

Primary hepatocytes or AML-12 cells are then lysed in a 20 mM HEPES buffer (Gibco), pH 7.2, containing 1 mM EGTA (Sigma), 210 mM mannitol (Sigma), and 70 mM sucrose (AMRESCO). Total protein concentration is determined using the Bradford assay (BioRad). SOD-2 activity is determined at various times after ACMSD inhibitor treatment by the SOD Assay Kit (Cayman Chemical) according to the manufacturer's instructions. In order to specifically detect the SOD2 activity 2 mM potassium cyanide is added to the assay, which inhibits both Cu/Zn-SOD and extracellular SOD, resulting in the detection of only Mn-SOD (SOD-2) activity. Absorbance is determined with a Victor X4 multi-label plate reader (Perkin-Elmer) at 450 nm. Results are expressed in U/ml/mg of protein according to the standard curve and measured protein concentration.

The oxidative stress resistance pathway is explored by measuring the activity of SOD2.

Biological Example 6: Determination of $NAD^+$ Content in Murine Primary Hepatocytes $NAD^+$ levels are determined in human primary hepatocytes treated with a compound of Formula (I) or a pharmaceutically acceptable salt thereof.

$NAD^+$ is extracted using acidic extraction method. Samples are collected and homogenized in 70% ice-cold perchloric acid ($HClO_4$). After insoluble protein parts are pelleted by adding potassium carbonate ($K_2CO_3$), the samples are separated by high-performance liquid chromatography (HPLC) and analyzed by mass-spectrometry. The proteins in the pellet are quantified by Bradford assay and were used for normalization.

The exposure of primary hepatocytes to 5 nM, 10 nM and 50 nM of an ACMSD inhibitor of Formula (I) or a pharmaceutically acceptable salt thereof, for 24 hours is examined for significant and dose-dependent increases in intra-cellular $NAD^+$ levels.

Biological Example 7: RT-qPCR Analysis of SIRT1-Regulated Genes in AML-12 Cells, Hepa-1.6 Cells and Primary Murine Hepatocytes Treated with a Compound of the Disclosure Gene expression of ACMSD and genes known to be regulated by SIRT1, (an enzyme that is strictly $NAD^+$ dependent) such as Pgc1a, Sod1, Sod2 (MnSOD), are analyzed in AML-12 cells, Hepa-1.6 cells and primary murine hepatocytes treated with a compound of Formula (I) or a pharmaceutically acceptable salt thereof.

Cells (AML-12, Hepa-1.6, HEK-293, primary human and murine hepatocytes) are treated with different concentrations of a compound of Formula (I) or a pharmaceutically acceptable salt thereof. Total RNA is extracted from cells using TRIzol (Invitrogen) according to the manufacturer's instructions. The RNA is treated with DNase, and 2 μg of RNA is used for reverse transcription (RT). 50× diluted cDNA is used for RT-quantitative PCR (RT-qPCR) reactions. The RT-qPCR reactions are performed using the Light-Cycler system (Roche Applied Science) and a qPCR Supermix (QIAGEN) with the indicated primers. The average of at least three technical repeats is used for each biological data point.

A dose-dependent increase in mRNA expression levels of genes is known to be regulated by SIRT1, (an enzyme that is strictly $NAD^+$ dependent) such as Pgc1a, Sod2 (MnSOD), but not Sod1 (Cu—Zn SOD). Primary mouse hepatocytes are treated for 24 hrs with a compound of Formula (I) or a pharmaceutically acceptable salt thereof, (5 nM-500 nM range) and are observed for changes in expression levels and mRNA levels of Pgc1a and Sod2 (MnSOD). Changes in mRNA expression are compatible with the activation of SIRT1, subsequent to the induction in $NAD^+$ levels by inhibition of ACMSD1 activity.

Biological Example 8: Modulation of Caspase 3/7 Activity in MDCK Cells

An in vitro study is performed to determine the effects of compounds of Formula (I) or a pharmaceutically acceptable salt thereof, on Acute Kidney Injury in MDCK cells.

MDCK cells (MDCK (NBL-2) ATCC® CCL-34™) are cultured in base medium ATCC-formulated Eagle's Minimum Essential Medium, Catalog No. 30-2003 with fetal bovine serum (FBS) to a final concentration of 10%. 10,000 cells are plated into 96 wells and 24 hours after cell plating the medium is changed with fresh medium supplemented with 1% FBS. Cisplatin (50 μM for 16 hrs) is then used to induce cell injury. Different concentrations (about 1 μM to about 125 μM) of a compound of Formula (I) or a pharmaceutically acceptable salt thereof, (in 1% DMSO) are added in combination with cisplatin or 1 hour prior adding cisplatin.

Caspase 3/7 activity (Promega) is determined according to standard procedures using a luminescent signal readout on a Victor V plate reader (PerkinElmer). Each experiment/condition is performed in triplicate.

Caspase activity is analyzed as percentage effect normalized to the cisplatin alone (100%) and vehicle treated cells as 0% of caspase activity. Data are analyzed by GraphPad Software. One-way analysis of variance (Dunnett's Multiple Comparison test) is used for statistical analyses.

MDCK cells are treated with different concentrations of a compound of Formula (I) or a pharmaceutically acceptable salt thereof.

Biological Example 9: Cytotoxicity and hERG Screening

Cytotoxicity: 20000 HePG2 and AML-12 cells are seeded in 96 well plate (Viewplate PerkinElmer). Dose-response of a compound of Formula (I) or a pharmaceutically acceptable salt thereof, is performed using HP D300 digital dispenser, ranging from 10 nM to 300 μM with constant DMSO 1% in medium. Cells are stimulated for 4 hrs at 37° C.; the supernatant is used to perform LDH release (Cytotox-one, Promega) as a measure of necrosis while the cells are lysed to detect ATP level for determining cell viability (Celltiter-glo, Promega) according to manufacturer's instructions.

The Predictor hERG assay kit (Invitrogen), containing membrane preparations from Chinese hamster ovary cells stably transfected with hERG potassium channel and a high-affinity red fluorescent hERG channel ligand (tracer), is used for the determination of hERG channel affinity binding of the compounds of Formula (I) or a pharmaceutically acceptable salt thereof. Compounds that bind to the hERG channel protein (competitors) are identified by their ability to displace the tracer, resulting in a lower fluorescence polarization. The final concentration of DMSO in each well is maintained at 1%. The assays are performed according to the manufacturer's protocol (Invitrogen).

Biological Example 10: Anti-Diabetic Effects in C57BL/6J and KK-Ay Mice

A glucose tolerance test is performed on male C57BL/6J and KK-Ay mice to determine the effects of compounds of Formula (I) or a pharmaceutically acceptable salt thereof, on glucose and insulin levels.

Male C57BL/6J and KK-Ay mice, 6-7 weeks of age, are obtained, e.g., from Charles River Laboratories France and CLEA Japan, respectively. Mice are fed from the age of 8 weeks onwards with regular chow (CD-Harlan 2018), a high fat diet (HFD-Harlan 06414). A compound of Formula (I) or a pharmaceutically acceptable salt thereof, is mixed with the HFD at 180 mg kg$^{-1}$ of food. On the basis of their daily food intake, this results in a daily dose of about 15 mg kg$^{-1}$ body weight. The mice are fasted for 4 hrs before blood and tissues are harvested for RNA isolation, lipid measurements and histology. Oxygen consumption is measured with the Oxymax apparatus (Columbus Instruments). Histological analysis and transmission electron microscopy are performed.

An oral glucose tolerance test is performed in the animals that are fasted overnight. Glucose is administered by gavage at a dose of 2 g/kg. An intraperitoneal insulin tolerance test is performed in animals fasted for 4 hrs. Insulin is injected at a dose of 0.75 U/kg body weight. Glucose is quantified with the Maxi Kit Glucometer 4 (Bayer Diagnostic) or Glucose RTU (bioMerieux Inc.) and plasma insulin concentrations are measured by ELISA (Cristal Chem Inc.). Statistical differences are determined by either ANOVA or Student's t-test.

Biological Example 11: Anti-Diabetic and Obesity Effects in db/db Mice with LepR Mutation A study of the anti-diabetic effects of the compounds of Formula (I) or a pharmaceutically acceptable salt thereof, is conducted in genetically obese Leprdb/J (db/db) mice.

Animals are bred and housed in a temperature- and humidity-controlled environment in compliance with FELASA-protocols. From an age of three weeks, mice are fed a high-fat diet (HFD) (Harlan 06414). Most pharmacological studies are started in diabetic eight-week-old db/db and wild type (wt) references.

Subchronic Intervention db/db mice are treated once/day with a compound of Formula (I) or a pharmaceutically acceptable salt thereof, for 14 days between 5-6 PM before dark-phase onset (6 PM). Blood samples are collected after 4 hrs of fasting the mice prior to the first dose and at 18±2 hrs after the last dose. Glucose concentrations of each blood sample are determined.

Acute Intervention Glucose

Initial blood samples are collected in random-fed db/db mice between 6-8 AM after light-phase-onset (6 AM), then compounds of Formula (I) or a pharmaceutically acceptable salt thereof, are administered, diet-access is restricted, and the second blood sample is collected 4 hrs post-treatment. Thereafter, mice are subjected to an oral glucose tolerance test (OGTT1: 1 g glucose/kg body mass) and blood glucose concentrations are determined at 0.5, 1, 2, 3, and 4 hrs after each glucose challenge.

Euglycemic-Hyperinsulinemic Clamps Assay db/db mice receive a permanent jugular vein catheter under ketamine/xylazine anesthesia. For six to seven days, later (after 6 AM) food-access is restricted. Conscious mice are placed in oversized rat-restrainers and warmed by warming pads. Catheter-ends are then connected to syringes in CMA402-pumps (Axel Semrau, Sprockhoevel, Germany). After 110 minutes of primed-continuous [3-$^3$H]glucose infusion (1.85 kBq/min), a blood sample is collected to determine plasma insulin, glucose and [3-$^3$H]glucose concentrations and to calculate basal endogenous glucose appearance rates. The mice then receive vehicle or a compound of Formula (I) or a pharmaceutically acceptable salt thereof, via gavage.

Subsequently, glucose-1 clamps are started with a [3-$^3$H] glucose infusion (3.7 kBq/min) containing insulin (36 pmol/kg*min$^{-1}$; HumulinR, Lilly, USA) causing a moderate net-increase in plasma insulin concentrations. Blood glucose concentrations are measured every 10 minutes and target glycemia is established by adjusting the rate of a 20% glucose infusion (GIR). At minute 120, 2-deoxy-D-[1-$^{14}$C] glucose (370 kBq) is given intravenously. Blood samples are collected at minute 30, 60, 90, 100, 110, 120, 122, 125, 130, and 140. The mice are then sacrificed (i.e., through an intravenous ketamine/xylazine-overdose). Gastrocnemius muscle and epididymal adipose tissue are collected, immediately snap-frozen in liquid nitrogen, and stored at −80° C. 2-[$^{14}$C]deoxyglucose-6-phosphate is extracted from the tissue and glucose uptake rates (R$^g$) are calculated.

Plasma [$^3$H]$^-$ and [$^{14}$C]-radioactivity is determined in deproteinized plasma after [$^3$H$_2$O] evaporation. Glucose fluxes under basal conditions and between glucose clamp minute 60 to 90 and 90 to 120 are estimated as follows: whole-body glucose disappearance rate (Rd)=[3-$^3$H]GIR (dpm/min)/plasma [3-$^3$H]glucose specific activity (dpm/min*mol); basal Endo R$^a$=[3-$^3$H]GIR (dpm/min)/plasma [3-$^3$H]glucose specific activity (dpm/min*mol); glucose-clamp Endo Ra=GIR-Rd. Ultima-Gold scintillation-cocktail, radioisotopes, and a Tri-Carb2910TR are obtained from Perkin Elmer (Germany).

Assays from Blood, Plasma, Urine

Blood samples are collected from lateral tail veins. Blood glucose is measured with a glucometer (Contour, Bayer Vital, Germany), urine and plasma glucose with a colorimetric Glucose LabAssay (Wako, Germany), and HbA1c with A1cNow+ (Bayer Vital) or Clover Analyzer (Inopia, South Korea).

Analyses of Disease Onset and Survival

Disease onset is defined as the last day of individual peak body weight before gradual loss occurs. The stages of disease are defined as follows: the early stage of disease is defined as the duration of time between peak body weight until loss of 10% of peak body weight. The late stage of disease is defined as the duration of time between 10% loss of peak body weight until the end stage of disease. The end stage of disease is defined as the day when an animal could no longer right itself within 30 s for three consecutive trials when placed on its side. Animals are euthanized at the end of stage of disease.

Body Composition Measurements

Body weights are assessed weekly for at least 13 weeks. Brown adipose tissue (BAT) and gonadal white adipose tissue (WAT) are dissected and weighed at the indicated age. Total lean mass, % of WAT and BMD (bone mineral density) are determined by DEXA (PIXImus DEXA; GE).

Indirect Calorimetry, Food Intake and Activity

Animals are initially weighed and acclimated to the test cage. Volume oxygen ($VO_2$) and volume carbon dioxide production ($VCO_2$) are measured every 20 min using the Oxymax Comprehensive Laboratory Animal Monitoring System (CLAMS) (Columbus Instruments) and are reported as average $VO_2$ per hour normalized to body weight (mL/h/kg). Using the CLAMS machine, activity counts by infrared beam interruptions and food intake are simultaneously measured. More specifically, food intake is measured by deducting the weight of powderized food pellets at the end of experimentation from the starting weight at the beginning of experimentation. To complement this experiment and to control for a novel environment that may affect feeding behaviour, we also perform a more 'manual' experiment, wherein a set weight of food pellets is placed at the same time each day into a clean home cage, which holds a mouse. The next day the weight of the remaining pellets is recorded and deducted from the starting weight. This experiment is performed for 14 days straight. The body weight of each mouse is also recorded daily. Results for each genotype are similar to that acquired from the CLAMS.

Statistical Analyses.

Considering a 1-β larger than 0.9 statistically powerful, we estimate appropriate group numbers from pilot studies a priori. One- or two-way Analyses of Variance (Bonferroni post-tests) or t-tests are performed.

Biological Example 12: Effects on Non-Alcoholic Fatty Liver Disease (NAFLD) and Non-Alcoholic Steatohepatitis (NASH) in Mice A study is performed to determine the effects of compounds of Formula (I) or a pharmaceutically acceptable salt thereof, on non-alcoholic fatty liver disease (NAFLD) and non-alcoholic steatohepatitis (NASH) in male C57BL/6J fed a high fat and high sucrose diet.

Male C57BL/6J mice (The Jackson Laboratory, Bar Harbor, Maine, USA) are housed under a 14 hrs light-10 hrs dark cycle at 21-23° C. and have ad libitum access to water during the entire experiment. From the age of 6 weeks, mice are fed a 'Western' HF-HSD with 44.6% of kcal derived from fat (of which 61% saturated fatty acids) and 40.6% of kcal derived from carbohydrates (primarily sucrose 340 g/kg diet) (TD.08811, 45% kcal Fat Diet, Harlan Laboratories Inc., Madison, Wisconsin, USA) or normal chow diet (NCD) as control (V1534-000 ssniff R/M–H, ssniff Spezialdiäten GmbH, Soest, Germany). The animals are then treated with a compound of Formula (I) or a pharmaceutically acceptable salt thereof, or a control for 4, 12 or 20 weeks (n=8 per group for every time point), after which they are sacrificed.

Body weight and food intake are monitored weekly on the same day. After sedation with sodium pentobarbital (intraperitoneal injection, 50 mg/kg body weight), total fat mass is analyzed by dual-energy X-ray absorptiometry (DEXA) (PIXImus densitometer, Lunar Corp., Madison, Wisconsin, USA). Intraperitoneal glucose tolerance test (IPGTT) is performed in 6 hrs fasted mice. Tail vein glucose levels are measured with a Bayer Contour glucometer immediately before (time point 0 min) and 15, 30, 60, 90 and 150 min after glucose administration (1 g glucose/kg body weight). Insulin resistance is calculated using the Homeostasis Model of Insulin Resistance (HOMA-IR) index: (fasting insulin (ng/mL)×fasting glucose (mg/dL))/405.

Sacrifice

After a 6 hrs fasting period, mice are anaesthetised with sodium pentobarbital (intraperitoneal injection, 50 mg/kg body weight) and sacrificed by blood sampling via cardiac puncture. Plasma is obtained by centrifugation of blood (6000 rpm for 5 min at 4° C.) that is collected in heparinised syringes. Tissues are either snap frozen in liquid nitrogen or stored at −80° C. together with the plasma until further biochemical and molecular analyses or preserved for histological analysis.

Histological Analyses

Liver samples are routinely fixed in buffered formalin (4%) and embedded in paraffin. Serial 4 mm thick sections are stained with H&E and picrosirius red to assess fibrosis. Frozen liver sections are stained with Oil Red O to assess lipid accumulation. All liver biopsies are analyzed by an expert liver pathologist, blinded to the dietary condition or surgical intervention. Steatosis, activity and fibrosis are semiquantitatively scored according to the NASH-Clinical Research Network criteria. The amount of steatosis (percentage of hepatocytes containing fat droplets) is scored as 0 (<5%), 1 (5-33%), 2 (>33-66%) and 3 (>66%). Hepatocyte ballooning is classified as 0 (none), 1 (few) or 2 (many cells/prominent ballooning). Foci of lobular inflammation are scored as 0 (no foci), 1 (<2 foci per 200×field), 2 (2-4 foci per 200× field) and 3 (>4 foci per 200× field). Fibrosis is scored as stage F0 (no fibrosis), stage F1a (mild, zone 3, perisinusoidal fibrosis), stage F1b (moderate, zone 3, perisinusoidal fibrosis), stage F1c (portal/periportal fibrosis), stage F2 (perisinusoidal and portal/periportal fibrosis), stage F3 (bridging fibrosis) and stage F4 (cirrhosis). Diagnosis of NASH is based on accepted histological criteria. Severity of the disease is assessed using the NAS (NAFLD activity score) as the unweighted sum of scores of steatosis, hepatocyte ballooning and lobular inflammation. Percentage of fibrosis is quantitated by morphometry from digitalised sirius red stained sections using the Aperio system after tuning the threshold of fibrosis detection under visual control. Results are expressed as collagen proportional area.

Biological Example 13: Effects on Non-Alcoholic Fatty Liver Disease (NAFLD) and Non-Alcoholic Steatohepatitis (NASH) in Methionine and Choline Deficient Mice A study is performed to determine the effects of compounds of Formula (I) or a pharmaceutically acceptable salt thereof, on non-alcoholic fatty liver disease (NAFLD) and non-alcoholic steatohepatitis (NASH) in male wildtype mice fed a methionine- and choline-deficient diet.

Wildtype mice housed in 12-hour light/dark cycles, with free access to food and water are used. At least 5 animals per time point are analyzed. All experiments are repeated at least three times. For dietary treatment, 8-12 weeks old male mice weighing 25 g are either fed a methionine- and choline-deficient diet (MCD to induce NASH) or chow diet (as a control). Animal experiments and evaluation of NAFLD and NASH as described above in Example 55 for mice fed the high fat and high sucrose diet.

Biological Example 14: Effects on Atherosclerosis in High Cholesterol Fed LDL-R Knockout Mice A study is performed to determine the effects of compounds of Formula (I) or a pharmaceutically acceptable salt thereof, on atherosclerosis in high cholesterol fed LDL-R knockout mice.

LDL-R knockout (KO) mice are backcrossed for ten generations with the C57BL/6J strain, yielding congenic C57BL/6J animals. The controls that are used are littermates in all experiments. The animals are treated with a compound of Formula (I) or pharmaceutically acceptable salt thereof, or a control. Mice are sacrificed 12 weeks after the initiation of the atherogenic diet (TD94059; Harlan), after which the heart and aorta are perfused with PBS and subsequently fixed (Shandon Formal Fixx, Thermo Scientific). Atherosclerosis is assessed by an Oil red O staining of the aortic root and quantified with MetaMorph software. Biochemistry parameters are measured with the appropriate kits in the COBAS C111 (Roche). For the in vivo lipopolysaccharide (LPS) study, mice are intraperitoneally injected with 100 mg of LPS, and blood is taken from the tail vein. TNFα levels are quantified with Mouse TNFα ELISA Ready-SET-Go! (eBioscience) assay. Blood cell counts are determined with Advia2120 (Siemens Healthcare Diagnostics).

The Student's t test is used to calculate the statistical significance. In case of multiple testing (i.e., the comparison of more than two groups), this test is preceded by the ANOVA test. P<0.05 is considered statistically significant. Results represent the mean SEM.

Biological Example 15: Effects on Inherited Mitochondrial Disease in $Sco2^{KO/KI}$ Mice A study is performed to determine the effects of compounds of Formula (I) or a pharmaceutically acceptable salt thereof, on inherited mitochondrial disease in $Sco2^{KO/KI}$ mice.

Anti-COI, anti-COX5a, anti-Ndufa9, anti-SDH-HA, and anti-Core 2 are from Invitrogen; anti-GAPDH is from Millipore; anti-FoxO1 and anti-acetylated-FoxO1 are from Cell Signaling and Santa Cruz, respectively. Anti-mouse secondary antibodies are from Amersham. Chemicals are from Sigma. Oligonucleotides are from PRIMM, Italy.

Compounds of Formula (I) or a pharmaceutically acceptable salt thereof, are dissolved in water and added to a standard powder diet (Mucedola, Italy) at the appropriate concentration of 50 mg/Kg/day. Pellets containing the compounds of Formula (I) or a pharmaceutically acceptable salt thereof, or the vehicles are reconstituted by hand and kept frozen at −20° C. until needed. The diet supply is changed every three days, and only the amount needed is thawed at each time and administered ad libitum for one month. $Sco2^{KO/KI}$ mice are maintained in a temperature- and humidity-controlled animal-care facility, with a 12 hrs light/dark cycle and free access to water and food. Animals are sacrificed by cervical dislocation.

Morphological Analysis

For histochemical analysis, tissues are frozen in liquid-nitrogen precooled isopentane. Series of 8 mm thick sections are stained for COX and SDH.

Biochemical Analysis of MRC Complexes

Muscle quadriceps samples stored in liquid nitrogen are homogenized in 10 mM phosphate buffer (pH 7.4), and the spectrophotometric activity of cI, cII, cIII, and cIV, as well as CS, is measured as described. Note that in all panels the activity of cII is multiplied by 10 for visualization clarity.

$NAD^+$ Determination $NAD^+$ is extracted using acidic and alkaline extraction methods, respectively. Tissue $NAD^+$ is analyzed with mass spectrometry as previously described.

Biological Example 16: Effects on Inherited Mitochondrial Disease in Deletor Mice A study is performed to determine the effects of compounds of Formula (I) or a pharmaceutically acceptable salt thereof, on inherited mitochondrial disease in Deletor mice.

The Deletor mouse model is generated in C57BL/6 congenic background and has been previously characterized (Tyynismaa et al, 2005); WT mice are littermates from the same congenic mouse strain C57BL/6J. Deletor and WT male mice are administered either chow diet (CD) or a compound of Formula (I) or a pharmaceutically acceptable salt thereof, admixed with the CD at the appropriate concentration. The food pellets are manually prepared by mixing a compound of Formula (I) or a pharmaceutically acceptable salt thereof, into the powdered food as described for the $Sco2^{KO/KI}$ mice in Example 58 and stored at −20° C. The mice are housed in standard animal facility, under a 12 hrs dark/light cycle. They have ad libitum access to food and water. The pre-manifestation group consists of 12 Deletors and 12 WT mice, and the post-manifestation group of 24 Deletors and 24 WT mice, receiving either a compound of Formula (I) or a pharmaceutically acceptable salt thereof, or CD diet. During the intervention, the mice are regularly monitored for weight, food consumption, and physical endurance. Their exercise capability is measured twice by treadmill exercise test (Exer-6M Treadmill, Columbus Instruments) at the start and the end of the diet. The exercise test protocol consists of the initial running speed of 7 m/s which is increased every 2 min by 2 m/s and continued until the animal is unable to run or repeatedly falls from the belt at the stimulus site.

Oxygen consumption and carbon dioxide production, as well as spontaneous moving and feeding activities, are recorded by Oxymax Lab Animal Monitoring System (CLAMS; Columbus Instruments, OH, USA). The mice are kept in individual cages inside a CLAMS chamber for 3 days; the first day and night is a nonrecording adjustment period followed by a 24 hrs recording at thermoneutrality (+30° C.). The results of 02 consumption and $CO_2$ production are used to calculate respiratory exchange rate and analyzed separately from the light (inactive) and dark (active) periods of the day.

Morphologic Analysis

Tissue sections are prepared from the quadriceps, liver, and BAT. Samples are embedded with OCT Compound Embedding Medium (Tissue-Tek) and snap-frozen in 2-methylbutane in liquid nitrogen. Frozen sections (12 lm) from quadriceps are assayed for in situ histochemical COX and succinate dehydrogenase (SDH) activities simultaneously. The activities from the quadriceps sections, the COX-negative and the COX-negative plus SDH positive and normal fibres are calculated. Approximately 2000 fibres are counted from each mouse sample. The intensity of COX histochemical activity from quadriceps for both oxidative and non-oxidative fibres is measured with Image J software. Frozen sections (8 μm) from liver and BAT are stained with Oil Red O. For plastic embedding, quadriceps, liver, and BAT samples are fixed in 2.5% glutaraldehyde, treated with 1% osmium tetroxide, dehydrated in ethanol, and embedded in epoxy resin. Semi-thin (1 μm) sections are stained with methyl blue (0.5% w/v) and boric acid (1% w/v). The interesting areas for the ultrastructural analyses are selected by inspection of the light microscopic sections. For transmission electron microscopy, ultrathin (60-90 nm) sections are cut on grids and stained with uranyl acetate and lead citrate and viewed with a Transmission Electron Microscope. Crista content in both BAT and muscle is determined from electron micrographs, utilizing a 1 μm "intra-mitochondrial measuring stick," placed perpendicular to cristae. Skeletal muscle samples are also analyzed for citrate synthase activity.

Biological Example 17: Effects on Kidney Disease

A study is performed to determine the effects of compounds of Formula (I) or a pharmaceutically acceptable salt thereof, on kidney disease in C57BL/6J WT mice. (Wei, Q., et al., "*Mouse model of ischemic acute kidney injury: technical notes and tricks*" American Journal of Physiology-Renal Physiology, 303(11), F1487-F1494)

C57BL/6J WT mice are purchased from Charles-River. All mice are fed a standard commercial diet while housed at an ambient temperature of 20-22° C. with a relative humidity of 50±5% under 12/12 hrs light-dark cycle in a specific pathogen-free facility. The experimental mice are 8 weeks old and are divided into four groups: (1) control (n=5); (2) cisplatin (20 mg/kg; Sigma Chemical, St Louis, MO; n=5); (3) a compound of Formula (I) or a pharmaceutically acceptable salt thereof, and cisplatin (n=5); and (4) a compound of Formula (I) or a pharmaceutically acceptable salt thereof, alone (40 mg/kg; n=5). The dose and time of cisplatin treatment for nephrotoxicity are chosen according to a published method. A compound of Formula (I) or a pharmaceutically acceptable salt thereof, is administered orally once a day for 4 days. Cisplatin is injected once at 12 hrs after the first administration of a compound of Formula (I) or a pharmaceutically acceptable salt thereof. The mice are sacrificed at 72 hrs after the single cisplatin injection.

Assays for Renal Functional Markers and Proinflammatory Cytokines

For renal function analysis, serum is isolated and stored at −80° C. until use. Serum creatinine and BUN levels are measured using an assay kit according to the manufacturer's instructions (BioVision, Milpitas, CA). In addition, the proinflammatory cytokines TNF-α, IL-1b, and IL-6 from serum or homogenates from kidney tissue are quantified by ELISA (Quantikine Kit; R&D Systems, Minneapolis, MN) according to the manufacturer's instructions. For measuring cytokines, kidney tissue is homogenized in phosphate buffered saline containing 0.05% Tween-20. Aliquots containing 300 mg of total protein are used. A metabolic cage is used for collecting urine to analyze the level of urinary cytokines. The sample size for each group is five.

Alternative Study of the Effects on Kidney Disease

Alternatively, C57BL/6J WT mice are numbered and kept in acclimatization for a period of 5-7 days before initiation of the experiment. (Wei, Q., et al. "*Mouse model of ischemic acute kidney injury: technical notes and tricks*" American Journal of Physiology-Renal Physiology, 303(11), F1487-F1494) Mice are randomized into different treatment groups based on their body weight. Different groups are maintained on Harlan diet 2916. Mice are then maintained on the respective diets for 10 days prior to bilateral Ischemic kidney injury. Body weight measurement is made once at randomization and once on day 7. Food consumption is evaluated once on day 7. Blood is collected by retro-orbital puncture under mild Isoflurane anesthesia and used for analysis of basal blood urea nitrogen levels (BUN) on day 9.

Mice are anesthetized with ketamine (80 mg/kg i.p) and/or Xylazine (10 mg/kg, i.p.) and placed on a surgical platform in a dorsal position. Both kidneys are exposed through flank incisions and renal pedicles are occluded using vascular clamps for 25 minutes. The clamp is then removed and the surgical site is sutured. 1 ml of physiological saline is administered intra-peritoneally after closing the wound to prevent dehydration. The sham-operated group is subjected to similar surgical procedures, except that the occluding clamp is not applied. Animals are monitored until recovery from anesthesia and returned to their home cage. Animals are observed every day for general clinical signs and symptoms and mortality.

One day prior to termination, animals are individually housed in metabolic cages for 12 h and urine is collected for estimation of urea, creatinine, sodium and potassium.

On days 12, 14, & 16 blood is collected by retro orbital puncture under mild isoflurane anesthesia and plasma is used for analysis of blood urea nitrogen levels (BUN) and serum creatinine. Animals are then euthanized by $CO_2$ inhalation and organs are collected. One kidney is fixed in 10% neutral buffered formalin and the other is flash frozen in liquid nitrogen, stored at −80° C. and used for the estimation of lipid peroxidation, GSH, KIM1, MPO, NGAL, and SOD levels.

Histological Analysis and Neutrophil Counting

Mouse kidneys are fixed in 4% formaldehyde and embedded in paraffin wax. The 5-mm-thick sections are deparaffinised in xylene and rehydrated through graded concentrations of ethanol. H&E and PAS staining are performed using standard protocols. Images are collected and analyzed using a light microscope (IX71, Olympus, Tokyo, Japan) with DP analyzer software (DP70-BSW, Tokyo, Japan). Tubular damage in PAS-stained kidney sections is examined under a light microscope and scored based on the percentage of cortical tubular necrosis: 0=normal, 1=1-10, 2=11-25, 3=26-45, 4=46-75, and 5=76-100%. Slides are scored in a blinded manner, and results are means±s.d. of 10 representative fields/group. Severity criterion for tubular necrosis displaying the loss of the proximal tubular brush border and cast formation are used to classify samples. The sample size for each group is 10. Neutrophil infiltration is quantitatively assessed on PAS stained tissue by a renal pathologist by counting the number of neutrophils per high-power field (×400). At least 10 fields are counted in the outer stripe of the outer medulla for each slide.

All values are represented as mean±s.d. One-way analysis of variance is used to calculate the statistical significance of the results of all assays and P-values<0.05 are considered statistically significant.

Biological Example 18: Effects on Ischemia/Reperfusion-induced Acute Kidney Injury A study is performed to determine the effects of compounds of Formula (I) or a pharmaceutically acceptable salt thereof, on Ischemia/Reperfusion-induced (I/R-induced) Acute Kidney Injury in CD-1 (ICR) mice.

CD-1 (ICR) mice are purchased from Charles River Laboratory (Wilmington, MA). Mice are housed in a temperature- and humidity-controlled environment with a 12:12 hrs light-dark cycle and are allowed freely access to standard rodent chow (TekLad, Madison, WI) and tap water.

Mice are subjected to a midline back incision, and both renal pedicles are clamped for 45 min with microaneurysm clamps (00396-01; Fine Science Tools, Foster City, CA). After removal of the clamp, the kidneys are inspected for the restoration of blood flow. The animals are allowed to recover, and they are sacrificed 48 hrs after reperfusion. Mice are treated with 100 mg/kg of a compound of Formula (I) or a pharmaceutically acceptable salt thereof, by oral gavage once per day. CD-1 mice are divided into four groups: (1) young mice with sham injury (n=4) (6-7 weeks old); (2) young mice with I/R injury (n=8); (3) adult mice with sham injury (n=4) (20-24 weeks old); and (4) adult mice with I/R injury (n=11). An additional 27 adult mice (20-24 weeks old) are randomized into two groups: 13 mice received a compound of Formula (I) or a pharmaceutically acceptable salt thereof, and the other 14 mice received the vehicle as a control.

The serum creatinine level is measured using the QuantiChrom Creatinine Assay Kit (DICT-500, BioAssay Systems, Hayward, CA). BUN measurements are recorded using the Infinity Urea (Nitrogen) Liquid Stable Reagent (TR12421; ThermoTrace, Victoria, AU).

Evaluation of Renal Tissue

Kidneys are fixed in 4% paraformaldehyde, embedded in paraffin, and stained with hematoxylin and eosin (4 mm thick). Tubular injury is scored on a scale of 0-4 on the basis of the percentage of tubules with necrosis, dilatation, or cell swelling: 0, less than 5%; 1, 5-25%; 2, 25-50%; 3, 50-75%; and 4, over 75%. All high-power fields (×400) in the cortex and outer medulla are evaluated by a pathologist in a blinded manner.

All values are expressed as mean±s.e. Statistical analysis is carried out using GraphPad Prism 4.00 (San Diego, CA) with unpaired Student's t testing for two sets of data and an analysis of variance with a Bonferroni post-test for multiple groups. $P<0.05$ was considered significant.

Biological Example 19: Effects on Cisplatin-Induced Acute Kidney Injury

A study is performed to determine the effects of compounds of Formula (I) or a pharmaceutically acceptable salt thereof, on Cisplatin-induced Acute Kidney Injury in C57BL6 mice.

C57BL6 mice. are purchased from Charles River Laboratory (Wilmington, MA). Mice are housed in a temperature- and humidity-controlled environment with a 12:12 hrs light-dark cycle and are allowed freely access to standard rodent chow (TekLad, Madison, WI) and tap water.

Mice are subjected to a midline back incision, and both renal pedicles are clamped for 45 min with microaneurysm clamps (00396-01; Fine Science Tools, Foster City, CA). Cisplatin was injected intraperitoneally 20 mg/kg body weight. The animals are allowed to recover, and they are sacrificed 48, 72, and 96 hrs post cisplatin injection. Mice are treated with 100 mg/kg of a compound of Formula (I) or a pharmaceutically acceptable salt thereof, by oral gavage once per day. C57BL6 mice are divided into four groups: (1) young mice with sham injury (n=4) (6-7 weeks old); (2) young mice with Cisplatin injury (n=8); (3) adult mice with sham injury (n=4) (20-24 weeks old); and (4) adult mice with Cisplatin injury (n=11). An additional 27 adult mice (20-24 weeks old) are randomized into two groups: 13 mice received a compound of Formula (I) or a pharmaceutically acceptable salt thereof, and the other 14 mice received the vehicle as a control.

The serum creatinine level is measured using the QuantiChrom Creatinine Assay Kit (DICT-500, BioAssay Systems, Hayward, CA). BUN measurements are recorded using the Infinity Urea (Nitrogen) Liquid Stable Reagent (TR12421; ThermoTrace, Victoria, AU).

Evaluation of Renal Tissue

Kidneys are fixed in 4% paraformaldehyde, embedded in paraffin, and stained with hematoxylin and eosin (4 mm thick). Tubular injury is scored on a scale of 0-4 on the basis of the percentage of tubules with necrosis, dilatation, or cell swelling: 0, less than 5%; 1, 5-25%; 2, 25-50%; 3, 50-75%; and 4, over 75%. All high-power fields (×400) in the cortex and outer medulla are evaluated by a pathologist in a blinded manner.

All values are expressed as mean±s.e. Statistical analysis is carried out using GraphPad Prism 4.00 (San Diego, CA) with unpaired Student's t testing for two sets of data and an analysis of variance with a Bonferroni post-test for multiple groups. $P<0.05$ was considered significant.

Biological Example 20: Effects on Sepsis-Induced Acute Kidney Injury

A study is performed to determine the effects of compounds of Formula (I) or a pharmaceutically acceptable salt thereof, against sepsis-induced Acute Kidney Injury in C57BL6 mice (12-15 weeks old). C57BL6 mice. are purchased from Charles River Laboratory (Wilmington, MA).

Mice are housed in a temperature- and humidity-controlled environment with a 12:12 hrs light-dark cycle and are allowed freely access to standard rodent chow (TekLad, Madison, WI) and tap water. Sepsis is induced by Cecal ligation and puncture (CLP). The procedure for CLP is as follows; the lower abdomen is shaved, and cleaned with 70% ethanol and a 1 cm laparotomy is performed whereby the cecum is identified and externalized. The cecum is measured from the ileo-cecal valve to the tip, ligated at the ~50% mark, punctured once (through-and-through) with a 21-gauge needle and returned into the abdomen after expressing to allow for fecal matter to extrude. The abdominal wall is then closed by planes using a running Silk 4-0. Control animals undergo the same laparotomy, identification and externalization of the cecum, but no ligation or perforation. Animals are then given 1 ml of saline and buprenorphine into the scruff of the neck subcutaneously and recovered on thermal blankets under monitoring. Animals are treated with ampicillin sulbactam (250 mg/kg Q12 hours IP for 3 days) and analgesic treatment (buprenorphine 0.05 mg/kg for 3 days).

A compound of Formula (I) or a pharmaceutically acceptable salt thereof, are administered at two different timepoints: A. At the time of CLP (early phase); and B. At 24 hours after CLP via IP injection.

Blood and kidney tissues are collected at the time of sacrificing for measurement of primary and secondary endpoints.

Primary endpoint (at 48 hrs):serum creatinine. Secondary endpoints (at 48 hours) include: Macrophage phenotype marker (IF stain), Plasma NGAL, Plasma and kidney markers of inflammation (IL-6, IL-18, TNF), and Kidney Injury markers (KIM-1, NGAL, TIMP2 and IGFBP7). Addition endpoints include; cell death (IF: Annexin V and Propidium Iodide; Caspase 3/7), autophagy, biogenesis (PGC-1α, mitochondrial DNA), OXPHOS (Complex I, III, IV activity), Sirt1 and Sirt3 expression, AMPK (Total, P-AMPK, P-ACC, and HIF-1α.

Histological Analysis

Mouse kidneys are fixed in 4% formaldehyde and embedded in paraffin wax. The 5-mm-thick sections are deparaffinised in xylene and rehydrated through graded concentrations of ethanol. H&E and PAS staining are performed using standard protocols. Images are collected and analyzed using a light microscope (IX71, Olympus, Tokyo, Japan) with DP analyzer software (DP70-BSW, Tokyo, Japan). Tubular damage in PAS-stained kidney sections is examined under a light microscope and scored based on the percentage of cortical tubular necrosis: 0=normal, 1=1-10, 2=11-25, 3=26-45, 4=46-75, and 5=76-100%. Slides are scored in a blinded manner, and results are means±s.d. of 10 representative fields/group. Severity criterion for tubular necrosis displaying the loss of the proximal tubular brush border and cast formation are used to classify samples. The sample size for each group is (n=6 per group in groups 2, 4-9 and n=3 for group 1, 45 total). A tubular injury score will be used to evaluate protection against kidney damage.

Biological Example 21: Effects on FoxO1 Phosphorylation Levels

AML-12 cells are treated with different concentrations of a compound of Formula (I) or a pharmaceutically acceptable salt thereof, for 24 hours. Cells are then lysed in lysis buffer (50 mM Tris, 150 mM KCl, EDTA 1 mM, NP40 1%) containing protease and phosphatase inhibitors, and analyzed by SDS-PAGE/western blot. Blocking and antibody incubations were done in 5% milk. Each protein present is detected with its specific antibody. Tubulin antibody is obtained from Sigma Inc, FoxO1 and phopho-FoxO1 (Ser256) antibodies were obtained from Cell Signaling. Antibody detection reactions are developed by enhanced chemiluminescence (Advansta, CA, USA) using X-ray films.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice of testing the present disclosure, suitable methods and materials are described below. All publications, patent applications, patents, and other references mentioned herein are hereby expressly incorporated by reference. The references cited herein are not admitted to be prior art of the claimed disclosure. In the case of conflict, the present specification, including definitions, will control. In addition, the materials, methods, and examples are illustrative only and are not intended to be limiting.

EQUIVALENTS

Those skilled in the art will recognize, or be able to ascertain using no more than routine experimentation, many equivalents to the specific embodiments and methods described herein. Such equivalents are intended to be encompassed by the scope of the present disclosure.

The invention claimed is:

1. A compound represented by Formula (II):

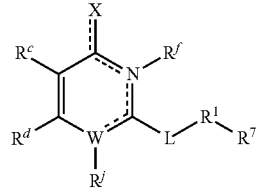

or a pharmaceutically acceptable salt or tautomer thereof, wherein:
X is O or $OR^h$;
W is N;
L is $-SCH_2-$;
$R^1$ is absent, $C_6$-$C_{10}$ arylene or heteroarylene, wherein the heteroarylene comprises one or two 5- to 7-membered rings and 1-4 heteroatoms selected from N, O, and S, and wherein the $C_6$-$C_{10}$ arylene and heteroarylene are unsubstituted or substituted with one to two $R^e$;
each $R^6$ is independently at each occurrence H or $C_1$-$C_4$ alkyl;
$R^7$ is A;
A is $-(C(R^6)_2)_r$tetrazole;
$R^c$ is H, halogen, or $-CN$;
$R^d$ is $-CF_3$, $-CR^fF_2$, $-(C(R^6)_2)_t$-$C_6$-$C_{10}$ aryl, $-(C(R^6)_2)_t$-5- or 6-membered heteroaryl;
each $R^e$ is independently at each occurrence $C_1$-$C_6$ alkyl, halogen, $C_1$-$C_6$ haloalkyl, $-NHR^z$, $-OH$, or $-CN$;
$R^f$ is H;
$R^h$ is H;
$R^j$ is absent;
$R^z$ is H, $C_1$-$C_6$ alkyl, or $C_1$-$C_6$ haloalkyl;
each r is independently 0, 1, or 2;
each t is independently 1 or 2; and
=== represents a single bond or a double bond.

2. The compound of claim 1, wherein $R^c$ is H.
3. The compound of claim 1, wherein $R^e$ is $-CN$.
4. The compound of claim 1, wherein $R^d$ is $-CF_3$.
5. The compound of claim 1, wherein $R^d$ is $-CR^fF_2$.
6. The compound of claim 1, wherein $R^d$ is $-(C(R^6)_2)_t$-$C_6$-$C_{10}$ aryl or $-(C(R^6)_2)_t$-5- or 6-membered heteroaryl.
7. The compound of claim 6, wherein $R^d$ is $-CH_2$-$C_6$-$C_{10}$ aryl.
8. The compound of claim 1, wherein $R^1$ is $C_6$-$C_{10}$ arylene.
9. The compound of claim 1, wherein $R^1$ is heteroarylene.
10. The compound of claim 1, wherein $R^1$ is absent.
11. A compound, or a pharmaceutically acceptable salt or tautomer thereof, selected from the group consisting of:

| Cpd No. | Structure |
|---|---|
| I-26 | 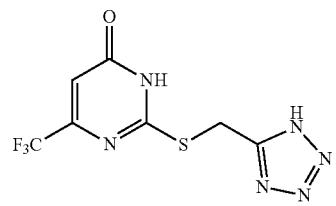 |

-continued
| Cpd No. | Structure |
|---|---|
| I-29 | 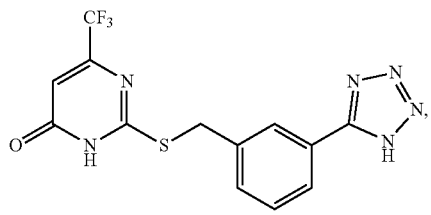 [SMILES: O=c1cc(C(F)(F)F)nc(SCc2cccc(-c3nnn[nH]3)c2)[nH]1] |
| I-32 | 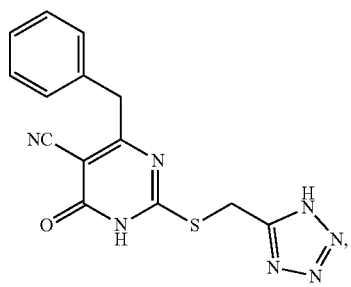 [SMILES: N#Cc1c(Cc2ccccc2)nc(SCc2nnn[nH]2)[nH]c1=O] |
| I-34 | 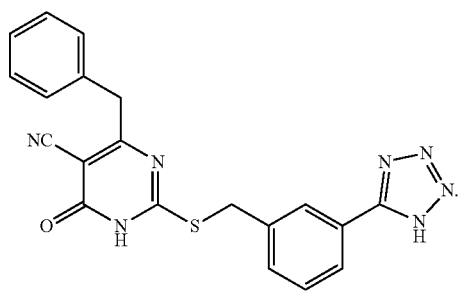 [SMILES: N#Cc1c(Cc2ccccc2)nc(SCc2cccc(-c3nnn[nH]3)c2)[nH]c1=O] |
12. A compound, or a pharmaceutically acceptable salt or tautomer thereof, selected from the group consisting of:
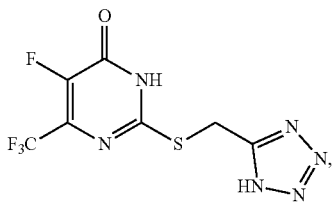
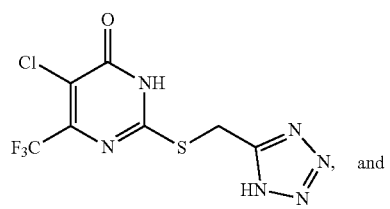 and
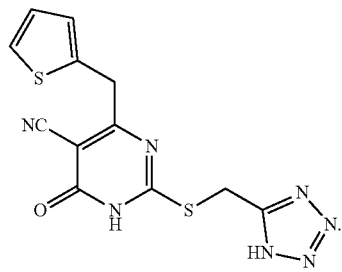
* * * * *